ns that Your may be useful in therapy.

(12) United States Patent
Traquandi et al.

(10) Patent No.: US 7,482,354 B2
(45) Date of Patent: Jan. 27, 2009

(54) PYRAZOLO-QUINAZOLINE DERIVATIVES, PROCESS FOR THEIR PREPARATION AND THEIR USE AS KINASE INHIBITORS

(75) Inventors: Gabriella Traquandi, Milan (IT); Maria Gabriella Brasca, Cusago (IT); Roberto D'Alessio, Cinisello Balsamo (IT); Paolo Polucci, Parabiago (IT); Fulvia Roletto, Busto Garolfo (IT); Anna Vulpetti, Brugherio (IT); Paolo Pevarello, Pavia (IT); Achille Panzeri, Merate (IT); Francesca Quartieri, Arona (IT); Ron Ferguson, Casale Litta (IT); Paola Vianello, Milan (IT); Daniele Fancelli, Milan (IT)

(73) Assignee: Nerviano Medical Sciences S.r.l., Milan (IT)

( * ) Notice: Subject to any disclaimer, the term of this patent is extended or adjusted under 35 U.S.C. 154(b) by 19 days.

(21) Appl. No.: 10/557,565

(22) PCT Filed: Apr. 27, 2004

(86) PCT No.: PCT/EP2004/050612

§ 371 (c)(1),
(2), (4) Date: Sep. 26, 2006

(87) PCT Pub. No.: WO2004/104007

PCT Pub. Date: Dec. 2, 2004

(65) Prior Publication Data

US 2007/0185143 A1    Aug. 9, 2007

Related U.S. Application Data

(60) Provisional application No. 60/472,661, filed on May 22, 2003.

(51) Int. Cl.
*A61K 31/505* (2006.01)
*A01N 43/54* (2006.01)
*C07D 239/00* (2006.01)
*C07D 471/00* (2006.01)
*C07D 487/00* (2006.01)
*C07D 491/00* (2006.01)

(52) U.S. Cl. .................... 514/267; 514/251
(58) Field of Classification Search ............ 544/251; 514/267
See application file for complete search history.

(56) References Cited

U.S. PATENT DOCUMENTS

2002/0119975 A1    8/2002    Snow et al.
2003/0100594 A1 *  5/2003    Masferrer et al. .......... 514/406

FOREIGN PATENT DOCUMENTS

| CA | 2 476 665 | * | 8/2003 |
|---|---|---|---|
| WO | WO 96/40142 | | 12/1996 |
| WO | WO 98/28281 | | 7/1998 |
| WO | WO 98/58926 | | 12/1998 |
| WO | WO 00/69846 | | 11/2000 |
| WO | WO 01/12188 A1 | | 2/2001 |
| WO | WO 01/12189 A1 | | 2/2001 |
| WO | WO 02/12242 A2 | | 2/2002 |
| WO | WO 02/48114 A1 | | 6/2002 |
| WO | WO 02/070515 A2 | | 9/2002 |
| WO | WO 03/028720 A1 | | 4/2003 |
| WO | WO 03/070706 A1 | | 8/2003 |
| WO | WO 03070706 | * | 8/2003 |
| WO | WO 2004/014352 A2 | | 2/2004 |

OTHER PUBLICATIONS

Webster K.R., "The Therapeutic Potential of Targeting the Cell Cycle", *Expert Opinion on Investigational Drugs*, 7(6):865-887 (1998).
Tanaka T. et al., "Centrosomal Kinase AIK1 Is Overexpressed in Invasive Ductal Carcinoma of the Breast", *Cancer Research*, 59:2041-2044 (1999).
Sen S. et al., "Amplification/Overexpression of a Mitotic Kinase Gene in Human Bladder Center", *Journal of the National Cancer Institute*, 94(17):1320-1329 (2002).
Warner S.L. et al., "Targeting Aurora-2 Kinase in Cancer", *Molecular Cancer Therapeutics*, 2:589-595 (2003).
Hosoi T. et al., "Evidence for cdk5 as a Major Activity Phosphorylating Tau Protein in Porcine Brain Extract", *J. Biochem.*, 117(4):741-749 (1995).

* cited by examiner

*Primary Examiner*—James O. Wilson
*Assistant Examiner*—Erich A Leeser
(74) *Attorney, Agent, or Firm*—Scully, Scott, Murphy & Presser, P.C.

(57) ABSTRACT

Pyrazolo-quinazoline derivatives of formula (Ia) or (Ib) as defined in the specification, and pharmaceutically acceptable salts thereof, process for their preparation and pharmaceutical compositions comprising them are disclosed; the compounds of the invention may be useful in therapy, in the treatment of diseases associated with a disregulated protein kinase activity, like cancer.

13 Claims, No Drawings

PYRAZOLO-QUINAZOLINE DERIVATIVES, PROCESS FOR THEIR PREPARATION AND THEIR USE AS KINASE INHIBITORS

CROSS REFERENCE TO RELATED APPLICATIONS

The present application is application is a 371 of PCT/EP04/50612, filed on Apr. 27, 2004 and claims benefit of U.S. Provisional Application No. 60/472,661, filed on May 22, 2003.

BACKGROUND OF THE INVENTION

1. Field of the Invention

The present invention relates to pyrazolo-quinazoline derivatives, to a process for their preparation, to pharmaceutical compositions comprising them, and to their use as therapeutic agents, particularly in the treatment of cancer and cell proliferation disorders.

2. Discussion of the Background

Several cytotoxic drugs such as, e.g., fluorouracil (5-FU), doxorubicin and camptothecins, damage DNA or affect cellular metabolic pathways and thus cause, in many cases, an indirect block of the cell cycle. Therefore, by producing an irreversible damage to both normal and tumor cells, these agents result in a significant toxicity and side-effects.

In this respect, compounds capable of functioning as highly specific antitumor agents by selectively leading to tumor cell arrest and apoptosis, with comparable efficacy but reduced toxicity than the currently available drugs, are desirable.

It is well known that progression through the cell cycle is governed by a series of checkpoint controls, otherwise referred to as restriction points, which are regulated by a family of enzymes known as the cyclin-dependent kinases (cdk). In turn, the cdks themselves are regulated at many levels such as, for instance, binding to cyclins.

The coordinated activation and inactivation of different cyclin/cdk complexes is necessary for normal progression through the cell cycle. Both the critical G1-S and G2-M transitions are controlled by the activation of different cyclin/cdk activities. In G1, both cyclin D/cdk4 and cyclin E/cdk2 are thought to mediate the onset of S-phase. Progression through S-phase requires the activity of cyclin A/cdk2 whereas the activation of cyclin A/cdc2 (cdk1) and cyclin B/cdc2 are required for the onset of mitosis. For a general reference to cyclins and cyclin-dependent kinases see, for instance, Kevin R. Webster et al, in Exp. Opin. Invest. Drugs, 1998, Vol. 7(6), 865-887.

Checkpoint controls are defective in tumor cells due, in part to disregulation of cdk activity. For example, altered expression of cyclin E and cdks has been observed in tumor cells, and deletion of the cdk inhibitor p27 KIP gene in mice has been shown to result in a higher incidence of cancer.

Increasing evidence supports the idea that the cdks are rate-limiting enzymes in cell cycle progression and, as such, represent molecular targets for therapeutic intervention.

In particular, the direct inhibition of cdk/cyclin kinase activity should be helpful in restricting the unregulated proliferation of a tumor cell.

Further protein kinases known in the art as being implicated in the growth of cancer cells are the Aurora kinases, in particular Aurora-2.

Aurora-2 was found to be over-expressed in a number of different tumor types. Its gene locus maps at 20q13, a chromosomal region frequently amplified in many cancers, including breast [Cancer Res. 1999, 59(9) 2041-4] and colon.

20q13 amplification correlates with poor prognosis in patients with node-negative breast cancer and increased Aurora-2 expression is indicative of poor prognosis and decreased survival time in bladder cancer patients [J. Natl. Cancer Inst., 2002, 94(17) 1320-9]. For a general reference to Aurora-2 role in the abnormal centrosome function in cancer see also Molecular Cancer Therapeutics, 2003, 2, 589-595.

SUMMARY OF THE INVENTION

It is an object of the invention to provide compounds which are useful in treating cell proliferative disorders caused by and/or associated with an altered protein kinase activity, for instance Aurora 2 inhibitory activity and cell cycle dependent kinase activity. It is another object to provide compounds which have protein kinase inhibitory activity.

The present inventors have now discovered that certain pyrazolo-quinazolines are endowed with protein kinase inhibitory activity and are thus useful in therapy as antitumor agents and lack, in terms of both toxicity and side effects, the aforementioned drawbacks associated with currently available antitumor drugs.

More specifically, the pyrazolo-quinazolines of the invention are useful in the treatment of a variety of cancers including, but not limited to: carcinoma such as bladder, breast, colon, kidney, liver, lung, including small cell lung cancer, esophagus, gall-bladder, ovary, pancreas, stomach, cervix, thyroid, prostate, and skin, including squamous cell carcinoma; hematopoietic tumors of lymphoid lineage including leukaemia, acute lymphocitic leukaemia, acute lymphoblastic leukaemia, B-cell lymphoma, T-cell-lymphoma, Hodgkin's lymphoma, non-Hodgkin's lymphoma, hairy cell lymphoma and Burkett's lymphoma; hematopoietic tumors of myeloid lineage, including acute and chronic myelogenous leukemias, myelodysplastic syndrome and promyelocytic leukaemia; tumors of mesenchymal origin, including fibrosarcoma and rhabdomyosarcoma; tumors of the central and peripheral nervous system, including astrocytoma neuroblastoma, glioma and schwannomas; other tumors, including melanoma, seminoma, teratocarcinoma, osteosarcoma, xeroderma pigmentosum, keratoxanthoma, thyroid follicular cancer and Kaposi's sarcoma.

Due to the key role of cell cycle kinases such as Aurora or cdks in the regulation of cellular proliferation, these pyrazolo-quinazoline derivatives are also useful in the treatment of a variety of cell proliferative disorders such as, for example, benign prostate hyperplasia, familial adenomatosis, polyposis, neurofibromatosis, psoriasis, vascular smooth cell proliferation associated with atherosclerosis, pulmonary fibrosis, arthritis, glomerulonephritis and post-surgical stenosis and restenosis.

The compounds of the invention may be useful in treatment of Alzheimer's disease, as suggested by the fact that cdk5 is involved in the phosphorylation of tau protein (J. Biochem. 117, 741-749, 1995).

The compounds of this invention, as modulators of apoptosis, may also be useful in the treatment of cancer, viral infections, prevention of AIDS development in HIV-infected individuals, autoimmune diseases and neurodegenerative disorders.

The compounds of this invention may be useful in inhibiting tumor angiogenesis and metastasis, as well as in the treatment of organ transplant rejection and host versus graft disease.

The compounds of the invention may also act as inhibitor of other protein kinases, e.g., protein kinase C in different isoforms, Met, PAK-4, PAK-5, ZC-1, STLK-2, DDR-2, Bub-1, PLK, Chk1, Chk2, HER2, raf1, MEK1, MAPK, EGF-R, PDGF-R, FGF-R, IGF-R, PI3K, wee1 kinase, Src, Ab1, Akt, MAPK, ILK, MK-2, IKK-2, Cdc7, Nek, and thus be effective in the treatment of diseases associated with other protein kinases.

The compounds of the invention are also useful in the treatment and prevention of radiotherapy-induced or chemotherapy-induced alopecia.

Accordingly, in a first embodiment, the present invention provides a method for treating cell proliferative disorders caused by and/or associated with an altered protein kinase activity, like for instance Aurora 2 activity and cell cycle dependent kinase activity, by administering to a mammal in need thereof an effective amount of a pyrazolo-quinazoline derivative represented by formula (Ia) or (Ib)

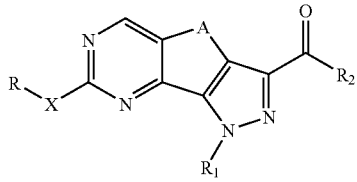

(Ia)

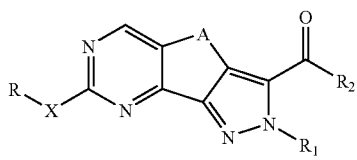

(Ib)

wherein

R is hydrogen or an optionally substituted group selected from amino, straight or branched $C_1$-$C_6$ alkyl, $C_3$-$C_{10}$ cycloalkyl, cycloalkyl-alkyl, aryl, arylalkyl, heterocyclyl or heterocyclylalkyl;

X is a single bond or a divalent radical selected from —NR'—, —CONR'—, —NH—CO—NH—, —O—, —S— or —SO$_2$—, wherein R' is hydrogen or an optionally substituted group selected from straight or branched $C_1$-$C_6$ alkyl, $C_3$-$C_6$ cycloalkyl, cycloalkyl-alkyl, aryl, arylalkyl, heterocyclyl, heterocyclylalkyl or, together with the nitrogen atom to which they are bonded, R and R' may form a 5 to 6 membered heteroaryl or heterocyclyl group optionally containing one additional heteroatom selected among N, O or S;

$R_1$, bonded to any one of the nitrogen atoms of the pyrazole ring as per formulae (Ia) or (Ib), represents a hydrogen atom or an optionally substituted group selected from straight or branched $C_1$-$C_6$ alkyl, $C_3$-$C_6$ cycloalkyl, aryl, arylalkyl, heterocyclyl or heterocyclylalkyl or, in formula (Ib), $R_1$ is a divalent —$(CH_2)_n$—NH— group being linked to $R_2$, wherein n is 2 or 3;

$R_2$ is a group selected from —NR"R'", —N(OH)R", —OR" or —R", wherein R" and R'" are, each independently, hydrogen or an optionally substituted group selected from straight or branched $C_1$-$C_6$ alkyl, $C_3$-$C_6$ cycloalkyl or cycloalkyl-alkyl, aryl, arylalkyl, heterocyclyl or heterocyclylalkyl or, together with the nitrogen atom to which they are bonded, R" and R'" may form a 5 to 6 membered heteroaryl or heterocyclyl group, optionally containing one additional heteroatom selected among N, O or S;

A is a divalent group selected from —$CH_2$—, —$(CH_2)_2$—, $CH_2$—$C(CH_3)_2$—, —$C(CH_3)_2$—$CH_2$— or —CH=CH—;

or a pharmaceutically acceptable salt thereof.

In another embodiment, the present invention also provides a method for treating cell proliferative disorders caused by and/or associated with an altered protein kinase activity, like cell cycle dependent kinase activity, by administering to a mammal in need thereof an effective amount of a pyrazolo-quinazoline derivative represented by the above formula (Ia) or (Ib).

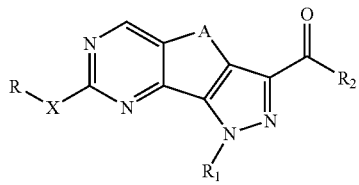

(Ic)

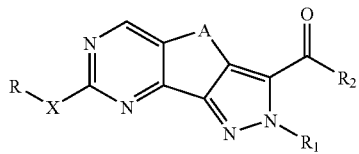

(Id)

In a preferred embodiment of the methods described above, the cell proliferative disorder is selected from the group consisting of cancer, Alzheimer's disease, viral infections, auto-immune diseases and neurodegenerative disorders.

Specific types of cancer that may be treated include carcinoma, squamous cell carcinoma, hematopoietic tumors of myeloid or lymphoid lineage, tumors of mesenchymal origin, tumors of the central and peripheral nervous system, melanoma, seminoma, teratocarcinoma, osteosarcoma, xeroderma pigmentosum, keratoxanthoma, thyroid follicular cancer, and Kaposi's sarcoma.

In another preferred embodiment of the method described above, the cell proliferative disorder is selected from the group consisting of benign prostate hyperplasia, familial adenomatosis, polyposis, neuro-fibromatosis, psoriasis, vascular smooth cell proliferation associated with atherosclerosis, pulmonary fibrosis, arthritis, glomerulonephritis and post-surgical stenosis and restenosis. In addition, the inventive method provides tumor angiogenesis and metastasis inhibition as well as treatment of organ transplant rejection and host versus graft disease. The inventive methods may also provide cell cycle inhibition or cdk/cyclin dependent inhibition.

In addition to the above, the methods object of the present invention provide treatment and prevention of radiotherapy-induced or chemotherapy-induced alopecia.

The present invention also provides a pyrazolo-quinazoline derivative represented by formula (Ia) or (Ib)

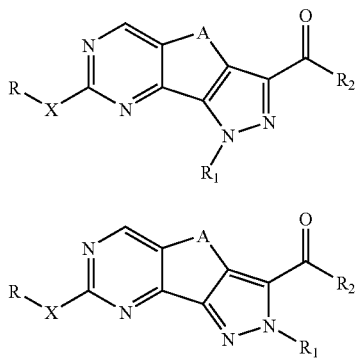

wherein

R is hydrogen or an optionally substituted group selected from amino, straight or branched $C_1$-$C_6$ alkyl, $C_3$-$C_{10}$ cycloalkyl, cycloalkyl-alkyl, aryl, arylalkyl, heterocyclyl or heterocyclylalkyl;

X is a single bond or a divalent radical selected from —NR'—, —CONR'—, —NH—CO—NH—, —O—, —S— or —SO$_2$—, wherein R' is hydrogen or an optionally substituted group selected from straight or branched $C_1$-$C_6$ alkyl, $C_3$-$C_6$ cycloalkyl, cycloalkyl-alkyl, aryl, arylalkyl, heterocyclyl, heterocyclylalkyl or, together with the nitrogen atom to which they are bonded, R and R' may form a 5 to 6 membered heteroaryl or heterocyclyl group optionally containing one additional heteroatom selected among N, O or S;

$R_1$, bonded to any one of the nitrogen atoms of the pyrazole ring as per formulae (Ia) or (Ib), represents a hydrogen atom or an optionally substituted group selected from straight or branched $C_1$-$C_6$ alkyl, $C_3$-$C_6$ cycloalkyl, aryl, arylalkyl, heterocyclyl or heterocyclylalkyl or, in formula (Ib), $R_1$ is a divalent —(CH$_2$)$_n$—NH— group being linked to $R_2$, wherein n is 2 or 3;

$R_2$ is a group selected from —NR"R'", —N(OH)R", —OR" or —R", wherein R" and R'" are, each independently, hydrogen or an optionally substituted group selected from straight or branched $C_1$-$C_6$ alkyl, $C_3$-$C_6$ cycloalkyl or cycloalkyl-alkyl, aryl, arylalkyl, heterocyclyl or heterocyclylalkyl or, together with the nitrogen atom to which they are bonded, R" and R'" may form a 5 to 6 membered heteroaryl or heterocyclyl group, optionally containing one additional heteroatom selected among N, O or S;

A is a divalent group selected from —CH$_2$—, —(CH$_2$)$_2$—, —CH$_2$—C(CH$_3$)$_2$—, —C(CH$_3$)$_2$—CH$_2$— or —CH=CH—;

or a pharmaceutically acceptable salt thereof.

The present invention also includes methods of synthesizing the pyrazolo-quinazoline derivatives represented by formulae (Ia) or (Ib) that, unless otherwise provided, may be conveniently grouped and defined as compounds of formula (I). Pharmaceutical compositions comprising the pyrazolo-quinazoline derivatives of formula (I) are also included in the present invention.

A more complete appreciation of the invention and many of the attendant advantages thereof will be readily obtained as the same becomes better understood by reference to the following detailed description.

DETAILED DESCRIPTION OF THE INVENTION

Several heterocyclic compounds are known in the art as protein kinase inhibitors. As an example, 2-carboxamido-pyrazoles and 2-ureido-pyrazoles, and derivatives thereof, have been disclosed as protein kinase inhibitors in the international patent applications WO 01/12189, WO 01/12188, WO 02/48114 and WO 02/70515, all in the name of the applicant itself.

Fused bicyclic compounds comprising pyrazole moieties and possessing kinase inhibitory activity have been also disclosed in WO 00/69846, WO 02/12242 as well as WO 03/028720 and still unpublished U.S. patent application 60/381,092 (filed in May 17, 2002), all in the name of the applicant itself.

Fused tricyclic derivatives possessing kinase inhibitory activity are also disclosed in two copending applications PCT/EP03/01594 and PCT/US03/04844 (both claiming Feb. 19, 2002 priority from U.S. applications No. 60/357,918 and No. 60/357,960, respectively) and herewith incorporated by reference; none of the said applications specifically disclose the derivatives in re.

In addition, fused polycyclic pyrimidine derivatives as protein kinase inhibitors are also disclosed in the international patent applications WO 98/58926 and WO 98/28281, both in the name of Celltech Therapeutics Ltd; though comprised within the general formula of both applications, no specific examples of pyrazolo-quinazolines of the present invention are exemplified therein.

Finally, heterocyclic ring fused pyrimidine derivatives for the treatment of hyperproliferative diseases are disclosed in WO 96/40142 in the name of Pfizer Inc. The compounds of formula (I) of the invention may have asymmetric carbon atoms and may therefore exist as individual optical isomers, as racemic admixtures or as any other admixture comprising a majority of one of the two optical isomers, which are all to be intended as within the scope of the present invention.

Likewise, the use as an antitumor agent of all the possible isomers and their admixtures and of both the metabolites and the pharmaceutically acceptable bio-precursors (otherwise referred to as pro-drugs) of the compounds of formula (I) are also within the scope of the present invention.

Prodrugs are any covalently bonded compounds which release the active parent drug, according to formula (I), in vivo.

In cases when compounds may exist in tautomeric forms, for instance keto-enol tautomers, each tautomeric form is contemplated as being included within this invention whether existing in equilibrium or predominantly in one form.

In the present description, unless otherwise specified, with the term straight or branched $C_1$-$C_6$ alkyl we intend any of the groups such as, for instance, methyl, ethyl, n-propyl, isopropyl, n-butyl, isobutyl, tert-butyl, sec-butyl, n-pentyl, n-hexyl, and the like.

With the term $C_3$-$C_{10}$ cycloalkyl we intend, unless otherwise provided, a cycloaliphatic ring such as cyclopropyl, cyclobutyl, cyclopentyl and cyclohexyl, as well as any bridged cycloalkyl group with up to 10 carbon atoms.

The term aryl includes carbocyclic or heterocyclic hydrocarbons with from 1 to 2 ring moieties, either fused or linked to each other by single bonds, wherein at least one of the rings is aromatic; if present, any aromatic heterocyclic hydrocarbon also referred to as heteroaryl group, comprises a 5 to 6 membered ring with from 1 to 3 heteroatoms selected among N, O or S.

Examples of aryl groups according to the invention are, for instance, phenyl, biphenyl, α- or β-naphthyl, dihydronaphthyl, thienyl, benzothienyl, furyl, benzofuranyl, pyrrolyl, imidazolyl, pyrazolyl, thiazolyl, isothiazolyl, oxazolyl, isoxazolyl, pyridyl, pyrazinyl, pyrimidinyl, pyridazinyl, indolyl, isoindolyl, purinyl, quinolyl, isoquinolyl, dihydroquinolinyl, quinoxalinyl, benzodioxolyl, indanyl, indenyl, triazolyl, and the like. Unless otherwise specified, the term heterocyclyl includes 5 to 6 membered saturated, partly unsaturated or fully unsaturated heterocycles with from 1 to 3 heteroatoms selected among N, O or S. Apart from the fully unsaturated heterocycles, previously referred to as aromatic heterocycles and encompassed by the term aryl, examples of saturated or partly unsaturated heterocycles according to the invention are, for instance, pyran, pyrrolidine, pyrroline, imidazoline, imidazolidine, pyrazolidine, pyrazoline, thiazoline, thiazolidine, dihydrofuran, tetrahydrofuran, 1,3-dioxolane, piperidine, piperazine, morpholine and the like.

From all of the above, it is clear to the skilled man that any compound of the invention wherein X represents a single bond has to be intended as having the R group directly linked to the pyrimidine moiety.

According to the above indicated substituent meanings and unless otherwise specified, any of the above R, R', $R_1$, R" and R'" group may be optionally substituted in any of their free positions by one or more groups, for instance 1 to 6 groups, independently selected from: halogen, nitro, oxo groups (=O), cyano, azido, alkyl, polyfluorinated alkyl, hydroxyalkyl, aryl, arylalkyl, heterocyclyl, heterocyclylalkyl, cycloalkyl, alkylaryl, alkylheterocyclyl, hydroxy, alkoxy, polyfluorinated alkoxy, aryloxy, arylalkyloxy, heterocyclyloxy, heterocyclylalkyloxy, methylenedioxy, alkylcarbonyloxy, alkylcarbonyloxyalkyl, arylcarbonyloxy, carboxy, alkoxycarbonyl, alkoxycarbonylalkyl, aryloxycarbonyl, cycloalkyloxycarbonyl, amino, aminoalkyl, alkylaminoalkyl, alkylaminoalkyloxy, ureido, alkylamino, dialkylamino, arylamino, diarylamino, formylamino, alkylcarbonylamino, arylcarbonylamino, heterocyclylcarbonylamino, alkoxycarbonylamino, alkoxyimino, alkylsulfonylamino, arylsulfonylamino, formyl, alkylcarbonyl, arylcarbonyl, heterocyclylcarbonyl, cycloalkylcarbonyl, heterocyclylcarbonyl, aminocarbonyl, alkylaminocarbonyl, dialkylaminocarbonyl, arylaminocarbonyl, alkylsulfonyl, arylsulfonyl, heterocyclylsulfonyl, aminosulfonyl, alkylaminosulfonyl, dialkylaminosulfonyl, arylthio and alkylthio.

In this respect, with the term halogen atom we intend a fluorine, chlorine, bromine or iodine atom.

With the term perfluorinated alkyl we intend any of the above straight or branched $C_1$-$C_6$ alkyl groups which are substituted by more than one fluorine atom such as, for instance, trifluoromethyl, trifluoroethyl, 1,1,1,3,3,3-hexafluoropropyl, and the like.

With the term alkoxy, aryloxy, heterocyclyloxy and derivatives thereof, e.g. perfluorinated alkoxy, we intend any of the above alkyl, aryl or heterocyclyl groups linked to the rest of the molecule through an oxygen atom (—O—).

From all of the above, it is clear to the skilled person that any group which name is a composite name such as, for instance, arylalkyl or heterocyclylalkyl has to be intended as conventionally construed by the parts from which it derives, e.g. by an alkyl group which is further substituted by aryl or heterocyclyl, wherein alkyl, aryl or heterocyclyl are as above defined.

Likewise, any of the terms such as, for instance, alkylthio, alkylamino, dialkylamino, alkoxycarbonyl, alkoxycarbonylamino, heterocyclylcarbonyl, heterocyclylcarbonylamino, cycloalkyloxycarbonyl and the like, include groups wherein the alkyl, alkoxy, aryl, cycloalkyl and heterocyclyl moieties are as above defined.

Pharmaceutically acceptable salts of the compounds of formula (I) include the acid addition salts with inorganic or organic acids, e.g., nitric, hydrochloric, hydrobromic, sulfuric, perchloric, phosphoric, acetic, trifluoroacetic propionic, glycolic, lactic, oxalic, malonic, malic, maleic, tartaric, citric, benzoic, cinnamic, mandelic, methanesulphonic, isethionic and salicylic acid, as well as the salts with inorganic or organic bases, e.g., alkali or alkaline-earth metals, especially sodium, potassium, calcium or magnesium hydroxides, carbonates or bicarbonates, acyclic or cyclic amines, preferably methylamine, ethylamine, diethylamine, triethylamine, piperidine and the like.

According to a first embodiment of the invention addressed to the compounds of formula (Ia) or (Ib), preferred derivatives are those wherein X is a group —NH— and $R_2$ is a group selected from —NHR", —N(OH)R", —OR" or —R", wherein R" is an optionally substituted group selected from $C_3$-$C_6$ cycloalkyl or cycloalkyl-alkyl, aryl, arylalkyl, heterocyclyl or heterocyclylalkyl; and R, $R_1$ and A are as above defined.

Also preferred are the compounds of formula (Ia) or (Ib) wherein X is a group —O— and $R_2$ is a group selected from —NHR", —N(OH)R", —OR" or —R", wherein R" is an optionally substituted group selected from $C_3$-$C_6$ cycloalkyl or cycloalkyl-alkyl, aryl arylalkyl, heterocyclyl or heterocyclylalkyl; and R, $R_1$ and A are as above defined.

Also preferred are the compounds of formula (Ia) or (Ib) wherein X is a group —S— and $R_2$ is a group selected from —NHR", —N(OH)R", —OR" or —R", wherein R" is an optionally substituted group selected from $C_3$-$C_6$ cycloalkyl or cycloalkyl-alkyl, aryl, arylalkyl, heterocyclyl or heterocyclylalkyl; and R, $R_1$ and A are as above defined.

Even more preferred, within the above classes of compounds (Ia) or (Ib) are those same derivatives wherein A is a group —$(CH_2)_2$—.

According to another embodiment of the invention addressed to the compounds of formula (Ia) or (Ib), a class of preferred compounds is represented by those derivatives wherein X is a group —NH— and $R_2$ is a group —NHR" or —N(OH)R" wherein R" is a hydrogen atom or a straight or branched $C_1$-$C_4$ alkyl group; and wherein A, R and $R_1$ are as above defined.

Another class of preferred compounds of the invention of formula (Ia) or (Ib) is represented by the derivatives wherein X is a group —O— and $R_2$ is a group —NHR" or —N(OH)R" wherein R" is a hydrogen atom or a straight or branched $C_1$-$C_4$ alkyl group; and wherein A, R and $R_1$ are as above defined.

Another class of preferred compounds of the invention of formula (Ia) or (Ib) is represented by the derivatives wherein X is a group —S— and $R_2$ is a group —NHR" or —N(OH)R" wherein R" is a hydrogen atom or a straight or branched $C_1$-$C_4$ alkyl group; and wherein A, R and $R_1$ are as above defined.

Another class of preferred compounds of the invention of formula (Ib) is represented by the derivatives wherein R, X and A are as above defined and $R_1$ and $R_2$ are linked together through a divalent —$(CH_2)_n$—NH— group so as to give rise to:

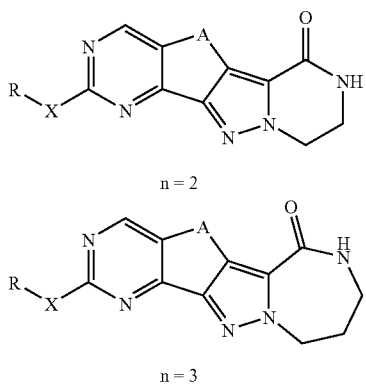

n = 2 n = 3

Also preferred, within the above class of derivatives of formula (Ia) and (Ib), are the compounds wherein A is a group selected from —CH$_2$—C(CH$_3$)$_2$— or —C(CH$_3$)$_2$—CH$_2$—.

For a reference to any specific compound of formula (Ia) or (Ib) of the invention, optionally in the form of a pharmaceutically acceptable salt, see the experimental section and claims.

As formerly indicated, a further object of the present invention is represented by the process for preparing the compounds of formula (I) which formula, unless otherwise specifically provided, has to be intended as comprising the derivatives of formula (Ia) and (Ib).

Therefore, the compounds of formula (I) or the pharmaceutically acceptable salts thereof may be obtained by a process comprising:

(1) when A is a —(CH$_2$)$_2$— group:

st.1) reacting 2-ethoxy-2-cyclohexen-1-one with diethyl oxalate, in the presence of lithium (bis-trimethylsilyl)amide [LiN(TMS)$_2$], so as to obtain a compound of formula (II)

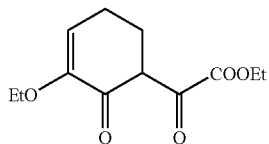
(II)

and treating it with a hydrazine derivative of formula (III)

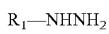
R$_1$—NHNH$_2$ (III)

wherein R$_1$ has the above reported meanings, according to the operative conditions set forth in any one of the steps (st.2a), (st.2b) or (st.2c)

st.2a) in the presence of a lower alcohol so as to obtain a mixture of the compounds of formula (IVa) and (IVb)

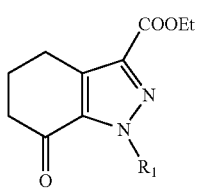
(IVa)

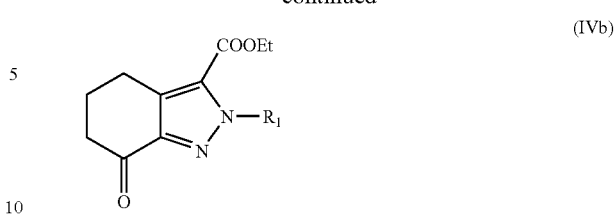
(IVb)

wherein R$_1$ is as above reported, and separating their mixture into the single compounds (IVa) and (IVb);

st.2b) in the presence of acetic acid so as to obtain a compound of formula (IVa);

st.2c) by alkylating a compound of formula (IVa) being obtained in step (st.2a) or (st.2b) and wherein R$_1$ is hydrogen with the compounds of formula (IVc)

R$_1$Y (IVc)

wherein Y is a suitable leaving group such as mesyl, tosyl, halogen, as to obtain a mixture of compounds of formula (IVa) and (IVb) wherein R$_1$ is as above reported and separating their mixture into the compounds (IVa) and (IVb);

st.3) reacting the compound of formula (IVa) prepared according to any one of steps (st.2a), (st.2b) or (st.2c), or of formula (IVb) prepared according to steps (st.2a) or (st.2c), with dimethylformamide-di-tert-butylacetale so as to obtain a compound of formula (Va) or (Vb)

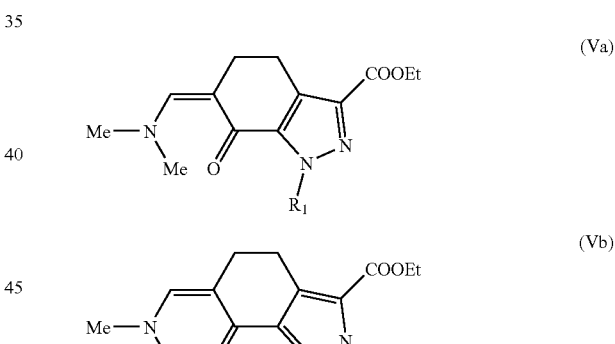
(Va)

(Vb)

wherein R$_1$ is as above reported; and reacting the compound of formula (Va) or (Vb) according to any one of the alternative steps (st.4a), (st.4b) or (st.4c)

st.4a) with guanidine so as to obtain a compound of formula (Ia) or (Ib)

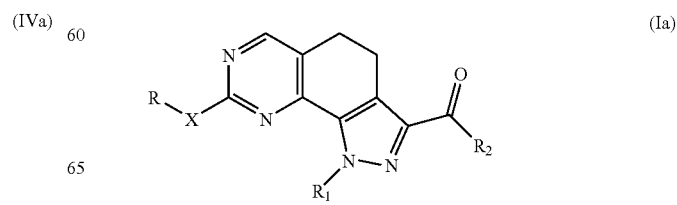
(Ia)

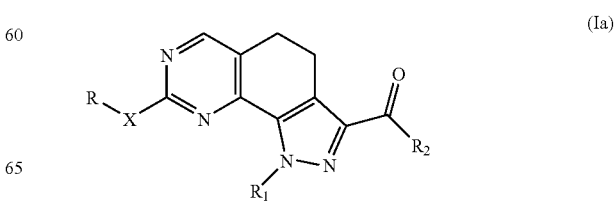

-continued

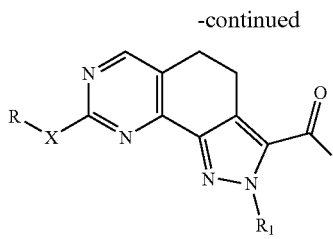
(Ib)

wherein R—X— is amino, $R_2$ is ethoxy, and $R_1$ is as above defined; and optionally converting them into other derivatives of formula (I);

st.4b) with a guanidine derivative of formula (VI)

R—NH—C(=NH)NH$_2$     (VI)

wherein R is as above reported, so as to obtain a compound of formula (Ia) or (Ib) wherein R and $R_1$ are as above reported, X is —NH—, and $R_2$ is ethoxy; and optionally converting them into other derivatives of formula (I);

st.4c) with an alkylisothiourea of formula (VII)

R—S—C(=NH)NH$_2$     (VII)

wherein R is as above reported, so as to obtain a compound of formula (Ia) or (Ib) wherein R and $R_1$ are as above reported, X is —S— and $R_2$ is ethoxy; and optionally converting them into other derivatives of formula (I);

st.4d) with methylisourea so as to obtain a compound of formula (Ia) or (Ib) wherein $R_1$ is as above reported R is methyl, X is —O— and $R_2$ is ethoxy; and optionally converting them into other derivatives of formula (I);

(2) when A is a —C(CH$_3$)$_2$—CH$_2$— group:

st.5) reacting 2-methoxy-4,4-dimethyl-2-cyclohexen-1-one with diethyl oxalate, in the presence of [LiN(TMS)$_2$], so as to obtain a compound of formula (VIII)

(VIII)

st.6) reacting the compound of formula (VIII) with a hydrazine derivative of formula (III) according to any one of previous steps (st.2a) or (st.2b) so as to obtain the compound of formula (IXa) or (IXb)

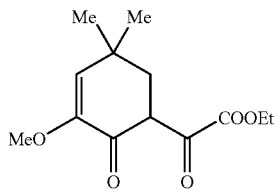
(IXa)

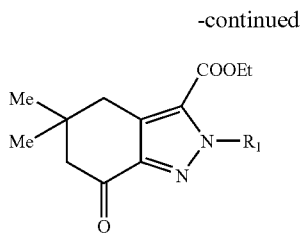
(IXb)

wherein $R_1$ is as above reported;

st.7) reacting the compound of formula (IXa) or (IXb) with ethyl formate under basic conditions, so as to obtain the compound of formula (Xa) or (Xb)

(Xa)

(Xb)

st.8) reacting the compound of formula (Xa) or (Xb) with guanidine or a guanidine derivative of formula (VI), so as to obtain a compound of formula (Ia) or (Ib)

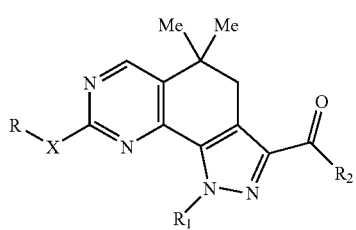
(Ia)

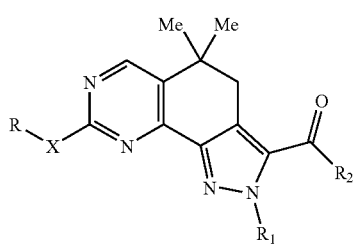
(Ib)

wherein R and $R_1$ are as above reported, X is —NH—, and $R_2$ is ethoxy; and optionally converting them into other derivatives of formula (I);

(3) when A is a —CH$_2$—C(CH$_3$)$_2$— group:

st.9) reacting 2-methoxy-5,5-dimethyl-2-cyclohexen-1-one with diethyl oxalate in the presence of sodium hydride, so as to obtain the compound of formula (XI)

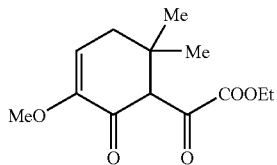

(XI)

st.10) reacting the compound of formula (XI) with a hydrazine derivative of formula (III) according to any one of previous steps (st.2a) or (st.2b) so as to obtain the compound of formula (XIIa) or (XIIb)

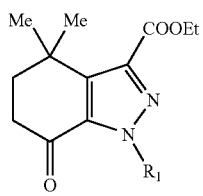

(XIIa)

(XIIb)

wherein R$_1$ is as above reported, st.11) reacting the compound of formula (XIIa) or (XIIb) with dimethylformamide-di-tert-butylacetale so as to obtain a compound of formula (XIIIa) or (XIIIb)

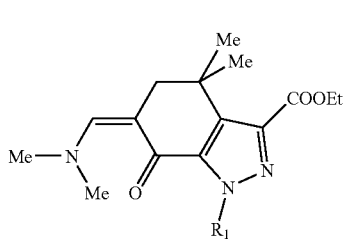

(XIIIa)

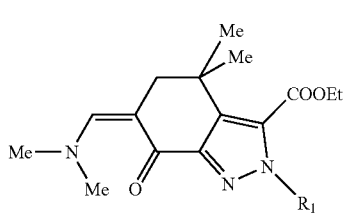

(XIIIb)

st.12) reacting the compound of formula (XIIIa) or (XIIIb) with guanidine or a guanidine derivative of formula (VI), so as to obtain a compound of formula (Ia) or (Ib)

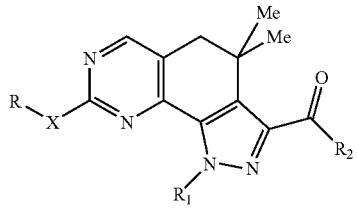

(Ia)

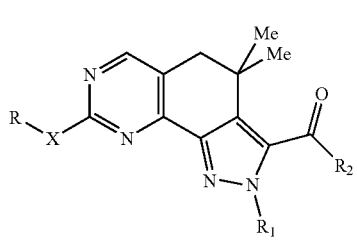

(Ib)

wherein R and R$_1$ are as above reported, X is —NH—, and R$_2$ is ethoxy; and optionally converting them into other derivatives of formula (I);

(4) when, in formula (Ib), A is a —(CH$_2$)$_2$— group, —CH$_2$—C(CH$_3$)$_2$— group, —C(CH$_3$)$_2$—CH$_2$— group, R$_1$ is directly linked to R$_2$ so as to yield a tetra-cyclic ring structure:

st.13) reacting a compound of formula (IV), (IX), (XI) wherein R$_1$ is hydrogen, obtained according to (st.2), (st.6), (st.10) of the process, with triphenylmethyl chloride so as to obtain a compound of formula (XIV)

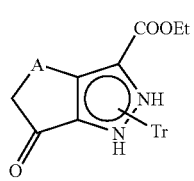

(XIV)

wherein Tr stands for trityl (triphenylmethyl);

st.14) reacting the compound of formula (XIV) with dimethylformamide-di-tert-butylacetale, as set forth in step (st.3), so as to obtain a compound of formula (XV)

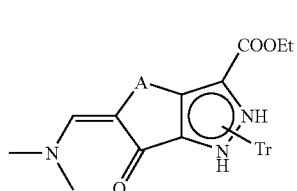

(XV)

st.15) reacting the compound of formula (XV) with a suitable guanidine derivative of formula (VI), as set forth in step (st.4b), so as to obtain a compound of formula (Ia) or (Ib)

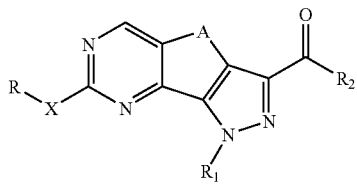

(Ia)

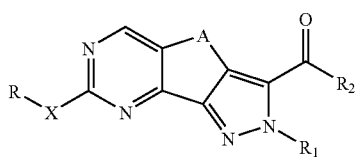

(Ib)

wherein R is as above defined, A is a —(CH$_2$)$_2$— group, —CH$_2$—C(CH$_3$)$_2$— group, —C(CH$_3$)$_2$—CH$_2$— group, X is NH, R$_1$ is trityl and R$_2$ is ethoxy;

st.16) reacting the above compound of formula (Ia) or (Ib) under acidic conditions, so as to obtain the corresponding compound of formula (Ia) or (Ib) wherein R$_1$ is hydrogen;

st.17) reacting the above compound of formula (Ia) or (Ib) with a suitable alkylating agent of formula (XVI) in the presence of litium tert-butylate

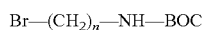

(XVI)

wherein n is 2 or 3, so as to obtain a compound of formula (Ib)

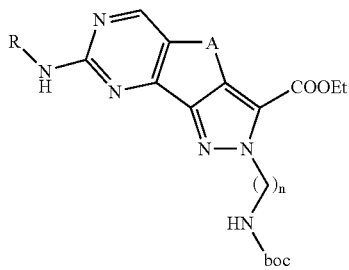

(Ib)

wherein A, n and R are as above defined;

st.18) reacting the above compound of formula (Ib) under acidic conditions, so as to convert the tert-butoxycarbonylamino group into amino (deprotection) and reacting it with cesium carbonate (CsCO$_3$) so as to obtain any one of the two compounds of formula (Ib)

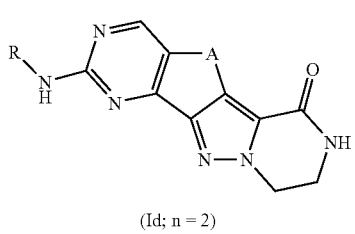

(Id; n = 2)

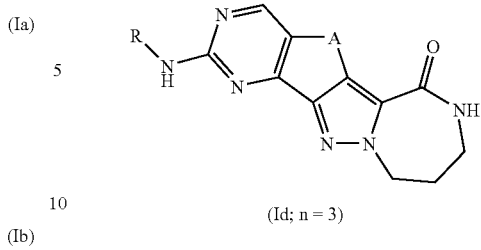

(Id; n = 3)

wherein A and R is as above defined, and optionally converting them into other derivatives of formula (I);

(5) when R$_2$ is a bulky group:

st.19) reacting 2-ethoxy-2-cyclohexenone with dimethylformamide-di-tert-butylacetale, as reported in step (st.3), so as to obtain a compound of formula (XVII)

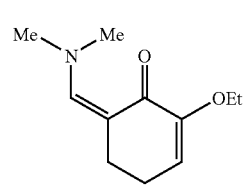

(XVII)

st.20) reacting the compound of formula (XVII) with a derivative of formula (VII), according to step (st.4c), so as to obtain a compound of formula (XVIII)

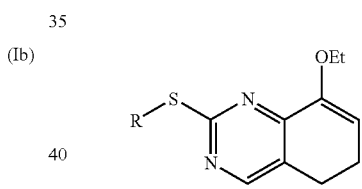

(XVIII)

wherein R is as above defined; and subsequently treating it under acidic conditions so as to obtain a compound of formula (XIX)

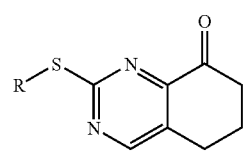

(XIX)

st.21) reacting the compound of formula (XIX) with a compound of formula (XX)

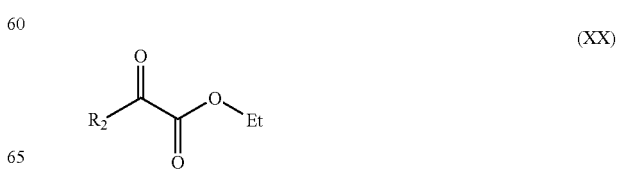

(XX)

wherein R₂ is a bulky group, so as to obtain a compound of formula (XXI)

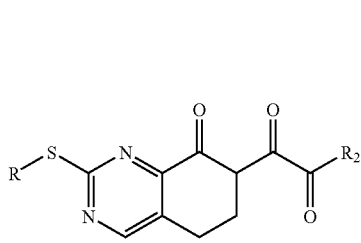
(XXI)

st.22) reacting the compound of formula (XXI) with a hydrazine derivative of formula (III), as per step (st.1) of the process, so as to obtain a compound of formula (I) wherein R and R₁ are as above defined, X is —S— and R₂ is a bulky group; and optionally converting them into other derivatives of formula (I).

As above reported, the compounds of formula (I) which are prepared according to the process object of the invention, for instance as set forth in steps (st.4a), (st.4b), (st.4c), (st.8), (st.12), (st.13), (st.18) and (st.22), can be conveniently converted into other compounds of formula (I) by operating according to well-known operative conditions.

As an example, the compounds of formula (I):

st.23) wherein R₂ is ethoxy may be converted into the compounds of formula (Ia) or (Ib) wherein R₂ is amino by treatment with ammonium hydroxide

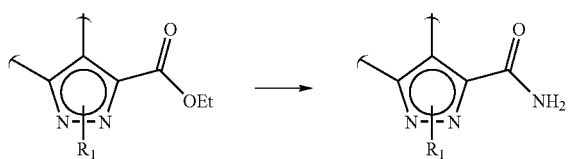

st.24) wherein R₂ is ethoxy may be converted into the compounds of formula (I) wherein R₂ is a group —NHR" by treatment with an amine of formula R"—NH₂ (XXII)

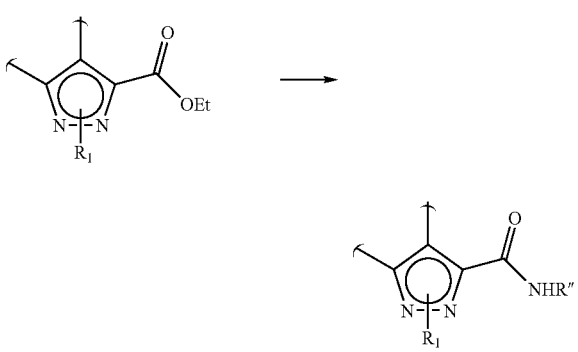

st.25) wherein R₂ is ethoxy may be converted into the compounds of formula (I) wherein R₂ is a group —OH through acidic or basic hydrolysis

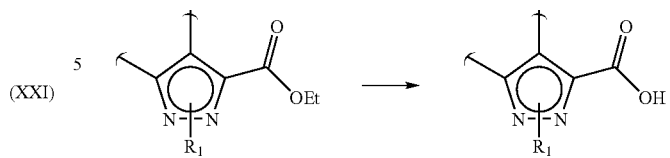

st.26) wherein R₂ is —OH may be converted into the compounds of formula (I) wherein R₂ is a group —NR"R'" or —N(OH)R", through reaction with a derivative of formula (XXIII) or (XXIV)

R"R'"NH     (XXIII)

R"NHOH     (XXIV)

under basic conditions and in the presence of a suitable condensing agent


st.27) wherein R is hydrogen and X is —NH— may be converted into the compounds of formula (I) wherein R is other than hydrogen, as above defined, and X is —CONH—, through reaction with an acid halide, for instance chloride, of formula R—COCl (XXV)

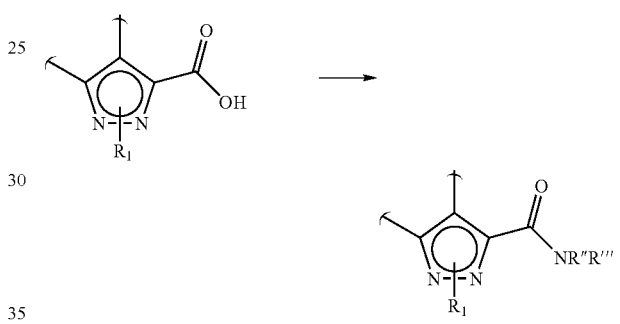

st.28) wherein R is hydrogen and X is —NH— may be converted into the compounds of formula (I) wherein R is other than hydrogen, as above defined, and X is —NH—CO—NH—, through reaction with an isocyanate of formula R—NCO (XXVI)

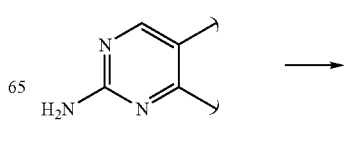

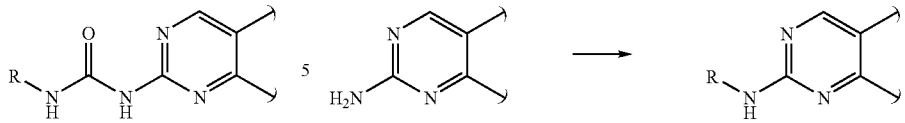

st.29) wherein R is hydrogen and X is —NH— may be converted into the compounds of formula (I) wherein R is aryl and X is —NH—, by first converting the amino group to iodine with iso-amylnitrite and diiodomethane or cesium iodide, in the presence of iodine and CuI, and by subsequently reacting the iododerivative with an arylamine of formula R—NH$_2$ (XXVII), in the presence of palladium acetate and (2,2'-bis(diphenylphosphino))-1,1'-binaphthalene (BINAP)

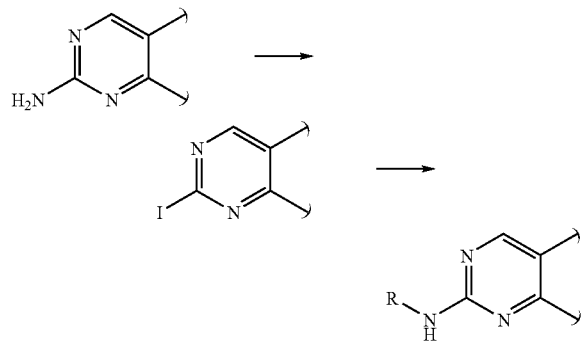

st.29a) wherein R is hydrogen and X is —NH— may be converted into the compounds of formula (I) wherein R is alkyl, cycloalkyl, cycloalkyl-alkyl, arylalkyl, heterocyclyl, heterocyclylalkyl, and X is —NH—, by first converting the amino group to iodine, as described in the previous step (st.29), and by subsequently reacting the iododerivative with an alkyl, cycloalkyl, cycloalkyl-alkyl, arylalkyl, heterocyclyl or heterocyclylalkyl amine of formula RNH$_2$ (XXVII), wherein R is as therein defined;

st.30) wherein R is hydrogen and X is —NH— may be converted into the compounds of formula (I) wherein R is aryl and X is a single bond, by first converting the amino group to iodine, as per the above step (st.29), and by subsequently reacting the iododerivative with an arylboronic acid of formula R—B(OH)$_2$ (XXVIII), in the presence of a palladium derivative

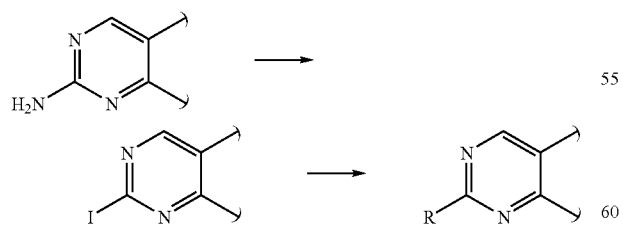

st.31) wherein R is hydrogen and X is —NH— may be converted into the compounds of formula (I) wherein R is alkyl or arylmethyl, by reaction with an alkyl aldehyde or aryl-aldehyde of formula R—CHO (XXIX) in the presence of sodium cyanoborohydride (NaBH$_3$CN) and acetic acid st.31a) wherein R is hydrogen and X is —NH— may be converted into the compounds of formula (I) wherein R is cycloalkyl or heterocycloalkyl, by reaction with an cycloalkyl ketone or heterocycloalkylketone in the presence of sodium triacetoxyborohydride NaBH(OAc)$_3$) and trifluoroacetic acid

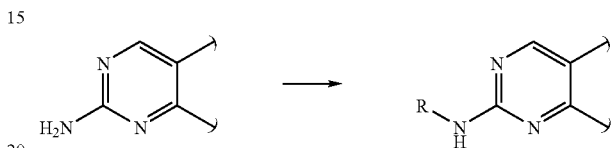

st.32) wherein R is as above defined, e.g. methyl, and X is —S— may be converted into the compounds of formula (I) wherein R is an optionally substituted alkyl, cycloalkyl, heterocyclyl, cycloalkyl-alkyl, arylalkyl or heterocyclylalkyl group, by first converting the RS— group into RSO$_2$— under oxidative conditions, and by then reacting the sulfonyl derivative with an amine of formula R—NH$_2$ (XXVII) wherein R is an optionally substituted alkyl, cycloalkyl, heterocyclyl, cycloalkyl-alkyl, arylalkyl or heterocyclylalkyl group

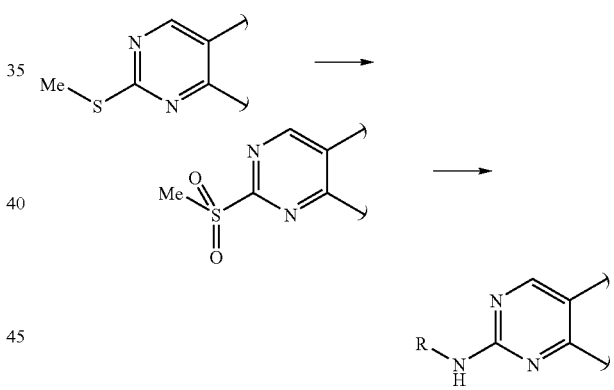

st.33) wherein R is as above defined, e.g. methyl, and X is —S— may be converted into the compounds of formula (I) wherein R is as defined in formula (I) and X is —O—, by first converting the RS— group into RSO$_2$— as per step (st.32) and by then reacting the sulfonyl derivative with a compound of formula R—OH (XXX)

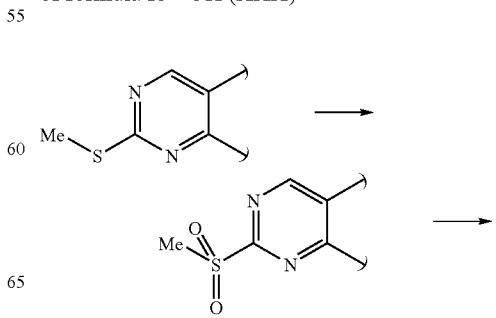

-continued

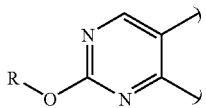

st.33a) wherein R is methyl, and X is —O— may be converted into the compounds of formula (I) wherein R is as defined in formula (I) and X is —O—, by first converting the MeO— group into HO—, then by reacting it with a triflating agent so as to obtain the corresponding trifluoromethansulfonate and finally by reacting it with a compound of formula R—OH (XXX)

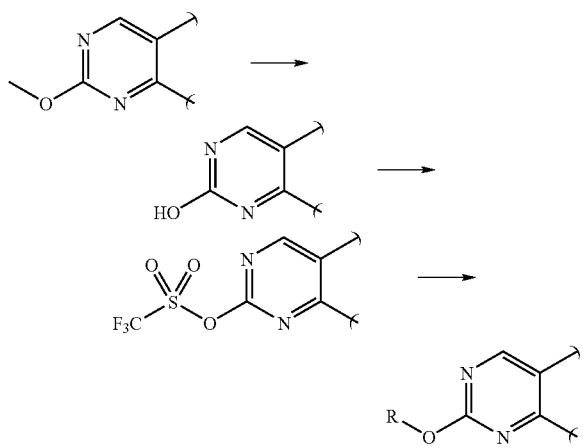

st.33b) wherein R is methyl and X is —O— may be converted into the compounds of formula (I) wherein R is an optionally substituted alkyl, cycloalkyl, heterocyclyl, cycloalkyl-alkyl, heterocyclylalkyl group, and X is —NH—, by first converting the MeO— group into HO—, then by reacting it with a triflating agent so as to obtain the corresponding trifluoromethansulfonate and finally by reacting it with an amine of formula R—NH$_2$ (XXVII) wherein R is an optionally substituted alkyl, cycloalkyl, heterocyclyl, cycloalkylalkyl, arylalkyl or heterocyclylalkyl group

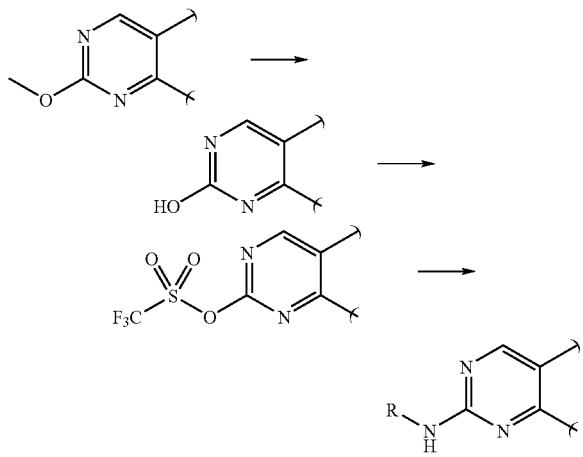

st. 33c) wherein R is methyl and X is —O— may be converted into the compounds of formula (I) wherein R is an aryl and X is —NH—, by first converting the MeO— group into —OH, then by reacting it with a triflating agent so as to obtain the corresponding trifluoromethansulfonate and finally by reacting it with an amine of formula RNH$_2$ (XXVII) wherein R is an optionally substituted aryl in the presence of palladium acetate and BINAP;

st.34) wherein A is a —(CH$_2$)$_2$— group may be converted into the compounds of formula (I) wherein A is a —CH═CH— group, under dehydrogenating operative conditions in the presence of a Pd or Pt catalyst.

The above process, in any one of the aforementioned variants, is an analogy process which can be carried out according to well known methods known in the art.

According to steps (st.1) of the process, 2-ethoxy-2-cyclohexen-1-one is reacted with diethyl oxalate in the presence of LiN(TMS)$_2$ and of a suitable solvent such as, for instance, dioxane, tetrahydrofuran or diethyl ether.

According to step (st.2a), the compound of formula (II) is reacted with a suitable hydrazine derivative of formula (III), in the presence of a lower alcohol such as methanol, ethanol or admixtures thereof. Preferably, the above reaction is carried out in ethanol at refluxing temperature, so as to obtain a mixture of both compounds of formula (IVa) and (IVb) wherein the former is present in major amounts. Their separation into the single compounds (IVa) and (IVb) is carried out under conventional methods, for instance through preparative HPLC.

By working according to step (st.2b) of the process, instead, that is by reacting the compound of formula (I) with the hydrazine derivative of formula (III) in the presence of acetic acid, a single compound of formula (IVa) is obtained. The reaction is preferably carried out at room temperature.

According to step (st.2c) of the process, the compound of formula (Iva) wherein R$_1$ is hydrogen, is reacted with a suitable compound of formula (IVc) in the presence of a base such as sodium hydride in a suitable solvent, for instance tetrahydrofaran, dioxane or dimethylformamide, at a temperature ranging from room temperature to 100° C., so as to obtain a mixture of compounds (IVa) and (Vb) wherein the former is present in major amounts, and by separating them under conventional methods, for instance through preparative HPLC.

According to step (st.3) of the process, the compound of formula (IVa) or (IVb) is reacted with dimethylformamide-1-tert-butylacetale, in the presence of a suitable solvent such as, for instance, dimethylformamide, so as to get the compounds of formula (Va) or (Vb), respectively. Preferably, the reaction is carried out at a temperature ranging from room temperature to about 70° C.

According to any one of the alternative steps (st.4a), (st.4b), (st.4c) or (st.4d) of the process, the compound of formula (Va) or (Vb) is reacted with guanidine, guanidine salts or derivatives thereof, alkylisothiourea or methylisourea so as to obtain the corresponding compound of formula (Ia) or (Ib) through pyrimidine ring formation. Any of the above reactions is carried out according to conventional methods. As an example, the reactions with guanidine or salts thereof such as hydrochloride, carbonate or nitrate, or with the guanidine derivative of formula (VI), as set forth in steps (st.4a) or (st.4b), are carried out in a lower alcoholic solvent under neutral or basic conditions, preferably with ethanol and sodium ethylate or with diazabicycloundecene (DBU) at is refluxing temperature or, alternatively, in dimethylformamide at a temperature ranging from 80° C. to refluxing temperature in the presence of potassium carbonate. The reaction with alkylisothiourea (VII), in (st.4c), is carried out in the presence of potassium acetate and in a suitable solvent such as dimethylformamide at refluxing temperature.

The reaction with methylisourea (st.4d) is carried out in a suitable solvent such as acetonitrile and in the presence of a base such as potassium carbonate at refluxing temperature.

The reactions of steps (st.5) and (st.6) are carried out under the operative conditions set forth in steps (st.1), (st.2a) or (st.2b) and lead to the desired compounds of formula (IXa) or (IXb), respectively.

Step (st.7) of the process is preferably carried out by reacting the derivative of formula (IXa) or (IXb) with ethyl formate under basic conditions, preferably in the presence of sodium ethylate or sodium hydride and of a suitable solvent such as, for instance, diethyl ether, tetrahydrofuran or dioxane, at a temperature ranging from room temperature to refluxing temperature.

The reaction conditions of step (st.8) are those previously reported for steps (st.4a and st.4b).

According to step (st.9), 2-methoxy-5,5-dimethyl-2-cyclohexen-1-one is reacted with diethyl oxalate in the presence of sodium hydride and in a suitable solvent such as diethyl ether, tetrahydrofuran or dioxane, at refluxing temperature.

The subsequent reaction conditions of steps (st.10) are essentially those previously reported for steps (st.2a) or (st.2b), and those of steps (st.11) and (st.12) correspond to those of (st.3) and (st.4a and st.4b), respectively.

According to step (st.13) of the process, it is clear to the skilled man that both compounds of formula (IVa) or (IVb) wherein $R_1$ is a hydrogen atom are tautomeric forms of a given compound which can be conveniently identified as having formula (IV). In this respect, this same derivative is reacted with triphenylmethyl chloride so as to obtain a compound of formula (XIV) wherein either one of the two pyrazole nitrogen atoms are alkylated with a trityl (e.g. triphenylmethyl) group.

The operative conditions in steps (st.14) and (st.15) of the process essentially correspond to those already reported for steps (st.3) and (st.4a and st.4b). According to step (st.16), the trityl group of the compounds of formula (I) is removed under acidic conditions, for instance with trifluoroacetic acid and in the presence of a suitable solvent such as dichloromethane, so as to give rise to the corresponding compound of formula (I) wherein $R_1$ is hydrogen, in both forms:

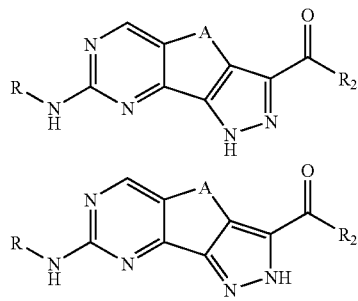

Its subsequent alkylation with a derivative of formula (XVI), according to step (st.17) of the process, allows to selectively alkylate the pyrazole nitrogen atom which is in proximity of the —COOEt group; this reaction may be carried out with lithium tert-butylate and in a suitable solvent, such as dioxane, diethyl ether or tetrahydrofuran. According to step (st.18), the above compound is first converted into the free amino derivative by working according to conventional methods, for instance under acidic conditions, preferably with hydrochloric acid, in a suitable solvent such as dioxane at refluxing temperature, and subsequently cyclised to the desired tetracyclic derivative in the presence of a base such as cesium carbonate ($CsCO_3$) and in a suitable solvent such as a lower alcohol, preferably methanol, ranging from room temperature to reflux. The operative conditions of steps (st.19) and (st.20) of the process essentially correspond to those already reported for steps (st.3) and (st.4c); the subsequent acidic treatment of the compound of formula (XVIII) to the compound of formula (XIX) is preferably carried out with an aqueous solution of acetic acid, at a temperature of about 100° C.

According to step (st.21), the compound of formula (XIX) is reacted with a suitable derivative of formula (XX) in the presence of sodium hydride and in a suitable solvent, e.g. diethyl ether, tetrahydrofuran or dioxane, at a temperature ranging from about −50° C. to room temperature.

The operative conditions of step (st.22) essentially correspond to those of step (st.1) of the process.

As formerly indicated, the compounds of formula (I) thus prepared may be easily converted into several other compounds of formula (I) of the invention.

As an example, compounds of formula (I) bearing $R_2$ as an ethoxy group, or even as an alkoxy group, can be converted into a variety of derivatives according to methods well-known in the art to convert carboxyester groups (—$COOR_2$) into carboxamides (—$CONH_2$), N-substituted carboxamides (—CONHR") and carboxylic acids (—COOH), for instance as reported in steps (st.23), (st.24) and (st.25).

The operative conditions are those widely known in the art and may comprise, for instance in the conversion of a carboxyester group into a carboxamide group, the reaction with ammonia or ammonium hydroxide in the presence of a suitable solvent such as a lower alcohol, dimethylformamide or mixtures thereof; preferably the reaction is carried out with ammonium hydroxide in a methanol/dimethylformamide mixture, at a temperature ranging from about 50° C. to about 100° C.

Analogous operative conditions apply in the preparation of N-substituted carboxamides wherein a suitable primary amine is used in place of ammonia or ammonium hydroxide. Likewise, carboxyester groups may be converted into carboxylic acid derivatives through basic or acidic hydrolysis conditions, widely known in the art.

According to step (st.26) of the process, compounds of formula (I) wherein $R_2$ is hydroxy (—COOH) may be converted into carboxamido derivatives (—CONR"R''') or [—CON(OH)R"] wherein R" and R''' are as formerly indicated, also inclusive of compounds wherein R" and R''' form, together with the nitrogen atom to which they are bonded, a 5 or 6 membered heteroaryl or heterocyclyl group optionally containing one additional heteroatom selected among N, O or S.

The reaction is carried out in the presence of an amine of formula (XXIII) or of a compound of formula (XXIV), as the case may be, under basic conditions, preferably with N,N-diisopropyl-N-ethylamine or triethylamine, in a suitable solvent such as dichloromethane, dimethylformamide, tetrahydrofuran, or dioxane, and in the presence of a suitable condensing agent such as N,N'-dicyclohexylcarbodiimide (DCC), N-(3-dimethylaminopropyl)-N'-ethylcarbodiimide hydrochloride (EDCI) or O-(benzotriazol-1-yl)-N,N,N',N'-tetramethylisouronium tetrafluoroborate (TBTU); catalytic amounts of (benzotriazol-1-yloxy)tripyrrolidinophosphonium hexafluorophosphate (PyBOP) ma be also required.

In addition, compounds of formula (I) wherein R—NH— is an amino (—$NH_2$) group may be easily converted into the corresponding carboxamido (—NHCOR) or ureido (—NH-CONHR) derivatives, as set forth in steps (st.27) or (st.28) of the process, respectively. Typically, the reaction with isocyanate is performed with sodium hydride in dimethylformamide whilst the one with the acid chloride may be carried out in a suitable solvent such as pyridine, tetrahydrofuran, ethyl acetate or dioxane, or a mixture of them at room temperature.

Compounds of formula (I) wherein R—NH— represents an arylamino or heteroarylamino group, can be obtained by the corresponding iodo derivatives which, in their turn, may be prepared by the corresponding compounds of formula (I) wherein R—NH— is amino, as per step (st.29) of the process.

The preparation of the iodo derivatives may be carried out in a suitable solvent such as tetrahydrofuran, diethyl ether or dimethoxyethane, at a temperature ranging from room temperature to about 70° C., and for a time of about 8 hours to about 48 hours.

The subsequent conversion of the iododerivative may be carried out in a suitable solvent such as dimethylformamide, dimethoxyethane or acetonitrile and in the presence of catalytic amounts of palladium acetate, (2,2'-bis(diphenylphosphino)-1,1'-binaphtalene (BINAP) and a base such as potassium carbonate, potassium phosphate or cesium carbonate, at a temperature ranging from room temperature to 110° C. and for a time ranging from about 2 to about 24 hours.

Compounds of formula (I) wherein R is aryl and X is a single bond can be obtained, as reported in step (st.30), from the iodo derivative above mentioned by reaction with arylboronic acids of formula (XXVIII) in a suitable solvent such as dimethylformamide, dichloromethane, methanol, dimethoxyethane or acetonitrile, in the presence of tris(dibenzylideneacetone)dipalladium (0) or tetrakis triphenylphosphino palladium [Pd(PPh$_3$)$_4$], optionally in the presence of cesium fluoride, at a temperature ranging from room temperature to 100° C.

Compounds of formula (I) wherein RNH— represents an alkylamino, cycloalkylamino, cycloalkyl-alkylamino, heterocyclylamino, heterocyclylalkylamino can be obtained from the corresponding iodo derivative as set forth in step (st.29a) of the process. The reaction may be carried out in a suitable solvent such as dimethylformamide, dioxane or acetonitrile or without solvent at a temperature ranging from 40° C. to 120° C. for a time ranging from 3 to 18 hours.

Compounds of formula (I) wherein R—NH— is amino may be also converted into the corresponding alkylamino or arylmethylamino derivatives of formula (I) as reported in (st.31), by operating in a suitable solvent or in a mixture of solvents, for instance comprising a 1:1:1 mixture of acetic acid, methanol and water.

Compounds of formula (I) wherein R—NH— is amino may be also converted into the corresponding cycloalkylamino or heterocycloalkylamino derivatives of formula (I) as reported in (st.31a), by operating in a suitable solvent such as methylene chloride, acetonitrile, dimethylformamide.

Compounds of formula (I) wherein R—X— represents an alkylthio group (R—S—) may be converted into a variety of compounds of formula (I) wherein X is —NH—, by first oxidizing the alkylthio to alkylsulfonyl group and by replacing it with a R—NH— group, as reported in (st.32). The oxidative step may be carried out with oxone in the presence of a suitable solvent, preferably dimethylformamide or dimethylsulfoxide at room temperature; the subsequent replacement of the alkylsulfonyl group with a suitable amino derivative is preferably carried out in the presence of dimethylsulfoxide, dimethylformamide, dimethoxyethane, dioxane, acetonitrile, N-methyl-pyrrolidone or diglyme, at a temperature ranging from room temperature to about 100° C.

Interestingly, when the last step is carried out in the presence of dimethylsulfoxide as a suitable solvent, this same solvent can also act as oxidizing agent capable of furnishing the desired compounds wherein A represents a group —CH═CH—. These latter derivatives are then separated from the reaction mixture according to conventional methods, for instance by chromatography or by preparative HPLC.

According to step (st.33) of the process, compounds of formula (I) wherein X is —O— may be easily obtained by reacting the sulfonyl derivative with an alcohol or phenol derivative of formula (XXX) wherein R is as in formula (I). The reaction may be carried out in the presence of a base such as potassium or sodium carbonate, butyl lithium, lithium amide, sodium hydride or the like, in a suitable solvent such as dimethylformamide or tetrahydrofuran, and by working at a temperature ranging from room temperature to about 100° C.

Alternatively, according to steps (st.4d) and (st.33a), compounds of formula (I) wherein X is —O— may be obtained by reacting the compounds of formula (Va) and (Vb) with methylisourea sulfate by operating in a suitable solvent such as dioxane, dimethylformamide or acetonitrile in the presence of a base such as sodium or potassium carbonate at a temperature ranging from 50° C. to 100° C. The compounds of formula (I) wherein X is —O— and R is hydrogen may be obtained by reacting the compounds of formula (I) wherein X is —O— and R is methyl with trimethylsilyl chloride in the presence of sodium iodide and in a suitable solvent such as dioxane, tetrahydrofuran or acetonitrile at room temperature. The compounds of formula (I) wherein X is —O— and R is a trifluorosulfonyl group may be obtained by reacting the compounds of formula (I) wherein X is —O— and R is hydrogen with a triflating agent such as trifluoromethanesulfonic anhydride, trifluoromethanesulfonylchloride or N-phenyl-bis(trifluoromethanesulfonimide), optionally in the presence of a base such as triethylamine or N,N-diisopropyl-N-ethylamine (DIPEA), in a suitable solvent such as dichloromethane, tetrahydrofuran or dioxane at a temperature ranging from −78° C. to room temperature.

The compounds of formula (I) wherein X is —O— and R is as described above may be obtained by reacting the compounds of formula (I) wherein X is —O— and R is a trifluoromethanesulfonyl group with an alcohol or phenol of formula (XXX) wherein R is as in formula (I), by operating in a suitable solvent such as dioxane, tetrahydrofuran, dimethoxyethane, acetonitrile, dimethylformamide or dimethylsulfoxide, at a temperature ranging from room temperature to about 90° C., optionally in the presence of a base such as potassium carbonate, potassium tertbutoxide or sodium hydride.

Alternatively the reaction may be carried out in a suitable solvent such as toluene, dimethylformamide, dimethoxyethane or acetonitrile, in the presence of palladium acetate, (±)-BINAP and a base such as potassium phosphate ($K_3PO_4$) or potassium or cesium carbonate ($K_2CO_3$ or $CsCO_3$) at a temperature ranging from 0° C. to 100° C. (st.33c).

The compounds of formula (I) wherein X is —NH— and R is an optionally substituted alkyl, cycloalkyl, heterocyclyl, cycloalkyl-alkyl or a heterocyclylalkyl group may be obtained by reacting the compounds of formula (I) wherein X is —O— and R is a trifluoromethanesulfonyl group with an amine of formula R—NH$_2$ (XXVII) wherein R is as in formula (I), by operating in a suitable solvent such as dioxane, tetrahydrofuran, dimethoxyethane, acetonitrile, dimethylformamide or dimethylsulfoxide, at a temperature ranging from room temperature to 90° C., optionally in the presence of a base such as potassium carbonate or triethylamine.

Finally, any of the above compounds of formula (I) wherein A represents a —CH₂—CH₂— group can undergo dehydrogenation in the presence of an optionally supported palladium or platinum catalyst, so as to give rise to the corresponding aromatic derivative wherein A is —CH═CH—, as per (st.34) of the process.

See the experimental section for any specific example concerning the preparation of the compounds of formula (I) of the invention and their conversion into other compounds of formula (I).

The intermediate compounds of formula (Va) or (Vb) according to step (st.3) of the process

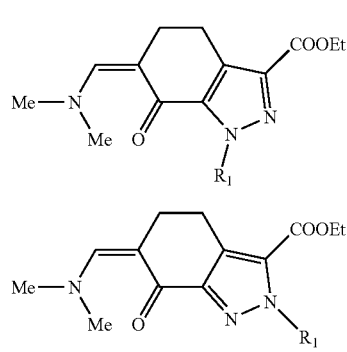

and wherein R₁ is a hydrogen atom or an optionally substituted group selected from straight or branched C₁-C₆ alkyl, C₃-C₆ cycloalkyl, aryl, arylalkyl, heterocyclyl or heterocyclylalkyl are novel and, hence, represent a further object of the invention.

According to any variant of the process for preparing the compounds of formula (I), the starting material and any other reactant is known or easily prepared according to known methods.

As an example, 2-ethoxy-2-cyclohexen-1-one is a known compound which can be easily obtained by refluxing cyclohexan-1,2-dione with ethanol in toluene, in the presence of catalytic amounts of p-toluenesulfonic acid (TsOH).

Likewise, 2-methoxy-4,4-dimethyl-2-cyclohexen-1-one is a known compound which can be prepared through epoxidation of commercially available 4,4-dimethyl-2-cyclohexen-1-one and subsequent treatment of the epoxide with potassium hydroxide in methanol.

Finally, 2-methoxy-5,5-dimethyl-2-cyclohexen-1-one may be prepared according to the following scheme from commercially available 5,5-dimethyl-cyclohexan-1,3-dione:

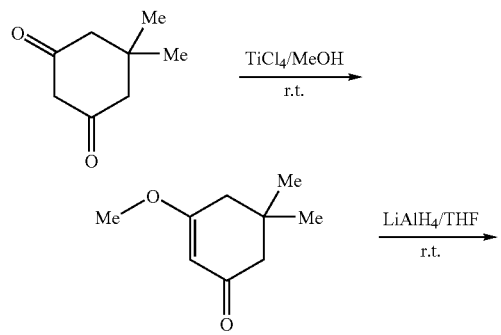

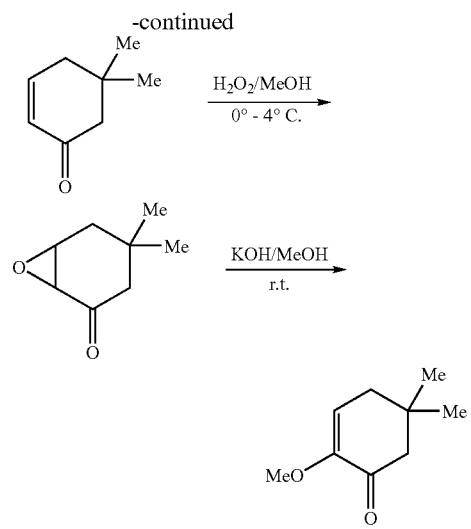

The compounds of formula (III), (VI), (VII), (XVI), (XXII), (XXIII), (XXIV), (XXV), (XXVI), (XXVII), (XXVIII), (XXIX), and (XXX) are known or easily prepared according to known methods.

Just as an example, when preparing given guanidino derivatives of formula (VI) wherein R is a rather complex chemical moiety, the following scheme may be followed:

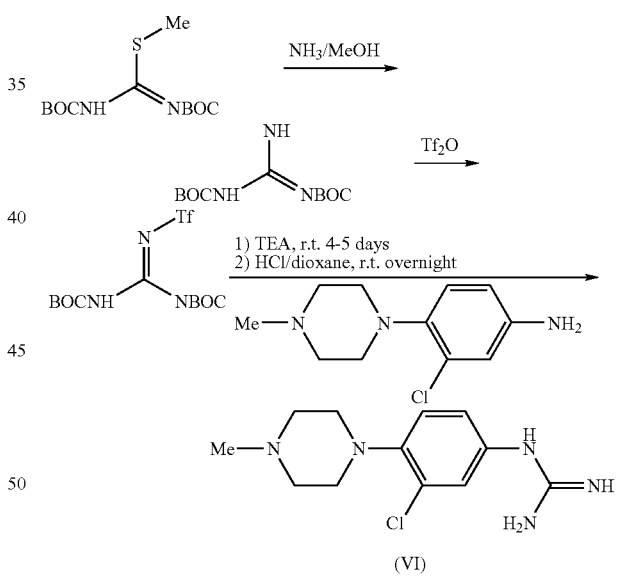

From all of the above, it is clear to the skilled man that when preparing the compounds of formula (I) according to any one of the aforementioned process variants, optional functional groups within the starting materials or the intermediates thereof and which could give rise to unwanted side reactions, need to be properly protected according to conventional techniques. Likewise, the conversion of these latter into the free deprotected compounds may be carried out according to known procedures.

As it will be readily appreciated, if the compounds of formula (I) prepared according to the process described above are obtained as an admixture of isomers, their separation into the single isomers of formula (I), according to conventional techniques, is within the scope of the present invention.

Conventional techniques for racemate resolution include, for instance, partitioned crystallization of diastereoisomeric salt derivatives or preparative chiral HPLC.

In addition, the compounds of formula (I) of the invention may be also prepared according to combinatorial chemistry techniques widely known in the art, for instance by accomplishing the aforementioned reactions between the several intermediates in a serial manner and by working under solid-phase-synthesis (SPS) conditions.

For a general reference to the preparation of the compounds of formula (I) of the invention according to combinatorial chemistry techniques, see the experimental section.

Hence, it is a further object of the present invention a library of two or more compounds of formula (Ia) or (Ib)

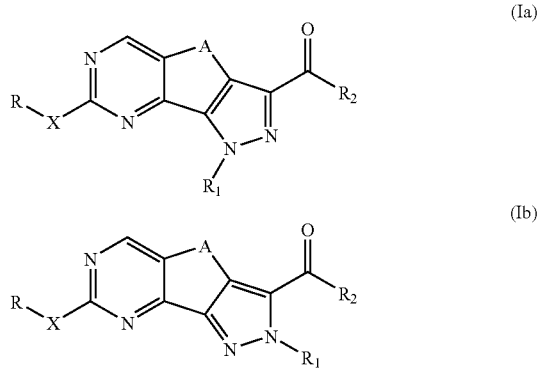

wherein

R is hydrogen or an optionally substituted group selected from amino, straight or branched $C_1$-$C_6$ alkyl, $C_3$-$C_{10}$ cycloalkyl, cycloalkyl-alkyl, aryl, arylalkyl heterocyclyl or heterocyclylalkyl;

X is a single bond or a divalent radical selected from —NR'—, —CONR'—, —NH—CO—NH—, —O—, —S— or —SO$_2$—, wherein R' is hydrogen or an optionally substituted group selected from straight or branched $C_1$-$C_6$ alkyl, $C_3$-$C_6$ cycloalkyl, cycloalkyl-alkyl, aryl arylalkyl, heterocyclyl, heterocyclylalkyl or, together with the nitrogen atom to which they are bonded, R and R' may form a 5 to 6 membered heteroaryl or heterocyclyl group optionally containing one additional heteroatom selected among N, O or S;

$R_1$, bonded to any one of the nitrogen atoms of the pyrazole ring as per formulae (Ia) or (Ib), represents a hydrogen atom or an optionally substituted group selected from straight or branched $C_1$-$C_6$ alkyl, $C_3$-$C_6$ cycloalkyl, aryl, arylalkyl, heterocyclyl or heterocyclylalkyl or, in formula (Ib), $R_1$ is a divalent —(CH$_2$)$_n$—NH— group being linked to $R_2$, wherein n is 2 or 3;

$R_2$ is a group selected from —NR"R'", —N(OH)R", —OR" or —R", wherein R" and R'" are, each independently, hydrogen or an optionally substituted group selected from straight or branched $C_1$-$C_6$ alkyl, $C_3$-$C_6$ cycloalkyl or cycloalkyl-alkyl, aryl, arylalkyl, heterocyclyl or heterocyclylalkyl or, together with the nitrogen atom to which they are bonded, R" and R'" may form a 5 to 6 membered heteroaryl or heterocyclyl group, optionally containing one additional heteroatom selected among N, O or S;

A is a divalent group selected from —CH$_2$—, —(CH$_2$)$_2$—, —CH$_2$—C(CH$_3$)$_2$—, —C(CH$_3$)$_2$—CH$_2$— or —CH=CH—;

or a pharmaceutically acceptable salt thereof.

Pharmacology

The compounds of formula (I) are active as protein kinase inhibitors and are therefore useful, for instance, to restrict the unregulated proliferation of tumor cells.

In therapy, they may be used in the treatment of various tumors, such as those formerly reported, as well as in the treatment of other cell proliferative disorders such as psoriasis, vascular smooth cell proliferation associated with atherosclerosis and post-surgical stenosis and restenosis and in the treatment of Alzheimer's disease.

The inhibiting activity of putative cdk/cyclin inhibitors and the potency of selected compounds is determined through a method of assay based on the use of the SPA technology (Amersham Pharmacia Biotech).

The assay consists of the transfer of radioactivity labelled phosphate moiety by the kinase to a biotinylated substrate. The resulting 33P-labelled biotinylated product is allowed to bind to streptavidin-coated SPA beads (biotin capacity 130 pmol/mg), and light emitted was measured in a scintillation counter.

Inhibition Assay of cdk2/Cyclin A Activity

Kinase reaction: 4 µM in house biotinylated histone H1 (Sigma # 1H-5505) substrate, 10 µM ATP (0.1 microCi P$^{33}$γ-ATP), 1.1 nM Cyclin A/CDK2 complex, inhibitor in a final volume of 30 µl buffer (TRIS HCl 10 mM pH 7.5, MgCl$_2$ 10 mM, DTT 7.5 mM+0.2 mg/ml BSA) were added to each well of a 96 U bottom. After incubation for 60 min at room temperature, the reaction was stopped by addition of 100 µl PBS buffer containing 32 mM EDTA, 500 µM cold ATP, 0.1% Triton X100 and 10 mg/ml streptavidin coated SPA beads. After 20 min incubation, 110 µL of suspension were withdrawn and transferred into 96-well OPTIPLATEs containing 100 µl of 5M CsCl. After 4 hours, the plates were read for 2 min in a Packard TOP-Count radioactivity reader.

IC$_{50}$ determination: inhibitors were tested at different concentrations ranging from 0.0015 to 10 µM. Experimental data were analyzed by the computer program GraphPad Prizm using the four parameter logistic equation:

$$y=\text{bottom}+(\text{top}-\text{bottom})/(1+10^{((\log IC50-x)*\text{slope})})$$

where x is the logarithm of the inhibitor concentration, y is the response; y starts at bottom and goes to top with a sigmoid shape.

Ki Calculation:

Experimental method: Reaction was carried out in buffer (10 mM Tris, pH 7.5, 10 mM MgCl$_2$, 0.2 mg/ml BSA, 7.5 mM DTT) containing 3.7 nM enzyme, histone and ATP (constant ratio of cold/labeled ATP 1/3000). Reaction was stopped with EDTA and the substrate captured on phosphomembrane (Multiscreen 96 well plates from Millipore). After extensive washing, the multiscreen plates were read on a top counter. Control (time zero) for each ATP and histone concentrations was measured.

Experimental design: Reaction velocities are measured at four ATP, substrate (histone) and inhibitor concentrations. An 80-point concentration matrix was designed around the respective ATP and substrate Km values, and the inhibitor IC50 values (0.3, 1, 3, 9 fold the Km or IC50 values). A preliminary time course experiment in the absence of inhibitor and at the different ATP and substrate concentrations allows the selection of a single endpoint time (10 min) in the linear range of the reaction for the Ki determination experiment Kinetic parameter estimates: Kinetic parameters were estimated by simultaneous nonlinear least-square regression using [Eq. 1] (competitive inhibitor respect to ATP, random mechanism) using the complete data set (80 points):

$$v = \frac{Vm \cdot A \cdot B}{\alpha \cdot Ka \cdot Kb + \alpha \cdot Ka \cdot B + a \cdot Kb \cdot A + A \cdot B + \alpha \cdot \frac{Ka}{Ki} \cdot I \cdot \left(Kb + \frac{B}{\beta}\right)} \quad [\text{Eq. 1}]$$

where A=[ATP], B=[Substrate], I=[inhibitor], Vm=maximum velocity, Ka, Kb, Ki the dissociation constants of ATP, substrate and inhibitor respectively. α and β the cooperativity factor between substrate and ATP binding and substrate and inhibitor binding respectively.

In addition the selected compounds are characterized on a panel of ser/thre kinases strictly related to cell cycle (cdk2/cyclin E, cdk1/cyclin B1, cdk5/p25, cdk4/cyclin D1), and also for specificity on MAPK, PKA, EGFR, IGF1-R, Aurora-2 and Cdc 7

Inhibition Assay of cdk2/Cyclin E Activity

Kinase reaction: 10 μM in house biotinylated histone H1 (Sigma # H-5505) substrate, 30 μM ATP (0.3 microCi $P^{33}\gamma$-ATP), 4 ng GST-Cyclin E/CDK2 complex, inhibitor in a final volume of 30 μl buffer (TRIS HCl 10 mM pH 7.5, $MgCl_2$ 10 mM, DTT 7.5 mM+0.2 mg/ml BSA) were added to each well of a 96 U bottom. After incubation for 60 min at room temperature, the reaction was stopped by addition of 100 μl PBS buffer containing 32 mM EDTA, 500 μM cold ATP, 0.1% Triton X100 and 10 mg/ml streptavidin coated SPA beads. After 20 min incubation, 110 μL of suspension were withdrawn and transferred into 96-well OPTIPLATEs containing 100 μd of 5M CsCl. After 4 hours, the plates were read for 2 min in a Packard TOP-Count radioactivity reader.

$IC_{50}$ Determination: see above

Inhibition Assay of cdk1/Cyclin B1 Activity

Kinase reaction: 4 μM in house biotinylated histone H1 (Sigma # H-5505) substrate, 20 μM ATP (0.2 microCi $P^{33}\gamma$-ATP), 3 ng Cyclin B/CDK1 complex, inhibitor in a final volume of 30 μl buffer (TRIS HCl 10 mM pH 7.5, $MgCl_2$ 10 mM, DTT 7.5 mM+0.2 mg/ml BSA) were added to each well of a 96 U bottom. After 20 min at r.t. incubation, reaction was stopped by 100 μl PBS+32 mM EDTA+0.1% Triton X-100+ 500 μM ATP, containing 1 mg SPA beads. Then a volume of 110 μl is transferred to Optiplate. After 20 min. incubation for substrate capture, 100 μl 5M CsCl were added to allow statification of beads to the top of the Optiplate and let stand 4 hours before radioactivity counting in the Top-Count instrument.

$IC_{50}$ Determination: see above

Inhibition Assay of cdk5/p25 Activity

The inhibition assay of cdk5/p25 activity is performed according to the following protocol.

Kinase reaction: 10 μM biotinylated histone H1 (Sigma # H-5505) substrate, 30 μM ATP (0.3 microCi $P^{33}\gamma$-ATP), 15 ng CDK5/p25 complex, inhibitor in a final volume of 30 μl buffer (TRIS HCl 10 mM pH 7.5, $MgCl_2$ 10 mM, DTT 7.5 mM+0.2 mg/ml BSA) were added to each well of a 96 U bottom. After incubation for 35 min at room temperature, the reaction was stopped by addition of 100 μl PBS buffer containing 32 mM EDTA, 500 μM cold ATP, 0.1% Triton X100 and 10 mg/ml streptavidin coated SPA beads. After 20 min incubation, 110 μL of suspension were withdrawn and transferred into 96-well OPTIPLATEs containing 100 μl of 5M CsCl. After 4 hours, the plates were read for 2 min in a Packard TOP-Count radioactivity reader.

$IC_{50}$ Determination: see above

Inhibition Assay of cdk4/Cyclin D1 Activity

Kinase reaction: 0.4 μM mouse GST-Rb (769-921) (# sc-4112 from Santa Cruz) substrate, 10 μM ATP (0.5 μCi $P^{33}\gamma$-ATP), 100 ng of baculovirus expressed GST-cdk4/GST-Cyclin D1, suitable concentrations of inhibitor in a final volume of 50 μl buffer (TRIS HCl 10 mM pH 7.5, $MgCl_2$ 10 mM, 7.5 mM DTT+0.2 mg/ml BSA) were added to each well of a 96 U bottom well plate. After 40 min at 37° C. incubation, reaction was stopped by 20 μl EDTA 120 mM.

Capture: 60 μl were transferred from each well to Multi-Screen plate, to allow substrate binding to phosphocellulose filter. Plates were then washed 3 times with 150 μl/well PBS $Ca^{++}/Mg^{++}$ free and filtered by MultiScreen filtration system.

Detection: filters were allowed to dry at 37° C., then 100 μl/well scintillant were added and $^{33}P$ labeled Rb fragment was detected by radioactivity counting in the Top-Count instrument.

$IC_{50}$ Determination: see above

Inhibition Assay of MAPK Activity

Kinase reaction: 10 μM in house biotinylated MBP (Sigma # M-1891) substrate, 15 μM ATP (0.15 microCi $P^{33}\gamma$-ATP), 30 ng GST-MAPK (Upstate Biothecnology # 14-173), inhibitor in a final volume of 30 μl buffer (IRIS HCl 10 mM pH 7.5, $MgCl_2$ 10 mM, DTT 7.5 mM+0.2 mg/ml BSA) were added to each well of a 96 U bottom. After incubation for 35 min at room temperature, the reaction was stopped by addition of 100 μl PBS buffer containing 32 mM EDTA, 500 μM cold ATP, 0.1% Triton X100 and 10 mg/ml streptavidin coated SPA beads. After 20 min incubation, 110 μL of suspension were withdrawn and transferred into 96-well OPTIPLATEs containing 100 μl of 5M CsCl. After 4 hours, the plates were read for 2 min in a Packard TOP-Count radioactivity reader.

$IC_{50}$ Determination: see above

Inhibition Assay of PKA Activity

Kinase reaction: 10 μM in house biotinylated histone H1 (Sigma # H-5505) substrate, 10 μM ATP (0.2 microM $P^{33}\gamma$-ATP), 0.45 U PKA (Sigma # 2645), inhibitor in a final volume of 30 μl buffer (TRIS HCl 10 mM pH 7.5, $MgCl_2$ 10 mM, DTT 7.5 mM+0.2 mg/ml BSA) were added to each well of a 96 U bottom. After incubation for 90 min at room temperature, the reaction was stopped by addition of 100 μl PBS buffer containing 32 mM EDTA, 500 μM cold ATP, 0.1% Triton X100 and 10 mg/ml streptavidin coated SPA beads. After 20 min incubation, 110 μL of suspension were withdrawn and transferred into 96-well OPTIPLATEs containing 100 μl of 5M CsCl. After 4 hours, the plates were read for 2 min in a Packard TOP-Count radioactivity reader.

$IC_{50}$ Determination: see above

Inhibition Assay of EGFR Activity

Kinase reaction: 10 μM in house biotinylated MBP (Sigma # M-1891) substrate, 2 μM ATP (0.04 microCi $P^{33}\gamma$-ATP), 36 ng insect cell expressed GST-EGFR, inhibitor in a final volume of 30 μl buffer (Repes 50 mM pH 7.5, $MgCl_2$ 3 mM, $MnCl_2$ 3 mM, DTT 1 mM, $NaVO_3$ 3 μM, +0.2 mg/ml BSA) were added to each well of a 96 U bottom. After incubation for 20 min at room temperature, the reaction was stopped by addition of 100 μl PBS buffer containing 32 mM EDTA, 500 μM cold ATP, 0.1% Triton X100 and 10 mg/ml streptavidin coated SPA beads. After 20 min incubation, 110 μL of suspension were withdrawn and transferred into 96-well OPTIPLATEs containing 100 μl of 5M CsCl. After 4 hours, the plates were read for 2 min in a Packard TOP-Count radioactivity reader.

$IC_{50}$ Determination: see above

Inhibition Assay of IGF1-R Activity

The inhibition assay of IGF1-R activity is performed according to the following protocol.

Enzyme activation: IGF1-R must be activated by autophosphorylation before starting the experiment. Just prior to the assay, a concentrated enzyme solution (694 nM) is incubated for half a hour at 28° C. in the presence of 100 μM ATP and then brought to the working dilution in the indicated buffer.

Kinase reaction: 10 μM biotinylated IRS1 peptide (PRIM) substrate, 0-20 μM inhibitor, 6 μM ATP, 1 microCi $^{33}$P-ATP, and 6 nM GST-IGF1-R (pre-incubated for 30 min at room temperature with cold 60 μM cold ATP) in a final volume of 30 μl buffer (50 mM HEPES pH 7.9, 3 mM $MnCl_2$, 1 mM DTT, 3 μM $NaVO_3$) were added to each well of a 96 U bottom well plate. After incubation for 35 min at room temperature, the reaction was stopped by addition of 100 μl PBS buffer containing 32 mM EDTA, 500 μM cold ATP, 0.1% Triton X100 and 10 mg/ml streptavidin coated SPA beads. After 20 min incubation, 110 μL of suspension were withdrawn and transferred into 96-well OPTIPLATEs containing 100 μl of 5M CsCl. After 4 hours, the plates were read for 2 min in a Packard TOP-Count radioactivity reader.

Inhibition Assay of Aurora-2 Activity

Kinase reaction: 8 μM biotinylated peptide (4 repeats of LRRWSLG), 10 μM ATP (0.5 μCi $P^{33}$γ-ATP), 7.5 ng Aurora 2, inhibitor in a final volume of 30 μl buffer (HEPES 50 mM pH 7.0, $MgCl_2$ 10 mM, 1 mM DTT, 0.2 mg/ml BSA, 3 μM orthovanadate) were added to each well of a 96 U bottom well plate. After 60 minutes at room temperature incubation, reaction was stopped and biotinylated peptide captured by adding 100 μl of bead suspension.

Stratification: 100 μl of CsCl2 5 M were added to each well and let stand 4 hour before radioactivity was counted in the Top-Count instrument.

$IC_{50}$ Determination: see above

Inhibition Assay of Cdc7/dbf4 Activity

The inhibition assay of Cdc7/dbf4 activity is performed according to the following protocol.

The Biotin-MCM2 substrate is trans-phosphorylated by the Cdc7/Dbf4 complex in the presence of ATP traced with $γ^{33}$-ATP. The phosphorylated Biotin-MCM2 substrate is then captured by Streptavidin-coated SPA beads and the extent of phosphorylation evaluated by β counting.

The inhibition assay of Cdc7/dbf4 activity was performed in 96 wells plate according to the following protocol.

To each well of the plate were added:
- 10 μl substrate (biotinylated MCM2, 6 μM final concentration)
- 10 μl enzyme (Cdc7/Dbf4, 17.9 nM final concentration)
- 10 μl test compound (12 increasing concentrations in the nM to μM range to generate a dose-response curve)
- 10 μl of a mixture of cold ATP (2 μM final concentration) and radioactive ATP (1/5000 molar ratio with cold ATP) was then used to start the reaction which was allowed to take place at 37° C.

Substrate, enzyme and ATP were diluted in 50 mM HEPES pH 7.9 containing 15 mM $MgCl_2$, 2 mM DTT, 3 μM $NaVO_3$, 2 mM glycerophosphate and 0.2 mg/ml BSA. The solvent for test compounds also contained 10% DMSO.

After incubation for 60 minutes, the reaction was stopped by adding to each well 100 μl of PBS pH 7.4 containing 50 mM EDTA, 1 mM cold ATP, 0.1% Triton X100 and 10 mg/ml streptavidin coated SPA beads.

After 20 min incubation, 110 μL of suspension were withdrawn and transferred into 96-well OPTIPLATEs containing 100 μl of 5M CsCl. After 4 hours, the plates were read for 2 min in a Packard TOP-Count radioactivity reader.

$IC_{50}$ Determination: see above.

The compounds of the present invention can be administered either as single agents or, alternatively, in combination with known anticancer treatments such as radiation therapy or chemotherapy regimen in combination with cytostatic or cytotoxic agents, antibiotic-type agents, alkylating agents, antimetabolite agents, hormonal agents, immunological agents, interferon-type agents, cyclooxygenase inhibitors (e.g. COX-2 inhibitors), matrixmetalloprotease inhibitors, telomerase inhibitors, tyrosine kinase inhibitors, anti-growth factor receptor agents, anti-HER agents, anti-EGFR agents, anti-angiogenesis agents (e.g. angiogenesis inhibitors), farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like.

If formulated as a fixed dose, such combination products employ the compounds of this invention within the dosage range described below and the other pharmaceutically active agent within the approved dosage range.

Compounds of formula (I) may be used sequentially with known anticancer agents when a combination formulation is inappropriate.

The compounds of formula (I) of the present invention, suitable for administration to a mammal, e.g., to humans, can be administered by the usual routes and the dosage level depends upon the age, weight, conditions of the patient and administration route.

For example, a suitable dosage adopted for oral administration of a compound of formula (I) may range from about 10 to about 500 mg per dose, from 1 to 5 times daily. The compounds of the invention can be administered in a variety of dosage forms, e.g., orally, in the form tablets, capsules, sugar or film coated tablets, liquid solutions or suspensions; rectally in the form suppositories; parenterally, e.g., intramuscularly, or through intravenous and/or intrathecal and/or intraspinal injection or infusion.

The present invention also includes pharmaceutical compositions comprising a compound of formula (I) or a pharmaceutically acceptable salt thereof in association with a pharmaceutically acceptable excipient, which may be a carrier or a diluent.

The pharmaceutical compositions containing the compounds of the invention are usually prepared following conventional methods and are administered in a suitable pharmaceutical form.

For example, the solid oral forms may contain, together with the active compound, diluents, e.g., lactose, dextrose saccharose, sucrose, cellulose, corn starch or potato starch; lubricants, e.g., silica, talc, stearic acid, magnesium or calcium stearate, and/or polyethylene glycols; binding agents, e.g., starches, arabic gum, gelatine methylcellulose, carboxymethylcellulose or polyvinyl pyrrolidone; disintegrating agents, e.g., starch, alginic acid, alginates or sodium starch glycolate; effervescing mixtures; dyestuffs; sweeteners; wetting agents such as lecithin, polysorbates, laurylsulphates;

and, in general, non-toxic and pharmacologically inactive substances used in pharmaceutical formulations. These pharmaceutical preparations may be manufactured in known manner, for example, by means of mixing, granulating, tabletting, sugar-coating, or film-coating processes.

The liquid dispersions for oral administration may be, e.g., syrups, emulsions and suspensions.

As an example, the syrups may contain, as carrier, saccharose or saccharose with glycerine and/or mannitol and sorbitol.

The suspensions and the emulsions may contain, as examples of carriers, natural gum, agar, sodium alginate, pectin, methylcellulose, carboxymethylcellulose, or polyvinyl alcohol.

The suspension or solutions for intramuscular injections may contain, together with the active compound, a pharmaceutically acceptable carrier, e.g., sterile water, olive oil, ethyl oleate, glycols, e.g., propylene glycol and, if desired, a suitable amount of lidocaine hydrochloride.

The solutions for intravenous injections or infusions may contain, as a carrier, sterile water or preferably they may be in the form of sterile, aqueous, isotonic, saline solutions or they may contain propylene glycol as a carrier.

The suppositories may contain, together with the active compound, a pharmaceutically acceptable carrier, e.g., cocoa butter, polyethylene glycol, a polyoxyethylene sorbitan fatty acid ester surfactant or lecithin.

With the aim to better illustrate the present invention, without posing any limitation to it, the following examples are now given.

EXAMPLES

Several compounds of formula (I), hence including those of formula (Ia) and (Ib) of the invention, have been prepared. Whilst some of them have been specifically named and listed in the following experimental section, most have been conveniently identified as per the coding system of the tables reported in the experimental section, together with their analytical data.

Each code, which unambiguosly identifies a single specific compound of formula (I) only, consists of five units B-X-M(C)-D.

Code B represents any R substituent, as per formula (I), being attached to the rest of the molecule through the X linkage; each B group is represented through the proper chemical formula in the following table I, also indicating its point of attachment to the rest of the molecule X-M.

Code X just represents the X group in formula (I); its meanings are represented in the following table II, also indicating its point of attachment to the rest of the molecule M.

Code C represents the $R_1$ group being attached to the rest of the molecule through any one of the pyrazole nitrogen atoms, as per formula (I). Each C group is represented through the proper chemical formula in the following table III, also indicating its point of attachment to the rest of the molecule M.

Code D represents the $R_2$ group being attached to the rest of the molecule through the carbonyl group, as per formula (I). Each D group is represented through the proper chemical formula in the following table IV, also indicating its point of attachment to the rest of the molecule M.

Finally, code M refers to the central core of the molecule (I) bearing a carbonyl group in position 3. From all of the above it is clear to the skilled person that M is substituted by groups —X— (code X), $R_1$ (code C) and $R_2$ (code D), as reported in formula (I); each M group is represented through the proper chemical formula, in table V, also indicating the positions of the other substituents.

Therefore, the coding system presently used for some compounds of formula (I) can be shortly summarised as follows:

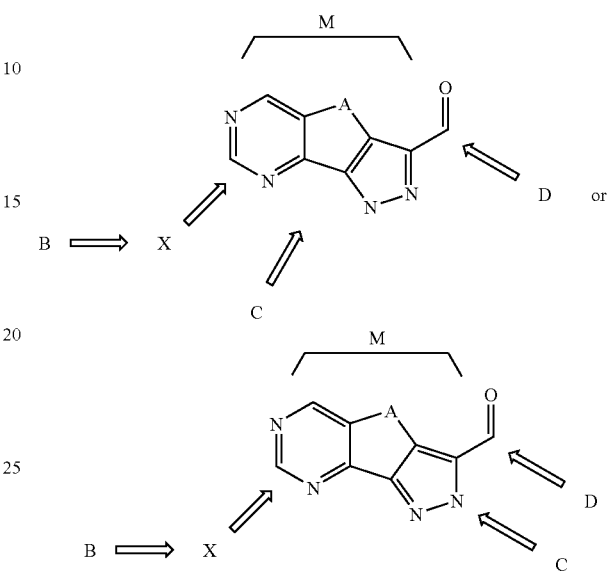

Just as an example, which is not intended to limit the scope of the present invention, the compound B66-X03-M00(C01)-D01 (see example 36) represents the pyrazolo-quinazoline derivative of formula (Ia) wherein the central core is represented by the moiety M00 of table V, R is the group of formula B66 of table I, X is the divalent group X03 of table II, $R_1$ is the group C01 of table III and $R_2$ is the group D01 of table IV, having formula

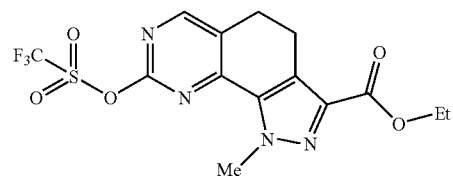

B66-X03-M00(C01)-D01

From all of the above, it is clear to the skilled person that when $R_1$ and $R_2$ are linked together as per formula (Ib), then this additional cycle is already included in the structure of the M moiety and, hence, codes C and D are missing.

TABLE I

TABLE OF B GROUPS

| Fragment | Code |
|---|---|
| M―X―H | B00 |
| M―X―⁀⁀OH | B01 |

TABLE I-continued
TABLE OF B GROUPS
| Fragment | Code |
|---|---|
| 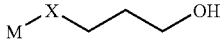 | B02 |
| 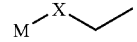 | B03 |
| 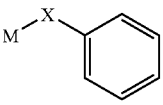 | B04 |
| 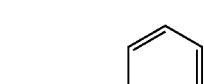 | B05 |
| 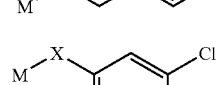 | B06 |
| 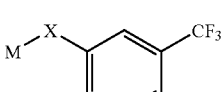 | B07 |
| 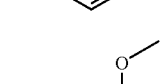 | B08 |
| 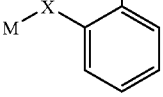 | B09 |
| 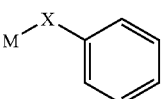 | B10 |
| 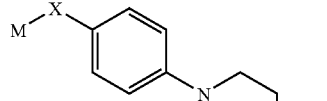 | B11 |
| 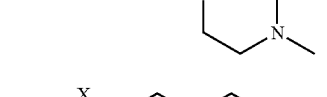 | B12 |
| 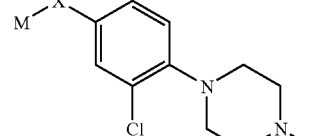 | B13 |
| 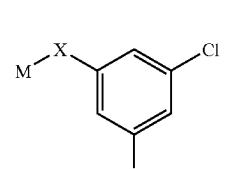 | B14 |
| 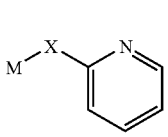 | B15 |
| 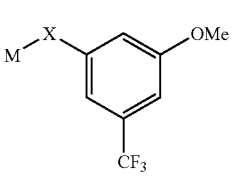 | B16 |
| 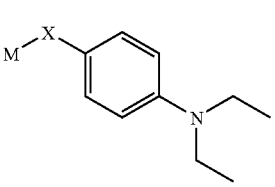 | B17 |
| 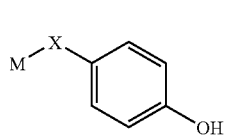 | B18 |
| 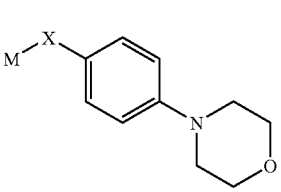 | B19 |
| 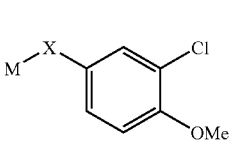 | B20 |
| 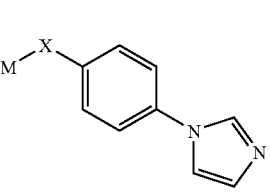 | B21 |

TABLE I-continued
TABLE OF B GROUPS
| Fragment | Code |
|---|---|
| 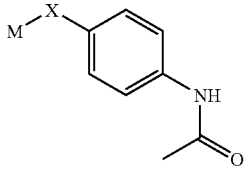 | B22 |
| 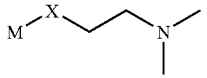 | B23 |
| 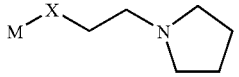 | B24 |
| 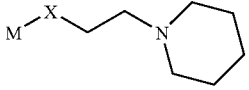 | B25 |
| 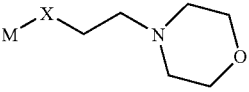 | B26 |
| 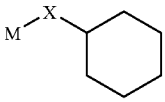 | B27 |
| 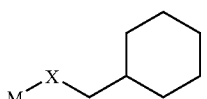 | B28 |
| 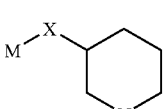 | B29 |
| 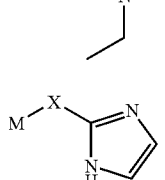 | B30 |
| 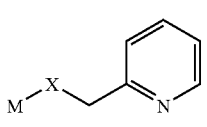 | B31 |
| 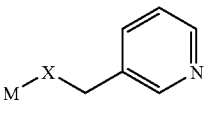 | B32 |
| 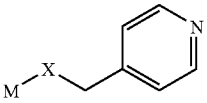 | B33 |
| 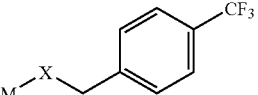 | B34 |
| 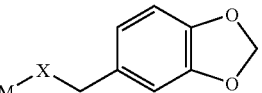 | B35 |
| 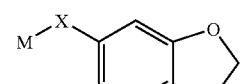 | B36 |
| 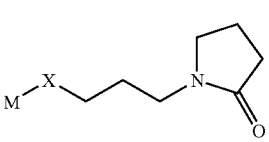 | B37 |
| 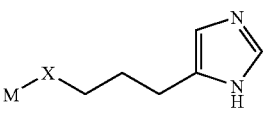 | B38 |
| 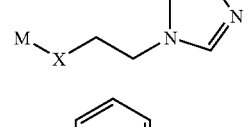 | B39 |
| 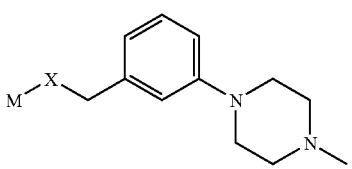 | B40 |
| 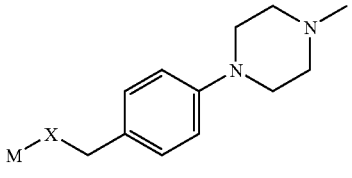 | B41 |
| 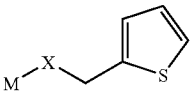 | B42 |
| 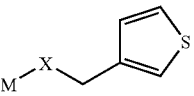 | B43 |
| 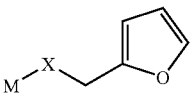 | B44 |
| 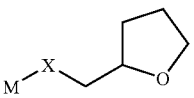 | B45 |

TABLE I-continued

TABLE OF B GROUPS

| Fragment | Code |
|---|---|
| 3-methoxybenzyl | B46 |
| adamantyl (with stereochemistry) | B47 |
| adamantyl | B48 |
| pinanyl-methyl | B49 |
| 1-benzylpiperidin-4-yl | B50 |
| 4-sulfamoylbenzyl | B51 |
| 4-(methylsulfonyl)benzyl | B52 |
| 1H-benzimidazol-2-ylmethyl | B53 |
| 3-iodobenzyl | B54 |
| cyclopropylmethyl | B55 |
| 2,3-dihydro-1,4-benzodioxin-2-ylmethyl | B56 |
| 3-fluoro-5-(trifluoromethyl)benzyl | B57 |
| 2-(pyridin-2-yl)ethyl | B58 |
| 3-(1H-pyrrol-1-yl)benzyl | B59 |
| 4-methoxybenzyl | B60 |
| 4-(3-(dimethylamino)propoxy)benzyl | B61 |
| 3,5-dihydroxybenzyl | B62 |
| 3-cyanobenzyl | B63 |

TABLE I-continued
TABLE OF B GROUPS
| Fragment | Code |
|---|---|
| 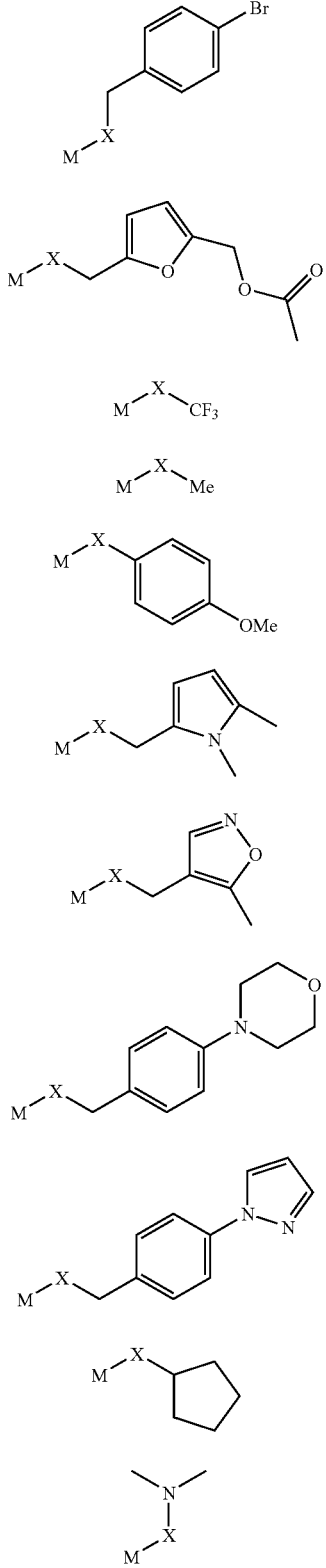 | B64 |
| | B65 |
| | B66 |
| | B67 |
| | B68 |
| | B69 |
| | B70 |
| | B71 |
| | B72 |
| | B73 |
| | B74 |
TABLE I-continued
TABLE OF B GROUPS
| Fragment | Code |
|---|---|
| 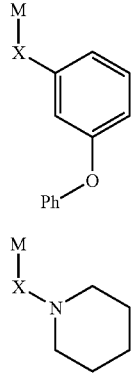 | B75 |
| | B76 |
| | B77 |
| | B78 |
| | B79 |
| | B80 |
| | B81 |
| | B82 |
| | B83 |
| | B84 |
| | B85 |

TABLE I-continued
TABLE OF B GROUPS
| Fragment | Code |
|---|---|
| 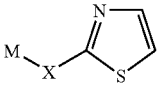 | B86 |
| 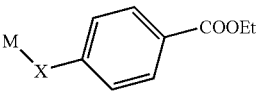 | B87 |
| 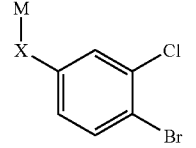 | B88 |
| 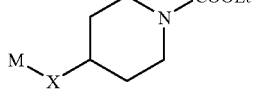 | B89 |
| 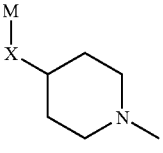 | B90 |
| 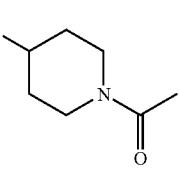 | B91 |
| 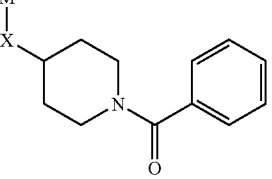 | B92 |
| 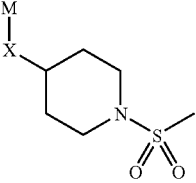 | B93 |
| 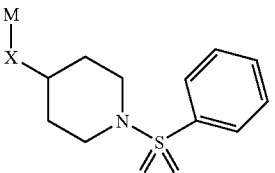 | B94 |
| 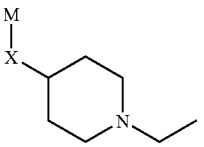 | B95 |
| 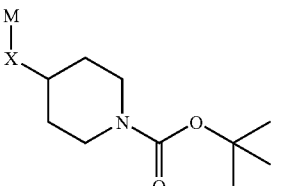 | B96 |
| 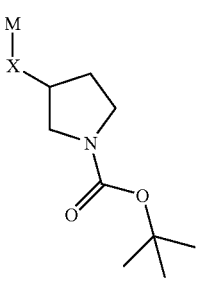 | B97 |
| 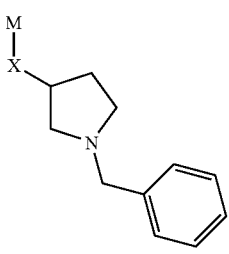 | B98 |
| 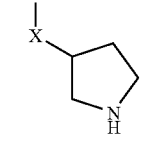 | B99 |
| 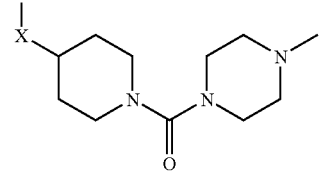 | B100 |
| 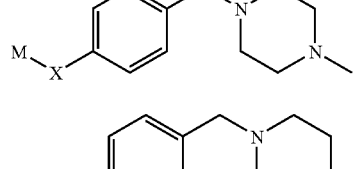 | B101 |
| 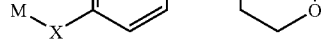 | B102 |

TABLE I-continued
TABLE OF B GROUPS
| Fragment | Code |
|---|---|
| 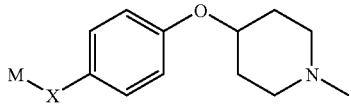 | B103 |
| 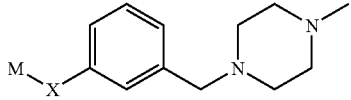 | B104 |
| 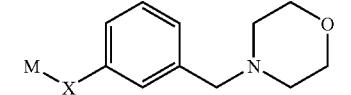 | B105 |
| 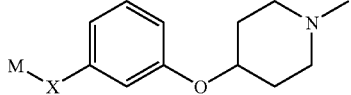 | B106 |
| 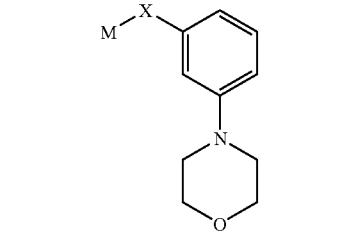 | B107 |
| 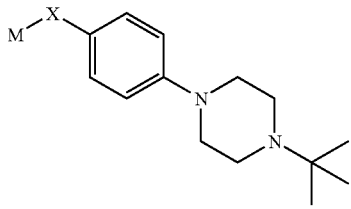 | B108 |
|  | B109 |
| 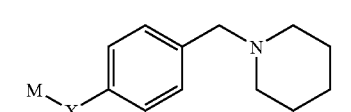 | B110 |
| 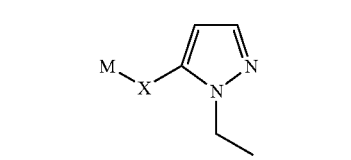 | B111 |
| 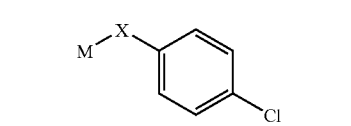 | B112 |
| 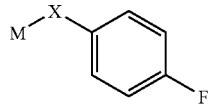 | B113 |
| 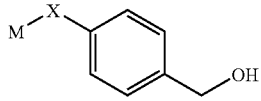 | B114 |
| 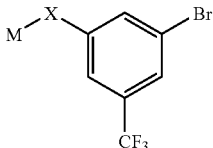 | B115 |
| 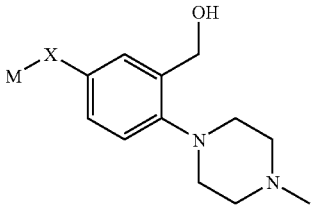 | B116 |
| 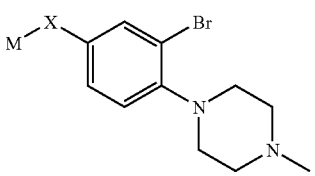 | B117 |
| 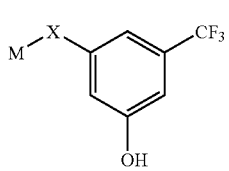 | B118 |
| 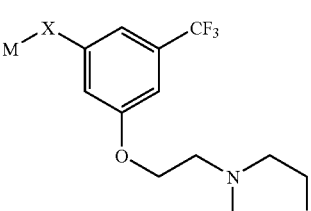 | B119 |
| 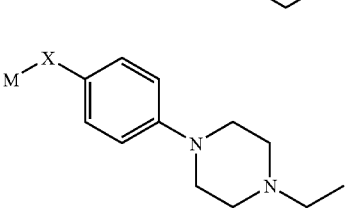 | B120 |

TABLE I-continued

TABLE OF B GROUPS

| Fragment | Code |
|---|---|
| (4-sulfamoylphenyl, M-X- at para) | B121 |
| (2-hydroxymethylphenyl, M-X- at ortho) | B122 |
| (3-hydroxypyridin-2-yl, M-X- at 2-position) | B123 |
| (3-hydroxyphenyl, M-X- at meta) | B124 |
| (4-dimethylaminophenyl, M-X- at para) | B125 |
| (2,6-dihydroxyphenyl, M-X- at 1-position) | B126 |
| (2-sulfamoylphenyl, M-X- at ortho) | B127 |
| (3-cyano-4,5-dimethylfuran-2-yl) | B128 |
| (3-carbamoylphenyl, M-X- at meta) | B129 |
| (4-carbamoylphenyl, M-X- at para) | B130 |
| (4-ethoxycarbonylmethylphenyl) | B131 |
| (2-morpholinophenyl) | B132 |
| (3-carbamoylthiophen-4-yl) | B133 |
| (2-(2-hydroxyethyl)phenyl) | B134 |
| (2-carbamoylphenyl) | B135 |
| (1-methyl-2-ethoxycarbonylimidazol-4-yl) | B136 |
| (3-hydroxy-4-methoxyphenyl) | B137 |
| (2-hydroxy-4-methylphenyl) | B138 |
| (3-(1-hydroxyethyl)phenyl) | B139 |

TABLE I-continued

TABLE OF B GROUPS

| Fragment | Code |
|---|---|
| (3-methyl-4-hydroxyphenyl with M-X) | B140 |
| (4-(2-hydroxyethyl)phenyl with M-X) | B141 |
| (2,5-dihydroxyphenyl with M-X) | B142 |
| (3-(dimethylamino)phenyl with M-X) | B143 |
| (4-(piperidin-1-yl)phenyl with M-X) | B144 |
| (4-((dimethylamino)methyl)phenyl with M-X) | B145 |
| (2-((N-cyclohexyl-N-methylamino)methyl)phenyl with M-X) | B146 |
| (3-((dimethylamino)methyl)phenyl with M-X) | B147 |
| (2-methyl-3-(hydroxymethyl)phenyl with M-X) | B148 |
| (4-methyl-3-(hydroxymethyl)phenyl with M-X) | B149 |
| (2-morpholino-5-carboxyphenyl with M-X) | B150 |
| (3-sulfamoyl-4-hydroxyphenyl with M-X) | B151 |
| (4-(piperidin-1-ylsulfonyl)phenyl with M-X) | B152 |
| (4-(morpholin-4-ylsulfonyl)phenyl with M-X) | B153 |
| (2-morpholino-5-propanoylphenyl with M-X) | B154 |
| (4-((2,6-dimethylmorpholin-4-yl)carbonyl)phenyl with M-X) | B155 |
| (4-(4-acetylpiperazin-1-yl)phenyl with M-X) | B156 |

TABLE I-continued
TABLE OF B GROUPS
| Fragment | Code |
|---|---|
| 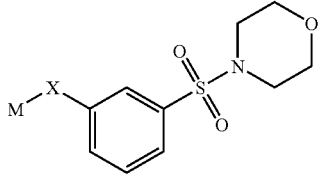 | B157 |
| 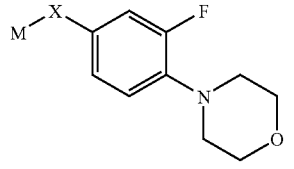 | B158 |
| 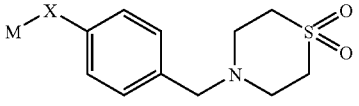 | B159 |
| 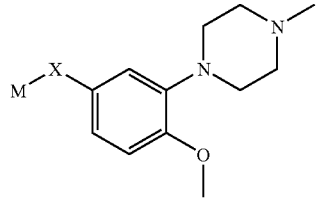 | B160 |
| 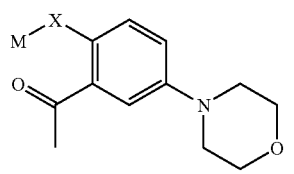 | B161 |
| 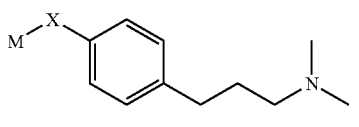 | B162 |
| 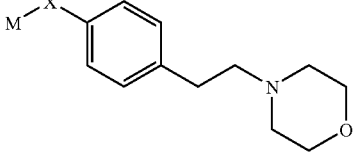 | B163 |
| 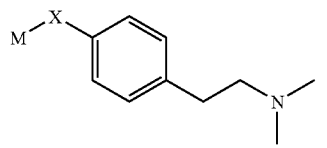 | B164 |
| 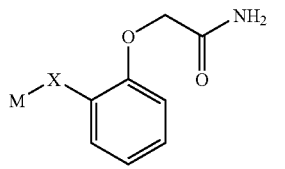 | B165 |
TABLE I-continued
TABLE OF B GROUPS
| Fragment | Code |
|---|---|
| 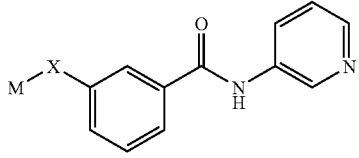 | B166 |
| 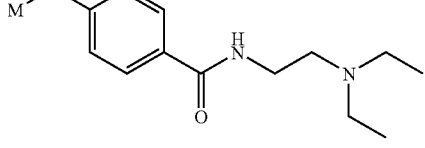 | B167 |
| 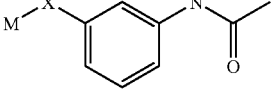 | B168 |
| 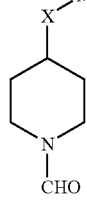 | B169 |
| 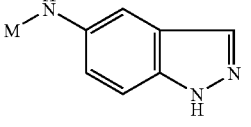 | B170 |
| 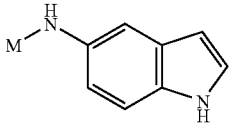 | B171 |
| 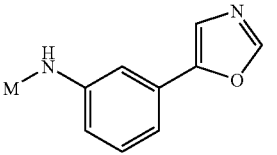 | B172 |
| 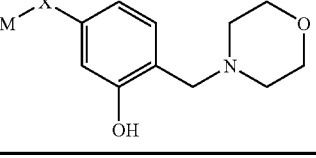 | B173 |
TABLE II
TABLE OF X LINKERS
| Fragment | Code |
|---|---|
| —NH—M | X00 |
| —CONH—M | X01 |

TABLE II-continued

TABLE OF X LINKERS

| Fragment | Code |
| --- | --- |
| —NHCONH—M | X02 |
| —O—M | X03 |
| —S—M | X04 |
| —SO$_2$—M | X05 |
| —M | X06 |

TABLE III

TABLE OF C GROUPS

| Fragment | Code |
| --- | --- |
| M—H | C00 |
| M—Me | C01 |
| M-tBu | C02 |
| M-CH$_2$-C(CH$_3$)$_3$ | C03 |
| M-CH$_2$CH$_2$-OH | C04 |
| M-CH$_2$-CF$_3$ | C05 |
| M-CH$_2$-COOEt | C06 |
| M-CH$_2$-CONH$_2$ | C07 |
| M-C$_6$H$_4$-SO$_2$NH$_2$ (para) | C08 |
| M-C$_6$H$_4$-OMe (para) | C09 |
| M-C$_6$H$_4$-CN (para) | C10 |
| M-(2-pyridyl) | C11 |
| M-CH$_2$CH$_2$-NH$_2$ | C12 |
| M-CH$_2$CH$_2$CH$_2$-NH$_2$ | C13 |
| M-CH$_2$-(2,5-diethyl-oxazole) | C14 |

TABLE III-continued

TABLE OF C GROUPS

| Fragment | Code |
| --- | --- |
| M-CH$_2$-(2-methyl-5-phenyl-oxazole) | C15 |
| M-phenyl | C16 |
| M-CH$_2$-phenyl | C17 |
| M-(4-piperidyl) (NH) | C18 |
| M-(1-methyl-4-piperidyl) | C19 |
| M-(1-formyl-4-piperidyl) | C20 |
| M-(1-benzyl-4-piperidyl) | C21 |
| M-(1-acetyl-4-piperidyl) | C22 |
| M-CH$_2$CH$_2$-N(CH$_3$)$_2$ | C23 |
| M-CH$_2$CH$_2$CH$_2$-N(CH$_3$)$_2$ | C24 |

TABLE IV
TABLE OF D GROUPS
| Fragment | Code |
|---|---|
| M—OMe | D00 |
| M—OEt | D01 |
| M—OH | D02 |
| M—NH₂ | D03 |
|  | D04 |
| M—NH—OH | D05 |
| 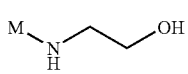 | D06 |
| M—Ph | D07 |
| 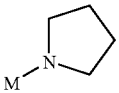 | D08 |
| 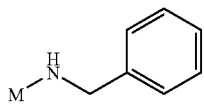 | D09 |
| 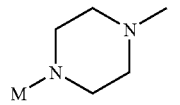 | D10 |
| 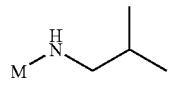 | D11 |
| 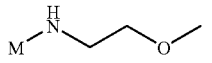 | D12 |
| 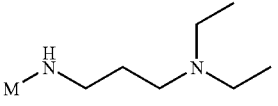 | D13 |
| 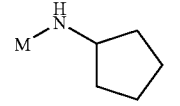 | D14 |
| 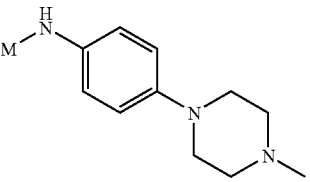 | D15 |
| 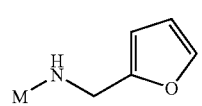 | D16 |
| 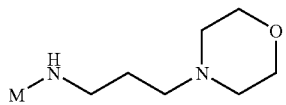 | D17 |
TABLE IV-continued
TABLE OF D GROUPS
| Fragment | Code |
|---|---|
| 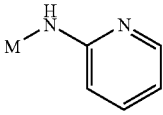 | D18 |
| 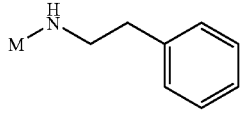 | D19 |
| 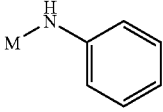 | D20 |
| 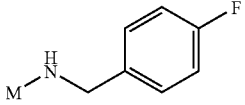 | D21 |
| 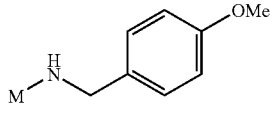 | D22 |
| 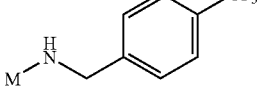 | D23 |
| 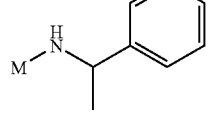 | D24 |
| 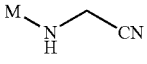 | D25 |
| 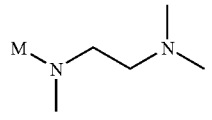 | D26 |
| 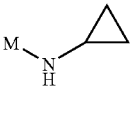 | D27 |
| 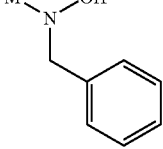 | D28 |

TABLE IV-continued
TABLE OF D GROUPS
| Fragment | Code |
|---|---|
|  | D29 |
|  | D30 |
|  | D31 |
|  | D32 |
|  | D33 |
|  | D34 |
|  | D35 |
|  | D36 |
|  | D37 |
|  | D38 |
TABLE IV-continued
TABLE OF D GROUPS
| Fragment | Code |
|---|---|
| | D39 |
| | D40 |
| | D41 |
| | D42 |
| | D43 |
| | D44 |
| | D45 |
| | D46 |
| | D47 |
| | D48 |

TABLE IV-continued
TABLE OF D GROUPS
| Fragment | Code |
|---|---|
| 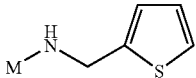 | D49 |
| 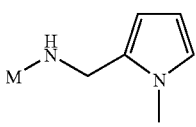 | D50 |
| 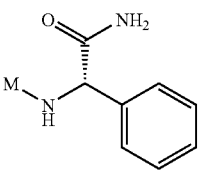 | D51 |
| 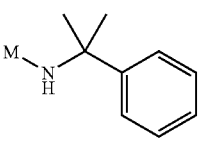 | D52 |
| 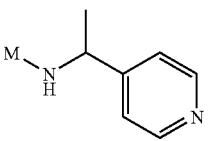 | D53 |
| 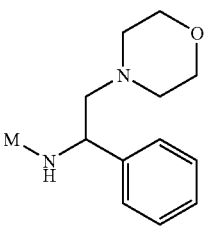 | D54 |
| 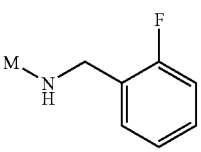 | D55 |
| 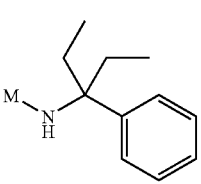 | D56 |
| 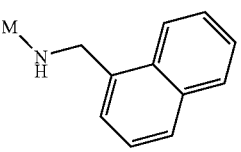 | D57 |
| 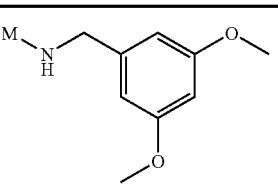 | D58 |
| 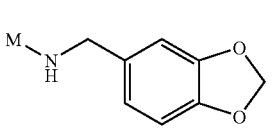 | D59 |
| 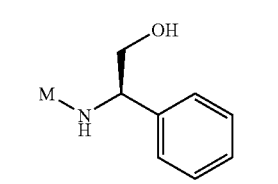 | D60 |
| 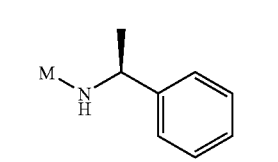 | D61 |
| 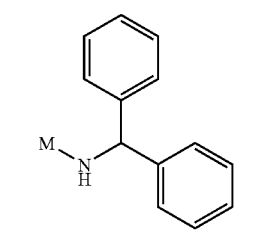 | D62 |
| 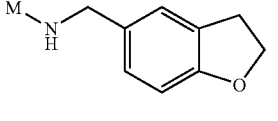 | D63 |
| 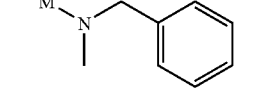 | D64 |
| 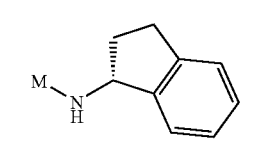 | D65 |
| 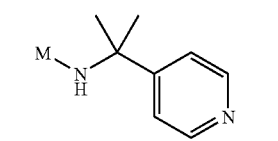 | D66 |

TABLE IV-continued
TABLE OF D GROUPS
| Fragment | Code |
|---|---|
| 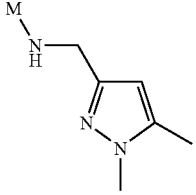 | D67 |
| 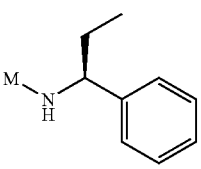 | D68 |
| 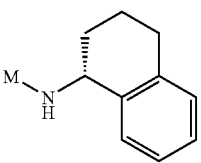 | D69 |
| 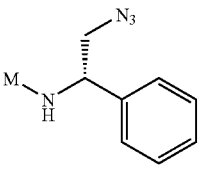 | D70 |
| 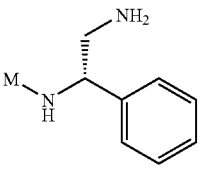 | D71 |
| 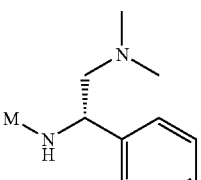 | D72 |
| 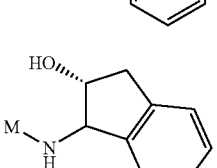 | D73 |
| 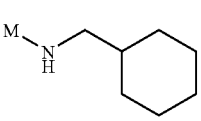 | D74 |
| 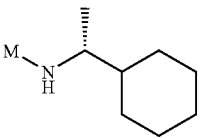 | D75 |
| 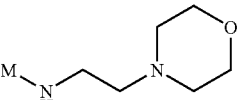 | D76 |
| 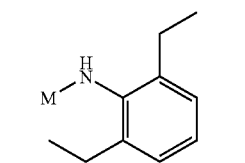 | D77 |
| 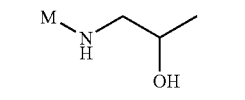 | D78 |
| 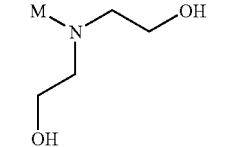 | D79 |
| 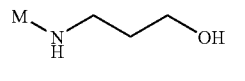 | D80 |
| 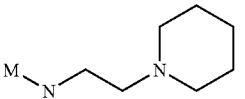 | D81 |
| 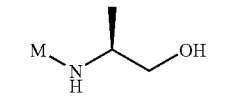 | D82 |
| 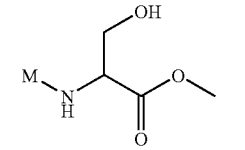 | D83 |
| 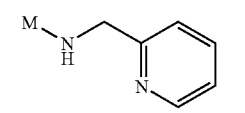 | D84 |
| 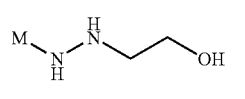 | D85 |
| 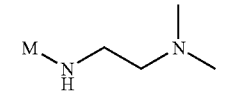 | D86 |
| 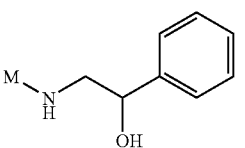 | D87 |

TABLE IV-continued
TABLE OF D GROUPS
| Fragment | Code |
|---|---|
| 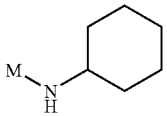 | D88 |
|  | D89 |
| 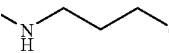 | D90 |
| 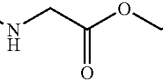 | D91 |
| 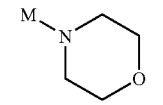 | D92 |
| 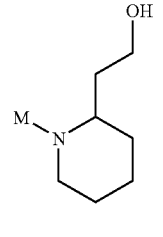 | D93 |
| 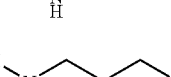 | D94 |
| 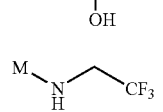 | D95 |
|  | D96 |
| 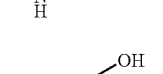 | D97 |
| 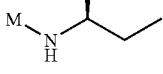 | D98 |
| 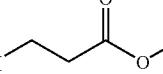 | D99 |
| 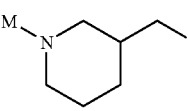 | D100 |
| 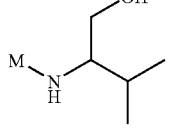 | D101 |
| 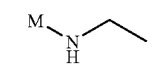 | D102 |
| 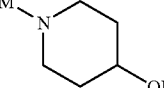 | D103 |
| 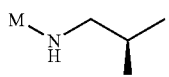 | D104 |
| 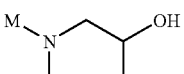 | D105 |
| 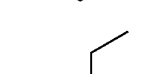 | D106 |
| 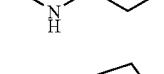 | D107 |
| 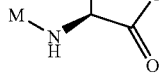 | D108 |
| 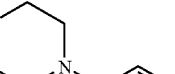 | D109 |
| 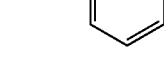 | D110 |
| 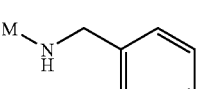 | D111 |

TABLE IV-continued

TABLE OF D GROUPS

| Fragment | Code |
|---|---|
| | D112 |
| | D113 |
| | D114 |
| | D115 |
| | D116 |
| | D117 |
| | D118 |
| | D119 |
| | D120 |
| | D121 |
| | D122 |
| | D123 |
| | D124 |
| | D125 |
| | D126 |
| | D127 |
| | D128 |
| | D129 |
| | D130 |
| | D131 |
| | D132 |

TABLE IV-continued
TABLE OF D GROUPS
| Fragment | Code |
|---|---|
| 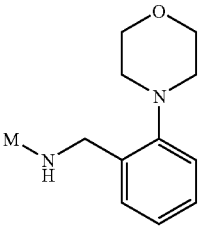 | D133 |
| 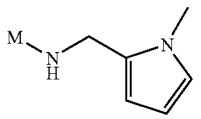 | D134 |
| 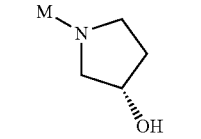 | D135 |
| 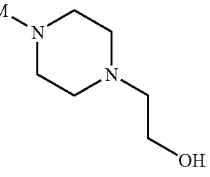 | D136 |
| 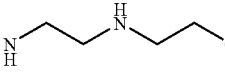 | D137 |
| 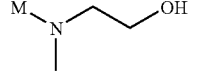 | D138 |
| 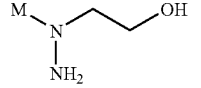 | D139 |
| 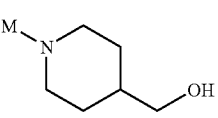 | D140 |
| 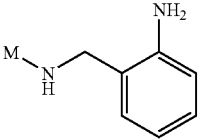 | D141 |
| 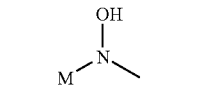 | D142 |
| 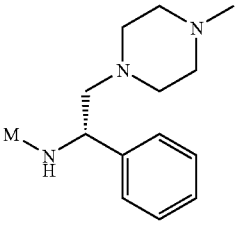 | D143 |
| 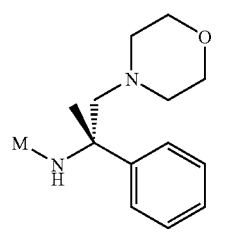 | D144 |
| 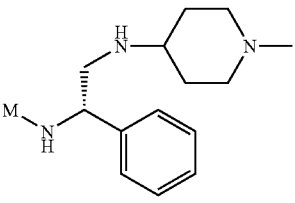 | D145 |
| 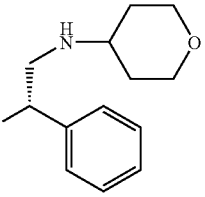 | D146 |
| 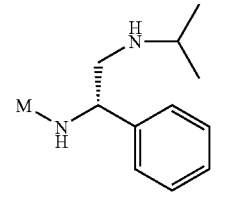 | D147 |
| 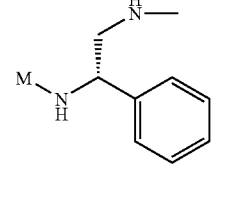 | D148 |
| 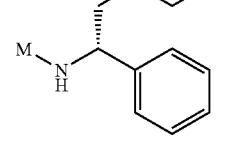 | D149 |

TABLE IV-continued

TABLE OF D GROUPS

| Fragment | Code |
|---|---|
| | D150 |
| | D151 |
| | D152 |
| | D153 |
| | D154 |
| | D155 |
| | D156 |
| | D157 |
| | D158 |
| | D159 |
| | D160 |
| | D161 |
| | D162 |
| | D163 |

TABLE IV-continued

TABLE OF D GROUPS

| Fragment | Code |
|---|---|
| (structure) | D164 |
| (structure) | D165 |

TABLE V

TABLE OF M CORE

| Structure | Code |
|---|---|
| (structure) | M00 |
| (structure) | M01 |
| (structure) | M02 |
| (structure) | M03 |
| (structure) | M04 |

TABLE V-continued

TABLE OF M CORE

| Structure | Code |
|---|---|
| (structure) | M05 |
| (structure) | M06 |
| (structure) | M07 |
| (structure) | M08 |
| (structure) | M09 |
| (structure) | M10 |
| (structure) | M11 |

The compounds of the present invention, as prepared according to the following examples, were also characterized by $^{1H}$ NMR and/or by HPLC/MS analytical data; HPLC/MS data were collected following any one of methods 1, 2 or 3.

HPLC/MS Method 1

The HPLC equipment consisted of a Waters 2790 HPLC system equipped with a 996 Waters PDA detector and Micromass mod. ZQ single quadrupole mass spectrometer, equipped with an electrospray (ESI) ion source. Instrument control, data acquisition and data processing were providen by Empower and MassLynx 4.0 software.

HPLC was carried out at 25° C. at a flow rate of 1 mL/min using a RP18 Waters X Terra (4.6×50 mm, 3.5 μm) column. Mobile phase A was ammonium acetate 5 mM buffer (pH 5.5 with acetic acid/acetonitrile 95:5), and Mobile phase B was H₂O/acetonitrile (5:95); the gradient was from 10 to 90% B in 8 minutes then hold 90% B 2 minutes. The injection volume was 10 μl.

The mass spectrometer was operated in positive and in negative ion mode, the capillary voltage was set up at 2.5 KV; the source temperature was 120° C.; cone was 10 V; full scan, mass range from 100 to 800 amu was set up.

HPLC/MS Method 2

The HPLC equipment consisted of a Waters 2790 HPLC system equipped with a 996 Waters PDA detector and Micromass mod. ZQ single quadrupole mass spectrometer, equipped with an electrospray (ESI) ion source. Instrument control, data acquisition and data processing were providen by Empower and MassLynx 4.0 software.

HPLC was carried out at 25° C. at a flow rate of 1 mL/min using a RP18 Waters X Terra (3.0×30 mm, 3.5 μm) column. Mobile phase A was ammonium acetate 5 mM buffer (pH 5.5 with acetic acid/acetonitrile 95:5), and Mobile phase B was H₂O/acetonitrile (5:95); the gradient was from 10 to 90% B in 4 min then hold 90% B 1 minute. The injection volume was 10 μl.

The mass spectrometer was operated in positive and in negative ion mode, the capillary voltage was set up at 2.5 KV; the source temperature was 120° C.; cone was 10 V; full scan, mass range from 100 to 800 amu was set up.

HPLC/MS Method 3

Mass spectra were recorded on a Finnigan LCQ ion trap mass spectrometer using the electrospray (ESI) ionization technique with positive and negative ion detection. The mass spectrometer is directly connected to a SSP4000HPLC system (Thermo Separation), equipped with an LcPal autosampler (CTC Analytics) and a UV 6000LP PDA detector (Thermo Separation). Instrument control, data acquisition and processing were performed by using Xcalibur 1.2 software. HPLC analysis were carried out at room temperature at a flow rate of 1 mL/min using an RP C18 Waters ZorbaxSB C18 column (4.6×50 mm; 1.8 μm).

Mobile phase A was ammonium acetate 5 mM buffer (pH 5.5 with acetic acid): acetonitrile 90:10, and Mobile phase B was ammonium acetate 5 mM buffer (pH 5.5 with acetic acid): acetonitrile 10:90; the gradient was from 0 to 100% B in 7 minutes then hold 100% B for 2 minutes before requilibration. Total LC time is 12 minutes. The injection volume was 10 μl. UV Detection was performed between 215 and 400 nm.

Ions were generated under the following conditions: ESI sprayer voltage 4.0 kV, heated capillary temperature 255° C., sheath gas nitrogen with a pressure of 5.0 Bar. A full scan detection mode (from 50 to 1000 amu) was used with an MS/MS analysis of the most intense ion (normalized collision energy: 35%).

UV Detection: 215-400 nm.

Example 1

2-ethoxycyclohex-2-en-1-one

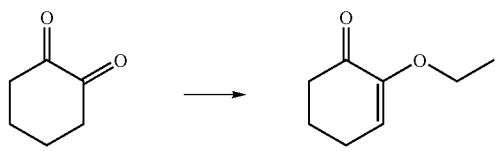

50 g (0.45 mol) of 1,2-dicyclohexandione were dissolved in a mixture of 1 L of toluene and 0.5 L of ethanol. 10 g of p-toluenesulfonic acid were added and the solution heated at reflux for 2 days. (TLC chloroform/methanol 6/1). The solvent was then evaporated, the residue redissolved with dichloromethane and washed with a saturated solution of NaHCO₃. The organic layer was dried over Na₂SO₄ and concentrated. The crude was purified by chromatography on a silica gel column by eluting with a mixture of cyclohexane/ethyl acetate 98/2 (66% yield as an oil).

$^{1}$H NMR (400 MHz, DMSO-d₆) δ ppm 1.20 (t, 3 H) 2.33-2.39 (m, 6 H) 3.67 (q, 2 H) 5.97 (t, 1 H).

Example 2

Ethyl (3-ethoxy-2-oxocyclohex-3-en-1-yl)(oxo)acetate

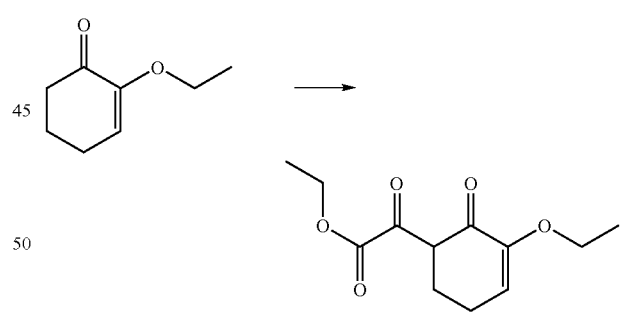

41.40 g (0.29 mol) of 2-ethoxycyclohex-2-en-1-one were dissolved in 310 mL of diethyl ether and 325 mL of 1M LiN(1MS)₂ in tetrahydrofuran were added dropwise at −50° C. After 30 minutes at the same temperature, 44.2 mL of diethyloxalate were also added under stirring. The solution was kept at room temperature overnight (TLC chloroform). 300 mL of water were then added, the pH adjusted to 4-5 by adding 1 N HCl and the resulting solution extracted with ethyl acetate. The organic layer was dried over Na₂SO₄ and evaporated to dryness. The crude was purified by chromatography on a silica gel column eluted by chloroform (76% yield as an oil).

$^1$H NMR (400 MHz, DMSO-d$_6$) δ ppm 1.12 (t, 3 H) 1.51 (t, 3 H) 2.06-2.58 (m, 4 H) 3.57 (m, 1 H) 3.86 (q, 2 H) 4.38 (q, 2 H) 6.09 (m, 1 H).

Example 3

Ethyl 1-methyl-7-oxo-4,5,6,7-tetrahydro-1H-indazole-3-carboxylate

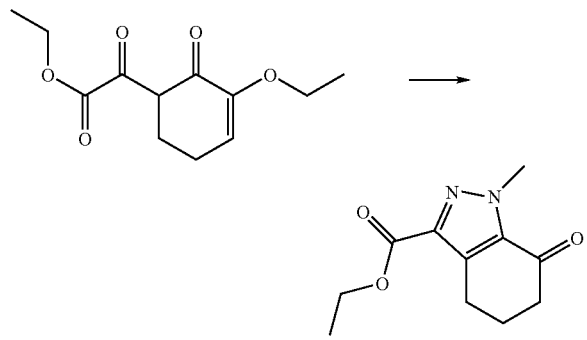

30 g (0.125 mol) of ethyl (3-ethoxy-2-oxocyclohex-3-en-1-yl)(oxo)acetate were dissolved in 150 mL of glacial acetic acid and 6.5 mL of methylhydrazine were added. The mixture was stirred at room temperature for 6 hours. The solvent was then evaporated and the crude redissolved with water, the solution made basic with 30% NH$_4$OH and extracted with chlorform. The organic layer was then dried over Na$_2$SO$_4$ and concentrated. The residue was chromatographed on a silica gel column (eluant: chloroform) and crystallized from a mixture n-hexane/diethyl ether (TLC chloroform; 63% yield as a white solid).

$^1$H NMR (400 MHz, DMSO-d$_6$) δ ppm 1.12 (t, J 6.89 Hz, 3 H) 1.51 (t, J 6.94 Hz, 3 H) 2.06-2.58 (m, 4 H) 3.57 (m, 1 H) 3.86 (q, J 6.83 Hz, 2 H) 4.38 (q, J 6.94 Hz, 2 H, 6.09 (m, 1 H).

According to the same method, but employing the suitable substituted hydrazine derivative, the following compounds were prepared:

ethyl 1-tert-butyl-7-oxo-4,5,6,7-tetrahydro-1H-indazole-3-carboxylate $^1$H NMR (400 MHz, DMSO-d$_6$) δ ppm 1.16 (t, J 6.83 Hz, 3 H) 1.58 (s, 9 H) 2.30-2.93 (3 m, 6 H) 4.18 (q, J 6.83 Hz, 2 H);

ethyl 1-(2-hydroxyethyl)-7-oxo-4,5,6,7-tetrahydro-1H-indazole-3-carboxylate $^1$H NMR (400 MHz), DMSO-d$_6$) δ ppm 1.3 (t, J 7.20 Hz, 3 H) 1.9-2.9 (3m, 6 H) 3.7 (m, 2 H) 4.3 (q, J 7.20 Hz, 2 H) 4.53 (t, J 5.85, 2 H) 4.77 (t, J 5.73, OH);

ethyl 1-(2-ethoxy-2-oxoethyl)-7-oxo-4,5,6,7-tetrahydro-1H-indazole-3-carboxylate $^1$H NMR (400 MHz), DMSO-d$_6$) δ ppm 1.18 (t, J 7.20 Hz, 3 H) 1.29 (t, J 7.20 Hz, 3 H) 2.04 (m, 2 H); 2.52 (m, 2 H) 2.93 (t, J 6.10 Hz, 2 H) 4.04 (q, J 7.07 Hz, 2 H) 4.37 (q, J 7.20 Hz, 2 H) 5.26 (s, 1 H);

ethyl 7-oxo-1-(2,2,2-trifluoroethyl)-4,5,6,7-tetrahydro-1H-indazole-3-carboxylate $^1$H NMR (400 MHz, DMSO-d$_6$) δ ppm 1.20 (t, J 7.07 Hz, 3 H) 2.05 (m, 2 H) 2.57 (m, 2 H) 2.95 (, 2 H) 4.2 (q, J 7.07 Hz, 2 H) 5.3 (2d, 2 H);

ethyl 7-oxo-2-(2,2,2-trifluoroethyl)-4,5,6,7-tetrahydro-2H-indazole-3-carboxylate $^1$H NMR (400 MHz, DMSO-d$_6$) δ ppm 1.29 (t, J 7.08 Hz, 3 H) 2.05 (m, 2 H) 2.57 (t, J 7.44 Hz, 2 H) 2.94 (t, 2 H) 4.30 (q, J 7.19 Hz, 2 H) 5.46 (2d, 2 H);

ethyl 7-oxo-4,5,6,7-tetrahydro-1H-indazole-3-carboxylate $^1$H NMR (400 MHz, DMSO-d$_6$) δ ppm 1.28 (t, J=7.07 Hz, 3 H) 2.04 (m, 2 H) 2.51 (m, 2 H) 2.87 (t, J=6.10 Hz, 2 H) 4.27 (q, J=7.11 Hz, 2 H) 14.39 (s, 1 H);

ethyl 1-[4-(aminosulfonyl)phenyl]-7-oxo-4,5,6,7-tetrahydro-1H-indazole-3-carboxylate $^1$H NMR (400 MHz, DMSO-d$_6$) δ ppm 1.34 (t, J=7.13 Hz, 3 H) 2.10-2.19 (m, 2 H) 2.57-2.63 (m, 2 H) 3.05 (t, J=6.10 Hz, 2 H) 4.37 (q, J=7.07 Hz, 2 H) 7.54 (s, 2 H) 7.77 (d, J=8.78 Hz, 2 H) 7.96 (d, J=8.90 Hz, 2 H);

ethyl 1-(4-methoxyphenyl)-7-oxo-4,5,6,7-tetrahydro-1H-indazole-3-carboxylate $^1$H NMR (400 MHz, DMSO-d$_6$) δ ppm 1.33 (t, J=7.07 Hz, 3 H) 2.05-2.17 (m, 2 H) 2.56 (dd, J=7.26, 5.55 Hz, 2 H) 3.03 (t, J=6.10 Hz, 2 H) 3.85 (s, 3 H) 4.34 (q, J=7.07 Hz, 2 H) 7.05 (d, J=9.02 Hz, 2 H) 7.44 (d, J=9.02 Hz, 2 H);

ethyl 1-(4-cyanophenyl)-7-oxo-4,5,6,7-tetrahydro-1H-indazole-3-carboxylate $^1$H NMR (400 M, DMSO-d$_6$) δ ppm 1.34 (t, J=7.07 Hz, 3 H) 2.09-2.19 (m, 2 H) 2.60 (dd, J=7.32, 5.49 Hz, 2 H) 3.04 (t, J=6.16 Hz, 2 H) 4.36 (q, J=7.11 Hz, 2 H) 7.80 (d, J=8.90 Hz, 2 H) 8.03 (d, J=8.78 Hz, 2 H);

ethyl 7-oxo-1-pyridin-2-yl-4,5,6,7-tetrahydro-1H-indazole-3-carboxylate $^1$H NMR (400 MHz, DMSO-d$_6$) δ ppm 1.34 (t, J=7.13 Hz, 3 H) 2.10-2.21 (m, 2 H) 2.58 (dd, J=7.32, 5.61 Hz, 2 H) 3.05 (t, J=6.16 Hz, 2 H) 4.36 (q, J=7.07 Hz, 2 H) 7.61 (ddd, J=7.41, 4.73, 1.04 Hz, 1 H) 7.64 (dt, J=7.93, 0.98 Hz, 1 H) 8.07 (td, J=7.74, 1.83 Hz, 1 H) 8.57 (ddd, J=4.79, 1.86, 0.79 Hz, 1 H);

ethyl 7-oxo-1-phenyl-4,5,6,7-tetrahydro-1H-indazole-3-carboxylate $^1$H NMR (400 MHz, DMSO-d$_6$) δ ppm 1.30 (t, 3 H, J 7.08) 2.08 (m, 2 H) 2.54 (m, 2 H) 4.30 (q, 2 H J 7.08) 7.49 (m, 5 H);

ethyl 1-benzyl-7-oxo-4,5,6,7-tetrahydro-1H-indazole-3-carboxylate ethyl 1-(1-methylpiperidin-4-yl)-7-oxo-4,5,6,7-tetrahydro-1H-indazole-3-carboxylate $^1$H NMR (400 MHz, DMSO-d$_6$) δ ppm 1.32 (t, J=7.07 Hz, 3 H) 1.84-2.11 (m, 6 H) 2.28 (s, 3 H) 2.48-2.53 (m, 2 H) 2.52-2.60 (m, 2 H) 2.91-3.00 (m, 2 H) 2.94 (t, J=6.16 Hz, 2 H) 4.32 (q, J=7.15 Hz, 2 H) 4.93-5.11 (m, 1 H)

(The hydrazino derivative being employed was not commercially available (CAS n° 53242-78-7) and was thus synthesized as described in the literature: WO 02/085906).

ethyl 7-oxo-1-piperidin-4-yl-4,5,6,7-tetrahydro-1H-indazole-3-carboxylate (The hydrazino derivative being employed was not commercially available and was thus synthesized as described in the literature: DE 3634942 A1).

ethyl 1-(1-benzylpiperidin-4-yl)-7-oxo-4,5,6,7-tetrahydro-1H-indazole-3-carboxylate $^1$H NMR (400 MHz, DMSO-d$_6$) δ ppm 1.32 (t, 3 H, J 7.07 Hz) 3.34 (s, 2 H) 4.31 (q, 2 H, J 7.07 Hz) 5.06 (m, 1 H) 7.35 (m, 5 H);

ethyl 1-(1-acetylpiperidin-4-yl)-7-oxo-4,5,6,7-tetrahydro-1H-indazole-3-carboxylate (The hydrazino derivative being employed was not commercially available and was thus synthesized as reported in example 69).

¹H NMR (400 MHz, DMSO-d₆) δ ppm 1.32 (bs, 3H) 2.59 (m, 1H) 2.71 (m, 1H) 2.95 (m, 1H) 3.29 (m, 1H) 3.94 (m, 1H) 4.30 (m, 2H) 4.48 (m, 1H) 5.29 (m, 1H)

ethyl 1-(2-dimethylaminoethyl)-7-oxo-4,5,6,7-tetrahydro-1H-indazole-3-carboxylate ethyl 1-(2-dimethylaminopropyl)-7-oxo-4,5,6,7-tetrahydro-1H-indazole-3-carboxylate

Example 4

Ethyl 1(2)-(3,3-dimethylbutyl)-7-oxo-4,5,6,7-tetrahydro-1H-indazole-3-carboxylate

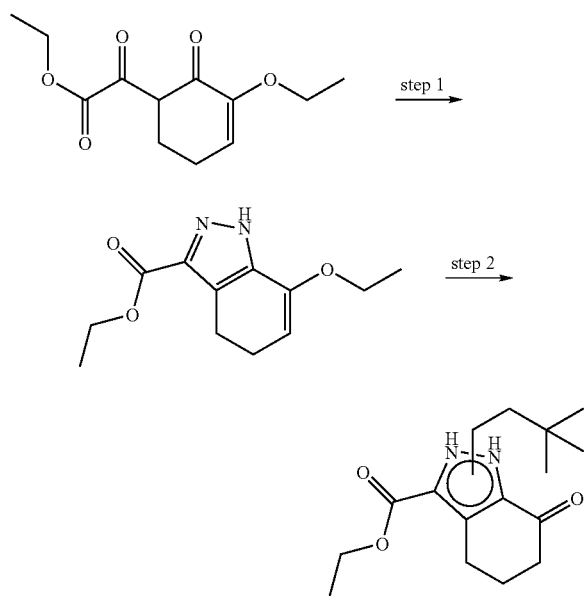

Step 1. Ethyl 7-ethoxy-4,5-dihydro-1H-indazole-3-carboxylate 1.2 g (5 mmol) of ethyl (3-ethoxy-2-oxocyclohex-3-en-1-yl)(oxo)acetate were dissolved in 20 mL of ethanol and 25 mL (5.2 mmol) of hydrazine hydrate 98% were added dropwise. The solution was stirred at room temperature for 5 hours, then heated at 60° C. for further 5 hours. The solvent was removed in vacuo and the residue taken up with diethyl ether and the resulting precipitate collected by filtration giving 0.8 g of the title compound, that was employed in the next step without any further purification.

Step 2. Ethyl 1(2)-(3,3-dimethylbutyl)-7-oxo-4,5,6,7-tetrahydro-1H-indazole-3-carboxylate 0.28 g (1.17 mmol) of ethyl 7-ethoxy-4,5-dihydro-1H-indazole-3-carboxylate were dissolved in 12 mL of dry dimethylformamide and 0.25 g (1.40 mmol) of 3,3-dimethylbutyl methanesulfonate were added. The resulting solution was treated with 0.06 g (1.40 mmol) of sodium hydride 60% in mineral oil and the reaction mixture stirred at 65° C. for 4 hours. Water was added to the reaction and the solution extracted with ethyl acetate. The solvent was evaporated in vacuo and the residue redissolved with 10 mL of methanol. Few drops of 1 N HCl were then added and after 3 hours the reaction was partitioned between water and ethyl acetate, giving a crude that, after drying over Na₂SO₄, was purified by chromatography on a silica gel column (eluant hexane/ethyl acetate 95/5) (75% yield).

Example 5

Ethyl 7-oxo-1(2)-[(5-phenyl-1,3-oxazol-2-yl)methyl]-4,5,6,7-tetrahydro-1H-indazole-3-carboxylate

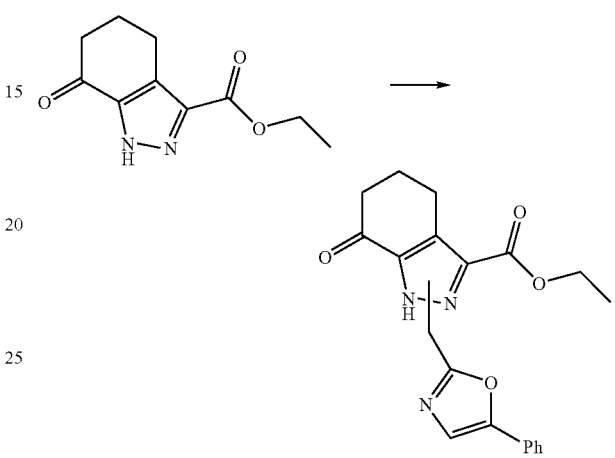

900 mg (4.3 mmol) of ethyl 7-oxo-4,5,6,7-tetrahydro-1H-indazole-3-carboxylate were dissolved in 26 mL of DMF and 712 mg (5.16 mmol) of K₂CO₃ and 995 mg (5.16 mmol) of 2-(chloromethyl)-5-phenyl-1,3-oxazole were added. The reaction mixture was stirred at room temperature for 5 hours then the solvent was removed under vacuo and the residue was dissolved in dichloromethane and washed with water. The organic layer was dried over Na₂SO₄ and evaporated to dryness. By chromatography, 405 mg (30% yield) of the two regioisomers were recovered.

ethyl 7-oxo-1-[(5-phenyl-1,3-oxazol-2-yl)methyl]-4,5,6,7-tetrahydro-1H-indazole-3-carboxylate ¹H NMR (400 MHz, DMSO-d₆) δ ppm 1.29 (t, 3 H) 2.09 (m, 2 H) 2.59 (m, 2 H) 2.97 (m, 2 H) 4.31 (q, 2 H) 6.04 (s, 2 H) 7.39 (m, 1 H) 7.49 (m, 2 H) 7.63 (s, 1 H) 7.66 (m, 2 H)

ethyl 7-oxo-2-[(5-phenyl-1,3-oxazol-2-yl)methyl]-4,5,6,7-tetrahydro-2H-indazole-3-carboxylate ¹H NMR (400 MHz, DMSO-d₆) δ ppm 1.32 (t, 3 H) 2.09 (m, 2 H) 2.60 (m, 2 H) 2.99 (m, 2 H) 4.31 (q, 2 H) 5.98 (s, 2 H) 7.39 (m, 1 H) 7.49 (m, 2 H) 7.62 (s, 1 H) 7.66 (m, 2 H).

Example 6

Ethyl 1-[(5-ethyl-1,3-oxazol-2-yl)methyl]-7-oxo-4,5,6,7-tetrahydro-1H-indazole-3-carboxylate -continued

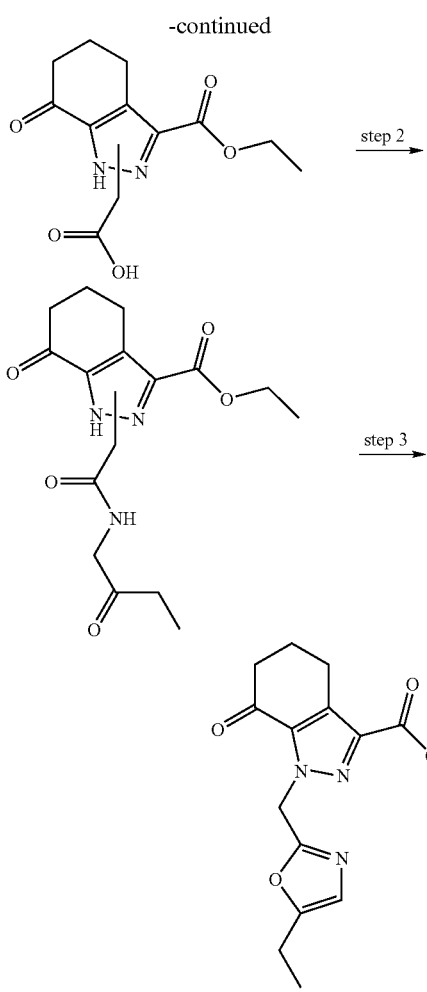

Step 1. [3-(ethoxycarbonyl)-7-oxo-4,5,6,7-tetrahydro-1H-indazol-1(2)-yl]acetic acid 1 g (4.8 mmol) of ethyl 7-oxo-4,5,6,7-tetrahydro-1H-indazole-3-carboxylate were dissolved in 30 mL of dry DMF and treated with 1.59 g (11.52 mmol) of $K_2CO_3$ and 800 mg (5.76 mmol) of bromoacetic acid at room temperature. After heating at 80° C. overnight the mixture was cooled and the solvent was removed under vacuo. The crude was dissolved in water and neutralized with HCl 37%. Three extractions with dichloromethane afforded 1.7 g of crude that was purified by flash chromatography (eluant dichloromethane) yielding 783 mg (61%) of the product as mixture of regioisomers.

Step 2. Ethyl 7-oxo-1(2)-{2-oxo-2-[(2-oxobutyl)amino]ethyl}-4,5,6,7-tetrahydro-1H-indazole-3-carboxylate 743 mg (2.79 mmol) of [3-(ethoxycarbonyl)-7-oxo-4,5,6,7-tetrahydro-1H-indazol-1(2)-yl]acetic acid as mixture of isomers were dissolved in 28 mL of DMF and 2.18 g (4.18 mmol) of benzotriazol-1-yloxytris(pyrrolidino)phosphonium hexafluorophosphate (PyBOP), 690 mg (5.58 mmol) of 1-aminobutan-2-one hydrochloride and 2.4 mL (13.95 mmol) of N-ethyl-N,N-diisopropylamine were added. After 2 hours the solvent was evaporated under vacuo, the crude was dissolved in dichloromethane and washed with saturated $NaHCO_3$, brine and water. Purification by flash chromatography (eluant hexane/ethylacetate 8/2) yielded 511 mg of ethyl 7-oxo-1-{2-oxo-2-[(2-oxobutyl)amino]ethyl}-4,5,6,7-tetrahydro-1H-indazole-3-carboxylate and 20 mg of ethyl 7-oxo-2-{2-oxo-2-[(2-oxobutyl)amino]ethyl}-4,5,6,7-tetrahydro-1H-indazole-3-carboxylate (57% overall yield).

ethyl 7-oxo-1-{2-oxo-2-[(2-oxobutyl)amino]ethyl}-4,5,6,7-tetrahydro-1H-indazole-3-carboxylate $^1$H NMR (400 MHz, DMSO-$d_6$) δ ppm 0.94 (t, 3 H) 1.32 (t, 3 H) 2.09 (m, 2 H) 2.44 (q, 2 H) 2.52 (t, 2 H) 2.96 (t, 2 H) 3.98 (d, 2 H) 4.31 (q, 2 H) 5.26 (s, 2 H) 8.44 (t, 1 H);

ethyl 7-oxo-2-{2-oxo-2[(2-oxobutyl)amino]ethyl}-4,5,6,7-tetrahydro-1H-indazole-3-carboxylate $^1$H NMR (400 MHz, DMSO-$d_6$) δ ppm 0.94 (t, 3 H) 1.31 (t, 3 H) 2.08 (m, 2 H) 2.44 (q, 2 H) 2.53 (t, 2 H) 2.94 (t, 2 H) 3.99 (d, 2 H) 4.29 (q, 2 H) 5.32 (s, 2 H). 8.48 (t, 1 H).

Step 3. Ethyl 1-[(5-ethyl-1,3-oxazol-2-yl)methyl]-7-oxo-4,5,6,7-tetrahydro-1H-indazole-3-carboxylate A solution of 506 mg (1.51 mmol) of ethyl 7-oxo-1-{2-oxo-2-[(2-oxobutyl)amino]ethyl}-4,5,6,7-tetrahydro-1H-indazole-3-carboxylate in toluene (45 mL) was treated with 0.422 mL (4.53 mmol) of phosphoric trichloride and heated at 90° C. for 15 hours. The mixture was cooled to room temperature, poured into ice and neutralized with NaOH 5N. The aqueous phase was extracted with dichloromethane and the organic layer afforded 425 mg of crude that was purified on silica gel (eluant hexane/ethylacetate 7/3). 285 mg of the title compound were thus isolated (60% yield).

$^1$H NMR (400 MHz, DMSO-$d_6$) δ ppm 1.16 (t, 3 H) 1.32 (t, 3 H) 2.08 (m, 2 H) 2.63 (m, 4 H) 2.97 (t, 2 H) 4.31 (q, 2 H) 5.84 (s, 2 H) 6.79 (s, 1 H).

Example 7

Ethyl 6-[(dimethylamino)methylene]-1-methyl-7-oxo-4,5,6,7-tetrahydro-1H-indazole-3-carboxylate

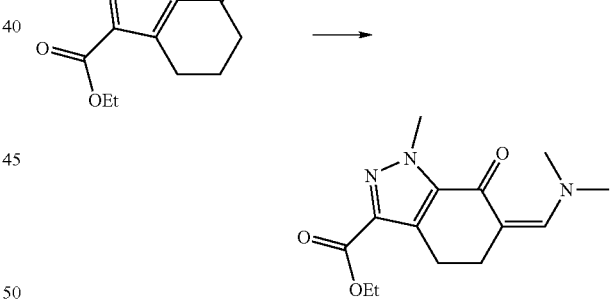

16 g (0.07 mol) of ethyl 1-methyl-7-oxo-4,5,6,7-tetrahydro-1H-indazole-3-carboxylate were dissolved in 100 mL of dimethylformamide and 32 mL of dimethylformamide ditertbutyl acetale were added. The mixture was stirred at 60° C. for 8 hours. The solvent was then evaporated in vacuo and the product crystallized from ethanol (90% yield).

$^1$H NMR (400 MHz), DMSO-$d_6$) δ ppm 2.72-2.95 (m, 4 H) 3.04-3.14 (m, 6 H) 4.10 (s, 3 H) 4.24 (q, J 7.20 Hz, 2 H) 7.46 (m, 1 H).

By working according to the same method the following compounds were prepared:

Ethyl 1-tert-butyl-6-[(dimethylamino)methylene]-7-oxo-4,5,6,7-tetrahydro-1H-indazole-3-carboxylate;

ethyl 6-[(dimethylamino)methylene]-1-(2-hydroxyethyl)-7-oxo-4,5,6,7-tetrahydro-1H-indazole-3-carboxylate $^1$H NMR (400 MHz), DMSO-d$_6$) δ ppm 2.80 (t, J 6.34 Hz, 2 H) 2.88 (t, J 6.21, 2 H) 3.70 (m, 2 H) 4.24 (q, J 7.07 Hz, 3 H) 4.58 (t, J 5.97 Hz, 2 H) 4.79 (bs, OH) 7.47 (bs, 1 H);

ethyl 6-[(dimethylamino)methylene]-1-(2-ethoxy-2-oxoethyo)-7-oxo-4,5,6,7-tetrahydro-1H-indazole-3-carboxylate $^1$H NMR (400 MHz, DMSO-d$_6$) δ ppm 1.17 (t, J 7.07 Hz, 3 H) 1.28 (t, J 7.13 Hz, 3 H) 2.86 (m, 4 H) 3.10 (s, 6 H) 4.10 (q, J 7.11 Hz, 2 H) 4.26 (q, J 7.11 Hz, 2 H) 5.33 (s, 2 H) 7.43 (s, 1 H);

ethyl 1-[4-(aminosulfonyl)phenyl]-6-[(dimethylamino)methylene]-7-oxo-4,5,6,7-tetrahydro-1H-indazole-3-carboxylate;

ethyl-6-[(dimethylamino)methylene]-1-(4-methoxyphenyl)-7-oxo-4,5,6,7-tetrahydro-1H-indazole-3-carboxylate $^1$H NMR (400 MHz, DMSO-d$_6$) δ ppm 1.32 (t, J=7.07 Hz, 3 H) 2.87-2.93 (m, 2 H) 2.95-3.00 (m, 2 H) 3.12 (s, 6 H) 3.83 (s, 3 H) 4.32 (q, J=7.07 Hz, 2 H) 7.00 (d, J=9.02 Hz, 2 H) 7.39 (d, J=9.02 Hz, 2 H) 7.42 (s, 1 H);

ethyl 1-(4-cyanophenyl)-6-[(dimethylamino)methylene]-7-oxo-4,5,6,7-tetrahydro-1H-indazole-3-carboxylate $^1$H NMR (400 MHz, DMSO-d$_6$) δ ppm 1.33 (t, J=7.13 Hz, 3 H) 2.88-2.94 (m, 2 H) 2.97-3.03 (m, 2 H) 3.14 (s, 6 H) 4.34 (q, J=7.15 Hz, 2 H) 7.48 (s, 1 H) 7.73 (d, J=8.90 Hz, 2 H) 7.96 (d, J=8.78 Hz, 2 H);

ethyl 6-[(dimethylamino)methylene]-7-oxo-1-pyridin-2-yl-4,5,6,7-tetrahydro-1H-indazole-3-carboxylate $^1$H NMR (400 MHz, DMSO-d$_6$) δ ppm 1.33 (t, J=7.07 Hz, 3 H) 2.87-2.93 (m, 2 H) 3.00 (t, J=6.71 Hz, 2 H) 3.13 (s, 6 H) 4.33 (q, J=67.07 Hz, 2 H) 7.40 (s, 1 H) 7.54 (ddd, J=7.47, 4.79, 1.04 Hz, 1 H) 7.56 (dt, J=8.02, 0.93 Hz, 1 H) 7.99-8.04 (m, 1 H) 8.52 (ddd, J=4.82, 1.89, 0.85 Hz, 1 H);

ethyl 6-(dimethylamino)methylene-1-(3,3-dimethylaminobutyl)-7-oxo-4,5,6,7-tetrahydro-1H-indazole-3-carboxylate;

ethyl 6-(dimethylamino)methylene-2-(3,3-dimethylaminobutyl)-7-oxo-4,5,6,7-tetrahydro-1H-indazole-3-carboxylate;

ethyl 6-[(dimethylamino)methylene]-7-oxo-1-(2,2,2-trifluoroethyl)-4,5,6,7-tetrahydro-1H-indazole-3-carboxylate $^1$H NMR (400 MHz, DMSO-d$_6$) δ ppm 1.30 (t, J 7.07 Hz, 3 H) 2.88 (2 m, 4 H) 3.10 (s, 6 H) 4.33 (q, J 7.07 Hz, 2 H) 5.45 (q, J 8.90 Hz, 2 H) 7.50 (bs, 1 H);

ethyl 6-[(dimethylamino)methylene]-7-oxo-2-(2,2,2-trifluoroethyl)-4,5,6,7-tetrahydro-2H-indazole-3-carboxylate $^1$H NMR (400 MHz, DMSO-d$_6$) δ ppm 1.28 (t, J 7.07 Hz, 3 H) 2.82 (2m, 4 H) 3.12 (s, 3 H) 4.29 (q, J 7.07 Hz, 2 H) 5.57 (q, J 9.02 Hz, 2 H) 7.53 (bs, 1 H), ethyl 6-[(dimethylamino)methylene]-7-oxo-1-phenyl-4,5,6,7-tetrahydro-1H-indazole-3-carboxylate ethyl 1-benzyl-6-[(dimethylamino)methylene]-7-oxo-4,5,6,7-tetrahydro-1H-indazole-3-carboxylate ethyl 6-[(dimethylamino)methylene]-1-(1-methylpiperidin-4-yl)-7-oxo-4,5,6,7-tetrahydro-1H-indazole-3-carboxylate ethyl 6-[(dimethylamino)methylene]-7-oxo-1-piperidin-4-yl-4,5,6,7-tetrahydro-1H-indazole-3-carboxylate ethyl 1-(1-benzylpiperidin-4-yl)-6-[(dimethylamino)methylene]-7-oxo-4,5,6,7-tetrahydro-1H-indazole-3-carboxylate $^1$H NMR (400 MHz, DMSO-d$_6$) δ ppm 1.31 (t, J=7.07 Hz, 3 H) 1.76-2.15 (m, 4 H) 2.79-3.01 (m, 4 H) 3.13 (s, 6 H) 3.24-3.64 (m, 6 H) 4.29 (q, J=7.07 Hz, 2 H) 5.30 (dd, J=17.01, 7.26 Hz, 1 H) 7.14-7.40 (m, 6 H);

ethyl 1-(1-acetylpiperidin-4-yl)-6-[(dimethylamino)methylene]-7-oxo-4,5,6,7-tetrahydro-1H-indazole-3-carboxylate ethyl 6-[(dimethylamino)methylene]-1-(1-formylpiperidin-4-yl)-7-oxo-4,5,6,7-tetrahydro-1H-indazole-3-carboxylate ethyl 1-(2-dimethylaminoethyl)-6-dimethylaminomethylene-7-oxo-4,5,6,7-tetrahydro-1H-indazole-3-carboxylate ethyl 1-(2-dimethylaminopropyl)-6-dimethylaminomethylene-7-oxo-4,5,6,7-tetrahydro-1H-indazole-3-carboxylate Example 8

Ethyl 1-methyl-8-(methylthio)-4,5-dihydro-1H-pyrazolo[4,3-h]quinazoline-3-carboxylate [B67-X04-M00(C01)-D01]

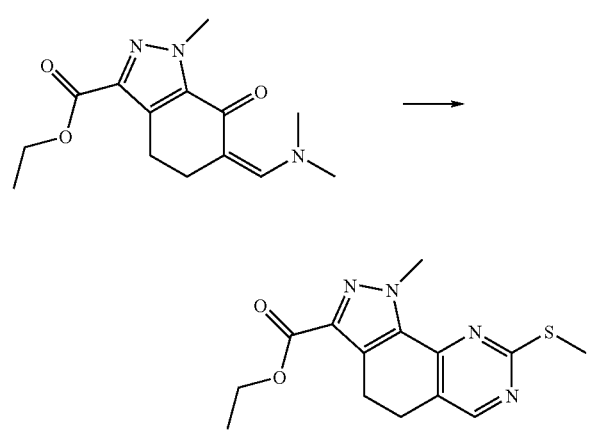

9 g (69 mmol) of ethyl-6-[(dimethylamino)methylene]-1-methyl-7-oxo-4,5,6,7-tetrahydro-1H-indazole-3-carboxylate were dissolved in 350 mL of anhydrous dimethylformamide and 13.4 g of anhydrous potassium acetate (138 mmol) and 19.18 g (69 mmol) of methylisothiourea sulfate were added. The mixture was maintained at 90° C. under stirring for 8 hours. The solvent was then evaporated, the residue redissolved with dichloromethane and washed with water. The organic layer was dried over Na$_2$SO$_4$ and evaporated. The crude was finally triturated with diethyl ether and collected by filtration to give 15.5 g (74% yield) of the title compound.

$^1$H NMR (400 MHz, DMSO-d$_6$) δ ppm 1.29 (t, J 7.07 Hz, 3 H) 2.54 (s, 3 H) 2.84-3.00 (m, 4 H) 4.26 (q, J 7.07 Hz, 2 H) 4.31 (s, 3 D) 8.53 (m, 1 H).

Following the same method, but employing the suitable substituted isothiourea derivative, the following compounds can be prepared:

ethyl 8-(benzylthio)-1-methyl-4,5-dihydro-1H-pyrazolo[4,3-h]quinazoline-3-carboxylate [B05-X04-M00(C01)-D01];

ethyl 1-methyl-8-(phenylthio)-4,5-dihydro-1H-pyrazolo[4,3-h]quinazoline-3-carboxylate [B04-X04-M00(C01)-D01].

Example 9

Ethyl 8-benzyl-1-methyl-4,5-dihydro-1H-pyrazolo[4,3-h]quinazoline-3-carboxylate [B05-X06-M00(C01)-D01]

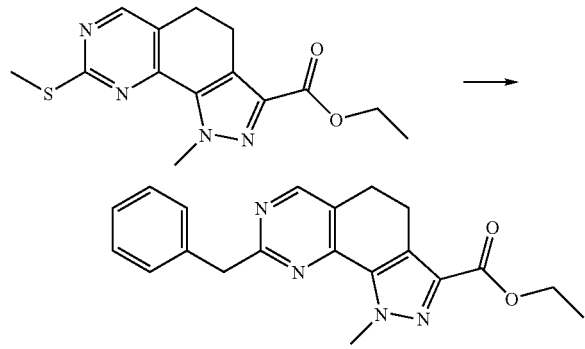

Under a nitrogen atmosphere, a 0.5 M solution of benzylzinc bromide in THF (3.11 mL, 1.556 mmol) was added to a mixture of ethyl 1-methyl-8-(methylthio)-4,5-dihydro-1H-pyrazolo[4,3-h]quinazoline-3-carboxylate (237 mg, 0.778 mmol) and Pd(PPh$_3$)$_4$ (9 mg, 0.0078 mmol, 1%). After 20 hours of heating at 60° C. under nitrogen, the mixture was cooled to room temperature, shaken with aqueous sodium bicarbonate and ethyl acetate and then filtered. The organic phase was then separated and the aqueous phase was extracted twice with ethyl acetate. The combined organic phase was dried over Na$_2$SO$_4$, evaporated and the crude was purified on silica gel (eluant dichloromethane/methanol 97/3). 20 mg of the title compound were isolated.

$^1$H NMR (400 MHz, DMSO-d$_6$) δ ppm 1.32 (t, 3 H) 2.99 (m, 4 H) 4.23 (s, 2 H) 4.27 (m, 5 H) 7.23 (m, 1 H) 7.32 (m, 2 H) 7.36 (, 2 H) 8.66 (s, 1 H)

Example 10 ethyl 1-methyl-8-(phenylthio)-4,5-dihydro-1H-pyrazolo[4,3-h]quinazoline-3-carboxylate [B04-X04-M00(C01)-D01]

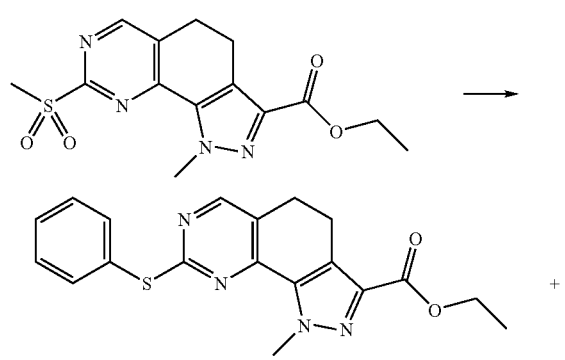

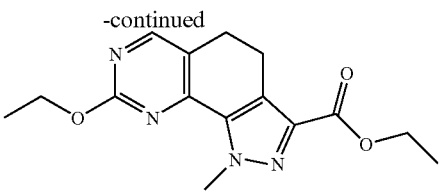

To a stirred suspension of ethyl 1-methyl-8-(methylsulfonyl)-4,5-dihydro-1H-pyrazolo[4,3-h]quinazoline-3-carboxylate (46 mg, 0.137 mmol) and phenylthiol (16 µl, 17 mg, 0.15 mmol) in ethanol (1 mL), 1N sodium hydroxide (150 µl, 0.15 mmol) was added at room temperature under an argon atmosphere. After the mixture was stirred for 3 days, 1N hydrochloric acid (150 µl, 0.15 mmol) was added and the solvent removed under vacuo. By chromatography on silica gel (eluant: dichloromethane/methanol 97/3), 13 mg of ethyl 1-methyl-8-(phenylthio)-4,5-dihydro-1H-pyrazolo[4,3-h]quinazoline-3-carboxylate and 10 mg of ethyl 8-ethoxy-1-methyl-4,5-dihydro-1H-pyrazolo[4,3-h]quinazoline-3-carboxylate were isolated.

B04-X04-M00(C01)-D01
$^1$H NMR (400 MHz, DMSO-d$_6$) δ ppm 1.26 (t, 3 H) 2.86 (t, 2 H) 2.93 (t, 2 H) 3.68 (s, 3 H) 4.25 (q, 2 H) 7.48 (m, 3 H) 7.64 (m, 2 H) 8.53 (s, 1 H);

B03-X03-M00(C01)-D01
$^1$H NMR (400 MHz, DMSO-d$_6$) δ ppm 1.33 (t, 3 H) 1.38 (t, 3 H) 2.91 (t, 2 H) 3.01 (t, 2 H) 4.33 (m, 5 H) 4.41 (q, 2 H).

Example 11

1-methyl-8-(methylthio)-4,5-dihydro-1H-pyrazolo[4,3-h]quinazoline-3-carboxamide [B67-X04-M00(C01)-D03]

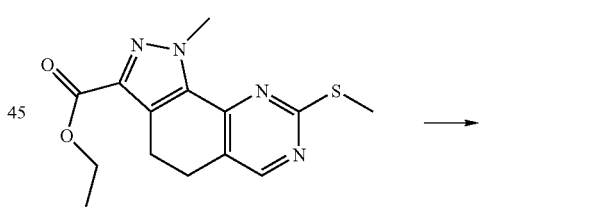

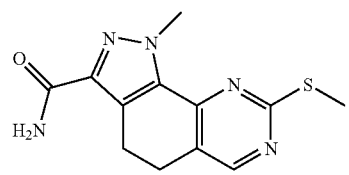

13.00 g (0.043 mol) of ethyl 1-methyl-8-(methylthio)-4,5-dihydro-1H-pyrazolo[4,3-h]quinazoline-3-carboxylate were suspended in a mixture of 200 mL of methanol, 200 mL of dimethylformamide and 200 mL of ammonium hydrate 30%. The mixture was stirred at 65° C. in a closed bottle for about 8 hours. The solvent was then evaporated to dryness, the residue redissolved with dichloromethane and washed with water. The organic layer was dried over Na$_2$SO$_4$ and evaporated. The crude was purified by chromatography on a silica gel column eluted by a mixture cyclohexane/ethyl acetate, giving 6.16 g (52% yield) of the title compound.

$^1$H NMR (400 MHz, DMSO-d$_6$) δ ppm 2.54 (s, 3 H) 2.75-3.05 (m, 4 H) 4.28 (s, 3 H) 7.47 (bs, 2 H) 8.51 (m, 1 H).

Example 12

1-methyl-8-(methylsulfonyl)-4,5-dihydro-1H-pyrazolo[4,3-h]quinazoline-3-carboxamide [B67-X05-M00(C01)-D03]

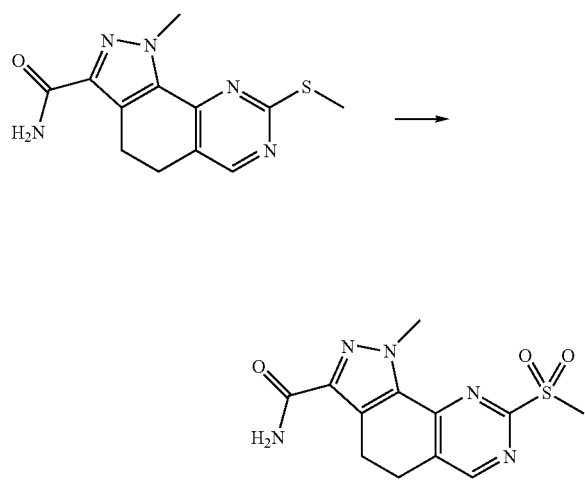

6.00 g (0.022 mol) of 1-methyl-8-(methylthio)-4,5-dihydro-1H-pyrazolo[4,3-h]quinazoline-3-carboxamide were dissolved in 1000 mL of dimethylformamide and 40.18 g of oxone were added. The mixture was stirred 16 hours at room temperature. Water and ethyl acetate were then added and the layers separated. The organic layer was finally dried over Na$_2$SO$_4$ and evaporated. The residue was triturated with diethyl ether and 5.40 g (80% yield) of the title compound were collected by filtration.

$^1$H NMR (400 MHz, DMSO-d$_6$) δ ppm 3.06 (m, 4 H) 3.43 (s, 3 H) 4.29 (s, 3 H) 7.45 (bs, 2 H) 8.91 (m, 1 H).

By working according to this methodology the following compound was prepared:

ethyl 1-methyl-8-(methylsulfonyl)-4,5-dihydro-1H-pyrazolo[4,3-h]quinazoline-3-carboxylate [B67-X05-M00(C01)-D01]

Example 13

8-(cyclohexylamino)-1-methyl-4,5-dihydro-1H-pyrazolo[4,3-h]quinazoline-3-carboxamide [B27-X00-M00(C01)-D03] and 8-(cyclohexylamino)-1-methyl-1H-pyrazolo[4,3-h]quinazoline-3-carboxamide [B27-X00-M01(C01)-D03]

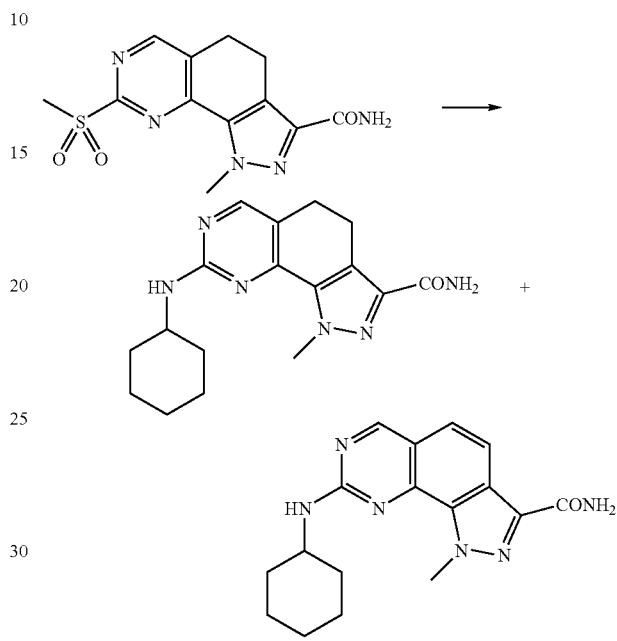

1.5 g of 1-methyl-8-(methylsulfonyl)-4,5-dihydro-1H-pyrazolo[4,3-h]quinazoline-3-carboxamide were dissolved in 100 mL of dry dimethylsulfoxide and 1.15 mL of cyclohexylamine were added. After 16 hours at 80° C. under nitrogen the solvent was evaporated at reduced pressure. The residue was then redissolved with dichloromethane and washed with water. The organic layer was dried over Na$_2$SO$_4$ and evaporated to dryness. By chromatography on a silica gel column (eluant dichloromethane/acetone 9/1) 300 mg of 8-(cyclohexylamino)-1-methyl-1H-pyrazolo[4,3-h]quinazoline-3-carboxamide and 200 mg of 8-(cyclohexylamino)-1-methyl-4,5-dihydro-1H-pyrazolo[4,3-h]quinazoline-3-carboxamide and were obtained (30% yield overall).

B27-X00-M00(C01)-D03

$^1$H NMR (400 MHz, DMSO-d$_6$) δ ppm 1.63 (m, 10 H) 2.73 (m, 2 H) 2.94 (m, 2 H) 3.69 (m, 1 H) 4.31 (m, 3 H) 6.94 (d, J 6.58 Hz, 1 H) 7.23 (s, 1 H) 7.43 (s, 1 H) 8.20 (s, 1 H);

B27-X00-M01(C01)-D03

$^1$H NMR (400 MHz DMSO-d$_6$) δ ppm 1.63 (m, 10 H) 3.88 (m, 1 H) 4.66 (s, 3 H) 7.40 (s, 1 H) 7.47 (d, J 8.66 Hz, 1 H) 7.59 (s, 1 H) 7.74 (s, 1 H) 7.87 (d, J 8.66 Hz, 1 H) 9.13 (s, 1 H)

By working according to this methodology, and by taking into account that when the amine is available as a salt, stoichiometric amounts of potassium carbonate were employed, the following compounds were prepared as coded in Table VI:

TABLE VI

| B76-X06-M00(C01)-D03 | $^1$H NMR(400MHz, DMSO-d$_6$) δ ppm 1.60(m, 6H) 2.75(m, 2H) 2.96(m, 2H) 3.76(m, 4H) 4.29(s, 3H) 7.24(s, 1H) 7.44(s, 1H) 8.29(s, 1H) |
|---|---|

TABLE VI-continued

| | |
|---|---|
| B23-X00-M00(C01)-D03 | $^1$H NMR(400MHz, DMSOd$_6$) δ ppm 2.21(s, 6H) 2.46(m,, 2H) 2.74(m, 2H) 2.95(m,, 2H) 3.41(m, 2H) 4.32(s, 3H) 6.90(t, J 5.73Hz, 1H) 7.24(s, 1H) 7.43(s, 1H) 8.21(s, 1H) |
| B24-X00-M00(C01)-D03 | $^1$H NMR(400MHz, DMSO-d$_6$) δ ppm 1.69(m, 4H); 2.49(m, 4H); 2.95 and 2.61(2m, 4H); 3.40(m, 2H); 4.32(s, 3H); 6.95(bs, NH); 7.2-7.4(2s, 2H); 8.21(s, 1H). |
| B25-X00-M00(C01)-D03 | $^1$H NMR(400MHz, DMSO-d$_6$) δ ppm 1.51(m, 6H) 2.52(m, 6H) 2.70(m, 2H,) 2.95(m, 2H), 3.42(m, 2H) 4.32(s, 3H) 7.2-7.4(2s, 2H) 8.21(s, 1H). |
| B26-X00-M00(C01)-D03 | $^1$H NMR(400MHz, DMSO-d$_6$) δ ppm 2.37-2.54(m, 6H) 2.74(m, 2H,) 2.95(m, 2H.) 3.45(m, 2H) 3.59(m, 4H) 4.32(s, 3H) 6.93(bs, NH) 8.22(s, 1H). |
| B28-X00-M00(C01)-D03 | $^1$H NMR(400MHz, DMSO-d$_6$) δ ppm 1.18(m, 11H) 2.72(m, 2H) 2.94(m, 2H,) 3.16(m, 2H) 4.31(s, 3H) 7.14-7.49(3bs, 3H) 8.19(s, 1H). |
| B29-X00-M00(C01)-D03 | $^1$H NMR(400MHz, DMSO-d$_6$) δ ppm 1.00(m, 3H) 2.60-3.20(m, 10H) 2.73(m, 2H) 2.95(m, 2H) 3.88(m, 1H) 4.31(s, 3H) 6.88(bs, 1H) 7.24(s, 1H) 7.43(s, 1H) 8.22(s, 1H). |
| B30-X00-M00(C01)-D03 | $^1$H NMR(400MHz, DMSO-d$_6$) δ ppm 2.98(m, 2H) 3.07(m, 2H) 4.34(s, 3H) 6.60(m, 2H) 7.44(m, 2H) 7.32(s, 1H) 8.71(s, 1H). |
| B31-X00-M00(C01)-D03 | $^1$H NMR(400MHz, DMSO-d$_6$) δ ppm 2.74(m, 2H) 2.94(m, 2H) 4.62(d, J 6.10Hz, 2H) 7.23(m, 2H) 7.34(m, 1H) 7.41(s, 1H) 7.73(m, 2H) 8.24(s, 1H) 8.50(m, 1H). |
| B32-X00-M00(C01)-D03 | $^1$H NMR(400MHz, DMSO-d$_6$) δ ppm 2.86(m, 4H) 4.17(s, 3H) 4.56(d, J 6.22Hz, 2H) 7.23(s, 1H) 7.34(dd, J 7.87, 4.69Hz, 1H) 7.42(s, 1H) 7.74(m, 1H) 7.74(dt, J 7.68, 1.83Hz, 1H) 8.24(s, 1H) 8.44(dd, J 4.76, 1.46Hz, 1H) 8.57(d, J 1.83Hz, 1H) |
| B33-X00-M00(C01)-D03 | $^1$H NMR(400MHz, DMSO-d$_6$) δ ppm 2.73(m, 2H) 2.93(m, 2H) 4.55(d, J 6.22Hz, 2H) 7.22(s, 1H) 7.32(m, 2H) 7.41(s, 1H) 7.78(bs, 1H) 8.24(s, 1H) 8.49(m, 2H). |
| B34-X00-M00(C01)-D03 | $^1$H NMR(400MHz, DMSO-d$_6$) δ ppm 2.73(m, 2H) 2.94(m, 2H) 4.62(d, J 6.22Hz, 2H) 7.23(s, 1H) 7.41(s, 1H) 7.54-7.76(2m, 4H) 7.82(bs. 1H) 8.24(s, 1H). |
| B35-X00-M00(C01)-D03 | $^1$H NMR(400MHz, DMSO-d$_6$) δ ppm 2.74(m, 2H) 2.94(m, 2H) 4.23(s, 3H) 4.44(d, J 6.22Hz, 2H) 5.97(s, 2H) 6.83(m, 2H) 6.91(s, 1H) 7.23(s, 1H); 7.42(s, 1H) 7.63(bs, 1H) 8.23(s, 1H). |
| B37-X00-M00(C01)-D03 | $^1$H NMR(400MHz, DMSO-d$_6$) δ ppm 1.73(m, 2H) 1.93(m, 2H) 2.22(m, 2H) 2.73(m, 2H) 295(m, 2H) 3.34(m, 4H) 4.32(s, 3H) 7.09(bs, 1H) 7.22(s, 1H) 7.43(s, 1H) 8.22(s, 1H). |
| B38-X00-M00(C01)-D03 | $^1$H NMR(400MHz, DMSO-d$_6$) δ ppm 2.74(m, 2H) 2.81(t, J 7.38Hz, 2H) 2.95(t, J 7.62Hz, 2H) 3.54(m, 2H) 4.32(s, 3H) 6.86(s, 1H) 7.16(t, J 5.55Hz, 1H) 7.24(s, 1H) 7.43(s, 1H) 7.61(s, 1H) 8.22(s, 1H) 12.00(s, 1H) |
| B39-X00-M00(C01)-D03 | $^1$H NMR(400MHz, DMSO-d$_6$) δ ppm 2.00(m, 2H) 2.73(m, 2H) 2.94(m, 2H) 3.33(m, 4H) 4.25(s, 3H) 6.99(s, 1H) 7.27(m, 3H) 7.24(s, 3H) 7.43(s, 1H) 7.80(s, 1H) 8.22(s, 1H). |
| B40-X00-M00(C01)-D03 | $^1$H NMR(400MHz, DMSO-d$_6$) δ ppm 2.22(s, 3H) 2.44(m, J 4.39Hz, 4H) 2.83(m, 4H) 3.10(m, 4H) 4.20(s, 3H) 4.47(d, J 6.22Hz, 2H) 6.78(m, 2H) 6.94(m, 1H) 7.13(m, 1H) 7.22(s, 1H) 7.41(s, 1H) 7.63(s, 1H) 8.22(s, 1H) |
| B41-X00-M00(C01)-D03 | $^1$H NMR(400MHz, DMSO-d$_6$) δ ppm 2.28(s, 3H) 2.52(m, 4H) 2.83(m, 4H) 3.11(s, 4H) 4.22(s, 3H) 4.43(d, J 6.22Hz, 2H) 6.88(d, J 8.78Hz, 2H) 7.20(d, J 8.66Hz, 2H) 7.23(s, 1H) 7.41(t, 1H) 7.57(t, J 6.10Hz, 1H) 8.21(s, 1H) |
| B42-X00-M00(C01)-D03 | $^1$H NMR(400MHz, DMSO-d$_6$) δ ppm 2.75(m, 2H) 2.95(m, 2H) 4.27(s, 3H) 4.71(d, J 6.22Hz, 2H) 6.96(m, 1H) 7.32(m, 1H) 7.24(s, 1H) 7.43(s, 1H) 7.73(s, 1H) 8.26(s, 1H). |
| B44-X00-M00(C01)-D03 | $^1$H NMR(400MHz, DMSO-d$_6$) δ ppm 2.85(m, 4H) 4.27(s, 3H) 4.52(d, J 5.97Hz, 2H) 6.24(d, J 2.68Hz, 1H) 6.38(dd, J 3.11, 1.89Hz, 1H) 7.23(m, J 0.49Hz, 1H) 7.43(s, 1H) 7.56(m, J 0.98Hz, 2H) 8.24(s, 1H) |
| B45-X00-M00(C01)-D03 | $^1$H NMR(400MHz, DMSO-d$_6$) δ ppm 1.5-1.9(3m, 4H) 2.73(m, 2H) 2.94(m, 2H) 3.33(m, 2H) |

TABLE VI-continued

| | |
|---|---|
| | 3.6-3.8(2m, 2H) 4.05(m, 1H) 4.31(s, 3H) 7.10(bs, 1H) 7.24(s, 1H) 7.44(s, 1H) 8.21(s, 1H). |
| B46-X00-M00(C01)-D03 | $^1$H NMR(400MHz, DMSO-$d_6$) δ ppm 2.73(t, J=7.62Hz, 2H) 2.93(t, J=7.68Hz, 2H) 3.73(s, 3H) 4.19(s, 3H) 4.51(d, J=6.34Hz, 2H) 6.74-6.82(m, 1H) 6.87-6.96(m, 2H) 7.16-7.30(m, 2H) 7.41(s, 1H) 7.68(t, J=6.65Hz, 1H) 8.23(s, 1H) |
| B47-X00-M00(C01)-D03 | $^1$H NMR(400MHz, DMSO-$d_6$) δ ppm 1.68(none, 2H) 2.81(m, 4H) 3.10(none, 1H) 4.34(s, 3H) 7.00(s, 1H) 7.23(s, 1H) 7.43(s, 1H) 8.18(s, 1H) |
| B48-X00-M01(C01)-D03 | $^1$H NMR(400MHz, DMSO-$d_6$) δ ppm 1.72(s, 6H) 2.14(s, 3H) 2.22(m, J 2.07Hz, 6H) 4.70(s, 3H) 7.19(s, 1H) 7.41(s, 1H) 7.48(d, J 8.66Hz, 1H) 7.76(s, 1H) 7.91(d, J 8.66Hz, 1H) 9.13(s, 1H) |
| B49-X00-M00(C01)-D03 | $^1$H NMR(400MHz, DMSO-$d_6$) δ ppm 0.99(s, 3H) 1.04(d, J 7.07Hz, 3H) 1.19(s, 3H) 1.4-2.4(5m, 8H) 2.70-3.00(2t, 4H) 3.34(bs, 2H) 4.35(s, 3H) 7.23-7.42(3bs, 3H) 8.20(s, 1H) |
| B50-X00-M00(C01)-D03 | $^1$H NMR(400MHz, DMSO-$d_6$) δ ppm 1.54(m, 2H) 1.91(d, J 11.71Hz, 2H) 2.06(m, 2H) 2.73(m, J 7.93, 7.44Hz, 2H) 2.83(d, J 11.34Hz, 2H) 2.94(t, J 7.62Hz, 2H) 3.48(s, 2H) 3.70(m, 1H) 4.30(s, 3H) 7.01(d, J 4.51Hz, 1H) 7.23(s, 1H) 7.30(m, 5H) 7.43(s, 1H) 8.20(s, 1H) |
| B51-X00-M00(C01)-D03 | $^1$H NMR(400MHz, DMSO-$d_6$) δ ppm 2.73(t, J=7.62Hz, 2H) 2.93(t, J=7.68Hz, 2H) 4.10(s, 3H) 4.60(d, J=6.10Hz, 2H) 7.22(s, 1H) 7.27(s, 2H) 7.41(s, 1H) 7.51(d, J=8.54Hz, 2H) 7.77(d, J=8.41Hz, 2H) 7.78-7.83(m, 1H) 8.23(s, 1H) |
| B52-X00-M00(C01)-D03 | $^1$H NMR(400MHz, DMSO-$d_6$) δ ppm 2.73(m, 2H) 2.93(m, 2H) 3.18(m, 3H) 4.63(d, J 6.22Hz, 2H) 7.23(s, 1H) 7.41(s, 1H) 7.59(m, 2H) 7.86(m, 3H) 8.24(s, 1H). |
| B53-X00-M00(C01)-D03 | $^1$H NMR(400MHz, DMSO-$d_6$) δ ppm 3.11(m, 4H) 4.37(s, 3H) 4.43(s, 3H) 7.37(m, 4H) 7.57(s, 1H) 7.74(m, 2H) 8.20(m, 2H) 8.92(s, 1H). |
| B54-X00-M00(C01)-D03 | $^1$H NMR(400MHz, DMSO-$d_6$) δ ppm 2.73 and 2.93(2t, 4H, J 8.04Hz) 4.18(s, 3H) 4.49(d, 2H, 6.34Hz) 7.13(m, 1H) 7.36(m, 1H) 7.42 and 7.23(2s, 2H) 7.58(m, 1H) 7.73(bs, 2H) 8.23(s, 1H). |
| B55-X00-M00(C01)-D03 | $^1$H NMR(400MHz, DMSO-$d_6$) δ ppm 0.24(m, 2H) 0.44(m, 2H) 1.13(m, 1H) 2.74(m, 2H) 2.95(t, J 7.68Hz, 2H) 3.20(m, 2H) 4.32(s, 3H) 7.17(t, J 5.79Hz, 1H) 7.23(s, 1H) 7.43(s, 1H) 8.21(s, 1H) |
| B56-X00-M00(C01)-D03 | $^1$H NMR(400MHz, DMSO-$d_6$) δ ppm 2.75(t, J=7.68Hz, 2H) 2.95(t, J=7.80Hz, 2H) 3.51-3.75(m, 2H) 4.04(dd, J=11.52, 6.77Hz, 1H) 4.27(s, 3H) 4.34(dd, J=11.58, 2.19Hz, 1H) 4.38-4.48(m, 1H) 6.74-6.94(m, 4H) 7.24(s, 1H) 7.36(t, J=5.97Hz, 1H) 7.44(s, 1H) 8.25(s, 1H) |
| B57-X00-M00(C01)-D03 | $^1$H NMR(400MHz, DMSO-$d_6$) δ ppm 2.74(m, 2H) 2.94(m, 2H) 4.14(bs, 3H) 4.62(d,, J 6.22Hz 2H) 7.23(s, 1H) 7.42(s, 1H) 7.51(m, 2H) 7.60(m, 1H) 7.83(bs, 1H) 9.26(s, 1H). |
| B58-X00-M00(C01)-D03 | $^1$H NMR(400MHz, DMSO-$d_6$) δ ppm 2.74(m, 2H) 2.95(m, 2H) 3.05(m, 2H) 3.69(m, 2H) 4.33(s, 3H) 7.24(3m, 3H) 7.32(m, 1H) 7.43/m, 1H) 8.22(s, 1H) 8.51(m, 1H). |
| B59-X00-M00(C01)-D03 | $^1$H NMR(400MHz, DMSO-$d_6$) δ ppm 2.73 and 2.93(2t, 4H, J 7.56) 4.18(s, 3H) 6.27(2s, 2H) 7.22(m, 1H) 7.31(2s, 2H) 7.37-7.43(2m, 2H) 7.55(s, 1H) 7.74(bs, 1H) 8.24(s, 1H). |
| B30-X00-M01(C01)-D03 | $^1$H NMR(400MHz, DMSO-$d_6$) δ ppm 4.72(s, 3H) 6.67(m, 1H) 7.56(m, 1H) 7.44(s, 1H) 7.63(s, 1H) 8.33(m, 1H) 8.35(m, 1H) 9.73). |
| B45-X00-M01(C01)-D03 | $^1$H NMR(400MHz, DMSO-$d_6$) δ ppm 1.50-2.00(2m, 4H) 3.34(m, 2H) 3.67-3.69(2m, 2H) 4.18(m, 1H) 4.67(s, 3H) 7.42(m, 1H) 7.74(m, 2H) 7.88(m, 1H) 7.88(m, 1H) 9.15(s, 1H). |
| B28-X00-M01(C01)-D03 | $^1$H NMR(400MHz, DMSO-$d_6$) δ ppm 0.90-2.00(6m, 11H) 3.34(m, 2H) 4.67(s, 3H) 7.41(bs, 1H) 7.48(m, 2H) 7.86(m, 1H) 9.12(s, 1H). |
| B29-X00-M01(C01)-D03 | $^1$H NMR(400MHz, DMSO-$d_6$) δ ppm 4.04(m, 1H) 4.66(s, 3H) 7.42(bs, 1H) 7.50(m, 1H) 7.70(s, 1H) 7.88(m, 1H) 9.15(s, 1H). |
| B50-X00-M01(C01)-D03 | $^1$H NMR(400MHz, DMSO-$d_6$) δ ppm 4.65(s, 3H) 7.00-8.00(m, 9H) 9.14(s, 1H). |
| B55-X00-M01(C01)-D03 | $^1$H NMR(400MHz, DMSO-$d_6$) δ ppm 0.31(m, 2H) 0.49(m, 2H) 1.25(m, 1H) 3.33(m, 2H) 4.68(s, 3H) |

TABLE VI-continued

| | |
|---|---|
| | 7.41(s, 1H) 7.49(m, 2H) 7.73(s, 1H) 7.75(s, 1H) 9.14(s, 1H) |
| B01-X00-M00(C01)-D03 | $^1$H NMR(400MHz, DMSO-$d_6$) δ ppm 2.84(m, 4H) 3.40(m, 4H) 4.31(s, 3H) 4.66(s, 1H) 6.96(t, J 5.67Hz, 1H) 7.23(s, 1H) 7.43(s, 1H) 8.21(s, 1H) |
| B02-X00-M00(C01)-D03 | $^1$H NMR(400MHz, DMSO-$d_6$) δ ppm 1.72(m, 2H) 2.73(m, 2H) 2.95(m, 2H) 3.50(m, 2H) 4.32(s, 3H) 4.45(m, 1H) 7.05(bs, 1H) 7.23(s, 1H) 7.42(s, 1H) 8.20(s, 1H). |
| B05-X00-M00(C01)-D03 | $^1$H NMR(400MHz, DMSO-$d_6$) δ ppm 2.73(m, 2H) 2.93(m, 2H) 4.17(bs, 3H) 4.55(d, J 6.22Hz, 2H) 7.15-7.40(m, 7H) 7.70(bs, 1H) 8.23(s, 1H). |
| B69-X00-M00(C01)-D03 | $^1$H NMR(400MHz, DMSO-$d_6$) δ ppm 2.15(s, 3H) 2.74(t, J=7.68Hz, 2H) 2.95(t, J=7.68Hz, 2H) 3.44(s, 3H) 4.32(s, 3H) 4.46(d, J=5.73Hz, 2H) 5.66(dd, J=3.41, 0.73Hz, 1H) 5.84(d, J=3.29Hz, 1H) 7.24(s, 1H) 7.28(t, J=4.94Hz, 1H) 7.43(s, 1H) 8.24(s, 1H) |
| B70-X00-M00(C01)-D03 | $^1$H NMR(400MHz, DMSO-$d_6$) δ ppm 2.75 and 2.95(2t, 4H, J 7.32Hz) 4.24(s, 3H) 4.57(d, 2H, J 6.22Hz) 6.13(s, 1H) 7.23 and 7.43(2s, 2H) 7.64(bs, 1H) 8.25(s, 1H) |
| B71-X00-M00(C01)-D03 | |
| B72-X00-M00(C01)-D03 | $^1$H NMR(400MHz, DMSO-$d_6$) δ ppm 2.74(t, J=7.62Hz, 2H) 2.94(t, J=7.62Hz, 2H) 4.20(s, 3H) 4.58(d, J=6.22Hz, 2H) 6.53(dd, J=2.50, 1.77Hz, 1H) 7.22(s, 1H) 7.41(s, 1H) 7.46(d, J=8.66Hz, 2H) 7.72(dd, J=1.71, 0.49Hz, 1H) 7.74-7.77(m, 1H) 7.77(d, J=8.66Hz, 2H) 8.24(s, 1H) 8.43(dd, J=2.50, 0.55Hz, 1H) |
| B74-X00-M00(C01)-D03 | $^1$H NMR(400MHz, DMSO-$d_6$) δ ppm 2.73(m, 2H) 2.96(m, 2H) 3.16(s, 6H) 4.43(s, 3H) 7.23(bs, 1H) 7.43(bs, 1H) 8.28(s, 1H). |

Example 14

Ethyl 6-[(dimethylamino)methylene]-1,4,4-trimethyl-7-oxo-4,5,6,7-tetrahydro-1H-indazole-3-carboxylate

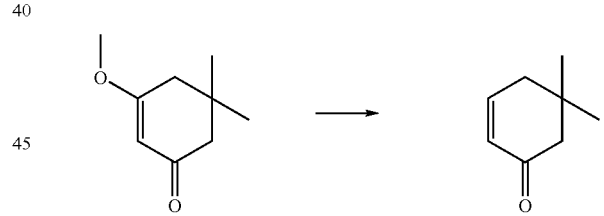

Step 1. 3-methoxy-5,5-dimethyl-cyclohex-2-enone

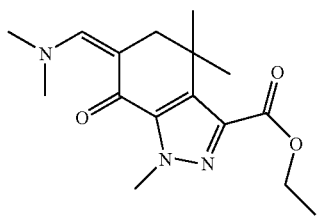

A solution of 5,5-dimethyl-cyclohexane-1,3-dione (80.0 g, 0.57 mol) in anhydrous methanol (600 mL) was treated with a 1 M solution of titanium chloride (TiCl$_4$) in dichloromethane (17.2 mL). After stirring 1 hour at room temperature, the mixture was slowly poured into cold 5% NaHCO$_3$ solution and extracted with diethyl ether (450 mL×6). The organic layers were collected, washed with brine, dried on Na$_2$SO$_4$ and evaporated to dryness affording the title compound (81.5 g, 92% yield) as a pale yellow oil.

$^1$H NMR (300 MHz, CHCl$_3$-d) δ ppm 1.05 (s, 6 H) 2.19 (s, 2 H) 2.26 (s, 2 H) 3.68 (s, 3 H) 5.35 (s, 1 H).

Step 2. 5,5-dimethyl-cyclohex-2-enone

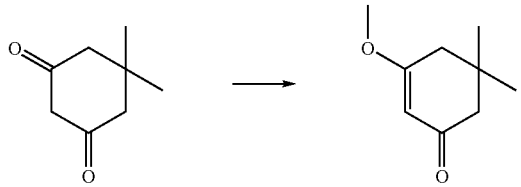

A solution of 3-methoxy-5,5-dimethyl-cyclohex-2-enone (80 g, 0.52 mol) in anhydrous tetrahydrofuran (270 mL) was treated dropwise with a 1 M solution of LiAlH$_4$ in tetrahydrofuran (182 mL), under argon atmosphere and keeping the temperature of the reaction between 0° C. and 5° C. The temperature was allowed to rise to 25° C. and the mixture was stirred for 4 hours. The resulting slurry was cooled with an ice bath, quenched with ethyl acetate (30 mL) and poured with caution into a cooled 2 M H$_2$SO$_4$ solution. The aqueous solution was then extracted with diethyl ether (300 mL×3), dried on Na$_2$SO$_4$ and evaporated under reduced pressure to remove most of the solvent. The crude material contained the title compound as a low boiling point oil that was used in the next step without further purification.

$^1$H NMR (300 MHz, CHCL$_3$-d) δ ppm 1.04 (s, 6 H) 2.23 (dd, J 4.10, 2.05 Hz, 2 H) 2.27 (s, 2 H) 6.02 (dt, J 9.96, 2.05 Hz, 1 H) 6.85 (dt, J 9.96, 4.10 Hz, 1 H).

Step 3. 4,4-dimethyl-7-oxa-bicyclo[4.1.0]heptan-2-one

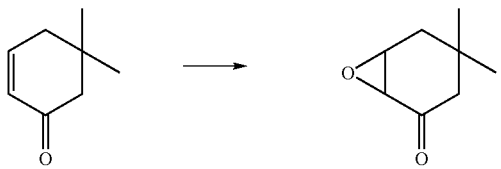

5,5-dimethyl-cyclohex-2-enone from the previous step (0.52 mol theoretically) was dissolved in methanol (500 mL), cooled to 0° C. and treated with 30% hydrogen peroxide (265 mL, 2.6 mol). The resulting solution was treated dropwise with a 2% NaOH solution (142 mL, 0.067 mol) keeping the reaction temperature around 0° C. The mixture was allowed to stay at 4° C. for twenty hours and was then diluted with water (900 mL) and extracted with ethyl ether (450 mL×4).

The extracts were collected, washed with 5% $Na_2S_2O_5$ solution, with brine, dried on $Na_2SO_4$ and concentrated under reduced pressure. The residue was purified by distillation under vacuum to obtain the title compound (56.8 g, 78.3% yield) as a colourless oil.

$^1$H NMR (300 MHz, CHCl$_3$-d) δ ppm 0.91 (s, 3 H) 1.01 (s, 3 H) 1.82 (m, 2 H) 2.03 (d, J 15.53 Hz, 1 H) 2.64 (d, J 13.77 Hz, 1 H) 3.20 (dt, J 3.74, 0.92 Hz, 1 H) 3.49 (t, J 4.10 Hz, 1 H).

Step 4. 2-methoxy-5,5-dimethyl-cyclohex-2-enone

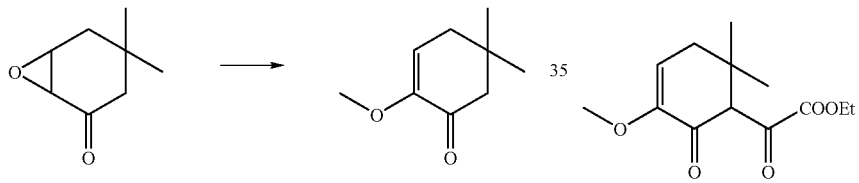

A solution of 4,4-dimethyl-7-oxa-bicyclo[4.1.0]heptan-2-one (44.0 g, 0.31 mol) in methanol (150 mL) was added to a solution of 85% potassium hydroxide (20.7 g, 0.31 mol) in methanol (450 mL) at room temperature. The mixture was kept at this temperature for 20 hours and was then heated to reflux for 30 minutes. After cooling, the solution was diluted with water (1.2 L) and extracted with ethyl ether (350 mL×5). The organic extracts were collected, washed with brine, dried on $Na_2SO_4$ and evaporated under vacuum to remove most of the solvent. The crude material was purified by distillation to obtain pure the title compound (32.8 g, 68% yield) as an oil.

$^1$H NMR (300 MHz, CHCl$_3$-d) δ ppm 1.04 (s, 6 H) 2.30 (d, J 4.69 Hz, 2 H) 2.35 (s, 2 H) 3.59 (t, 3 H) 5.67 (t, J 4.54 Hz, 1 H).

Step 5. Ethyl (3-methoxy-6,6-dimethyl-2-oxocyclohex-3-en-1-yl)(oxo)acetate

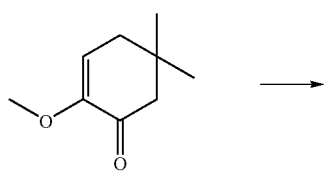

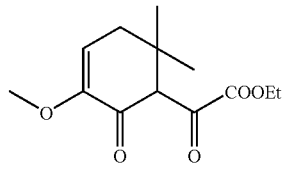

60% sodium hydride in mineral oil (2.41 g, 60.3 mmol) was suspended in anhydrous tetrahydrofuran (60 mL) under argon atmosphere and treated with a solution of 2-methoxy-5,5-dimethyl-cyclohex-2-enone (6.20 g, 40.2 mmol) in anhydrous tetrahydrofuran (50 mL). After 15 minutes, a solution of diethyl oxalate (8.17 mL, 60.3 mmol) in anhydrous tetrahydrofuran (50 mL) was added and the mixture was refluxed for 1 hour. The slurry was diluted with water (800 mL), acidified with 1 N HCl (50 mL) and extracted with ethyl acetate (500 mL×2). The organic layers were collected, washed with brine, dried on $Na_2SO_4$ and evaporated to dryness to obtain the crude title compound (10.60 g) as an orange oil, which was used without further purification.

$^1$H NMR (300 MHz, CHCl$_3$-d) δ ppm 1.41 (t, 3 H) 2.77 (s, 2 H) 3.13 (s, 6 H) 4.23 (s, 3 H) 4.40 (q, J 7.13 Hz, 2 H) 7.58 (s, 1 H).

Step 6. Ethyl 1,4,4-trimethyl-7-oxo-4,5,6,7-tetrahydro-1H-indazole-3-carboxylate

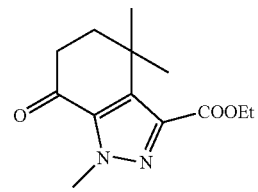

A solution of ethyl (3-methoxy-6,6-dimethyl-2-oxocyclohex-3-en-1-yl)(oxo)acetate from the previous step (40.2 mmol theoretically) in acetic acid (65 mL) was treated dropwise with a solution of methyl hydrazine (2.14 mL, 40.2 mmol) in acetic acid (20 mL) and allowed to stand at room temperature overnight. The mixture was then diluted with water (800 mL) and extracted with ethyl acetate (500 mL×2). The organic extracts were washed with brine, dried on $Na_2SO_4$ and evaporated to dryness. The crude material was chromatographed on silica gel eluted with dichloromethane/ethyl acetate 100:5 to obtain the pure title compound (4.8 g, 47.7% yield).

$^1$H NMR (300 MHz, CHCl$_3$-d) δ ppm 1.42 (t, J 7.18 Hz, 3 H) 1.49 (s, 3 H) 1.98 (t, J 6.45 Hz, 2 H) 2.61 (t, J 6.45 Hz, 2 H) 4.19 (s, 3) 4.43 (q, J 7.03 Hz, 2 H)

Step 7. Ethyl 6-[(dimethylamino)methylene]-1,4,4-trimethyl-7-oxo-4,5,6,7-tetrahydro-1H-indazole-3-carboxylate

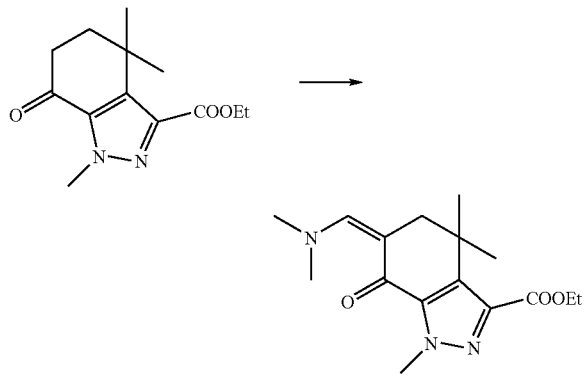

A solution of ethyl 1,4,4-trimethyl-7-oxo-4,5,6,7-tetrahydro-1H-indazole-3-carboxylate (4.8 g, 19.18 mmol) in anhydrous dimethylformamide (30 mL) was treated with dimethylformamide di-tert-butylacetal (9.19 mL, 38.35 mmol) at 65° C. for 2 hours. The mixture was evaporated to dryness and the crude material was crystallized from hexane to give the title compound (5.1 g, 87% yield).

$^1$H NMR (300 MHz, CHCl$_3$-d) δ ppm 1.21 (m, 9H) 2.76 (s, 2 H) 3.15 (s, 6 H) 4.22 (s, 3 H) 4.41 (q, 2 H).

Example 15

Ethyl 6-(hydroxymethylene)-1,5,5-trimethyl-7-oxo-4,5,6,7-tetrahydro-1H-indazole-3-carboxylate

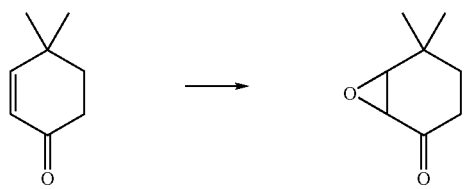

Step 1. 5,5-dimethyl-7-oxabicyclo[4.1.0]heptan-2-one

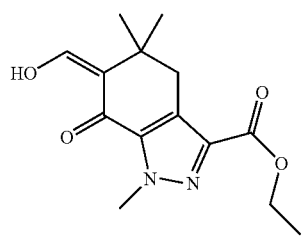

A solution of 4,4-dimethyl-cyclohex-2-enone (32.0 g, 0.26 mol) and 30% hydrogen peroxide (132 mL, 1.29 mol) in methanol (250 mL) was treated dropwise with a 2% sodium hydroxide solution (70 mL, 0.035 mol) keeping the reaction temperature around 0° C. The mixture was allowed to stay at 4° C. for 20 hours and was then diluted with water (400 mL) and extracted with diethyl ether (250 mL×4).

The extracts were collected, washed with 5% Na$_2$S$_2$O$_5$ solution, with brine, dried on Na$_2$SO$_4$ and concentrated under reduced pressure. The residue was purified by distillation under vacuum to obtain the title compound (27.6 g, 76.4% yield) as an oil.

$^1$H NMR (300 MHz, CHCl$_3$-d) δ ppm 1.05 (s, 3 H) 1.21 (s, 3 H) 1.20-2.50 (m, 5 H) 3.20 (m, 1 H).

Step 2. 2-methoxy-4,4-dimethylcyclohex-2-en-1-one

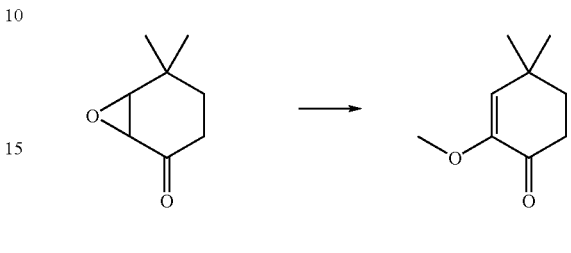

A solution of 5,5-dimethyl-7-oxabicyclo[4.1.0]heptan-2-one (19.4 g, 138.4 mmol) in methanol (95 mL) was added to a solution of 85% potassium hydroxide (9.1 g, 138.4 mmol) in methanol (285 mL) at room temperature. The mixture was kept at this temperature for 20 hours and was then heated to reflux for 30 minutes. After cooling, the solution was diluted with water (750 mL) and extracted with diethyl ether (350 mL×4). The organic extracts were collected, washed with brine, dried on Na$_2$SO$_4$ and evaporated to dryness. The crude material was taken up with hexane (380 mL), maintained under vigorous stirring for 30 minutes and filtered to remove the solid material. The filtrate was evaporated under vacuum to obtain the pure title compound (9.8 g, 45.9% yield) as a pale yellow oil.

$^1$H NMR (CDCl$_3$ 400 MHz) δ ppm 1.23 (s, 6 H) 1.87 (t, 2 H) 2.61 (t, 2 H) 3.60 (s, 3 H) 5.57 (s, 1 H)

Step 3. Ethyl (3-methoxy-5,5-dimethyl-2-oxocyclohex-3-en-1-yl)(oxo)acetate

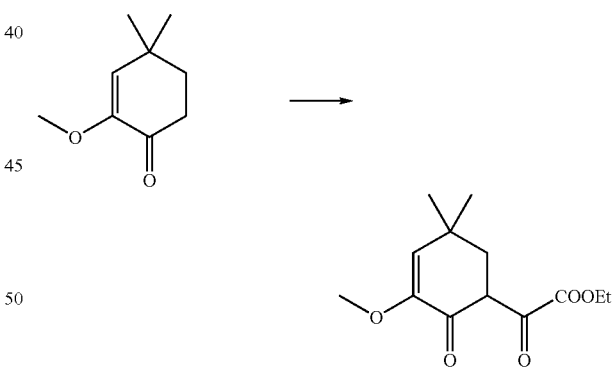

A solution of 2-methoxy-4,4-dimethyl-cyclohex-2-enone (12.5 g, 81.1 mmol) and diethyl oxalate (12.1 mL, 89.2 mmol) in ethyl ether was treated with a 1 M solution of lithium bis(trimethylsilyl)amide in tetrahydrofuran under argon atmosphere. The reaction was stirred at room temperature for 2 hours, poured into a 10% NaH$_2$PO$_4$ solution (500 mL) and extracted with diethyl ether (300 mL×2). The organic extracts were washed with brine, dried on Na$_2$SO$_4$ and evaporated to dryness. The crude material was taken up with hexane, stirred and filtered to give the title compound (16.8 g, 81.5% yield) as a yellow crystalline solid.

$^1$H NMR (300 MHz, CHCl$_3$-d) δ ppm 1.15 (s, 6 H) 1.38 (t, 3 H) 2.77 (s, 2 H) 3.63 (s, 3 H) 4.35 (q, 2 H) 5.62 (s, 1 H).

Step 4. Ethyl 1,5,5-trimethyl-7-oxo-4,5,6,7-tetrahydro-1H-indazole-3-carboxylate

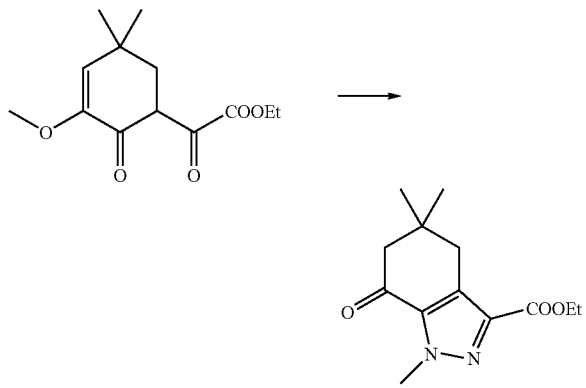

A solution of ethyl (3-methoxy-5,5-dimethyl-2-oxocyclohex-3-en-1-yl)(oxo)acetate (15.50 g, 0.061 mol) in acetic acid (100 mL) was treated dropwise with a solution of methyl hydrazine (3.49 mL, 0.066 mol) dissolved in acetic acid (50 mL). After 24 hours at room temperature, the reaction mixture was diluted with water (2 L) under vigorous stirring. The resulting precipitate was filtered and washed with water to obtain the title compound (10.30 g, 67.6% yield) as a yellow solid.

$^1$H NMR (300 MHz, CHCl$_3$-d) δ ppm 1.20 (s, 6 H) 1.42 (t, 3 H) 2.43 (s, 2 H) 2.93 (s, 2 H) 4.21 (s, 3 H) 4.41 (q, 2 H).

Step 5. Ethyl 6-(hydroxymethylene)-1,5,5-trimethyl-7-oxo-4,5,6,7-tetrahydro-1H-indazole-3-carboxylate

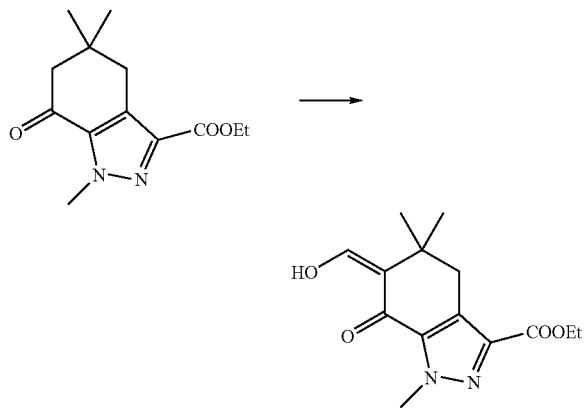

A solution of ethyl 1,5,5-trimethyl-7-oxo-4,5,6,7-tetrahydro-1H-indazole-3-carboxylate (1.00 g, 4 mmol) in anhydrous ethyl formate (10 mL) was treated with sodium ethoxide (0.54 g, 8 mmol) and refluxed for 3 hours. The mixture was cooled to room temperature and poured into cold water (40 mL). The aqueous layer was washed with diethyl ether (40 mL) to remove unreacted staring material, acidified with a 20% NaH$_2$PO$_4$ solution and extracted with ethyl acetate (50 mL×2). The organic extracts were collected, dried on Na$_2$SO$_4$ and evaporated to dryness to obtain the title compound (0.88 g, 78.8% yield) as a brown solid.

$^1$H NMR (400 MHz, DMSO-d$_6$) δ ppm 1.21 (s, 6 H) 1.32 (t, 3 H) 2.87 (s, 2 H) 4.19 (s, 3 H) 4.30 (q, 2 H) 7.74 (s, 1 H) 14.00 (br, 1 H)

Example 16

Ethyl 8-amino-1-methyl-1H-pyrazolo[4,3-h]quinazoline-3-carboxylate [B00-X00-M00(C01)-D01]

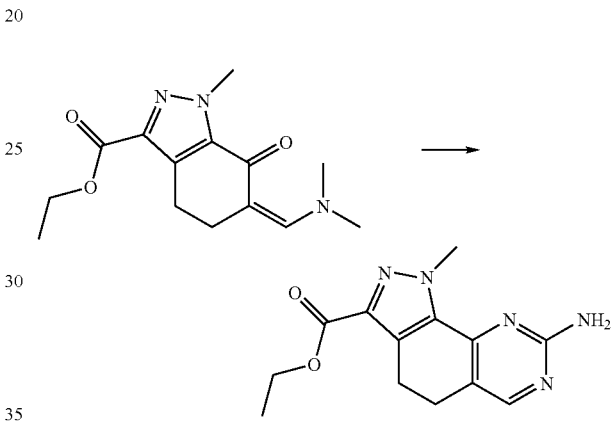

16.00 g (0.06 mol) of ethyl-6-[(dimethylamino)methylene]-1-methyl-7-oxo-4,5,6,7-tetrahydro-1H-indazole-3-carboxylate were dissolved in 600 mL of ethanol and 3.90 g of sodium ethylate, and 5.44 g of guanidine hydrochloride were added consecutively. The solution was stirred at reflux for 12 hours. The solvent was then evaporated, the residue redissolved with dichloromethane and washed with water. The organic layer was then dried over anhydrous Na$_2$SO$_4$ and concentrated. The residue was triturated with diethyl ether and the product collected by filtration (85% yield as a white solid).

$^1$H NMR (400 MHz, DMSO-d$_6$) δ ppm: 1.28 (t, J 7.07 Hz, 3 H) 2.68-2.93 (m, 4 H) 4.25 (q, J 7.07 Hz, 2 H) 4.30 (s, 3 H) 6.54 (bs, 2 H) 8.15 (m, 1 H).

According to this same methodology, but employing a suitable substituted guanidine derivative, the following compounds were prepared, as reported in table VII:

TABLE VII

| | |
|---|---|
| B04-X00-M00(C01)-D01 | $^1$H NMR(400MHz, DMSO-d$_6$) δ ppm 1.29(t, J 7.07Hz, 3H) 2.82(m, 2H) 2.95(m, 2H) 4.27(q, J 7.07Hz, 2H) 4.32(s, 3H) 6.93(m, 2H) 7.37(m, 2H) 7.77(m, 2H) 8.39(s, 1H) 9.49(s, 1H). |
| B06-X00-M00(C01)-D01 | $^1$H NMR(400MHz, DMSO-d$_6$) δ ppm 1.29(t, J 7.07Hz, 3H) 2.84(m, 2H) 2.96(m, 2H) 4.27(q, J 7.07Hz, 2H) 6.97(m, 1H) 7.30(m, 1H) 7.54(m, 1H) 7.97(m, 1H) 8.42(s, 1H) 9.74(s, 1H). |

TABLE VII-continued

| | |
|---|---|
| B07-X00-M00(C01)-D01 | ¹H NMR(400MHz, DMSO-d₆) δ ppm 1.29(t, J 7.07Hz, 3H) 2.85(m, 2H) 2.97(m, 2H) 4.28(q, J 7.07Hz, 2H) 4.33(s, 3H) 7.28(m, 1H) 7.51(m, 1H) 7.89(m, 2H) 8.18(bs, 1H) 8.47(s, 1H) 9.88(s, 1H). |
| B08-X00-M00(C01)-D01 | |
| B09-X00-M00(C01)-D01 | ¹H NMR(400MHz, DMSO-d₆) δ ppm 1.29(t, J 7.07Hz, 3H) 2.21(s, 3H,) 2.45(m, 2H) 2.81(m, 2H) 2.95(m, 2H) 3.69(m, 4H) 4.26(q, J 7.07Hz, 2H) 4.33(s, 3H) 6.65(m, 1H) 7.10(m, 1H) 7.19(m, 1H) 7.21(m, 1H) 8.38(s, 1H) 9.31(bs, 1H). |
| B10-X00-M00(C01)-D01 | ¹H NMR(400MHz, DMSO-d₆) δ ppm 1.34(t, J=7.19Hz, 3H) 2.25(s, 3H) 2.48(m, 4H) 2.84(t, J=7.74Hz, 2H) 2.99(t, J=7.74Hz, 2H) 3.10(m, 4H) 4.32(q, J=7.19Hz, 2H) 4.36(s, 3H) 6.93(d, J=9.34Hz, 2H) 7.53(d, J=9.34Hz, 2H) 8.37(s, 1H) 9.29(s, 1H) |
| B04-X00-M00(C02)-D01 | |
| B04-X00-M00(C04)-D01 | ¹H NMR(400MHz, DMSO-d₆) δ ppm 1.30(t, J 7.07Hz, 3H) 2.82(m, 2H) 2.96(m, 2H) 3.79(m, 2H) 4.28(q, J 7.07Hz, 2H) 4.78(t, J 5.25Hz, OH) 4.88(t, J 5.73Hz, 2H) 6.95(m, 1H) 7.29(m, 2H) 7.65(m, 2H) 8.39(s, 1H) 9.44(bs, 1H). |
| B04-X00-M00(C06)-D01 | ¹H NMR(400MHz, DMSO-d₆) δ ppm 1.12(t, 3H, J=7.07Hz) 1.33(t, 3H, J=7.07Hz) 2.90(m, 2H) 3.03(m, 2H) 4.07(q, 2H, J=7.07Hz) 4.31(q, 2H, J=7.07Hz) 5.73(s, 2H) 7.01(m, 1H) 7.31(m, 2H) 7.57(m, 2H) 8.44(s, 1H) 9.49(bs, 1H). |
| B04-X00-M00(C08)-D01 | |
| B04-X00-M00(C09)-D01 | |
| B04-X00-M00(C10)-D01 | |
| B04-X00-M00(C05)-D01 | ¹H NMR(400MHz, DMSO-d₆) δ ppm 1.33(t, J 7.07Hz, 3H) 2.87(m, 2H) 3.02(m, 2H) 4.36(q, J 7.07Hz, 2H) 5.53(q, J 8.90 H, 2H) 6.90(m, 1H) 7.24(m, 2H) 7.79(m, 2H) 8.42(s, 1H) 9.74(bs, 1H). |
| B04-X00-M04(C05)-D01 | ¹H NMR(400MHz, DMSO-d₆) δ ppm 1.30(t, J 7.07Hz, 3H) 2.87(m, 2H) 2.98(m, 2H) 4.29(q, J 7.07Hz, 2H) 5.85(q, J 8.90Hz, 2H) 6.80-7.60(3m, 5H) 8.43(s, 1H) 9.58(bs, 1H). |
| B04-X00-M00(C11)-D01 | |
| B36-X00-M00(C01)-D01 | |
| B12-X00-M00(C01)-D01 | ¹H NMR(400MHz, DMSO-d₆) δ ppm 1.33(t, J 7.07Hz, 3H) 2.25(s, 3H) 2.52(m, 4H) 2.93(m, 8H) 4.31(q, J 7.07Hz, 2H) 4.36(s, 3H) 7.54(d, J 8.90Hz, 1H) 7.93(dd, J 8.84, 2.50Hz, 1H) 8.07(d, J 2.56Hz, 1H) 8.46(s, 1H) 9.78(s, 1H) |
| B13-X00-M00(C01)-D01 | ¹H NMR(400MHz, DMSO-d₆) δ ppm 1.33(t, J 7.07Hz, 3H) 2.28(s, 3H) 2.53(m, 4H) 2.94(m, 8H) 4.31(q, J 7.15Hz, 2H) 4.38(s, 3H) 7.14(d, J 8.90Hz, 1H) 7.53(dd, J 8.72, 2.50Hz, 1H) 7.96(d, J 2.44Hz, 1H) 8.44(s, 1H) 9.60(s, 1H) |
| B00-X00-M00(C00)-D01 | ¹H NMR(400MHz, DMSO-d₆) δ ppm 1.33(t, J=7.2Hz, 3H) 2.78(m, 2H) 2.96(m, 2H) 4.31(q, J=7.2Hz, 2H) 6.64(m, 2H) 8.19(bs, 1H) |
| B00-X00-M00(C03)-D01 | |
| B00-X00-M04(C03)-D01 | |
| B00-X00-M00(C04)-D01 | ¹H NMR(400MHz, DMSO-d₆) δ ppm 1.32(t, J=7.07Hz, 3H) 2.76(t, J=7.68Hz, 2H) 2.94(t, J=7.50Hz, 2H) 3.79-3.88(m, 2H) 4.30(q, J=7.07Hz, 2H) 4.80(t, J=5.79Hz, 1H) 4.84(t, J=5.97Hz, 2H) 6.55(s, 2H) 8.19(s, 1H) |
| B00-X00-M00(C05)-D01 | |
| B00-X00-M00(C08)-D01 | ¹H NMR(400MHz, DMSO-d₆) δ ppm 1.35(t, J=7.07Hz, 3H) 2.83(t, J=7.56Hz, 2H) 3.02(t, J=7.38Hz, 2H) 4.36(q, J=7.07Hz, 2H) 6.14(s, 2H) 7.44(s, 2H) 7.83(d, J=8.78Hz, 2H) 7.92-7.99(m, 2H) 8.25(s, 1H) |
| B00-X00-M00(C09)-D01 | ¹H NMR(400MHz, DMSO-d₆) δ ppm 1.34(t, J=7.13Hz, 3H) 2.80(t, J=7.50Hz, 2H) 3.00(t, J=7.38Hz, 2H) 3.85(s, 3H) 4.34(q, J=7.11Hz, 2H) 6.10(s, 2H) 7.03(d, J=9.02Hz, 2H) 7.50(d, J=9.02Hz, 2H) 8.20(s, 1H) |
| B00-X00-M00(C10)-D01 | ¹H NMR(400MHz, DMSO-d₆) δ ppm 1.34(t, J=7.07Hz, 3H) 2.83(t, J=7.56Hz, 2H) 3.01(t, J=7.68Hz, 2H) 4.36(q, J=7.15Hz, 2H) 6.24(s, 2H) 7.83(d, J=8.78Hz, 2H) 7.97(d, J=8.78Hz, 2H) 8.23(s, 1H) |
| B00-X00-M00(C10)-D01 | ¹H NMR(400MHz, DMSO-d₆) δ ppm 1.34(t, J=7.07Hz, 3H) 2.83(t, J=7.50Hz, 2H) 3.01(t, J=7.56Hz, 2H) 4.35(q, J=7.07Hz, 2H) 6.02(s, 2H) |

TABLE VII-continued

| | |
|---|---|
| B00-X00-M00(C16)-D01 | 7.57(ddd, J=7.53, 4.85, 1.04Hz, 1H) 7.68(dt, J=7.99, 0.95Hz, 1H) 8.05(td, J=7.74, 1.95Hz, 1H) 8.21(s, 1H) 8.53(ddd, J=4.88, 1.83, 0.85Hz, 1H) |
| | $^1$H NMR(400MHz, DMSO-$d_6$) δ ppm 1.34(t, 3H, J=7.07Hz) 2.82 and 3.01(2t, 4H, J=7.68Hz) 4.34(q, 2H, J=7.68Hz) 6.06(s, 2H) 7.46-7.60(2m, 5H) 8.22(s, 1H) |
| B00-X00-M00(C17)-D01 | $^1$H NMR(400MHz, DMSO-$d_6$) δ ppm 1.32(t, 3H, J=7.20Hz) 2.76 and 2.96(2t, 4H, J=7.31Hz) 4.29(q, 2H, J=7.20Hz) 6.09(s, 2H) 6.64(s, 2H) 7.34(m, 5H) 8.19(s, 1H) |
| B00-X00-M00(C20)-D01 | $^1$H NMR(400MHz, DMSO-$d_6$) δ ppm 1.32(t, 3H, J 7.19Hz) 2.09(m, 4H) 3.85(m, 4H) 4.31(q, 2H, J 7.19Hz) 5.88(m, 1H) 6.67(bs, 2H) 8.08(s, 1H) 8.21(s, 1H). |
| B00-X00-M00(C19)-D01 | $^1$H NMR(400MHz, DMSO-$d_6$) δ ppm 1.32(t, J=7.07Hz, 3H) 1.93-2.16(m, 4H) 2.24-2.43(m, 5H) 2.74(t, J=7.62Hz, 2H) 2.88-3.02(m, 4H) 4.31(q, J=7.07Hz, 2H) 5.48-5.69(m, 1H) 6.56(s, 2H) 8.20(s, 1H) |
| B00-X00-M00(C21)-D01 | |
| B00-X00-M00(C22)-D01 | $^1$H NMR(400MHz, DMSO-$d_6$) δ ppm 1.32(t, J=7.07Hz, 3H) 1.74-2.06(m, 4H) 2.08(s, 3H) 2.73-2.78(m, 2H) 2.74-2.86(m, 1H) 2.94(t, J=7.62Hz, 2H) 3.28-3.36(m, 1H) 3.91-4.04(m, 1H) 4.30(q, J=7.11Hz, 2H) 4.48-4.59(m, 1H) 5.78-5.97(m, 1H) 6.61(s, 2H) 8.20(s, 1H) |
| B00-X00-M00(C23)-D01 | $^1$H NMR(400MHz, DMSO-$d_6$) δ ppm 1.32(t, J=7.07Hz, 3H) 2.32(s, 6H) 2.76(t, J=7.68Hz, 2H) 2.94(t, J=7.50Hz, 2H) 3.34(m, 2H) 4.30(q, J=7.07Hz, 2H) 4.61(m, 2H) 6.55(s, 2H) 8.19(s, 1H) |
| B00-X00-M00(C24)-D01 | $^1$H NMR(400MHz, DMSO-$d_6$) δ ppm 1.32(t, J=7.07Hz, 3H) 1.71(m, 2H) 2.32(s, 6H) 2.76(t, J=7.68Hz, 2H) 2.94(t, J=7.50Hz, 2H) 3.34(m, 2H) 4.30(q, J=7.07Hz, 2H) 4.61(m, 2H) 6.55(s, 2H) 8.19(s, 1H) |
| B10-X00-M00(C19)-D01 | $^1$H NMR(400MHz, DMSO-$d_6$) δ ppm 1.33(m, 3H) 2.53-2.51(m, 6H) 2.97 and 2.51(2t, 4H J 7.44Hz) 3.13(m, 4H) 4.30(q, 2H) 6.96(m, 2H) 7.37(m, 2H) 8.37(s, 1H) 9.14(s, 1H). |
| B04-X00-M00(C21)-D01 | $^1$H NMR(400MHz, DMSO-$d_6$) δ ppm 1.34(t, J=7.07Hz, 3H) 1.89-1.96(m, 2H) 2.00-2.15(m, 4H) 2.79-2.89(m, 4H) 2.98(t, J=7.87Hz, 2H) 3.52(s, 2H) 4.32(q, J=7.15Hz, 2H) 5.48-5.66(m, 1H) 6.99-7.09(m, 1H) 7.21-7.43(m, 7H) 7.59(dd, J=8.60, 1.04Hz, 2H) 8.43(s, 1H) 9.45(s, 1H) |
| B10-X00-M04(C15)-D01 | $^1$H NMR(400MHz, DMSO-$d_6$) δ ppm 1.32(t, 3H) 2.26(m, 7H) 2.98(m, 6H) 3.33(m, 2H) 4.30(q, 2H) 6.32(s, 2H) 6.70(d, 2H) 7.33(d, 2H) 7.39(m, 1H) 7.47(m, 2H) 7.67(m, 3H) 8.42(m, 1H) 9.29(m, 1H) |
| B10-X00-M00(C15)-D01 | $^1$H NMR(400MHz, DMSO-$d_6$) δ ppm 1.31(t, 3H) 2.30(m, 4H) 2.52(m, 5H) 2.86(m, 2H) 3.07(m, 4H) 4.33(q, 2H) 6.03(s, 1H) 6.88(d, 2H) 7.39(m, 1H) 7.51(m, 2H) 7.65(m, 5H) 8.36(s, 1H) 9.42(s, 1H) |

Example 17

Step 8. Ethyl 8-{[3-chloro-4-(4-methylpiperazin-1-yl)phenyl]amino}-1,4,4-trimethyl-4,5-dihydro-1H-pyrazolo[4,3-h]quinazoline-3-carboxylate [B13-X00-M03(C01)-D01]

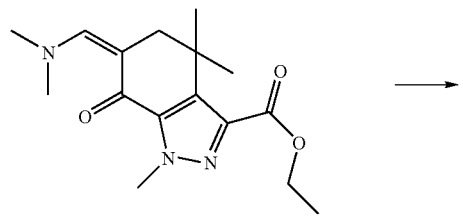

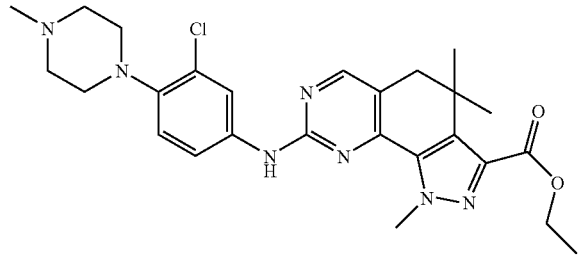

-continued

A solution of ethyl 6-[(dimethylamino)methylene]-1,4,4-trimethyl-7-oxo-4,5,6,7-tetrahydro-1H-indazole-3-carboxylate (0.50 g, 1.6 mmol) and N-[3-chloro-4-(4-methyl-piperazin-1-yl)-phenyl]-guanidine (0.48 g, 1.8 mmol) in anhydrous dimethylformamide was heated to 100° C. and kept at this temperature for 37 hours. After cooling, the mixture was diluted with water (50 mL) and the resulting precipitate was collected by filtration and dried to give the title compound (0.72 g, 85% yield) as a yellow solid.

¹H NMR (400 Hz, DMSO-d₆) δ ppm 1.33 (m, 9 H) 2.75 (s, 2 H) 2.84 (s, 3 H) 3.33 (m, 8 H) 4.32 (q, J 7.07 Hz, 2 H) 4.37 (s, 3 H) 7.20 (d, J 8.78 Hz, 1 H) 7.57 (dd, J 8.84, 2.50 Hz, 1 H) 8.01 (d, J 2.44 Hz, 1 H) 8.44 (s, 1 H) 9.68 (s, 1 H).

By working according to this methodology, and by taking into account that when the guanidine derivative is available as a salt, stoichiometric amounts of potassium carbonate were employed, the following compounds were prepared:

Ethyl 1,4,4-trimethyl-8-{[4-(4-methylpiperazin-1-yl)-3-(trifluoromethyl)phenyl]amino}-4,5-dihydro-1H-pyrazolo[4,3-h]quinazoline-3-carboxylate [B12-X00-M03(C01)-D01]

¹H NMR (400 MHz, DMSO-d₆) δ ppm 1.33 (t, J 7.13 Hz, 3 H) 1.34 (s, 6 H) 2.24 (s, 3 H) 2.46 (s, 4 H) 2.75 (s, 2 H) 2.84 (t, J 4.63 Hz, 4 H) 4.32 (q, J 7 11 Hz, 2 H) 4.34 (s, 3 H) 7.54 (d, J 8 78 Hz, 1 H) 7.93 (dd, J 8.84, 2.50 Hz, 1 H) 8.06 (d, J 2.44 Hz, 1 H) 8.45 (s, 1 H) 9.78 (s, 1 H);

Ethyl 8-anilino-1,4,4-trimethyl-4,5-dihydro-1H-pyrazolo[4,3-h]quinazoline-3-carboxylate [B04-X00-M03(C01)-D01]

¹H NMR (400 MHz, DMSO-d₆) δ ppm 1.33 (m, 9 H) 2.74 (s, 2 H) 4.32 (q, J 7.15 Hz, 2 H) 4.36 (s, 3 H) 6.98 (tt, J 7.36, 1.07, 1.04 Hz, 1 H) 7.31 (dd, J 8.47, 7.38 Hz, 2 H) 7.71 (dd, J 8.60, 0.91 Hz, 2 H) 8.42 (s, 1 H) 9.54 (s, 1 H);

Ethyl 8-[4-(4-methyl-piperazin-1-yl)-phenylamino]-1,4,4-trimethyl-4,5-dihydro-1H-pyrazolo[4,3-h]quinazoline-3-carboxylate [B10-X00-M03(C01)-D01]

¹H NMR (400 MHz, DMSO-d₆) δ ppm 1.33 (t, J=7.07 Hz, 3 H) 1.33 (s, 6 H) 2.27 (s, 3 H) 2.52 (m, 4 H) 2.71 (s, 2 H) 3.03-3.15 (m, 4 H) 4.32 (q, J=7.07 Hz, 2 H) 4.33 (s, 3 H) 6.91 (d, J=9.02 Hz, 2 H) 7.53 (d, J=9.02 Hz, 2 H) 8.35 (s, 1 H) 9.28 (s, 1 H);

Ethyl 8-amino-1,4,4-trimethyl-4,5-dihydro-1H-pyrazolo[4,3-h]quinazoline-3-carboxylate [B00-X00-M03(C01)-D01]

¹H NMR (400 MHz, DMSO-d₆) δ ppm 1.32 (t, J=7.07 Hz, 3 H) 1.31 (s, 6 H) 2.64 (s, 2 H) 4.31 (q, J=7.07 Hz, 2 H) 4.33 (s, 3 H) 6.61 (s, 2 H) 8.18 (s, 1 H).

Example 18

Ethyl 8-{[3-chloro-4-(4-methylpiperazin-1-yl)phenyl]amino}-1,5,5-trimethyl-4,5-dihydro-1H-pyrazolo[4,3-h]quinazoline-3-carboxylate [B13-X00-M02(C01)-D01]

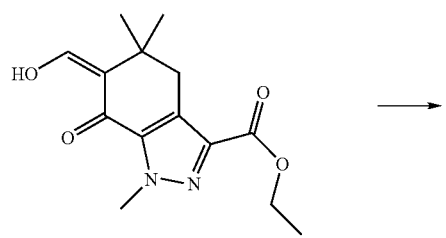

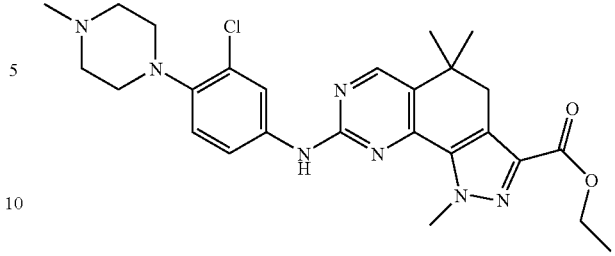

A solution of ethyl 6-(hydroxymethylene)-1,5,5-trimethyl-7-oxo-4,5,6,7-tetrahydro-1H-indazole-3-carboxylate (400 mg, 1.44 mmol) and N-[3-chloro-4-(4-methyl-piperazin-1-yl)-phenyl]-guanidine (424 mg, 1.58 mmol) in anhydrous dimethylformamide (5 mL) was heated at 100° C. for 3 hours. After cooling, the reaction mixture was poured into brine (50 mL) and extracted with ethyl acetate (50 mL×2). The extracts were collected, dried on Na₂SO₄ and evaporated to dryness. The crude material was purified by flash chromatography on silica gel eluted with dichloromethane/methanol 9:1 to give the pure title compound (240 mg, 33% yield).

¹H NMR (400 MHz, DMSO-d₆) δ ppm 1.33 (m, 9 H) 2.27 (s, 3 H) 2.52 (m, 4 H) 2.92 (s, 2 H) 2.95 (t, J 4.63 Hz, 4 H) 4.31 (q, J 7.07 Hz, 2 H) 4.39 (s, 3 H) 7.14 (d, J 8.78 Hz, 1 H) 7.52 (dd, J 8.78, 2.44 Hz, 1 H) 7.98 (d, J 2.44 Hz, 1 H) 8.54 (s, 1 H) 9.63 (s, 1 H).

By working according to this methodology, and by taking into account that when the guanidine derivative is available as a salt, stoichiometric amounts of potassium carbonate were employed, the following compounds were prepared:

Ethyl 1,5,5-trimethyl-8-{[4-(4-methylpiperazin-1-yl)-3-(trifluoromethyl)phenyl]amino}-4,5-dihydro-1H-pyrazolo[4,3-h]quinazoline-3-carboxylate [B12-X00-M02(C01)-D01]

¹H NMR (400 MHz, DMSO-d₆) δ ppm 1.32 (m, 9 H) 2.27 (s, 3 H) 2.52 (m, 4 H) 2.86 (t, J 4.51 Hz, 4 H) 2.93 (s, 2 H) 4.32 (q, J 7.15 Hz, 2 H) 4.37 (s, 3 H) 7.54 (d, J 8.66 Hz, 1 H) 7.93 (dd, J 8.78, 2.56 Hz, 1 H) 8.09 (d, J 2.44 Hz, 1 H) 8.56 (s, 1 H) 9.81 (s, 1 H);

Ethyl 8-anilino-1,5,5-trimethyl-4,5-dihydro-1H-pyrazolo[4,3-h]quinazoline-3-carboxylate [B04-X00-M02(C01)-D01]

¹H NMR (400 MHz, DMSO-d₆) δ ppm 1.32 (m, 9 H) 2.93 (s, 2 H) 4.31 (q, J 7.15 Hz, 2 H) 4.38 (s, 3 H) 6.98 (tt, J 7.36, 1.07, 1.04 Hz, 1 H) 7.32 (dd, J 8.47, 7.50 Hz, 2 H) 7.72 (dd, J 8.60, 1.04 Hz, 2 H) 8.53 (s, 1 H) 9.57 (s, 1 H);

Ethyl 1,5,5-trimethyl-8-{[4-(4-methylpiperazin-1-yl)-phenyl]amino}-4,5-dihydro-1H-pyrazolo[4,3-h]quinazoline-3-carboxylate [B10-X00-M02(C01)-D01]

¹H NMR (400 MHz, DMSO-D6) δ ppm 1.30 (s, 6 H) 1.34 (t, J=7.07 Hz, 3 H) 2.25 (s, 3 H) 2.48 (m, 4 H) 2.91 (s, 2 H) 3.09 (m, 4 H), 4.31 (q, J=7.19 Hz, 2 H) 4.35 (s, 3 H) 6.92 (d, J=9.29 Hz, 2 H) 7.52 (d, J=9.29 Hz, 2 H) 8.46 (s, 1 H) 9.30 (s, 1 H);

Ethyl 1,5,5-trimethyl-8-amino-4,5-dihydro-1H-pyrazolo[4,3-h]quinazoline-3-carboxylate [B00-X00-M02(C01)-D01]

$^1$H NMR (400 MHz, DMSO-d$_6$) δ ppm 1.25 (s, 6 H) 1.32 (t, J=7.13 Hz, 3 H) 2.86 (s, 2 H) 4.30 (q, J=7.07 Hz, 2 H) 4.35 (s, 3 H) 6.61 (s, 2 H) 8.29 (s, 1 H).

Example 19

Ethyl 8-(1-acetyl-piperidin-4-yl)amino-1-methyl-4,5-dihydro-1H-pyrazolo[4,3-h]quinazoline-3-carboxylate [B91-X00-M00(C01)-D01]

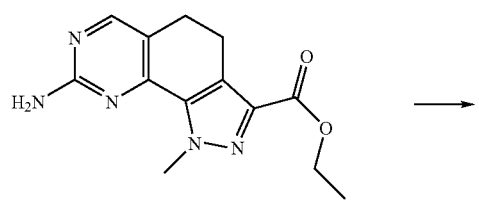 → 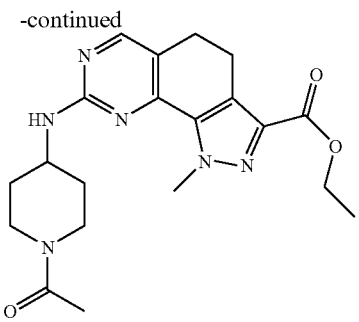

To a suspension of 5.187 g (19 mmol) of ethyl 8-amino-1-methyl-4,5-dihydro-1H-pyrazolo[4,3-h]quinazoline-3-carboxylate in dry dimethylformamide (120 mL), were added 1-acetyl-4-piperidone (4.7 mL, 38 mmol), CF$_3$COOH (10 mL, 128 mmol) and NaBH(OAc)$_3$ (8.862 g, 42 mmol). After 18 hours, NaOH 0.33N (800 mL, 264 mmol) was added dropwise to the mixture. The precipitate was filtered, washed with water and dried in oven to dryness to give 5.3 g (70% yield) of the title compound.

$^1$H NMR (400 MHz), DMSO-d$_6$) δ ppm 1.34 (t, J 7.07 Hz, 3 H) 1.47 (m, 2 H) 1.95 (m, 2 H) 2.02 (s, 3 H) 2.73 (m, 1 H) 2.77 (m, 2 H) 3.17 (m, 1 H) 3.83 (m, 1 H) 3.95 (m, 1 H) 4.30 (q, J 7.07 Hz, 2 H) 4.31 (m, 1 H) 4.33 (s, 3 H) 7.14 (m, 1 H) 8.24 (s, 1 H)

By working according to the above method the following compounds were prepared:

TABLE VIII

| | |
|---|---|
| B73-X00-M00(C01)-D01 | $^1$H NMR(400MHz, DMSO-d$_6$) δ ppm 1.32(t, J 7.13Hz, 3H) 1.54(m, 4H) 1.70(m, 2H) 1.94(m, 2H) 2.77(m, 2H) 2.94(t, J 7.74Hz, 2H) 4.17(m, 1H) 4.30(q, J 7.07Hz, 2H) 4.35(s, 3H) 7.11(d, J 6.34Hz, 1H) 8.22(s, 1H) |
| B89-X00-M00(C01)-D01 | $^1$H NMR(400MHz, DMSO-d$_6$) δ ppm 1.20(t, J 7.07Hz, 3H) 1.32(t, J 7.13Hz, 3H) 1.41(m, 2H) 1.92(dd, J 12.62, 2.99Hz, 2H) 2.89(m, 6H) 3.94(m, 3H) 4.05(q, J 7.07Hz, 2H) 4.30(q, J 7.19Hz, 2H) 4.33(s, 3H) 7.13(d, J 5.85Hz, 1H) 8.24(s, 1H) |
| B27-X00-M00(C01)-D01 | $^1$H NMR(400MHz, DMSO-d$_6$) δ ppm 1.08-1.37(m, 5H) 1.32(t, J=7.07Hz, 3H) 1.53-1.99(m, 5H) 2.76(t, J=7.62Hz, 2H) 2.94(t, J=7.50Hz, 2H) 3.62-3.77(m, 1H) 4.30(q, J=7.15Hz, 2H) 4.34(s, 3H) 6.98(d, J=5.37Hz, 1H) 8.21(s, 1H) |
| B90-X00-M00(C01)-D01 | $^1$H NMR(400MHz, DMSO-d$_6$) δ ppm 1.32(t, J=7.07Hz, 3H) 1.54(m, 2H) 1.89(d, J=12.80Hz, 2H) 1.96(m, 2H) 2.18(s, 3H) 2.77(m, 4H) 2.94(t, J=7.74Hz, 2H) 3.66(m, 1H) 4.30(q, J=7.19Hz, 2H) 4.33(s, 3H) 7.03(d, J=6.46Hz, 1H) 8.22(s, 1H) |
| B94-X00-M00(C01)-D01 | $^1$H NMR(400MHz, DMSO-d$_6$) δ ppm 1.31(t, J=7.2Hz, 3H); 1.58(m, 2H); 1.98(m, 2H); 2.75(m, 2H); 2.92(m, 2H); 3.30(m, 2H); 3.59(m, 2H); 3.72(m, 1H); 4.26(s, 3H); 4.29(q, J=7.2Hz, 2H); 7.13(d, J=7.2Hz, 1H); 7.68(m, 2H); 7.75(m, 1H); 7.78(m, 2H); 8.20(s, 1H) |
| B100-X00-M00(C01)-D01 | $^1$H NMR(400MHz, DMSO-d$_6$) δ ppm 1.32(t, J=7.2Hz, 3H); 1.45(m, 2H); 1.90(m, 2H); 2.19(m, 3H); 2.31(m, 4H); 2.77(m, 2H); 2.87(m, 2H); 2.94(m, 2H); 3.15(m, 4H); 3.60(m, 2H); 3.87(m, 1H); 4.30(q, J=7.2Hz, 2H); 4.33(s, 3H), 7.13(bs, 1H); 8.23(s, 1H) |
| B73-X00-M00(C09)-D01 | $^1$H NMR(400MHz, DMSO-d$_6$) δ ppm 1.10-1.24(m, 4H) 1.34(t, J=7.13Hz, 3H) 1.40-1.62(m, 4H) 2.83(t, J=7.62Hz, 2H) 3.03(t, J=7.44Hz, 2H) 3.83(s, 3H) 3.85-3.87(m, 1H) 4.34(q, J=7.15Hz, 2H) 6.94(s, 1H) 7.05(d, J=8.90Hz, 2H) 7.46(d, J=9.02Hz, 2H) 8.18(s, 1H) |

TABLE VIII-continued

| | |
|---|---|
| B73-X00-M00(C10)-D01 | $^1$H NMR(400MHz, DMSO-d$_6$) δ ppm 1.06-1.67(m, 8H) 1.34(t, J=7.13Hz, 3H) 2.85(t, J=7.68Hz, 2H) 3.03(t, J=7.68Hz, 2H) 3.28-3.44(m, 1H) 4.35(q, J=7.07Hz, 2H) 6.93(s, 1H) 7.82(d, J=8.78Hz, 2H) 8.04(d, J=8.66Hz, 2H) 8.22(s, 1H) |
| B73-X00-M00(C08)-D01 | $^1$H NMR(400MHz, DMSO-d$_6$) δ ppm 1.05-1.54(m, 8H) 1.34(t, J=7.13Hz, 3H) 2.85(t, J=7.62Hz, 2H) 3.03(t, J=7.44Hz, 2H) 3.25-3.42(m, 1H) 4.30-4.41(m, J=7.07, 7.07, 7.07Hz, 2H) 6.87(s, 1H) 7.48(s, 2H) 7.79(d, J=8.78Hz, 2H) 7.95(d, J=8.78Hz, 2H) 8.22(s, 1H) |
| B73-X00-M00(C11)-D01 | |
| B73-X00-M00-(C19)-D01 | |
| B91-X00-M00(C19)-D01 | $^1$H NMR(400MHz, DMSO-d$_6$) δ ppm 1.32(t, 3H, J=7.08) 2.04(s, 3H) 2.75 and 2.94(2t, 4H, J=7.32) 4.31(q, 2H, J=7.08) 8.26(s, 1H) |
| B73-X00-M00 (C20)-D01 | $^1$H NMR(400MHz, DMSO-d$_6$) δ ppm 1.29-1.35(m, 3H) 1.50-1.63(m, 4H) 1.66-2.17(m, 8H) 2.72-2.86(m, 1H) 2.76-2.81(m, 2H) 2.94(t, J=7.74Hz, 2H) 3.11-3.27(m, 1H) 3.86-3.97(m, 1H) 4.12-4.23(m, 1H) 4.30(q, J=7.15Hz, 2H) 4.34-4.44(m, 1H) 5.82-5.98(m, 1H) 7.14(s, 1H) 8.08(s, 1H) 8.24(s, 1H) |
| B73-X00-M00(C22)-D01 | $^1$H NMR(400MHz, DMSO-d$_6$) δ ppm 1.32(t, 3H, J=7.07) 2.09(s, 3H) 2.94 and 2.76(2t, 4H, J=7.68) 3.18(m, 1H) 4.02(m, 1H) 4.18(m, 1H) 4.30(q, 2H, J=7.07Hz) 4.56(m, 1H) 5.88(m, 1H) 7.13(bs, 1H) 8.24(s, 1H) |
| B91-X00-M00(C22)-D01 | |
| B73-X00-M00(C023)-D01 | $^1$H NMR(400MHz, DMSO-d$_6$) δ ppm 1.32(t, J=7.07Hz, 3H) 1.65(m, 6H) 1.94(m, 2H) 2.32(s, 6H) 2.73(m, 2H) 2.95(t, J 7.62Hz, 2H) 3.34(m, 2H) 4.17(m, 1H) 4.31(q, J=7.03Hz, 2H) 4.61(m, 2H) 8.20(s, 1H) |
| B73-X00-M00(C024)-D01 | $^1$H NMR(400MHz, DMSO-d$_6$) δ ppm 1.32(t, J=7.07Hz, 3H) 1.65(m, 6H) 1.94(m, 2H) 2.29(s, 6H) 2.50(m, 2H) 2.73(m, 2H) 2.95(t, J 7.62Hz, 2H) 4.17(m, 1H) 4.31(q, J=7.03Hz, 2H) 4.54(m, 2H) 8.20(s, 1H) |
| B95-X00-M00(C01)-D01 | |
| B91-X00-M03(C01)-D01 | $^1$H NMR(400MHz), DMSO-d$_6$) δ ppm 1.31(s, 6H) 1.32(t, J=7.07Hz, 3H) 1.49(m, 2H) 1.96(m, 2H) 2.02(s, 3H) 2.65(s, 2H) 2.76(m, 1H) 3.16(m, 1H) 3.83(m, 1H) 3.95(m, 1H) 4.30(m, 1H) 4.31(q, J=7.03Hz, 2H) 4.32(s, 3H) 7.17(s, 1H) 8.24(s, 1H) |
| B89-X00-M03(C01)-D01 | $^1$H NMR(400MHz, DMSO-d$_6$) δ ppm 1.23(t, J=7.07Hz, 3H) 1.33(s, 6H) 1.35(t, J=7.14Hz, 3H) 1.43(m, 2H) 1.95(dd, J=12.43, 2.54Hz, 2H) 2.67(s, 2H) 2.98(m, 2H) 3.92(m, 1H) 3.99(m, 2H) 4.08(q, J=7.00Hz, 2H) 4.33(q, J=7.10Hz, 2H) 4.34(s, 3H) 7.17(s, 1H) 8.25(s, 1 |
| B73-X00-M03(C01)-D01 | $^1$H NMR(400MHz, DMSO-d$_6$) δ ppm 1.31(s, 6H) 1.32(t, J=7.13Hz, 3H) 1.55(m, 4H) 1.70(m, 2H) 1.94(m, 2H) 2.64(s, 2H) 4.17(m, 1H) 4.31(q, J=7.11Hz, 2H) 4.34(s, 3H) 7.12(d, J=7.19Hz, 1H) 8.21(s, 1H) |
| B92-X00-M03(C01)-D01 | $^1$H NMR(400MHz, DMSO-d$_6$) δ ppm 1.32(t, J=7.07Hz, 3H) 1.31(s, 6H) 1.46(m, 2H) 1.96(m, 2H) 2.65(s, 2H) 3.18(m, 2H) 3.62(m, 1H) 4.01(m, 1H) 4.31(q, J=7.03Hz, 2H) 4.32(s, 3H) 4.40(m, 1H) 7.18(s, 1H) 7.34-7.49(m, 5H) 8.23(s, 1H) |
| B93-X00-M03(C01)-D01 | $^1$H NMR(400MHz, DMSO-d$_6$) δ ppm 1.29(s, 6H) 1.31(t, J=7.19Hz, 3H) 1.59(m, 2H) 2.01(m, 2H) 2.89(s, 3H) 2.90(m, 2H) 3.56(m, 2H) 3.87(m, 1H) 4.30(q, J=7.03Hz, 2H) 4.32(s, 3H) 8.24(s, 1H) |
| B94-X00-M03(C01)-D01 | $^1$H NMR(400MHz, DMSO-d$_6$) δ ppm 1.29(s, 6H) 1.31(t, J=7.19Hz, 3H) 1.59(m, 2H) 1.99(m, 2H) 2.56(m, 2H) 2.63(s, 2H) 3.59(m, 2H) 3.73(m, 1H) 4.25(s, 3H) 4.30(q, J=7.03Hz, 2H) 7.14(d, J=6.83Hz, 1H) 7.68(m, 2H) 7.73(m, 1H) 7.77(m, 2H) 8.19(s, 1H) |
| B91-X00-M05 | $^1$H NMR(400MHz, DMSO-d$_6$) δ ppm 1.37(m, 2H) 1.89(m, 2H) 2.02(s, 3H) 2.75(m, 1H) 2.93(m, 2H) 3.17(m, 1H) 3.64(m, 2H) 3.81(m, 1H) 4.01(m, 1H) 4.26(m, 1H) 4.36(m, 2H) 6.54(bs, 1H) 7.17(s, 1H) 8.23(s, 1H) |

Example 20

Ethyl 8-methoxy-1-methyl-4,5-dihydro-1H-pyrazolo[4,3-h]quinazoline-3-carboxylate [B67-X03-M00(C01)-D01]

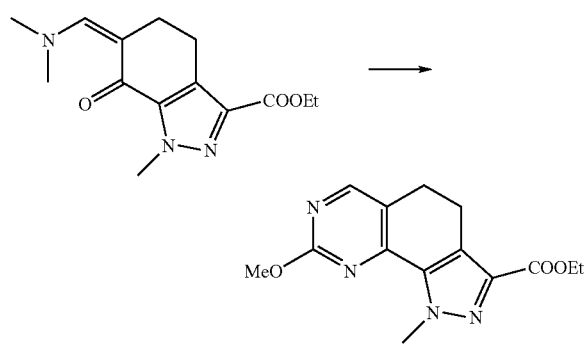

2.0 g (7.2 mmol) of ethyl 6-[(dimethylamino)methylene]-1-methyl-7-oxo-4,5,6,7-tetrahydro-1H-indazole-3-carboxylate were dissolved in 200 mL of acetonitrile and 17.4 g (70.6 mmol) of methylisourea sulfate and 10.0 g (72.4 mmol) of potassium carbonate were added. The reaction mixture was stirred at reflux for 16 hours. The solvent was then evaporated, the residue redissolved with dichloromethane and washed with water. The organic layer was dried over anhydrous $Na_2SO_4$ and concentrated. After a chromatography on a silica gel column (eluant dichloromethane) 1.7 g of product were obtained (86% yield).

$^1$H NMR (400 MHz, DMSO-$d_6$) δ ppm 1.33 (t, J 7.07 Hz, 3 H) 2.98 (m, 4 H) 3.97 (s, 3 H) 4.31 (q, J 7.07 Hz, 2 H) 4.34 (s, 3 H) 8.54 (s, 1 H).

Example 21

Ethyl 8-hydroxy-1-methyl-4,5-dihydro-1H-pyrazolo[4,3-h]quinazoline-3-carboxylate [B00-X03-M00(C01)-D01]

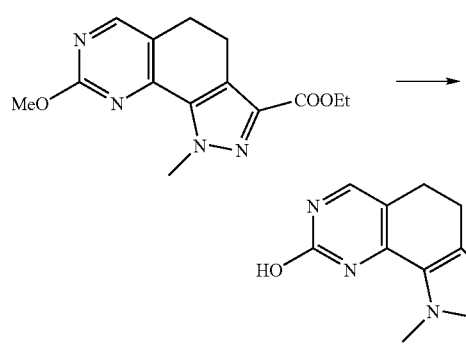

1.5 g (5.2 mmol) of ethyl 8-methoxy-1-methyl-4,5-dihydro-1H-pyrazolo[4,3-h]quinazoline-3-carboxylate were dissolved in 90 mL of acetonitrile and 1.6 g (10.6 mmol) of sodium iodide and 1.5 mL of trimethylsilylchloride were added. After a day under stirring and nitrogen atmosphere at room temperature the solvent was evaporated, the residue redissolved with a mixture dichloromethane/methanol 4/1 and washed with a saturated aqueous solution of $Na_2S_2O_3$. The organic layer was dried over $Na_2SO_4$ and evaporated to dryness. The residue crystallized from methanol leading 1.1 g of the title compound (78% yield).

$^1$H NMR (400 MHz, DMSO-$d_6$) δ ppm 1.32 (t, J 7.07 Hz, 3 H) 2.84 (m, 4 H) 4.31 (q, J 7.07 Hz, 2 H) 4.29 (s, 3 H) 7.87 (s, 1 H) 11.70 (s, 1 H).

Example 22

Ethyl 1-methyl-8-{[(trifluoromethyl)sulfonyl]oxy}-4,5-dihydro-1H-pyrazolo[4,3-h]quinazoline-3-carboxylate [B66-X03-M00(C01)-D01]

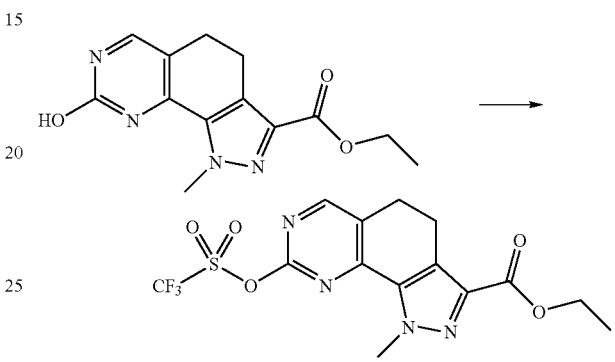

0.60 g (2.19 mmol) of ethyl 8-hydroxy-1-methyl-4,5-dihydro-1H-pyrazolo[4,3-h]quinazoline-3-carboxylate and 0.31 mL (2.19 mmol) of triethylamine were dissolved in 60 mL of dichloromethane and stirred for 5 hours at −78° C.; then, 0.72 mL (2.19 mmol) of triflic anhydride were added. The reaction was stirred overnight and allowed to come to room temperature, washed with aqueous $NaHCO_3$, dried over $Na_2SO_4$ and evaporated to dryness. The residue was triturated with diethyl ether/acetone and the product collected by filtration giving 0.60 g (67% yield) of the title compound.

$^1$H NMR (400 z, DMSO-$d_6$) δ ppm 1.33 (t, J 7.13 Hz, 3 H) 3.09 (s, 4 H) 4.28 (s, 3 H) 4.32 (q, J 7.11 Hz, 2 H) 8.86 (s, 1 H).

Example 23

Ethyl 8-{[1-(tert-butoxycarbonyl)pyrrolidin-3-yl]amino}-1-methyl-4,5-dihydro-1H-pyrazolo[4,3-h]quinazoline-3-carboxylate [B97-X00-M00(C01)-D01]

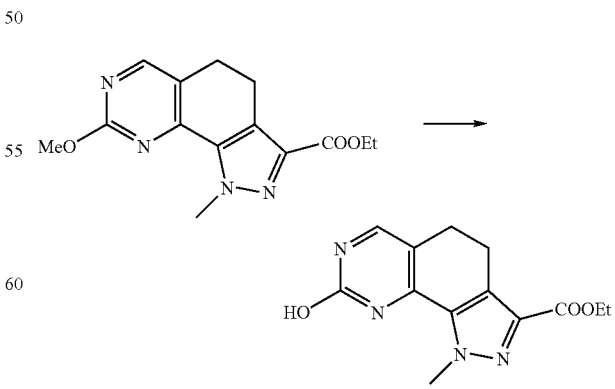

1.5 g (5.2 mmol) of ethyl 8-methoxy-1-methyl-4,5-dihydro-1H-pyrazolo[4,3-h]quinazoline-3-carboxylate were dissolved in 90 mL of acetonitrile and 1.6 g (10.6 mmol) of sodium iodide and 1.5 mL of trimethylsilylchloride were added. After a day under stirring and nitrogen atmosphere at room temperature the solvent was evaporated, the residue redissolved with a mixture dichloromethane/methanol 4/1 and washed with a saturated aqueous solution of $Na_2S_2O_3$. The organic layer was dried over $Na_2SO_4$ and evaporated to dryness. The residue crystallized from methanol leading 1.1 g of the title compound (78% yield).

$^1$H NMR (400 M DMSO-$d_6$) δ ppm 1.32 (t, J 7.07 Hz, 3 H) 2.84 (m, 4 H) 4.31 (q, J 7.07 Hz, 2 H) 4.29 (s, 3 H) 7.87 (s, 1 H) 11.70 (s, 1 H).

Example 22

Ethyl 1-methyl-8-{[(trifluoromethyl)sulfonyl]oxy}-4,5-dihydro-1H-pyrazolo[4,3-h]quinazoline-3-carboxylate [B66-X03-M00(C01)-D01]

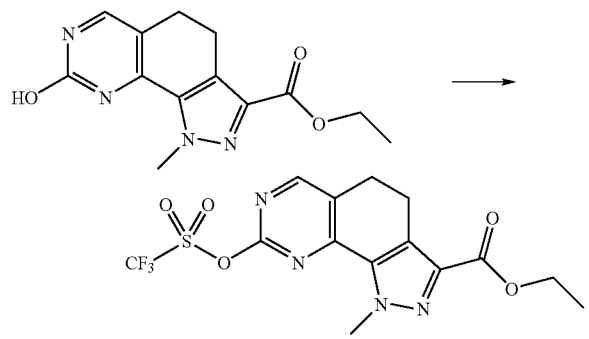

0.60 g (2.19 mmol) of ethyl 8-hydroxy-1-methyl-4,5-dihydro-1H-pyrazolo[4,3-h]quinazoline-3-carboxylate and 0.31 mL (2.19 mmol) of triethylamine were dissolved in 60 mL of dichloromethane and stirred for 5 hours at −78° C.; then, 0.72 mL (2.19 mmol) of triflic anhydride were added. The reaction was stirred overnight and allowed to come to room temperature, washed with aqueous $NaHCO_3$, dried over $Na_2SO_4$ and evaporated to dryness. The residue was triturated with diethyl ether/acetone and the product collected by filtration giving 0.60 g (67% yield) of the title compound.

$^1$H NMR (400 MHz, DMSO-$d_6$) δ ppm 1.33 (t, J 7.13 Hz, 3 H) 3.09 (s, 4 H) 4.28 (s, 3 H) 4.32 (q, J 7.11 Hz, 2 H) 8.86 (s, 1 H).

Example 23

Ethyl 8-{[1-(tert-butoxycarbonyl)pyrrolidin-3-yl]amino}-1-methyl-4,5-dihydro-1H-pyrazolo[4,3-h]quinazoline-3-carboxylate [B97-X00-M00(C01)-D01]

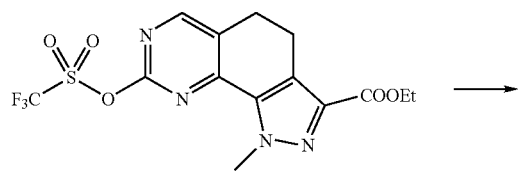

-continued

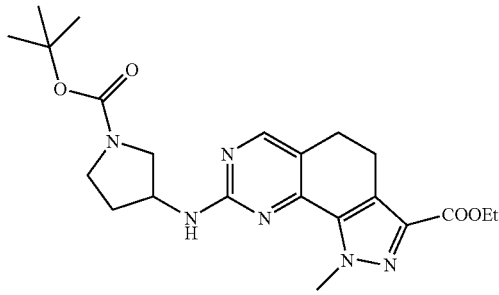

To a solution of 1.5 g (3.7 mmol) of ethyl 1-methyl-8-{[(trifluoromethyl)sulfonyl]oxy}-4,5-dihydro-1H-pyrazolo[4,3-h]quinazoline-3-carboxylate in 150 mL of anhydrous dioxane, 756 mg (4.1 mmol) of tert-butyl 3-aminopyrrolidine-1-carboxylate were added. The reaction mixture was stirred at room temperature overnight. The solvent was then removed under reduced pressure, the residue redissolved with dichloromethane and washed with water. The organic layer was dried over sodium sulfate and evaporated. 1.2 g (88% yield) of the title compound was collected by filtration after trituration with diethylether.

$^1$H NMR (400 MHz, DMSO-$d_6$) δ ppm 1.32 (t, J=7.07 Hz, 3 H) 1.38-1.44 (m, 9 H) 1.81-1.99 (m, 1 H) 2.09-2.23 (m, 1 H) 2.79 (t, J=7.68 Hz, 2 H) 2.95 (t, J=7.80 Hz, 2 H) 3.13-3.66 (m, 4 H) 4.30 (q, J=7.07 Hz, 2 H) 4.32-4.41 (m, 1 H) 4.34 (s, 3 H) 7.40 (s, 1 H) 8.27 (s, 1 H)

Analogously, but employing the suitable amino derivative, the following compounds was prepared:

ethyl 8-[(1-benzylpyrrolidin-3-yl)amino]-1-methyl-4,5-dihydro-1H-pyrazolo[4,3-h]quinazoline-3-carboxylate [B98-X00-M00(C01)-D01]

$^1$H NMR (400 MHz, DMSO-$d_6$) δ ppm 1.32 (t, 3 H, J 7.07 Hz) 2.21 and 1.79 (2m, 2 H) 2.51 and 2.69 (2m, 4 H) 2.93 and 2.74 (2t, 4 H, J 7.68 Hz) 4.30 (m, 5 H) 7.33 (m, 6 H) 8.23 (s, 1 H).

Example 24

8-amino-1-methyl-1H-pyrazolo[4,3-h]quinazoline-3-carboxamide [B00-X00-M00(C01)-D03]

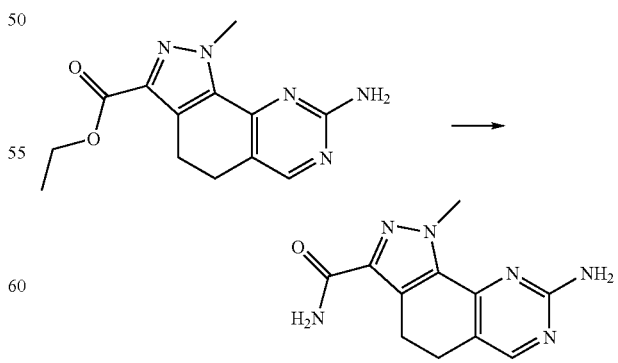

2.5 g of ethyl 8-amino-1-methyl-1H-pyrazolo[4,3-h]quinazoline-3-carboxylate (9.16 mmol) were dissolved in 40 mL of methanol, 40 mL of dimethylformamide and 50 mL of NH$_4$OH 30% mixture. The mixture was maintained at 65° C. under stirring for a day. The solvent was then evaporated to dryness, the residue redissolved with dichloromethane and washed with water. The organic layer was dried over Na$_2$SO$_4$ and evaporated. The crude was triturated with diethyl ether and the product collected by filtration (50% yield).

$^1$H NMR (400 MHz, DMSO-d$_6$) δ ppm 2.68 and 2.90 (2m, 4 H) 4.28 (s, 3 H) 6.50 (bs, 2 H) 7.13-7.42 (bs, 2 H) 8.15 (s, 1 H).

By working according to this method, the following compounds were prepared:

TABLE IX

| | |
|---|---|
| B04-X00-M00(C01)-D03 | $^1$H NMR(400MHz, DMSO-d$_6$) δ ppm 2.79(m, 2H) 2.96(m, 2H) 4.31(s, 3H) 6.94(m, 1H) 7.22(bs, 1H) 7.28(m, 2H) 7.68(m, 2H) 8.88(s, 1H) 9.48(bs, 1H). |
| B06-X00-M00(C01)-D03 | $^1$H NMR(400MHz, DMSO-d$_6$) δ ppm 2.81(m, 2H) 2.97(m, 2H) 4.33(s, 3H) 6.97(m, 1H) 7.29(m, 1H) 7.44(bs, 1H) 7.66(m, 1H) 7.98(m, 1H) 8.43(s, 1H) 9.73(bs, 1H). |
| B07-X00-M00(C01)-D03 | $^1$H NMR(400MHz, DMSO-d$_6$) δ ppm 2.81(t, J 7.68Hz, 2H) 2.98(t, J 7.74Hz, 2H) 4.30(s, 3H) 7.24(s, 1H) 7.26(dd, J 8.66, 0.85Hz, 1H) 7.44(s, 1H) 7.51(t, J 7.93Hz, 1H) 7.90(d, J 8.05Hz, 1H) 8.19(s, 1H) 8.45(s, 1H) 9.87(s, 1H) |
| B08-X00-M00(C01)-D03 | |
| B09-X00-M00(C01)-D03 | $^1$H NMR(400MHz, DMSO-d$_6$) δ ppm 2.73(m, 2H) 2.97(m, 2H) 4.31(s, 3H) 6.58(m, 1H) 7.00-7.40(3m, 4H) 8.37(s, 1H) 9.32(bs, 1H). |
| B10-X00-M00(C01)-D03 | $^1$H NMR(400MHz, DMSO-d$_6$) δ ppm 2.64(s, 3H) 2.76(m, 2H) 2.95(m, 2H) 4.29(s, 3H) 6.92(m, 2H) 7.23(bs, 1H) 7.41(bs, 1H) 7.54(m, 2H) 8.32(s, 1H) 9.27(bs, 1H). |
| B36-X00-M00(C01)-D03 | $^1$H NMR(400MHz, DMSO-d$_6$) δ ppm 2.76(m, 2H) 2.95(m, 2H) 4.28(s, 3H) 5.95(s, 2H) 6.84(m, 1H) 7.06(m, 1H) 7.34(m, 1H) 7.22(bs, 1H) 7.42(bs, 1H) 8.34(s, 1H) 9.34(bs, 1H). |
| B04-X00-M00(C02)-D03 | $^1$H NMR(400MHz, DMSO-d$_6$) δ ppm 1.77(s, 9H) 2.72(m, 2H) 2.96(m, 2H) 7.02(m, 1H) 7.20-7.40(m, 3H) 7.65(m, 1H) 7.67(m, 1H) 8.40(s, 1H) 9.21(bs, 1H). |
| B04-X00-M00(C04)-D03 | $^1$H NMR(400MHz, DMSO-d$_6$) δ ppm 2.78(t, J 7.68Hz, 2H) 2.96(t, J 7.74Hz, 2H) 3.83(q, J 5.69Hz, 2H) 4.78(t, J 5.49Hz, 1H) 4.84(t, J 5.79Hz, 2H) 6.94(t, J 7.38Hz, 1H) 7.23(s, 1H) 7.28(m, 2H) 7.43(s, 1H) 7.67(d, J 7.68Hz, 2H) 8.37(s, 1H) 9.42(s, 1H) |
| B04-X00-M00(C07)-D03 | $^1$H NMR(400MHz, DMSO-d$_6$) δ ppm 2.98(m, 4H) 5.47(s, 2H) 6.97(t, J 7.32Hz, 1H) 7.31(t, 4H) 7.49(s, 1H) 7.65(t, J 7.68Hz, 3H) 8.41(s, 1H) 9.48(s, 1H) |
| B04-X00-M00(C08)-D03 | |
| B04-X00-M00(C09)-D03 | |
| B04-X00-M00(C10)-D03 | |
| B04-X00-M00(C05)-D03 | $^1$H NMR(400MHz, DMSO-d$_6$) δ ppm 2.86(m, 2H) 2.92(m, 2H) 5.44(q, J 9.02, 2H) 6.90(m, 1H) 7.24(m, 2H) 7.80(m, 3H) 7.93(bs, 1H) 8.40(s, 1H) 9.72(bs, 1H). |
| B04-X00-M04(C05)-D03 | $^1$H NMR(400MHz, DMSO-d$_6$) δ ppm 2.83(m, 2H) 3.00(m, 2H) 5.75(q; J 8.90Hz, 2H) 6.97(m, 1H) 7.28(m, 2H) 7.40(bs, 1H) 7.56(m, 2H) 8.42(s, 1H) 9.56(bs, 1H) |
| B04-X00-M00(C11)-D03 | |
| B04-X00-M00(C00)-D03 | $^1$H NMR(400MHz, DMSO-d$_6$) δ ppm 2.86(m, 2H) 3.03(m, 2H) 6.95(m, 1H) 7.30(m, 3H) 7.51(bs, 1H) 7.89(m, 2H) 8.40(s, 1H) 9.45(bs, 1H) 14.03(bs, 1H). |
| B12-X00-M00(C01)-D03 | $^1$H NMR(400MHz, DMSO-d$_6$) δ ppm 2.27(s, 3H) 2.52(m, 4H) 2.90(m, 8H) 4.33(s, 3H) 7.27(s, 1H) 7.47(s, 1H) 7.53(d, J 8.78Hz, 1H) 7.93(dd, J 8.90, 2.44Hz, 1H) 8.08(d, J 2.56Hz, 1H) 8.45(s, 1H) 9.76(s, 1H) |
| B13-X00-M00(C01)-D03 | $^1$H NMR(400MHz, DMSO-d$_6$) δ ppm 2.26(s, 3H) 2.52(m, 4H) 2.92(m, 8H) 4.35(s, 3H) 7.14(d, J 8.78Hz, 1H) 7.27(s, 1H) 7.47(s, 1H) 7.53(dd, J=8.78, 2.44Hz, 1H) 7.97(d, J=2.56Hz, 1H) 8.42(s, 1H) 9.58(s, 1H) |
| B27-X00-M00(C03)-D03 | |
| B27-X00-M04(C03)-D03 | $^1$H NMR(400MHz, DMSO-d$_6$) δ ppm 0.79(s, 3H) 1.64(m, 2H) 4.85(m, 2H) 6.67(m, 1H) 7.16-7.24(m, 3H) 7.25-7.42(2 bs, 2H) 9.25(bs, 1H). |

TABLE IX-continued

| | |
|---|---|
| B04-X00-M00(C21)-D03 | ¹H NMR(400MHz, DMSO-d₆) δ ppm 1.92(dd, J=11.58, 4.15Hz, 2H) 2.01-2.10(m, 2H) 2.12-2.23(m, 2H) 2.80(t, J=7.56Hz, 2H) 2.88(d, J=11.10Hz, 2H) 2.98(t, J=7.50Hz, 2H) 3.52(s, 2H) 5.48-5.61(m, 1H) 6.99-7.07(m, 1H) 7.26(s, 1H) 7.27-7.39(m, 7H) 7.43(s, 1H) 7.60(dd, J=8.54, 1.10Hz, 2H) 8.41(s, 1H) 9.43(s, 1H) |
| B00-X00-M00(C21)-D03 | ¹H NMR(400MHz, DMSO-d₆) δ ppm 1.94(d, J=11.95Hz, 2H) 2.10-2.33(m, 4H) 2.70(t, J=7.74Hz, 2H) 2.93(t, J=7.56Hz, 4H) 3.55(s, 2H) 5.41-5.69(m, 1H) 6.51(s, 2H) 7.15-7.43(m, 7H) 8.17(s, 1H) |
| B10-X00-M00(C19)-D03 | ¹H NMR(400MHz, DMSO-d₆) δ ppm 2.51(m, 4H) 2.79(m, 4H) 3.13(m, 4H) 5.46(m, 1H) 6.95(m, 2H) 7.38(m, 2H) 7.36 and 7.26(2s, 2H) 8.34(s, 1H) 9.12(s, 1H). |
| B04-X00-M04(C01)-D03 | ¹H NMR(400MHz, DMSO-d₆) δ ppm 2.83(t, J=7.68Hz, 2H) 3.00(t, J=7.62Hz, 2H) 4.34(s, 3H) 6.92-7.03(m, 1H) 7.26(s, 1H) 7.31(dd, J=8.41, 7.44Hz, 2H) 7.47(s, 1H) 7.72(dd, J=8.60, 0.91Hz, 2H) 8.42(s, 1H) 9.51(s, 1H) |
| B73-X00-M00(C05)-D03 | ¹H NMR(400MHz, DMSO-d₆) δ ppm 1.42-1.78(m, 6H) 1.84-2.00(m, 2H) 2.78(t, J=7.74Hz, 2H) 2.98(t, J=7.74Hz, 2H) 4.02-4.20(m, 1H) 5.81(q, J=8.82Hz, 1H) 7.22(d, J=6.95Hz, 1H) 7.41(s, 1H) 7.45(s, 1H) 8.25(s, 1H) |
| B73-X00-M00(C04)-D03 | ¹H NMR(400MHz, DMSO-d₆) δ ppm 1.41-1.77(m, 6H) 1.84-2.01(m, 2H) 2.73(t, J=7.74Hz, 2H) 2.95(t, J=7.56Hz, 2H) 3.85(t, J=6.10Hz, 2H) 4.09-4.25(m, 1H) 4.73-4.90(m, 1H) 4.82(t, J=6.16Hz, 2H) 7.04(d, J=5.98Hz, 1H) 7.24(s, 1H) 7.43(s, 1H) 8.20(s, 1H) |
| B73-X00-M00(C21)-D03 | ¹H NMR(400MHz, DMSO-d₆) δ ppm 2.71 AND 2.94(2T, 4H, J 7.80Hz) 3.55(s, 2H) 4.15(m, 1H) 5.62(m, 1H) 7.25-7.36(m, 5H) 7.23 and 7.39(2s, 2H) 8.20(s, 1H). |
| B97-X00-M00(C01)-D03 | ¹H NMR(400MHz, DMSO-d₆) δ ppm 1.4(s, 9H) 1.8-2.2(2m, 2H) 2.75 and 2.96(2t, 4H) 3.2-3.7(m, 4H) 4.2-4.4(m, 4H) 7.38(s, 1H) 7.24 and 7.44(2s, 2H) 8.25(s, 1H). |
| B98-X00-M00(C01)-D03 | ¹H NMR(400MHz, DMSO-d₆) δ ppm 1.6-2.2(m, 2H) 2.72(m, 4H) 2.94(m, 4H) 4.27(s, 3H) 4.32(m, 1H) 7.33(m, 6H) 7.43(2s, 2H) 8.21(s, 1H). |
| B95-X00-M00(C01)-D03 | ¹H NMR(400MHz, DMSO-d₆) δ ppm 1.02(t, J=7.19Hz, 3H) 1.44-1.58(m, 2H) 1.87-1.94(m, 2H) 1.95-2.03(m, 2H) 2.35(q, J=7.07Hz, 2H) 2.73(t, J=7.56Hz, 2H) 2.89(d, J=11.71Hz, 2H) 2.94(t, J=7.62Hz, 2H) 3.59-3.78(m, 1H) 4.30(s, 3H) 7.00(d, J=7.93Hz, 1H) 7.23(s, 1H) 7.44(s, 1H) 8.21(s, 1H) |
| B73-X00-M00(C19)-D03 | ¹H NMR(400MHz, DMSO-d₆) δ ppm 2.72 and 2.94(2t, 4H, J 7.94Hz) 4.20(m, 1H) 5.60(m, 1H) 7.25(s, 1H) 1.10 and 7.35(2s, 2H) 8.21(s, 1H). |
| B91-X00-M00(C19)-D03 | ¹H NMR(400MHz, DMSO-d₆) δ ppm 2.04(s, 3H) 2.28(s, 3H) 3.18(m, 4H) 4.30(m, 4H) 5.50(m, 1H) 7.26(s, 1H) 7.10 and 7.36(2s, 2H) 8.24(s, 1H). |
| B91-X00-M00(C22)-D03 | |
| B73-X00-M00(C22)-D03 | ¹H NMR(400MHz, DMSO-d₆) δ ppm 2.07(s, 3H) 2.94 and 2.72(2t, 4H, J=7.93) 4.18(m, 1H) 5.83(m, 1H) 7.09(s, 1H) 7.42 and 7.23(2s, 2H) 8.22(s, 1H |
| B73-X00-M00(C20)-D03 | ¹H NMR(400MHz, DMSO-d₆) δ ppm 1.48-1.63(m, 4H) 1.66-2.15(m, 8H) 2.66-2.84(m, 1H) 2.72(t, J=7.62Hz, 2H) 2.94(t, J=7.68Hz, 2H) 3.08-3.39(m, 1H) 3.86-3.97(m, 1H) 4.10-4.25(m, 1H) 4.31-4.42(m, 1H) 5.77-5.95(m, 1H) 7.08(s, 1H) 7.23(s, 1H) 7.43(s, 1H) 8.09(s, 1H) 8.22(s, 1H) |
| B73-X00-M00(C16)-D03 | ¹H NMR(400MHz, DMSO-d₆) δ ppm 1.03-1.64(m, 8H) 2.80(t, J=7.62Hz, 2H) 3.03(t, J=7.62Hz, 2H) 3.27-3.33(m, 1H) 6.77(s, 1H) 7.33(s, 1H) 7.44-7.57(m, 5H) 7.61(s, 1H) 8.17(s, 1H) |
| B73-X00-M00(C17)-D03 | ¹H NMR(400MHz, DMSO-d₆) δ ppm 1.31-1.87(m, 8H) 2.76(t, J=7.68Hz, 2H) 2.99(t, J=7.62Hz, 2H) 3.99(s, 1H) 6.07(s, 2H) 7.06(d, J=7.44Hz, 1H) 7.13-7.35(m, 6H) 7.44(s, 1H) 8.21(s, 1H) |
| B73-X00-M00(C09)-D03 | ¹H NMR(400MHz, DMSO-d₆) δ ppm 1.00-1.68(m, 8H) 2.79(t, J=7.62Hz, 2H) 3.02(t, J=7.62Hz, 2H) 3.21-3.44(m, 1H) 3.82(s, 3H) 6.79(d, |

TABLE IX-continued

| | |
|---|---|
| | J=5.85Hz, 1H) 7.04(d, J=9.02Hz, 2H) 7.31(s, 1H) 7.46(d, J=8.90Hz, 2H) 7.58(s, 1H) 8.16(s, 1H) |
| B73-X00-M00(C10)-D03 | $^1$H NMR(400MHz, DMSO-$d_6$) δ ppm 1.05-1.65(m, 8H) 2.82(t, J=7.62Hz, 2H) 3.03(t, J=7.68Hz, 2H) 3.25-3.44(m, 1H) 6.90(s, 1H) 7.42(s, 1H) 7.70(s, 1H) 7.84(d, J=8.66Hz, 2H) 8.03(d, J=8.78Hz, 2H) 8.21(s, 1H) |
| B73-X00-M00(C11)-D03 | $^1$H NMR(400MHz, DMSO-$d_6$) δ ppm 1.06-1.65(m, 8H) 2.82(t, J=7.62Hz, 2H) 3.03(t, J=7.68Hz, 2H) 3.13-3.62(m, 1H) 6.78(s, 1H) 7.37(s, 1H) 7.58(ddd, J=7.53, 4.85, 1.04Hz, 1H) 7.65(s, 1H) 7.68(dt, J=7.93, 0.91Hz, 1H) 8.04-8.10(m, 1H) 8.18(s, 1H) 8.57(ddd, J=4.85, 1.86, 0.85Hz, 1H) |
| B73-X00-M00(C08)-D03 | $^1$H NMR(400MHz, DMSO-$d_6$) δ ppm 1.07-1.55(m, 8H) 2.82(t, J=7.62Hz, 2H) 3.03(t, J=7.56Hz, 2H) 3.26-3.42(m, 1H) 6.82(s, 1H) 7.41(s, 1H) 7.44(s, 2H) 7.64(s, 1H) 7.80(d, J=8.66Hz, 2H) 7.93(d, J=8.78Hz, 2H) 8.21(s, 1H) |

Example 25

1-methyl-8-[(phenylacetyl)amino]-1H-pyrazolo[4,3-h]quinazoline-3-carboxamide [B05-X01-M00(C01)-D03]

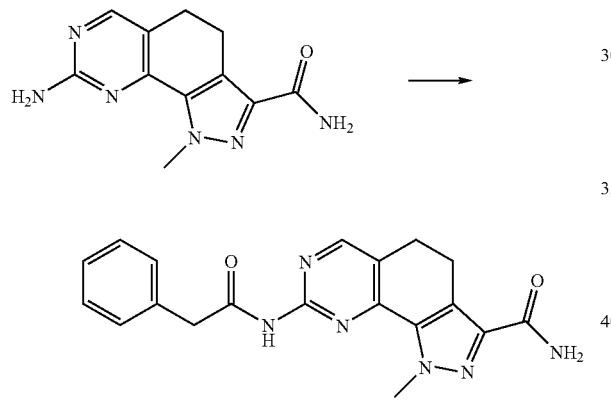

0.40 g (1.47 mmol) of 8-amino-1-methyl-1H-pyrazolo[4,3-h]quinazoline-3-carboxamide were suspended in 20 mL of tetrahydrofuran and 5 mL of pyridine and 0.42 mL (3.22 mmol) of phenylacetylchloride were added. The reaction mixture was stirred at room temperature for 16 hours. The solvent was evaporated, the residue redissolved with dichloromethane, washed with aqueous NaHCO$_3$ and then with water. After drying over anhydrous Na$_2$SO$_4$ the solvent was removed under reduced pressure and the crude purified by chromatography on a silica gel column (eluant cyclohexane/acetone) giving 0.35 mg of the title compound (60% yield).

$^1$H NMR (400 MHz), DMSO-$d_6$) δ ppm 2.62-3.02 (2m, 4 H) 3.76 (m, 2 H) 4.3 (s, 3 H) 7.00-7.50 (m, 7 H) 8.50 (s, 1 H) 10.80 (bs, 1 H).

By working according to this method, the following compound was prepared:

8-(benzoylamino)-1-methyl-4,5-dihydro-1H-pyrazolo[4,3-h]quinazoline-3-carboxamide [B04-X01-M00(C01)-D03]

$^1$H NMR (400 MHz), DMSO-$d_6$) δ ppm 2.87-3.04 (2m, 4 H) 4.33 (s, 3 H) 7.20-7.46 (bs, 2 H) 7.47-7.53 (m, 3 H) 7.90-8.00 (m, 2 H) 8.60 (s, 1 H) 10.97 (m, 1 H).

Example 26

Ethyl 8-[(aminocarbonyl)amino]-1-methyl-1H-pyrazolo[4,3-h]quinazoline-3-carboxylate [B00-X02-M00(C01)-D01]

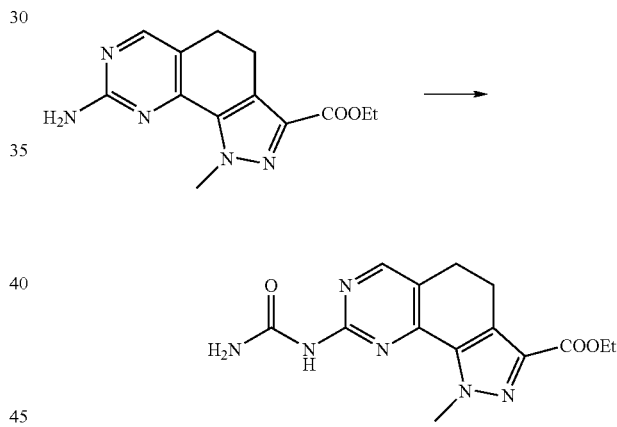

1.00 g (3.7 mmol) of ethyl 8-amino-1-methyl-1H-pyrazolo[4,3-h]quinazoline-3-carboxylate were dissolved in 50 mL of pyridine and 1 mL (8.0 mmol) of trichloroacetylisocyanate were added. The mixture was stirred overnight at room temperature. The solvent was then evaporated under reduced pressure and the residue was treated with 50 mL of methanol. After 2 hours under stirring the solvent was removed, the residue redissolved with dichloromethane and washed with a diluted solution of ammonium hydrate. After drying over anhydrous Na$_2$SO$_4$ the organic layer was evaporated to dryness and the residue purified by chromatography on a silica gel column (eluant: dichloromethane/acetone 4/1) leading 0.40 g (34% yield) of the title compound.

$^1$H NMR (400 MHz), DMSO-$d_6$) δ ppm 1.28 (t, J 7.07 Hz, 3 H) 2.8-3.0 (2m, 4 H) 4.19-4.34 (1s and 1q, J 7.07 Hz, 3 H) 7.04 (bs, 2 H) 8.44 (bs, 1 H) 9.91 (bs, 1 H).

Example 27

Ethyl 8-{[(ethylamino)carbonyl]amino}-1-methyl-1H-pyrazolo[4,3-h]quinazoline-3-carboxylate [B03-X02-M00(C01)-D01]

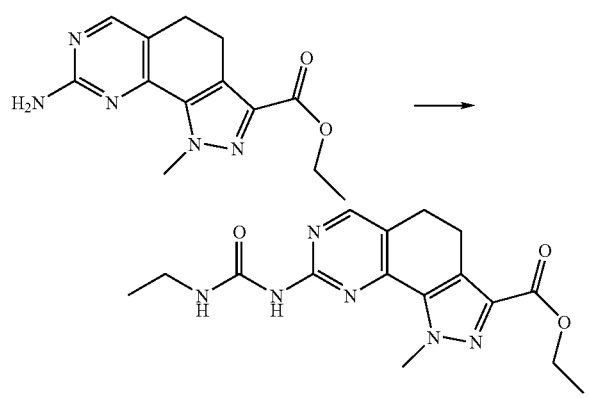

To a suspension of 18 mg (0.44 mmol) of sodium hydride 60% in mineral oil (0.37 mmol) in dry dimethylformamide, a solution of 100 mg of ethyl 8-amino-1-methyl-1H-pyrazolo[4,3-h]quinazoline-3-carboxylate (0.37 mmol) in 5 mL of the same solvent was added dropwise at 0° C. under stirring. After 5 minutes, 0.070 mL (0.88 mmol) of ethylisocyanate were added to the mixture and the reaction allowed to come to room temperature. After 8 hours the solvent was evaporated under reduced pressure, the residue redissolved with dichloromethane and washed with water. After drying over Na$_2$SO$_4$ the solvent was removed and the product purified by chromatography on a silica gel column (eluant dichloromethane/acetone) leading 64 mg (50% yield) of the title compound.

$^1$H NMR (400 MHz), DMSO-d$_6$) δ ppm 1.10 (t, J 7.20 Hz, 3 H) 1.29 (t, J 7.07 Hz, 3 H) 2.76-3.04 (2m, 4 H) 3.12 (m, 2 H) 4.21 (q, J 7.07 Hz, 2 H) 4.32 (s, 3 H) 8.45 (m, 1 H) 8.71 (t, 1 H) 9.70 (bs, 1 H).

Example 28

8-[(aminocarbonyl)amino]-1-methyl-1H-pyrazolo[4,3-h]quinazoline-3-carboxamide [B00-X02-M00(C01)-D03]

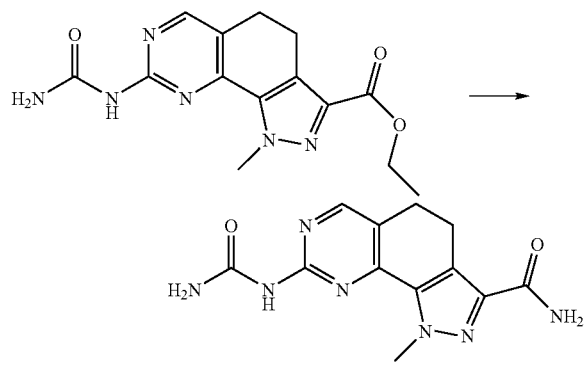

A suspension of 0.20 g (0.63 mmol) of ethyl 8-[(aminocarbonyl)amino]-1-methyl-1H-pyrazolo[4,3-h]quinazoline-3-carboxylate in 15 mL of a mixture methanol/dimethylformamide/ammonium hydroxide 30% 1/1/1 was stirred in a close bottle at 65° C. for 48 hours. The solvent was then evaporated under reduced pressure, the residue redissolved with a mixture dichloromethane/methanol 9/1 and washed with water. The organic layer was dried over anhydrous Na$_2$SO$_4$ and evaporated to dryness. The product was purified by chromatography on a silica gel column (eluant dichloromethane/acetone/methanol) giving 0.09 g (50% yield) of the title compound.

$^{1H}$ NMR (400 MHz), DMSO-d$_6$), δ ppm 2.91-3.09 (m, 4 H) 3.81 (s, 3 H) 6.47 (m, 3 H) 7.83 (bs, 2 H) 8.58 (m, 1 H).

By working according to the above method, the following compound was prepared:

8-{[(ethylamino)carbonyl]amino}-1-methyl-4,5-dihydro-1H-pyrazolo[4,3-h]quinazoline-3-carboxamide [B03-X02-M00(C01)-D03]

$^1$H NMR (400 MHz), DMSO-d$_6$), δ ppm 1.10 (t, J 7.19 Hz, 3 H) 2.82 (t, J 7.62 Hz, 2 H) 2.97 (t, J 7.74 Hz, 2 H) 3.23 (m, 2 H) 4.28 (s, 3 H) 7.24 (s, 1 H) 7.45 (s, 1 H) 8.42 (s, 1 H) 8.75 (t, J 5.61 Hz, 1 H) 9.67 (s, 1 H).

Example 29

Ethyl 8-iodo-1-methyl-4,5-dihydro-1H-pyrazolo[4,3-h]quinazoline-3-carboxylate

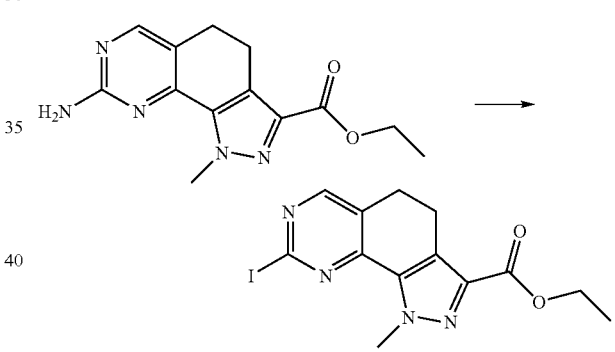

To a well stirred, warm suspension of ethyl 8-amino-1-methyl-4,5-dihydro-1H-pyrazolo[4,3-h]quinazoline-3-carboxamide (8.8 g, 0.032 mol) in dimethoxyethane (1.2 L) maintained in an inert atmosphere of argon, cesium iodide (9.13 g, 0.035 mol), bisublimated iodine (4.45 g, 0.018 mol), copper iodide (2.01 g, 0.01 mol) and isopentyl nitrite (7.00 mL, 6.14 g, 0.052 mol) were added in sequence. The reaction mixture was stirred vigorously at 65-70° C. for 18 hours. After cooling in a ice-water bath, the solid was filtered off and the filtrate was diluted with dichloromethane (2.0 L), washed with 30% ammonium hydroxide (150 mL), sodium thiosulphate (300 mL), brine and dried over anhydrous Na$_2$SO$_4$. Concentrating to a volume of about 100 mL of dimethoxyethane, the crude ethyl 8-iodo-1-methyl-4,5-dihydro-1H-pyrazolo[4,3-h]quinazoline-3-carboxylate precipitated; it was then filtered and washed with dimethoxyethane.

Flash chromatography on silica gel (eluant: dichloromethane/methanol 98:2) yielded 5.69 g of the title compound. (46% yield)

$^1$H NMR (400 MHz), DMSO-d$_6$), δ ppm 1.28 (t, J 7.07 Hz, 3 H) 2.81-3.07 (2t, J 8.90 Hz, 4 H) 4.24 (s, 3 H) 4.27 (q, J 7.07 Hz, 2 H) 8.5 (bs, 1 H).

By working according to this method, the following compounds were prepared:

ethyl 8-iodo-1,4,4-trimethyl-4,5-dihydro-1H-pyrazolo[4,3-h]quinazoline-3-carboxylate $^1$H NMR (400 M, DMSO-d$_6$) δ ppm 1.3 (t, J 7.1 Hz, 3 H) 1.3 (s, 6 H) 2.8 (s, 2 H) 4.3 (s, 3 H) 4.3 (q, J 7.1 Hz, 2 H) 8.5 (s, 1 H);

ethyl 8-iodo-1,5,5-trimethyl-4,5-dihydro-1H-pyrazolo[4,3-h]quinazoline-3-carboxylate $^1$H NMR (400 MHz, DMSO-d$_6$) δ ppm 1.32 (t, J=7.19 Hz, 3 H) 1.32 (s, 6 H) 2.96 (s, 2 H) 4.31 (q, J=7.07 Hz, 2 H) 4.28 (s, 3 H) 8.58 (s, 1 H);

ethyl 1-(3,3-dimethylbutyl)-8-iodo-4,5-dihydro-1H-pyrazolo[4,3-h]quinazoline-3-carboxylate;

ethyl 2-(3,3-dimethylbutyl)-8-iodo-4,5-dihydro-1H-pyrazolo[4,3-h]quinazoline-3-carboxylate.

Example 30

Ethyl 8-(cyclopentylamino)-1-methyl-4,5-dihydro-1H-pyrazolo[4,3-h]quinazoline-3-carboxylate [B73-X00-M00(C01)-D01]

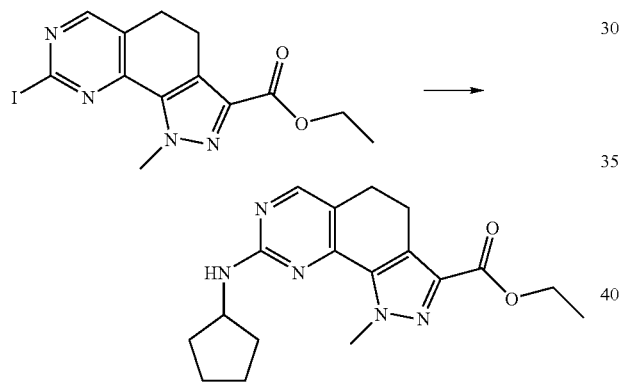

Ethyl 8-iodo-1-methyl-4,5-dihydro-1H-pyrazolo[4,3-h]quinazoline-3-carboxylate (0.5 g, 1.3 mmol) and cyclopentylamine (0.65 mL, 6.5 mmol) were heated at 100° C. under nitrogen for 3 hours. The mixture was concentrated under reduced pressure and the residue was purified by chromatography on a silica gel column (eluant: ethyl acetate/cyclohexane 70/30) to give 0.24 g of 8-(cyclopentylamino)-1-methyl-1H-pyrazolo[4,3-h]quinazoline-3-carboxylate (54% yield).

$^1$H NMR (400 MHz, DMSO-d$_6$) δ ppm 1.32 (t, J 7.13 Hz, 3 H) 1.54 (m, 4 H) 1.70 (m, 2 H) 1.94 (m, 2 H) 2.77 (m, 2 H) 2.94 (t, J 7.74 Hz, 2 H) 4.17 (m, 1 H) 4.30 (q, J 7.07 Hz, 2 H) 4.35 (s, 3 H) 7.11 (d, J 6.34 Hz, 1 H) 8.22 (s, 1 H)

By working according to this method, the following compounds were prepared:

8-{[1-(ethoxycarbonyl)piperidin-4-yl]amino}-1-methyl-4,5-dihydro-1H-pyrazolo[4,3-h]quinazoline-3-carboxylate [B89-X00-M00(C01)-D01]

$^1$H NMR (400 MHz, DMSO-d$_6$) δ ppm 1.20 (t, J 7.07 Hz, 3 H) 1.32 (t, J 7.13 Hz, 3 H) 1.41 (m, 2 H) 1.92 (dd, J 12.62, 2.99 Hz, 2 H) 2.89 (m, 6 H) 3.94 (m, 3 H) 4.05 (q, J 7.07 Hz, 2 H) 4.30 (q, J 7.19 Hz, 2 H) 4.33 (s, 3 H) 7.13 (d, J 5.85 Hz, 1 H) 8.24 (s, 1 H);

B27-X00-M00(C03)-D01

B27-X00-M04(C03)-D01

Example 31

Potassium 8-(cyclopentylamino)-1-methyl-4,5-dihydro-1H-pyrazolo[4,3-h]quinazoline-3-carboxylate [B73-X00-M00(C01)-D02]

Ethyl 8-(cyclopentylamino)-1-methyl-4,5-dihydro-1H-pyrazolo[4,3-h]quinazoline-3-carboxylate (230 mg, 0.67 mmol) was suspended in anhydrous ethanol (5 mL) and treated with a 1.5 M solution of potassium hydroxide in ethanol (1.33 mL, 3 eq.) at reflux temperature for 1.5 hours. After cooling in ice bath, the resulting precipitate was collected by filtration to give the title compound (193 mg, 82% yield) as a crystalline solid.

$^1$H NMR (400 MHz, DMSO-d$_6$) δ ppm 1.61 (m, 6 H) 1.94 (m, 2 H) 2.67 (m, 2 H) 2.90 (m, 2 H) 4.16 (m, 1 H) 4.21 (s, 3 H) 6.90 (d, J 6.83 Hz, 1 H) 8.12 (s, 1 H)

By working according to the above method the following compounds were prepared:

TABLE X

| | |
|---|---|
| B89-X00-M00(C01)-D02 | $^1$H NMR(400MHz, DMSO-d$_6$) δ ppm 1.20(t, J 7.07Hz, 3H) 1.41(m, 2H) 1.92(dd, J 12.62, 2.99Hz, 2H) 2.66(m, 4H) 2.91(m, 2H) 3.94(m, 3H) 4.04(q, J 7.07Hz, 2H) 4.18(s, 3H) 7.13(d, 1H, J 5.85Hz, 2H) 8.24(s, 1H). |

TABLE X-continued

| | |
|---|---|
| B04-X00-M00(C01)-D02 | $^1$H NMR(400MHz, DMSO-$d_6$) δ ppm 2.78-2.98(m, 1H) 6.91-6.97(m, 1H) 7.25-7.30(m, 1H) 7.66-7.71(m, 1H) |
| B04-X00-M04(C01)-D02 | $^1$H NMR(400MHz, DMSO-$d_6$) δ ppm 2.74(t, J=7.62Hz, 2H) 2.95(t, J=7.68Hz, 2H) 4.23(s, 3H) 6.95(tt, J=7.35, 1.13Hz, 1H) 7.30(dd, J=8.60, 7.38Hz, 2H) 7.73(dd, J=8.72, 1.04Hz, 2H) 8.32(s, 1H) 9.39(s, 1H) |
| B91-X00-M00(C01)-D02 | $^1$H NMR(400MHz, DMSO-$d_6$) δ ppm 1.41(m, 2H) 1.92(m, 2H) 2.02(s, 3H) 2.67(m, 1H) 2.75(m, 1H) 2.90(m, 2H) 3.16(m, 1H) 3.82(m, 1H) 3.94(m, 1H) 4.19(s, 3H) 4.28(m, 1H) 6.94(m, 1H) 8.14(s, 1H) |
| B94-X00-M00(C01)-D02 | $^1$H NMR(400MHz, DMSO-$d_6$) δ ppm 1.57(m, 2H) 1.99(m, 2H) 2.55(m, 2H) 2.63(m, 2H) 2.88(m, 2H) 3.58(m, 2H) 3.70(m, 1H) 4.11(s, 3H) 6.92(d, J=6.95Hz, 1H) 7.68(t, J=7.32Hz, 2H) 7.72-7.76(m, 1H) 7.76-7.80(m, 2H) 8.09(s, 1H) |
| B94-X00-M03(C01)-D02 | $^1$H NMR(400MHz, DMSO-$d_6$) δ ppm 1.29(s, 6H) 1.59(m, 2H) 1.99(m, 2H) 2.56(m, 2H) 3.58(m, 2H) 3.70(m, 1H) 4.08(s, 3H) 6.93(s, 1H) 7.68(m, 2H) 7.77(m, 3H) 8.08(m, 1H) 8.18(s, 1H) |
| B93-X00-M03(C01)-D02 | |
| B73-X00-M00(C04)-D02 | $^1$H NMR(400MHz, DMSO-$d_6$) δ ppm 1.46-1.99(m, 8H) 2.75(t, J=7.68Hz, 2H) 2.93(t, J=7.50Hz, 2H) 3.83(t, 2H) 4.10-4.22(m, 1H) 4.77-4.87(m, 3H) 7.04(d, J=5.97Hz, 1H) 8.21(s, 1H) 12.61(s, 1H) |
| B90-X00-M00(C01)-D02 | |
| B00-X00-M00(C21)-D02 | |
| B04-X00-M00(C21)-D02 | $^1$H NMR(400MHz, DMSO-$d_6$) δ ppm 1.81-1.90(m, 2H) 2.00-2.20(m, 4H) 2.72(t, J=7.68Hz, 2H) 2.88(d, J=10.00Hz, 2H) 2.94(t, J=7.50Hz, 2H) 3.53(s, 2H) 5.40-5.54(m, 1H) 6.96-7.04(m, 1H) 7.21-7.39(m, 5H) 7.26-7.31(m, 2H) 7.62(dd, J=8.54, 0.98Hz, 2H) 8.32(s, 1H) 9.31(s, 1H) |
| B10-X00-M00(C19)-D02 | |

Example 32

8-(cyclopentylamio)-1-methyl-4,5-dihydro-1H-pyrazolo[4,3-h]quinazoline-3-carboxamide [B73-X00-M00(C01)-D03]

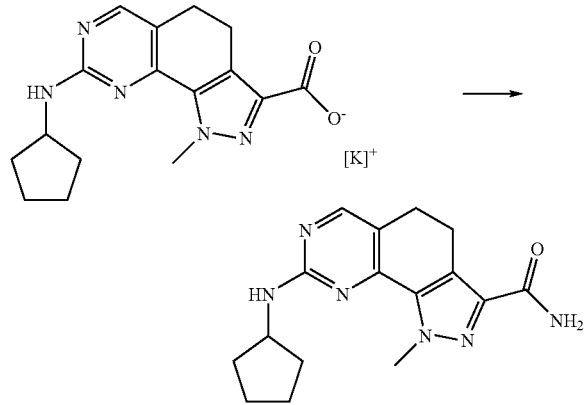

A suspension of potassium 8-(cyclopentylamino)-1-methyl-4,5-dihydro-1H-pyrazolo[4,3-h]quinazoline-3-carboxylate (180 mg, 0.51 mmol) in anhydrous dimethylformamide (3.0 mL) and anhydrous tetrahydrofuran (3.0 mL) was treated with N-ethyl-N,N-diisopropylamine (0.175 mL, 2 eq.) and N-ethyl-N',N'-diisopropyl carbodiimide hydrochloride (EDCI) (195 mg, 2 eq). The mixture was then cooled to 0° C. and treated with ammonium 1H-1,2,3-benzotriazol-1-ate (137 mg, 2 eq). After 5 minutes the reaction was warmed to room temperature and kept at this temperature overnight. The reaction was diluted with water and the resulting precipitate was collected by filtration to afford the title compound (143 mg, 90% yield).

$^1$H NMR (400 MHz, DMSO-$d_6$) δ ppm 1.65 (m, 6 H) 1.94 (m, 2 H) 2.73 (m, 2 H) 2.95 (t, J 7.62 Hz, 2 H) 4.17 (m, 1 H) 4.32 (s, 3 H) 7.08 (d, J 6.83 Hz, 1 H) 7.23 (s, 1 H) 7.43 (s, 1 H) 8.20 (s, 1 H)

By working according to the above method the following compounds were prepared:

TABLE XI

| | |
|---|---|
| B89-X00-M00(C01)-D03 | $^1$H NMR(400MHz, DMSO-$d_6$) δ ppm 1.20(t, J 7.07Hz, 3H) 1.41(m, 2H) 1.92(dd, J 12.62, 2.99, 2H) 2.74(m, 2H) 2.91(m, 2H) 2.95(m, 4H) 3.94(m, 3H) 4.04(q, J 7.07Hz, 2H) 4.30(s, 3H) 7.09(bs, 1H) 7.23(s, 1H) 7.44(s, 1H) 8.22(s, 1H). |
| B91-X00-M00(C01)-D03 | $^1$H NMR(400MHz, DMSO-$d_6$) δ ppm 1.37(m, 2H) 1.92(m, 2H) 2.02(s, 3H), 2.74(m, 2H) 2.76(m, 1H) 2.95(m, 2H) 3.16(m, 1H) 3.81(m, 1H) 3.94(m, 1H) 4.27(m, 1H) 4.31(s, 3H) 7.11(d, J 6.83Hz, 1H) 7.23(s, 1H) 7.44(s, 1H) 8.23(s, 1H) |

TABLE XI-continued

| | |
|---|---|
| B100-X00-M00(C01)-D03 dihydrochloride | $^1$H NMR(400MHz, DMSO-d$_6$) δ ppm 1.44-1.57(m, 2H) 1.95(d, J=12.19Hz, 2H) 2.74-2.83(m, 5H) 2.89-3.53(m, 10H) 3.65(dd, J=12.50, 7.87Hz, 4H) 3.96(t, J=10.61Hz, 1H) 4.30(s, 3H) 7.29(s, 1H) 7.47(s, 1H) 7.64(s, 1H) 8.26(s, 1H) 10.39(s, 1H) |
| B93-X00-M00(C01)-D03 | $^1$H NMR(400MHz, DMSOd$_6$) δ ppm 1.60(m, 2H) 2.01(m, 2H) 2.74(m, 2H) 2.89(m, 7H,) 3.55(m, 2H.) 3.86(m, 1H) 4.31(s, 3H) 7.15(bd, 1H) 7.24(s, 1H) 7.44(s, 1H) 8.24(s, 1H) |
| B92-X00-M00(C01)-D03 hydrochloride | $^1$H NMR(400MHz, DMSO-d$_6$) δ ppm 1.52(s, 2H) 1.99(s, 2H) 2.78(t, J=7.56Hz, 2H) 2.98(t, J=7.62Hz, 2H) 3.01-3.76(m, 3H) 4.05(m, 1H) 4.30(s, 3H) 4.41(m, 1H) 7.27(s, 1H) 7.40(s, 1H) 7.47(s, 4H) 7.60(s, 1H) 8.25(s, 1H) |
| B95-X00-M00(C01)-D03 | $^1$H NMR(400MHz, DMSO-d$_6$) δ ppm 1.02(t, J=7.19Hz, 3H) 1.52(m, 2H) 1.90(m, 2H) 1.98(m, 2H) 2.35(q, J=7.07Hz, 2H) 2.73(t, J=7.56Hz, 2H) 2.89(d, J=11.71Hz, 2H) 2.94(t, J=7.62Hz, 2H) 3.66(m, 1H) 4.30(s, 3H) 7.00(d, J=7.93Hz, 1H) 7.23(s, 1H) 7.44(s, 1H) 8.21(s, 1H) |
| B73-X00-M00(C00)-D03 | $^1$H NMR(400MHz, DMSO-d$_6$) δ ppm 1.65(m, 6H) 1.94(m, 2H) 2.73(m, 2H) 2.95(t, J 7.62Hz, 2H) 4.17(m, 1H) 7.08(d, J 6.83Hz, 1H) 7.23(s, 1H) 7.43(s, 1H) 8.20(s, 1H) |
| B91-X00-M00(C00)-D03 | $^1$H NMR(400MHz, DMSO-d$_6$) δ ppm 1.36(m, 1H); 1.46(m, 1H); 1.90(m, 1H); 1.96(m, 1H); 2.02(s, 3H); 2.74(d, J=5Hz, 3H); 2.74(m, 2H); 2.75(m, 1H); 2.95(m, 2H); 3.16(m, 1H); 3.82(m, 1H); 3.95(m, 1H); 4.29(m, 1H); 4.31(s, 3H); 7.11(bs, 1H); 8.05(q, J=4.5Hz, 1H); 8.23(s, 1H) |
| B94-X00-M00(C01)-D03 | $^1$H NMR(400MHz, DMSO-d$_6$) δ ppm 1.53-1.68(m, 2H) 1.92-2.05(m, 2H) 2.52-2.62(m, 2H) 2.71(t, J=7.62Hz, 2H) 2.89-2.98(m, 2H) 3.53-3.63(m, 2H) 3.65-3.79(m, 1H) 4.24(s, 3H) 7.10(d, J=7.32Hz, 1H) 7.23(s, 1H) 7.41(s, 1H) 7.65-7.70(m, 2H) 7.72-7.78(m, 1H) 7.76-7.80(m, 2H) 8.19(s, 1H) |
| B73-X00-M00(C023)-D03 | $^1$H NMR(400MHz, DMSO-d$_6$) δ ppm 1.65(m, 6H) 1.94(m, 2H) 2.32(s, 6H) 2.73(m, 2H) 2.95(t, J 7.62Hz, 2H) 3.34(m, 2H) 4.17(m, 1H) 4.61(m, 2H) 7.08(d, J 6.83Hz, 1H) 7.23(s, 1H) 7.43(s, 1H) 8.20(s, 1H) |
| B73-X00-M00(C024)-D03 | $^1$H NMR(400MHz, DMSO-d$_6$) δ ppm 1.65(m, 6H) 1.94(m, 2H) 2.29(s, 6H) 2.50(m, 2H) 2.73(m, 2H) 2.95(t, J 7.62Hz, 2H) 4.17(m, 1H) 4.54(m, 2H) 7.08(d, J 6.83Hz, 1H) 7.23(s, 1H) 7.43(s, 1H) 8.20(s, 1H) |
| B79-X00-M00(C01)-D04 | $^1$H NMR(400MHz, DMSO-d$_6$) δ ppm 1.65-1.82(m, 2H) 2.05-2.16(m, 2H) 2.75(d, J=4.76Hz, 3H) 2.75-2.80(m, 2H) 2.97(t, J=7.68Hz, 2H) 3.01-3.09(m, 2H) 3.27-3.49(m, 2H) 3.93-4.10(m, 1H) 4.31(s, 3H) 7.59(s, 1H) 8.07(q, J=4.47Hz, 1H) 8.26(s, 1H) 8.44-8.63(m, 1H) 8.69-8.90(m, 1H) |
| B90-X00-M00(C01)-D04 | $^1$H NMR(400MHz, DMSO-d$_6$) δ ppm 1.48-1.62(m, 2H) 1.90(d, J=13.05Hz, 2H) 2.00-2.08(m, 2H) 2.21(s, 3H) 2.70-2.76(m, 2H) 2.74(d, J=4.76Hz, 3H) 2.78-2.84(m, 2H) 2.95(t, J=7.56Hz, 2H) 3.62-3.75(m, 1H) 4.31(s, 3H) 7.01(d, J=7.68Hz, 1H) 8.06(q, J=4.59Hz, 1H) 8.21(s, 1H) |
| B90-X00-M00(C01)-D27 | $^1$H NMR(400MHz, DMSO-d$_6$) δ ppm 2.68-2.82(m, 4H) 2.73 and 2.95(2t, 4H J 7.44Hz) 3.67(m, 1H) 4.30(s, 3H) 7.01(bs, 1H) 8.11(d, 1H, J 4.51Hz) 8.21(s, 1H) |
| B89-X00-M00(C01)-D04 | $^1$H NMR(400MHz, DMSO-d$_6$) δ ppm 1.20(t, J=7.07Hz, 3H) 1.41(m, 2H) 1.92(dd, J=12.68, 2.68Hz, 2H) 2.70-2.79(m, 5H) 2.95(t, J=7.68Hz, 4H) 3.84-3.99(m, 3H) 4.05(q, J=7.07Hz, 2H) 4.30(s, 3H) 7.09(d, J=5.98Hz, 1H) 8.06(q, J=4.39Hz, 1H) 8.22(s, 1H) |
| B91-X00-M00(C01)-D04 | $^1$H NMR(400MHz, DMSO-d$_6$) δ ppm 1.40(m, 2H) 1.94(m, 2H) 2.02(s, 3H), 2.74(m, 5H) 2.96(m, 2H) 3.16(m, 1H) 3.83(m, 1H) 3.94(m, 1H) 4.27(m, 1H) 4.31(s, 3H) 7.11(d, J 6.83Hz, 1H) 7.23(s, 1H) 7.44(s, 1H) 8.23(s, 1H) |
| B73-X00-M00(C01)-D04 hydrochloride | $^1$H NMR(400MHz, DMSO-d$_6$) δ ppm 1.58(m, 4H) 1.73(m, 2H) 1.97(m, 2H) 2.75(d, J=4.76Hz, 3H) 2.79(t, J=7.62Hz, 2H) 2.99(t, J=7.68Hz, 2H) 4.21(s, 1H) 4.32(s, 3H) 7.68-7.92(m, 1H) 8.12(q, J=4.39Hz, 1H) 8.24(s, 1H) |
| B100-X00-M00(C01)-D04 | $^1$H NMR(400MHz, DMSO-d$_6$) δ ppm 1.43-1.51(m, 2H) 1.91(dd, J=12.68, 3.17Hz, 2H) 2.21(s, 3H) 2.33(s, 4H) 2.71-2.76(m, 2H) 2.75(d, J=4.76Hz, 3H) 2.82-2.91(m, 2H) 2.95(t, J=7.62Hz, 2H) |

TABLE XI-continued

| | |
|---|---|
| | 3.12-3.18(m, 4H) 3.60(dt, J=13.32, 3.34Hz, 2H) 3.80-3.95(m, 1H) 4.30(s, 3H) 7.09(s, 1H) 8.06(q, J=4.63Hz, 1H) 8.22(s, 1H) |
| B92-X00-M00(C01)-D04 hydrochloride | $^1$H NMR(400MHz, DMSO-d$_6$) δ ppm 1.52(s, 2H) 1.99(s, 2H) 2.75(d, J=4.76Hz, 3H) 2.78(m, 2H) 2.98(t, J=7.68Hz, 2H) 3.06-3.79(m, 3H) 4.05(m, 1H) 4.30(s, 3H) 4.41(m, 1H) 7.37-7.43(m, 2H) 7.45-7.49(m, 3H) 7.60(s, 1H) 8.10(q, J=4.63Hz, 1H) 8.25(s, 1H) |
| B93-X00-M00(C01)-D04 | $^1$H NMR(400MHz, DMSOd$_6$) δ ppm 1.60(m, 2H) 2.01(m, 2H) 2.74(m, 5H) 289(m, 3H,) 2.95(m, 4H) 3.56(m, 2H.) 3.86(m, 1H) 4.31(s, 3H) 7.15(bd, 1H) 8.05(m, 1H) 8.24(s, 1H) |
| B96-X00-M00(C01)-D04 | $^1$H NMR(400MHz, DMSO-d$_6$) δ ppm 1.34-1.46(m, 2H) 1.42(s, 9H) 1.84-1.94(m, 2H) 2.71-2.77(m, 2H) 2.75(d, J=4.76Hz, 3H) 2.93(m, 4H) 3.94(m, 3H) 4.30(s, 3H) 7.09(d, J=4.15Hz, 1H) 8.07(m, 1H) 8.22(s, 1H) |
| B94-X00-M00(C01)-D04 | $^1$H NMR(400MHz, DMSO-d$_6$) δ ppm 1.60(m, 2H) 1.98(m, 2H) 2.53-2.61(m, 2H) 2.67-2.77(m, 2H) 2.74(d, J=4.76Hz, 3H) 2.93(m, 2H) 3.58(d, J=13.90Hz, 2H) 3.72(m, 1H) 4.24(s, 3H) 7.10(d, J=7.07Hz, 1H) 7.64-7.71(m, 2H) 7.72-7.77(m, 1H) 7.76-7.80(m, 2H) 8.04(q, J=4.59Hz, 1H) 8.19(s, 1H) |
| B73-X00-M00(C01)-D26 dihydrochloride | $^1$H NMR(400MHz, DMSO-d$_6$) δ ppm 1.58(m, 4H) 1.72(m, 2H) 1.97(m, 2H) 2.79(m, 2H) 2.86(m, 11H) 3.01(m, 2H) 3.81(s, 1H) 4.03(s, 1H) 4.21(m, 1H) 4.33(s, 3H) 7.70(m, 1H) 8.25(s, 1H) |
| B73-X00-M00(C01)-D10 dihydrochloride | $^1$H NMR(400MHz, DMSO-d$_6$) δ ppm 1.58(m, 4H) 1.72(m, 2H) 1.96(m, 2H) 2.79(m, 2H) 2.82(d, J=2.2Hz, 3H) 2.87(m, 2H) 3.0-3.7(m, 6H) 4.21(m, 1H) 4.32(s, 3H) 4.60(m, 1H) 4.80(m, 1H) 7.70(m, 1H) 8.26(s, 1H) |
| B73-X00-M00(C01)-D25 | $^1$H NMR(400MHz, DMSO-d$_6$) δ ppm 1.55(m, 4H) 1.71(m, 2H) 1.94(m, 2H) 2.76(m, 2H) 2.94(m, 2H) 4.17(m, 1H) 4.22(d, J=5.68Hz, 2H) 4.36(s, 3H) 7.10(bd, 1H) 8.22(s, 1H) 8.35(t, J=5.68Hz, 1H) |
| B73-X00-M00(C01)-D30 | $^1$H NMR(400MHz, DMSO-d$_6$) δ ppm 1.55(m, 4H) 1.71(m, 2H) 1.93(m, 2H) 2.74(m, 2H) 2.96(m, 2H) 3.81(d, J=5.68Hz, 2H) 4.17(m, 1H) 4.35(s, 3H) 7.07(m, 2H) 7.38(bs, 1H) 8.015(t, J=5.68Hz, 1H) 8.21(s, 1H) |
| B73-X00-M00(C01)-D05 | $^1$H NMR(400MHz, DMSO-d$_6$) δ ppm 1.46-1.61(m, 4H) 1.64-1.78(m, 2H) 1.87-2.01(m, 2H) 2.67-2.89(m, 4H) 3.35(s, 3H) 4.11-4.23(m, 1H) 4.31(s, 3H) 7.06(d, J=6.58Hz, 1H) 8.20(s, 1H) 9.88(s, 1H) |
| B73-X00-M00(C01)-D72 | $^1$H NMR(400MHz, DMSO-d$_6$) δ ppm 1.55(m, 4H) 1.71(m, 2H) 1.92(m, 2H) 2.23(s, 6H) 2.52(m, 2H) 2.71(m, 2H) 2.91(m, 4H) 4.37(s, 3H) 4.17(m, 1H) 5.09(m, 1H) 7.07(d, J 6.83Hz, 1H) 7.24(m, 1H) 7.33(s, 2H) 7.42(m, 2H) 8.20(s, 1H) 8.28(m, 1H) |
| B73-X00-M00(C01)-D163 | $^1$H NMR(400MHz, DMSO-d$_6$) δ ppm 1.08(m, 3H) 1.65(m, 6H) 1.94(m, 2H) 2.17(s, 6H) 2.45(m, 2H) 2.73(m, 2H) 2.95(m, 2H) 4.04(m, 1H) 4.17(m, 1H) 4.32(s, 3H) 7.08(d, J 6.83Hz, 1H) 7.91(d, 1H) 8.20(s, 1H) |
| B94-X00-M00(C01)-D72 | $^1$H NMR(400MHz, DMSO-d$_6$) δ ppm 1.61(m, 2H) 1.97(m, 2H) 2.23(s, 6H) 2.52(m, 2H) 2.55(m, 2H) 2.70(m, 2H) 2.90(m, 4H) 3.56(m, 2H) 3.72(m, 1H) 4.28(s, 3H) 5.10(m, 1H) 7.11(d, J 6.83Hz, 1H) 7.24(m, 1H) 7.33(m, 2H) 7.40(m, 2H) 7.68(m, 2H) 7.77(m, 3H) 8.18(s, 1H) 8.27(m, 1H) |
| B94-X00-M00(C01)-D163 | $^1$H NMR(400MHz, DMSO-d$_6$) δ ppm 1.14(m, 3H) 1.61(m, 2H) 2.00(m, 2H) 2.19(s, 6H) 2.52(m, 2H) 2.55(m, 2H) 2.72(m, 2H) 2.94(m, 2H) 3.57(m, 2H) 3.73(m, 1H) 4.10(m, 1H) 4.25(s, 3H) 7.09(m, 1H) 7.68(m, 2H) 7.77(m, 3H) 8.19(s, 1H) |
| B91-X00-M03(C01)-D03 | $^1$H NMR(400MHz, DMSO-d$_6$) δ ppm 1.32(s, 6H) 1.43(m, 2H) 1.94(m, 2H) 2.02(s, 3H) 2.62(s, 2H) 2.76(m, 1H) 3.16(m, 1H) 3.83(m, 1H) 3.94(m, 1H) 4.28(m, 1H) 4.29(s, 3H) 7.12(d, J=4.15Hz, 1H) 7.27(s, 1H) 7.53(s, 1H) 8.21(s, 1H) |
| B89-X00-M03(C01)-D03 hydrochloride | $^1$H NMR(400MHz, DMSO-d$_6$) δ ppm 1.20(t, J=7.07Hz, 3H) 1.34(s, 6H) 1.38-1.49(m, 2H) 1.89-1.99(m, 2H) 2.65(s, 2H) 2.90-3.04(m, 2H) 3.90-4.00(m, 3H) 4.06(q, J=7.07Hz, 2H) 4.29(s, 3H) 7.31(s, 1H) 7.57(s, 1H) 8.24(s, 1H) 8.41(s, 2H) |
| B73-X00-M03(C01)-D03 hydrochloride | $^1$H NMR(400MHz, DMSO-d$_6$) δ ppm 1.35(s, 6H) 1.51-1.77(m, 6H) 1.85-2.04(m, 2H) 2.67(s, 2H) |

TABLE XI-continued

| | |
|---|---|
| | 4.14-4.25(m, 1H) 4.31(s, 3H) 7.34(s, 1H) 7.60(s, 1H) 7.86(s, 1H) 8.23(s, 1H) |
| B92-X00-M03(C01)-D03 | $^1$H NMR(400MHz, DMSO-$d_6$) δ ppm 1.32(s, 6H) 1.50(m, 2H) 1.99(m, 2H) 2.62(s, 2H) 3.10(m, 2H) 3.62(m, 1H) 4.01(m, 1H) 4.29(s, 3H) 4.40(m, 1H) 7.15(s, 1H) 7.27(s, 1H) 7.38(m, 2H) 7.47(m, 3H) 7.53(s, 1H) 8.22(s, 1H) |
| B94-X00-M03(C01)-D03 | $^1$H NMR(400MHz, DMSO-$d_6$) δ ppm 1.29(s, 6H) 1.60(m, 2H) 1.99(m, 2H) 2.52(s, 2H) 2.59(m, 2H) 2.75(d, J=4.51Hz, 3H) 3.57(m, 2H) 3.71(m, 1H) 4.22(s, 3H) 7.11(s, 1H) 7.68(m, 2H) 7.77(m, 3H) 8.11(m, 1H) 8.18(s, 1H) |
| B93-X00-M03(C01)-D03 | $^1$H NMR(400MHz, DMSO-$d_6$) δ ppm 1.32(s, 6H) 1.60(m, 2H) 2.02(m, 2H) 2.62(s, 2H) 2.89(m, 5H) 3.55(m, 2H) 3.85(m, 1H) 4.30(s, 3H) 7.15(bd, 1H) 7.27(s, 1H) 7.53(s, 1H) 8.22(s, 1H) |
| B91-X00-M03(C01)-D04 | $^1$H NMR(400MHz, DMSO-$d_6$) δ ppm 1.32(s, 6H) 1.34-1.52(m, 2H) 1.87-2.00(m, 2H) 2.02(s, 3H) 2.62(s, 2H) 2.71-2.84(m, 1H) 2.76(d, J=4.76Hz, 3H) 3.10-3.22(m, 2H) 3.83(d, J=12.93Hz, 1H) 3.89-4.02(m, 1H) 4.23-4.35(m, 1H) 4.30(s, 3H) 7.13(d, J=4.88Hz, 1H) 8.13(q, J=4.72Hz, 1H) 8.22(s, 1H) |
| B73-X00-M03(C01)-D04 hydrochloride | $^1$H NMR(400MHz, DMSO-$d_6$) δ ppm 1.34(s, 6H) 1.50-1.65(m, 4H) 1.67-1.78(m, 2H) 1.88-2.08(m, 2H) 2.67(s, 2H) 2.76(d, J=4.63Hz, 3H) 4.09-4.24(m, 1H) 4.31(s, 3H) 7.84(s, 1H) 8.20(q, J=4.51Hz, 1H) 8.23(s, 1H) |
| B92-X00-M03(C01)-D04 | $^1$H NMR(400MHz, DMSO-$d_6$) δ ppm 1.31(s, 6H) 1.50(m, 2H) 1.99(m, 2H) 2.62(s, 2H) 2.75(d, J=4.51Hz, 3H) 3.14(m, 2H) 3.63(m, 1H) 4.01(m, 1H) 4.29(s, 3H) 4.43(m, 1H) 7.15(s, 1H) 7.39(m, 2H) 7.47(m, 3H) 8.13(m, 1H) 8.22(s, 1H) |
| B94-X00-M03(C01)-D04 | $^1$H NMR(400MHz, DMSO-$d_6$) δ ppm 1.29(s, 6H) 1.60(m, 2H) 1.99(m, 2H) 2.52(s, 2H) 2.59(m, 2H) 2.75(d, J=4.51Hz, 3H) 3.57(m, 2H) 3.71(m, 1H) 4.22(s, 3H) 7.11(s, 1H) 7.68(m, 2H) 7.77(m, 3H) 8.11(m, 1H) 8.18(s, 1H) |
| B93-X00-M03(C01)-D04 | $^1$H NMR(400MHz, DMSO-$d_6$) δ ppm 1.32(s, 6H) 1.60(m, 2H) 2.02(m, 2H) 2.62(s, 2H) 2.75(d, 3H) 2.89(m, 5H) 3.55(m, 2H) 3.85(m, 1H) 4.30(s, 3H) 7.16(bd, 1H) 8.13(d, 1H) 8.22(s, 1H) |
| B89-X00-M03(C01)-D25 | $^1$H NMR(400MHz, DMSO-$d_6$) δ ppm 1.20(t, J=7.13Hz, 3H) 1.33(s, 6H) 1.35-1.50(m, 2H) 1.93(m, 2H) 2.64(s, 2H) 2.86-3.06(m, 2H) 3.84-4.00(m, 3H) 4.05(q, J=7.07Hz, 2H) 4.25(d, J=5.73Hz, 2H) 4.33(s, 3H) 7.14(s, 1H) 8.23(s, 1H) 8.92(t, J=5.79Hz, 1H) |
| B89-X00-M03(C01)-D138 | $^1$H NMR(400MHz, DMSO-$d_6$) δ ppm 1.20(t, J=7.13Hz, 3H) 1.22(s, 6H) 1.42(m, 2H) 1.94(m, 2H) 2.62(s, 2H) 3.0(m, 5H) 3.54(m, 2H) 3.63(m, 2H) 3.95(m, 3H) 4.05(q, J=7.07Hz, 2H) 4.33(s, 3H) 7.14(s, 1H) 8.23(s, 1H) 8.92(t, J=5.79Hz, 1H) |

In Table XII below See the HPLC/Mass Data for some Representative Compounds of the Invention

TABLE XII

| | M + H | Time | Method |
|---|---|---|---|
| B89-X00-M03(C01)-D05 | 444.23 | 2.07 | 2 |
| B89-X00-M03(C01)-D31 | 500.29 | 2.6 | 2 |
| B89-X00-M03(C01)-D32 | 500.29 | 2.44 | 2 |
| B89-X00-M03(C01)-D33 | 498.24 | 2.85 | 2 |
| B89-X00-M03(C01)-D136 | 541.32 | 1.73 | 2 |
| B89-X00-M03(C01)-D137 | 515.3 | 1.79 | 2 |
| B89-X00-M03(C01)-D17 | 555.33 | 1.88 | 2 |
| B89-X00-M03(C01)-D76 | 541.32 | 2 | 2 |
| B89-X00-M03(C01)-D78 | 486.28 | 2.29 | 2 |
| B89-X00-M03(C01)-D79 | 516.29 | 1.91 | 2 |
| B89-X00-M03(C01)-D14 | 496.3 | 3.16 | 2 |
| B89-X00-M03(C01)-D80 | 486.28 | 2.21 | 2 |
| B89-X00-M03(C01)-D44 | 519.28 | 2.49 | 2 |
| B89-X00-M03(C01)-D81 | 539.34 | 1.98 | 2 |
| B89-X00-M03(C01)-D12 | 486.28 | 2.55 | 2 |
| B89-X00-M03(C01)-D25 | 467.24 | 2.66 | 2 |
| B89-X00-M03(C01)-D82 | 486.28 | 2.27 | 2 |
| B89-X00-M03(C01)-D83 | 530.26 | 2.41 | 2 |
| B89-X00-M03(C01)-D84 | 519.28 | 2.66 | 2 |
| B89-X00-M03(C01)-D85 | 487.27 | 2.18 | 2 |
| B89-X00-M03(C01)-D60 | 548.29 | 2.83 | 2 |
| B89-X00-M03(C01)-D86 | 499.31 | 1.8 | 2 |
| B89-X00-M03(C01)-D87 | 548.29 | 2.94 | 2 |
| B89-X00-M03(C01)-D88 | 510.31 | 3.37 | 2 |
| B89-X00-M03(C01)-D89 | 481.26 | 2.51 | 2 |
| B89-X00-M03(C01)-D90 | 504.24 | 3.03 | 2 |
| B89-X00-M03(C01)-D91 | 514.27 | 2.82 | 2 |
| B89-X00-M03(C01)-D92 | 498.28 | 2.25 | 2 |
| B89-X00-M03(C01)-D93 | 540.32 | 2.49 | 2 |
| B89-X00-M03(C01)-D94 | 474.26 | 2.65 | 2 |
| B89-X00-M03(C01)-D04 | 442.25 | 2.48 | 2 |
| B89-X00-M03(C01)-D95 | 502.27 | 2 | 2 |
| B89-X00-M03(C01)-D34 | 548.29 | 2.8 | 2 |
| B89-X00-M03(C01)-D96 | 510.24 | 3.09 | 2 |
| B89-X00-M03(C01)-D97 | 486.28 | 2.27 | 2 |
| B89-X00-M03(C01)-D45 | 519.28 | 2.52 | 2 |

TABLE XII-continued

| | M + H | Time | Method |
|---|---|---|---|
| B89-X00-M03(C01)-D98 | 500.29 | 2.43 | 2 |
| B89-X00-M03(C01)-D99 | 528.29 | 2.86 | 2 |
| B89-X00-M03(C01)-D100 | 526.31 | 2.22 | 2 |
| B89-X00-M03(C01)-D06 | 472.26 | 2.15 | 2 |
| B89-X00-M03(C01)-D101 | 514.31 | 2.62 | 2 |
| B89-X00-M03(C01)-D102 | 456.26 | 2.67 | 2 |
| B89-X00-M03(C01)-D103 | 512.29 | 2.03 | 2 |
| B89-X00-M03(C01)-D104 | 486.28 | 2.27 | 2 |
| B89-X00-M03(C01)-D105 | 512.2 | 2.15 | 2 |
| B89-X00-M03(C01)-D106 | 498.31 | 3.22 | 2 |
| B89-X00-M03(C01)-D107 | 512.25 | 2.52 | 2 |
| B89-X00-M03(C01)-D108 | 615.33 | 2.98 | 2 |
| B89-X00-M03(C01)-D109 | 561.32 | 3.4 | 2 |
| B89-X00-M03(C01)-D110 | 515.27 | 1.99 | 2 |
| B89-X00-M03(C01)-D111 | 528.32 | 2.76 | 2 |
| B89-X00-M03(C01)-D112 | 533.29 | 2.76 | 2 |
| B89-X00-M03(C01)-D113 | 512.29 | 2.27 | 2 |
| B89-X00-M03(C01)-D114 | 583.33 | 2.9 | 2 |
| B89-X00-M03(C01)-D115 | 525.32 | 1.91 | 2 |
| B89-X00-M03(C01)-D116 | 539.34 | 1.95 | 2 |
| B89-X00-M03(C01)-D117 | 514.31 | 2.64 | 2 |
| B89-X00-M03(C01)-D118 | 500.29 | 2.52 | 2 |
| B89-X00-M03(C01)-D119 | 502.27 | 2.02 | 2 |
| B89-X00-M03(C01)-D120 | 482.28 | 3.06 | 2 |
| B89-X00-M03(C01)-D121 | 553.32 | 2.32 | 2 |
| B89-X00-M03(C01)-D122 | 526.31 | 2.38 | 2 |
| B89-X00-M03(C01)-D123 | 498.28 | 2 | 2 |
| B89-X00-M03(C01)-D124 | 456.26 | 2.25 | 2 |
| B89-X00-M03(C01)-D125 | 602.26 | 3.64 | 2 |
| B89-X00-M03(C01)-D126 | 584.3 | 3.2 | 2 |
| B89-X00-M03(C01)-D127 | 603.33 | 3.08 | 2 |
| B89-X00-M03(C01)-D128 | 565.35 | 1.99 | 2 |
| B89-X00-M03(C01)-D129 | 527.34 | 1.91 | 2 |
| B89-X00-M03(C01)-D130 | 541.35 | 1.93 | 2 |
| B89-X00-M03(C01)-D131 | 525.32 | 1.78 | 2 |
| B89-X00-M03(C01)-D132 | 616.36 | 2.25 | 2 |
| B89-X00-M03(C01)-D133 | 603.33 | 3.37 | 2 |
| B89-X00-M03(C01)-D134 | 521.29 | 3.11 | 2 |
| B89-X00-M03(C01)-D135 | 498.28 | 2.03 | 2 |

Example 33

Ethyl 1-methyl-8-(pyrrolidin-3-ylamino)-4,5-dihydro-1H-pyrazolo[4,3-h]quinazoline-3-carboxylate [B99-X00-M00(C01)-D03]

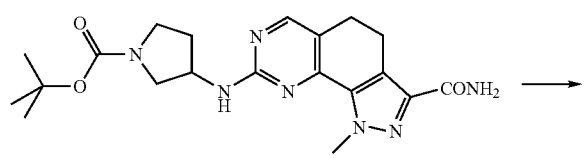

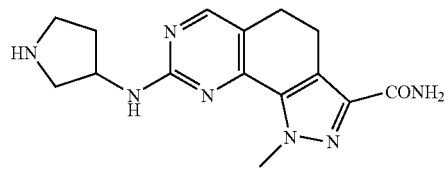

A solution of 110 mg (0.27 mmol) of ethyl 8-{[1-(tert-butoxycarbonyl)pyrrolidin-3-yl]amino}-1-methyl-4,5-dihydro-1H-pyrazolo[4,3-h]quinazoline-3-carboxylate in a mixture dichoromethane-trifluoroacetic acid 9/1 was stirred at room temperature for 6 hours. The solvent was then removed in vacuo and the resulting oil taken up with dichloromethane and washed with aqueous NaHCO$_3$. The organic layer was dried over Na$_2$SO$_4$ and evaporated. The residue was triturated with diethylether giving 83 mg (60% yield) of the title compound.

$^1$H NMR (400 MHz, DMSO-d$_6$) δ ppm 1.98-2.11 (m, 1 H) 2.22 (s, 1 H) 2.77 (t, J=7.62 Hz, 2 H) 2.92-3.02 (m, 2 H) 3.14-3.55 (m, 4 H) 4.31 (s, 3 H) 4.44-4.57 (m, 1 H) 7.27 (s, 2 H) 8.29 (s, 1 H) 8.76 (s, 1 H)

Analogously the following compound was prepared:

N,1-dimethyl-8-(piperidin-4-ylamino)-4,5-dihydro-1H-pyrazolo[4,3-h]quinazoline-3-carboxamide [B79-X00-M00(C01)-D03]

$^1$H NMR (400 Hz, DMSO-d$_6$) δ ppm 1.65-1.82 (m, 2 H) 2.05-2.16 (m, 2 H) 2.75 (d, J=4.76 z, 3 H) 2.75-2.80 (m, 2 H) 2.97 (t, J=7.68 Hz, 2 H) 3.01-3.09 (m, 2 H) 3.27-3.49 (m, 2 H) 3.93-4.10 (m, 1 H) 4.31 (s, 3 H) 7.59 (s, 1 H) 8.07 (q, J=4.47 Hz, 1 H) 8.26 (s, 1 H) 8.44-8.63 (m, 1 H) 8.69-8.90 (m, 1 H).

Example 34

1-methyl-8-(piperidin-4-ylamino)-4,5-dihydro-1H-pyrazolo[4,3-h]quinazoline-3-carboxamide [B79-X00-M00(C01)-D03]

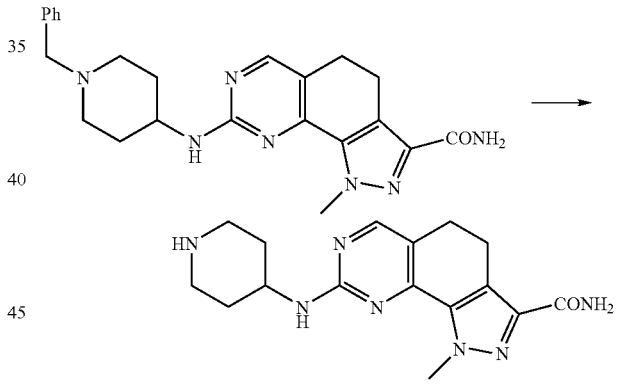

To a solution of 1 g (2.4 mmol) of 8-[(1-benzylpiperidin-4-yl)amino]-1-methyl-4,5-dihydro-1H-pyrazolo[4,3-h]quinazoline-3-carboxamide in 90 mL of absolute ethanol 1 g of palladium on charcoal 10% w and 30 mL of 98% formic acid were added. The resulting mixture was stirred at 60° C. for 12 hours. The catalyst was then filtered on celite and the filtrate evaporated. The crude was purified by chromatography on a silica gel column eluted with a mixture CH$_2$Cl$_2$-MeOH-Et$_3$N, giving 350 mg (45% yield) of the title compound.

$^1$H NMR (400 MHz, DMSO-d$_6$) δ ppm 1.65-1.77 (m, 2 H) 2.04-2.17 (m, 2 H) 2.75 (t, J=7.56 Hz, 2 H) 2.96 (t, J=7.56 Hz, 2 H) 2.99-3.09 (m, 2 H) 3.28-3.44 (m, 2 H) 3.93-4.08 (m, 1 H) 4.31 (s, 3 H) 7.25 (s, 1 H) 7.31 (d, J=7.56 Hz, 1 H) 7.43 (s, 1 H) 8.25 (s, 1 H).

Example 35

8-[(1-formylpiperidin-4-yl)amino]-1-methyl-4,5-dihydro-1H-pyrazolo[4,3-h]quinazoline-3-carboxamide [B169-X00-M00(C01)-D03]

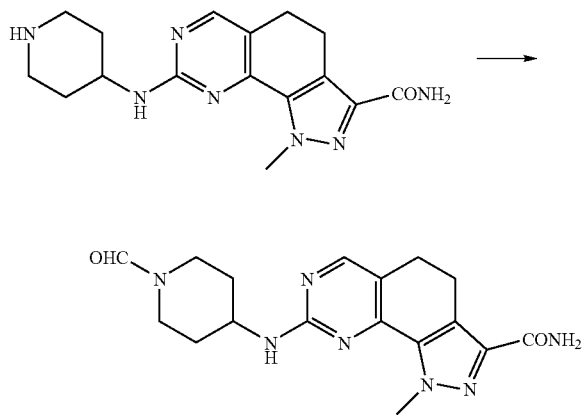

500 mg (1.53 mmol) of 1-methyl-8-(piperidin-4-ylamino)-4,5-dihydro-1H-pyrazolo[4,3-h]quinazoline-3-carboxamide were dissolved in 10 mL of dimethylformamide, containing 253 mg (1.68 mmol) of tert-butyldimethylsilyl chloride, 0.26 mL of triethylamine and 7 mg of 4-dimethylaminopyridine (0.06 mmol), and the mixture stirred at 35-40° C. for 25 hours under nitrogen. The mixture was then partitioned between dichloromethane and water, the organic layer was separated, washed with brine and dried over sodium sulfate. Evaporation of the volatiles in vacuo afforded 435 mg (80% yield) of the title compound.

$^1$H NMR (400 MHz, DMSO-$d_6$) δ ppm 1.25-1.48 (m, 2 H) 1.88-2.03 (m, 2 H) 2.74 (t, J=7.68 Hz, 2 H) 2.77-2.87 (m, 1 H) 2.95 (t, J=7.62 Hz, 2 H) 3.10-3.20 (m, 1 H) 3.66-3.79 (m, 1 H) 3.93-4.05 (m, 1 H) 4.09-4.17 (m, 1 H) 4.31 (s, 3 H) 7.13 (d, J=6.83 Hz, 1 H) 7.23 (s, 1 H) 7.44 (s, 1 H) 8.01 (s, 1 H) 8.23 (s, 1 H).

Example 36

8-(cyclopentylamino)-1-piperidin-4-yl-4,5-dihydro-1H-pyrazolo[4,3-h]quinazoline-3-carboxamide [B73-X00-M00(C18)-D03]

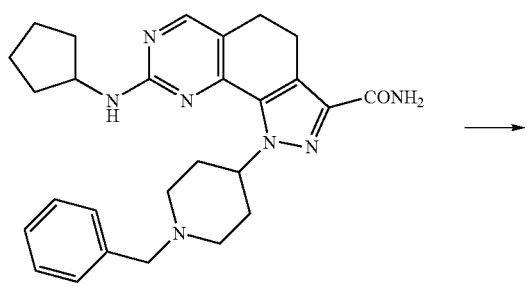

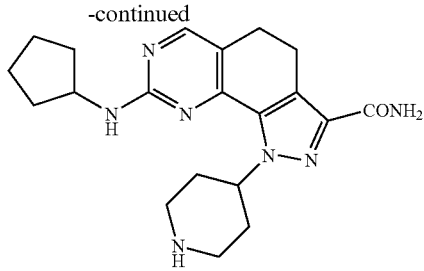

500 mg (1.1 mmol) of 1-(1-benzylpiperidin-4-yl)-8-(cyclopentylamino)-4,5-dihydro-1H-pyrazolo[4,3-h]quinazoline-3-carboxamide were dissolved in 50 mL of acetic acid and 50 mg of PtO$_2$ were added. The mixture was submitted to hydrogenation at 60 psi at room temperature. After 12 hors the catalyst was filtered on celite and the filtrate evaporated. The residue was redissolved with dicholoromethane and washed with aqueous NaHCO$_3$. The organic layer was dried over sodium sulfate and the solvent removed under reduced pressure. The title compound (80% yield) was collected by filtration after trituration with diethylether.

Example 37

8-(cyclopentylamino)-N-hydroxy-N,1-dimethyl-4,5-dihydro-1H-pyrazolo[4,3-h]quinazoline-3-carboxamide [B73-X00-M00(C01)-D142]

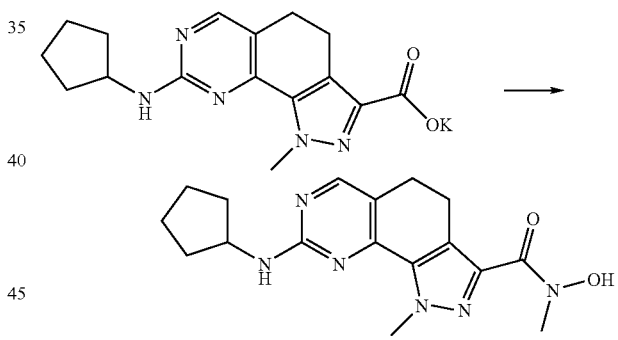

To a suspension of 400 mg (1.14 mmol) of potassium 8-(cyclopentylamino)-1-methyl-4,5-dihydro-1H-pyrazolo[4,3-h]quinazoline-3-carboxylate in 80 mL of dichloromethane and a few drops of dimethylformamide 0.11 mL (0.13 mmol) of oxalyl chloride were added at 0° C. The mixture was stirred at room temperature for 6 hours and then evaporated, redissolved in anhydrous dichloromethane and dropped into a solution of 344 mg (2.28 mmol) of N-methylhydroxylamine hydrochloride and 0.33 mL of triethylamine in 20 mL of the same solvent, cooled to 0° C. After 4 hours the mixture was washed with a saturated solution of sodium hydrogenocarbonate, dried over sodium sulfate and evaporated to dryness. The residue was triturated with diethylether and filtered to give 780 mg (60% yield) of the title compound.

$^1$H NMR (400 MHz, DMSO-$d_6$) δ ppm 1.46-1.61 (m, 4 H) 1.64-1.78 (m, 2 H) 1.87-2.01 (m, 2 H) 2.67-2.89 (m, 4 H) 3.35 (s, 3 H) 4.11-4.23 (m, 1 H) 4.31 (s, 3 H) 7.06 (d, J=6.58 Hz, 1 H) 8.20 (s, 1 H) 9.88 (s, 1 H).

Analogously, but employing the suitable hydroxylamino derivatives, the following compounds were prepared:

N-cyclohexyl-8-(cyclopentylamino)-N-hydroxy-1-methyl-4,5-dihydro-1H-pyrazolo[4,3-h]quinazoline-3-carboxamide [B73-X00-M00(C01)-D29]

$^1$H NMR (400 MHz, DMSO-$d_6$) δ ppm 0.96-2.04 (m, 18 H) 2.67-2.81 (m, 4 H) 4.04-4.45 (m, 2 H) 4.30 (s, 3 H) 6.97-7.10 (m, 1 H) 8.20 (s, 1 H) 9.45 (s, 1 H);

N-benzyl-8-(cyclopentylamino)-N-hydroxy-1-methyl-4,5-dihydro-1H-pyrazolo[4,3-h]quinazoline-3-carboxamide [B73-X00-M00(C01)-D28]

$^1$H NMR (400 MHz, DMSO-$d_6$) δ ppm 1.51-1.61 (m, 4 H) 1.64-1.79 (m, 2 H) 1.87-2.00 (m, 2 H) 2.70-2.88 (m, 4 H) 4.08-4.22 (m, 1 H) 4.31 (s, 3 H) 5.01 (s, 2 H) 7.06 (d, J=6.58 Hz, 1 H) 7.22-7.43 (m, 5 H) 8.21 (s, 1 H) 9.89 (s, 1 H).

Example 38

8-anilino-N-hydroxy-1-methyl-4,5-dihydro-1H-pyrazolo[4,3-h]quinazoline-3-carboxamide [B04-X00-M00(C01)-D05]

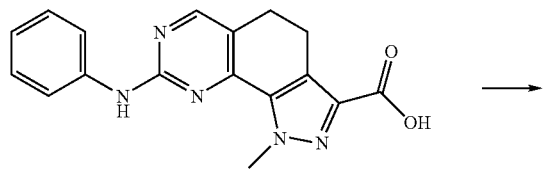

To a solution of 260 mg (0.81 mmol) of 8-anilino-1-methyl-4,5-dihydro-1H-pyrazolo[4,3-h]quinazoline-3-carboxylic acid in 50 mL of anhydrous dimethylformamide 111 mg of N-hydroxybenzotriazole (0.81 mmol), 0.16 mL of N-methylmorpholine, 205 mg (1.07 mmol) of N-(3-dimethylaminopropyl)-N'-ethylcarbodiimide hydrochloride and 585 mg (2.13 mmol) of triphenylmethylhydroxylanine were added consecutively. After 48 hours at room temperature the solvent was removed under reduced pressure and the residue taken up with dichoromethane and washed with water. The organic layer was then dried over sodium sulfate and evaporated. The crude was treated with 10 mL of a mixture dichloromethane-trifluoroacetic acid and after 4 hours the volatiles were removed in vacuo. The residue was redissolved with dichloromethane and washed with aqueous NaHCO$_3$ and the product purified by chromatography on a silica gel column, eluted with CH$_2$Cl$_2$—CH$_3$COCH$_3$ 4/1, to give 180 mg (66% yield) of the title compound.

$^1$H NMR (400 MHz, DMSO-$d_6$) δ ppm 2.80-2.91 (m, 2 H) 2.93-3.06 (m, 2 H) 4.33 (s, 3 H) 6.97 (tt, J=7.35, 1.07 Hz, 1 H) 7.31 (dd, J=8.47, 7.38 Hz, 2 H) 7.72 (dd, J=8.66, 1.10 Hz, 2 H) 8.42 (s, 1 H) 8.91 (s, 1 H) 9.52 (s, 1 H) 10.93 (s, 1 H)

Example 39

8-iodo-1-methyl-4,5-dihydro-1H-pyrazolo[4,3-h]quinazoline-3-carboxamide [B73-X00-M00(C01)-D03]

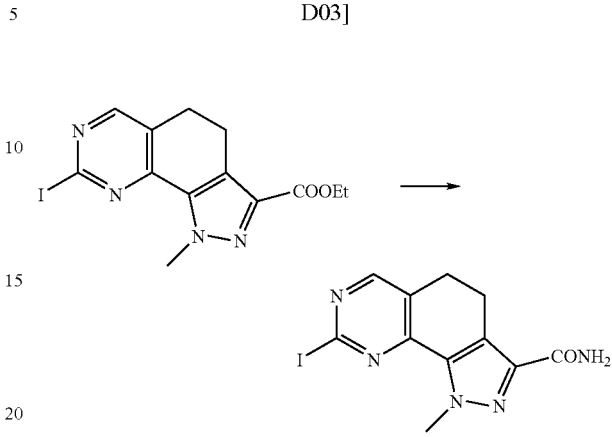

1.0 g (2.6 mmol) of ethyl 8-iodo-1-methyl-4,5-dihydro-1H-pyrazolo[4,3-h]quinazoline-3-carboxylate were dissolved in a mixture of 100 mL of methanol and 100 mL of ammonium hydrate 33%. The solution was stirred in a close bottle at 60° C. for 4 hours. The resulting precipitate was collected giving 0.5 g (54% yield) of the title compound.

$^1$H NMR (400 MHz, DMSO-$d_6$) δ ppm 2.99 (m, 4 H) 4.25 (s, 3 H) 7.31 (s, 1 H) 7.51 (s, 1 H) 8.47 (s, 1 H)

Example 40

1-methyl-8-[(1-methylpiperidin-4-yl)amino]-4,5-dihydro-1H-pyrazolo[4,3-h]quinazoline-3-carboxamide [B90-X00-M00(C01)-D03]

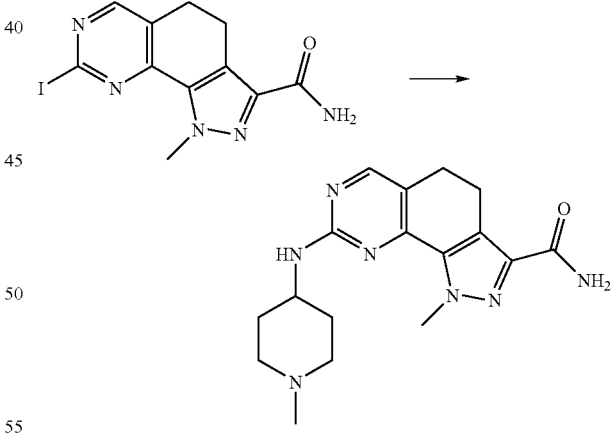

8-iodo-1-methyl-4,5-dihydro-1H-pyrazolo[4,3-h]quinazoline-3-carboxamide (0.10 g, 0.28 mmol) and 1-methylpiperidin-4-amine (0.19 g, 1.7 mmol) were heated at 80° C. under nitrogen for 3 hours. The mixture was concentrated under reduced pressure and the residue was purified by chromatography on a silica gel column (eluant: dichloromethane/ethanol/ammonium hydroxide 90/10/1) to give 0.047 mg of 1-methyl-8-[(1-methylpiperidin-4-yl)amino]-4,5-dihydro-1H-pyrazolo[4,3-h]quinazoline-3-carboxamide (50% yield).

$^1$H NMR (400 MHz, DMSO-$d_6$) δ ppm 1.54 (m, 2 H) 1.91 (m, 2 H) 2.06 (m, 2 H) 2.4 (s, 3 H) 2.73 (m, 2 H) 2.83 (m, 2 H)

2.94 (m, 2 H) 3.70 (m, 1 H) 4.30 (s, 3 H) 7.01 (m, 1 H) 7.25 (s, 1 H) 7.44 (s, 1 H) 8.29 (s, 1 H)

Example 41

[8-(cyclohexylamino)-1-methyl-4,5-dihydro-1H-pyrazolo[4,3-h]quinazolin-3-yl](phenyl)methanone [B27-X00-M01(C01)-D07] and [8-(cyclohexylamino)-1-methyl-1H-pyrazolo[4,3-h]quinazolin-3-yl](phenyl)methanone [B27-X00-M01(C01)-D07]

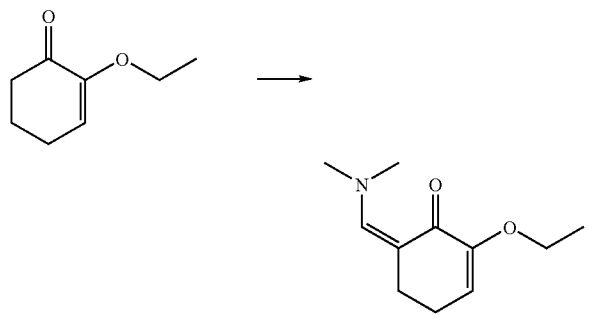

Step 1. 6-[(dimethylamino)methylene]-2-ethoxycyclohex-2-en-1-one

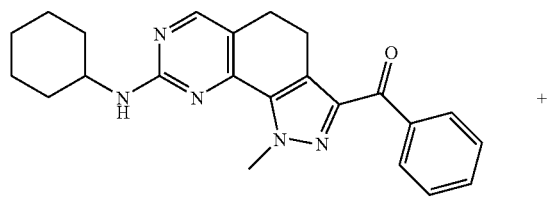

3.4 g (0.02 mmol) of 2-ethoxycyclohex-2-en-1-one were dissolved in 30 mL of dry dimethylformamide and 30 mL (0.05 mmol) of dimethylformamide dimethyl acetale were added. The solution was stirred at 60° C. for 2 hours. The solvent was then evaporated under vacuum, the residue triturated with diethyl ether and collected by filtration to give 6.6 g of the title compound (80% yield).

Step 2. 2-(benzylthio)-4-ethoxy-5,6-dihydroquinazoline

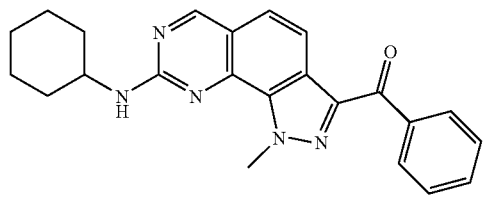

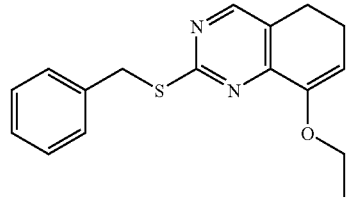

To a solution of 2.0 g (0.01 mol) of 6-[(dimethylamino)methylene]-2-ethoxycyclohex-2-en-1-one in 20 mL of dimethylformamide 2.6 g of S-benzylisothiourea (2 eq.mol.) were added. The reaction mixture was stirred at 95° C. for 4 hours. The solvent was then evaporated under reduced pressure and the crude purified by chromatography on a silica gel column (eluant dichloromethane/methanol 9/1) leading 1.5 g (50% yield) of the title compound.

Step 3. 2-(benzylthio)-6,7-dihydroquinazolin-8(5 H)-one

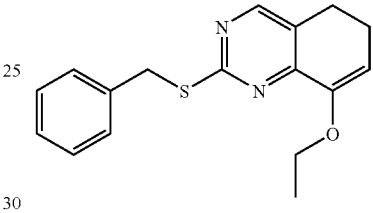

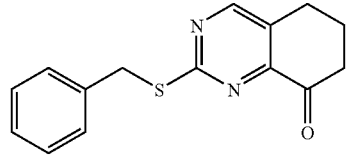

1.5 g (5 mmol) of 2-(benzylthio)-8-ethoxy-5,6-dihydroquinazoline were dissolved in 50 mL of acetic acid and 3 mL of water. The solution was stirred at refluxing temperature for 4 hours. The solvent was then removed under vacuum, the residue partitioned between dichloromethane and a NaHCO$_3$ saturated solution. The organic layer was dried over anhydrous Na$_2$SO$_4$ and concentrated, giving 1.0 g (74% yield) of the title compound.

Step 4. 1-[2-(benzylthio)-8-oxo-5,6,7,8-tetrahydroquinazolin-7-yl]-2-phenylethane-1,2-dione

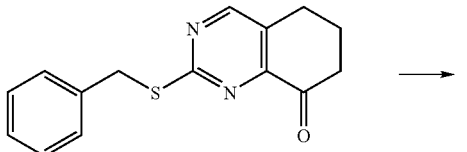

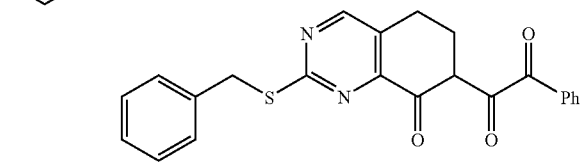

To a solution of 0.22 g (0.81 mmol) of 2-(benzylthio)-6,7-dihydroquinazolin-8(5 H)-one in 5 mL of dry tetrahydrofuran cooled to −50° C., 0.10 g of sodium hydride 60% in mineral oil were added. The resulting suspension was maintained at the same temperature for 30 minutes and then 0.59 mL of ethyl α-oxobenzeneacetate (PhCOCOOEt) were added and the reaction mixture allowed to come to room temperature. After 16 hours the mixture was partitioned between water and ethyl acetate and the organic layer was dried over $Na_2SO_4$ and evaporated to dryness. The residue was purified by chromatography on a silica gel column (eluant hexane/ethyl acetate 7/3) giving 0.22 g (68% yield) of the title compound.

Step 5. [8-(benzylthio)-1-methyl-4,5-dihydro-1H-pyrazolo[4,3-h]quinazolin-3-yl](phenyl)methanone [B05-X04-M00(C01)-D07]

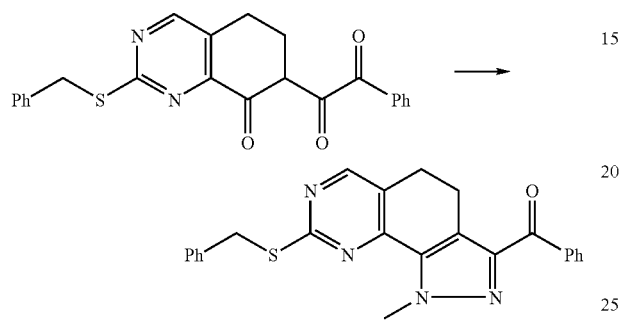

0.22 g (0.55 mmol) of 1-[2-(benzylthio)-8-oxo-5,6,7,8-tetrahydroquinazolin-7-yl]-2-phenylethane-1,2-dione were dissolved in 6 mL of ethanol and 0.03 g (0.66 mmol) of is methyl hydrazine were added. The reaction mixture was maintained under stirring at refluxing temperature for 5 hours. After that time the solvent was removed under reduced pressure, the residue redissolved with dichloromethane and washed with water. The organic layer was dried over $Na_2SO_4$ and concentrated, giving 0.16 g of the title compound (70% yield).

Step 6. [8-(benzylsulfonyl)-1-methyl-4,5-dihydro-1H-pyrazolo[4,3-h]quinazolin-3-yl](phenyl)methanone [B05-X05-M00(C01)-D07]

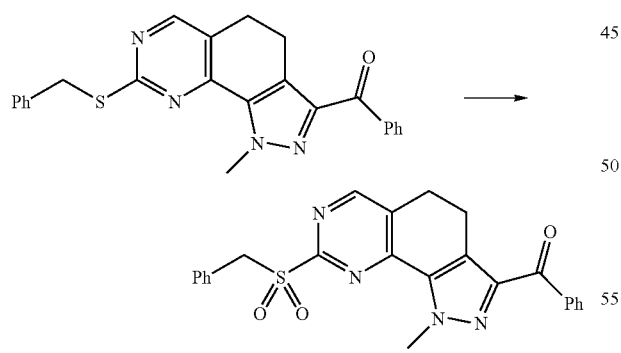

To a solution of 70 mg (0.17 mmol) of [8-(benzylthio)-1-methyl-4,5-dihydro-1H-pyrazolo[4,3-h]quinazolin-3-yl](phenyl)methanone in 3 mL of dichloromethane, 115 mg (0.34 mmol) of m-chloroperbenzoic acid were added. The reaction mixture was maintained at room temperature for 1 hour. The solution was then washed with aqueous $NaHCO_3$ and the organic layer was dried over $Na_2SO_4$ and evaporated in vacuo, giving 70 mg (93% yield) of the title compound.

Step 7. [8-(cyclohexylamino)-1-methyl-4,5-dihydro-1H-pyrazolo[4,3-h]quinazolin-3-yl](phenyl)methanone [B27-X00-M00(C01)-D07] and [8-(cyclohexylamino)-1-methyl-1H-pyrazolo[4,3-h]quinazolin-3-yl](phenyl)methanone [B27-X00-M01(C01)-D07]

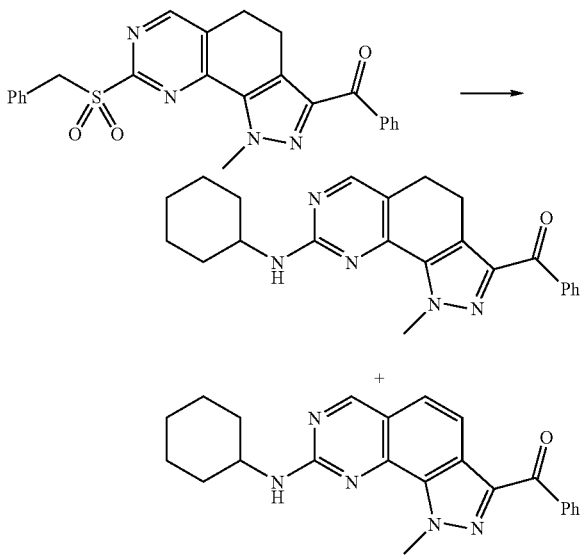

83 mg (0.19 mmol) of [8-(benzylsulfonyl)-1-methyl-4,5-dihydro-1H-pyrazolo[4,3-h]quinazolin-3-yl](phenyl)methanone were dissolved in 3 mL of dimethylsulfoxide and cyclohexylamine (0.033 mL, 0.29 mmol) and the solution was heated at 100° C. under stirring for 16 hours. The solvent was then removed under reduced pressure and the crude purified by chromatography on a silica gel column (eluant dichloromethane/acetone) giving 31 mg of [8-(cyclohexylamino)-1-methyl-4,5-dihydro-1H-pyrazolo[4,3-h]quinazolin-3-yl](phenyl)methanone and 15 mg of [8-(cyclohexylamino)-1-methyl-1H-pyrazolo[4,3-h]quinazolin-3-yl](phenyl)methanone (70% yield overall).

B27-X00-M00(C01)-D07

$^1$H NMR (400 MHz, DMSO-$d_6$) δ ppm 1.00-2.00 (5m, 11 H) 2.61 (m, 2 H) 2.66 (m, 2 H) 3.80 (s, 3 M) 7.17 (bs, 1 H) 7.34-7.37 (m, 3 H) 7.41-7.51 (m, 3 H) 8.27 (s, 1 H);

B27-X00-M01(C01)-D07

$^1$H NMR (400 MHz, DMSO-$d_6$) δ ppm 1.20-2.20 (5m, 11 H) 4.02 (bs, 3 H) 6.69 (m, 1 H) 7.37-7.58 (2m, 6 H) 7.93 (bs, 1 H) 8.83 (bs, 1 H).

Example 42

Ethyl 1-methyl-8-pyridin-2-ylamino)-4,5-dihydro-1H-pyrazolo[4,3-h]quinazoline-3-carboxylate [B15-X00-M00(C01)-D01]

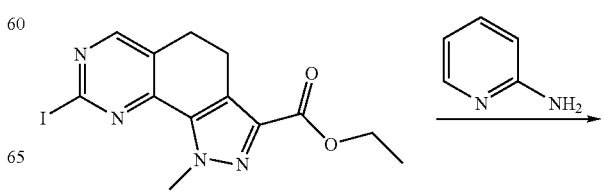

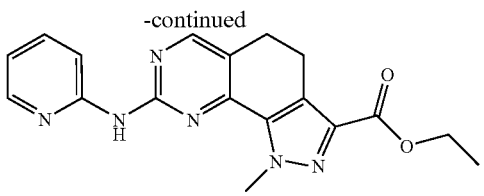

Palladium acetate [Pd(OAc)₂] (15.3 mg, 0.07 mmol, 10%), (±)-BINAP (42.6 mg, 0.07 mmol, 10%) and dimethylformamide (12 mL) were charged in a round-bottom flask flushed with argon. The mixture was stirred under argon for 30 minutes. Then 2-aminopyridine (70.4 mg, 0.75 mmol), ethyl 8-iodo-1-methyl-4,5-dihydro-1H-pyrazolo[4,3-h]quinazoline-3-carboxylate (250 mg, 0.65 mmol), potassium carbonate (1.89 g, 13.67 mmol) and dimethylformamide (5 mL) were added. The resulting mixture was stirred at room temperature for 1 hour and then heated to 120° C. in an oil bath under argon with good stirring for 18 hours.

After cooling to room temperature, the reaction mixture was poured into water and extracted with dichloromethane. The organic extracts were washed with brine and dried over Na₂SO₄. The solvent was removed under vacuum, the crude solid was taken up with diethyl ether, filtered, washed with diethyl ether and purified by flash chromatography on silica gel (eluant: dichloromethane/methanol 97.5:2.5) to afford 145 mg (63.8% yield) of the title compound.

¹H NMR (400 MHz, DMSO-d₆) δ ppm 1.3 (t, J 7.1 Hz, 3 H) 3.0 (m, 4 H) 4.3 (q, J 7.2 Hz, 2 H) 4.4 (s, 3 H) 7.0 (ddd, J 7.2, 4.9, 1.0 Hz, 1 H) 7.8 (ddd, 1 H) 8.2 (d, J 8.4 Hz, 1 H) 8.3 (ddd, J 4.8, 2.0, 0.9 Hz, 1 H) 8.5 (s, 1 H) 9.9 (s, 1 H).

By working according to the above method, the following compounds were prepared:

ethyl 8-[(3,5-dichlorophenyl)amino]-1-methyl-4,5-dihydro-1H-pyrazolo[4,3-h]quinazoline-3-carboxylate [B14-X00-M00(C01)D01]

¹H NMR (400 Hz, DMSO-d₆) δ ppm 1.3 (t, J 7.1 Hz, 3 H) 2.9 (m, 4 H) 4.3 (q, J 7.2 Hz, 2 H) 4.4 (s, 3 H) 7.1 (m, 1 H) 7.4 (m, 2 H) 8.5 (s, 1 H) 10 (s, 1 H);

ethyl 8-{[3-methoxy-5-(trifluoromethyl)phenyl]amino}-1-methyl-4,5-dihydro-1H-pyrazolo[4,3-h]quinazoline-3-carboxylate [B16-X00-M00(C01)D01]

¹H NMR (400 MHz, DMSO-d₆) δ ppm 1.3 (t, J 7.1 Hz, 3 H) 2.9 (m, 4 H) 3.8 (s, 3 H) 4.3 (q, J 7.2 Hz, 2 H) 4.4 (s, 3 H) 6.8 (s, 1 H) 7.6 (s, 1 H) 7.8 (s, 1 H) 8.5 (s, 1 H) 9.9 (s, 1 H);

ethyl 8-[(4-hydroxyphenyl)amino]-1-methyl-4,5-dihydro-1H-pyrazolo[4,3-h]quinazoline-3-carboxylate [B18-X00-M00(C01)D01]

¹H NMR (400 Hz, DMSO-d₆) δ ppm 1.3 (t, J 7.1 Hz, 3 H) 2.9 (m, 4 H) 4.3 (m, 5 H) 6.7 (d, J 8.8 Hz, 2 H) 7.4 (d, J 8.9 Hz, 2 H) 8.3 (s, 1 H) 9.1 (s, 1 H) 9.2 (s, 1 H);

ethyl 8-(1H-imidazol-1-ylamino)-1-methyl-4,5-dihydro-1H-pyrazolo[4,3-h]quinazoline-3-carboxylate [B21-X00-M00(C01)D01]

¹H NMR (400 MHz, DMSO-d₆) δ ppm 1.3 (m, 3 H) 2.9 (m, 4 H) 4.3 (d, J 7.1 Hz, 2 H) 4.4 (s, 3 H) 7.1 (s, 1 H) 7.6 (d, J 8.9 Hz, 2 H) 7.7 (s, 1 H) 7.9 (d, J 8.9 Hz, 2 H) 8.2 (s, 1 H) 8.5 (s, 1 H) 9.7 (s, 1 H);

ethyl 1-methyl-8-(1,3-thiazol-2-ylamino)-4,5-dihydro-1H-pyrazolo[4,3-h]quinazoline-3-carboxylate [B86-X00-M00(C01)D01]

¹H NMR (400 MHz, DMSO-d₆) δ ppm 1.3 (m, 3 H) 3.0 (m, 4 H) 4.3 (q, J 7.1 Hz, 2 H) 4.4 (s, 3 H) 7.1 (d, J 3.5 H, 1 H) 7.5 (d, J 3.7 Hz, 1 H) 8.6 (s, 1 H) 11.6 (s, 1 H);

ethyl 1-methyl-8-(1H-pyrazol-3-ylamino)-4,5-dihydro-1H-pyrazolo[4,3-h]quinazoline-3-carboxylate [B77-X00-M00(C01)D01]

¹H NMR (400 MHz, DMSO-d₆) δ ppm 1.3 (t, J 7.1 Hz, 3 H) 2.9 (m, 4 H) 4.3 (q, J 7.1 Hz, 2 H) 4.4 (s, 3 H) 6.5 (s, 1 H) 7.6 (s, 1 H) 8.4 (s, 1 H) 9.6 (s, 1 H) 12.2 (s, 1 H);

ethyl 1-methyl-8-[(4-morpholin-4-ylphenyl)amino]-4,5-dihydro-1H-pyrazolo[4,3-h]quinazoline-3-carboxylate [B19-X00-M00(C01)D01]

¹H NMR (400 MHz, DMSO d₆) δ ppm 1.3 (t, J 7.1 Hz, 3 H) 2.9 (m, 4 H) 3.1 (m, 4 H) 3.8 (m, 4 H) 4.3 (q, J 7.2 Hz, 2 H) 4.3 (s, 3 H) 6.9 (d, J 9.0 Hz, 2 H) 7.6 (d, J 9.0 Hz, 2 H) 8.4 (s, 1 H) 9.3 (s, 1 H);

ethyl 8-{[4-(ethoxycarbonyl)phenyl]amino}-1-methyl-4,5-dihydro-1H-pyrazolo[4,3-h]quinazoline-3-carboxylate [B87-X00-M00(C01)-D01]

¹H NMR (400 MHz, DMSO-d₆) δ ppm 1.3 (t, J 7.1 Hz, 6 H) 3.0 (m, 4 H) 4.3 (m, 4 H) 4.4 (s, 3 H) 7.9 (m, 4 H) 8.5 (s, 1 H) 10.0 (s, H);

ethyl 8-{[4-(N,N-diethylamino)phenyl]amino}-}-1-methyl-4,5-dihydro-1H-pyrazolo[4,3-h]quinazoline-3-carboxylate [B17-X00-M00(C01)-D01]

¹H NMR (400 MHz, DMSO-d₆) δ ppm 1.1 (t, J 7.0 Hz, 6 H) 1.3 (t, J 7.1 Hz, 3 H) 2.9 (m, 4 H) 3.3 (m, 4 H) 4.3 (q, J 7.1, 7.1 Hz, 2 H) 4.3 (s, 3 H) 6.7 (d, J 9.1 Hz, 2 H) 7.4 (d, J 9.0 Hz, 2 H) 8.3 (s, 1 H) 9.1 (s, 1 H);

ethyl 8-{[4-(acetylamino)phenyl]amino}-1-methyl-4,5-dihydro-1H-pyrazolo[4,3-h]quinazoline-3-carboxylate [B22-X00-M00(C01)-D01]

¹HNMR (400 MHz, DMSO-d₆) δ ppm 1.3 (t, J 7.1 Hz, 3 H) 2.0 (s, 3 H) 2.9 (m, 4 H) 4.3 (q, J 7.1 Hz, 2 H) 4.4 (s, 3 H) 7.5 (d, J 9.0 Hz, 2 H) 7.6 (d, J 9.0 Hz, 2 H) 8.4 (s, 1 H) 9.4 (s, 1 H) 9.8 (s, 1 H);

ethyl 8-{[3-(hydroxymethyl)phenyl]amino}-1-methyl-4,5-dihydro-1H-pyrazolo[4,3-h]quinazoline-3-carboxylate [B11-X00-M00(C01)-D01]

¹H NMR (400 MHz, DMSO-d₆) δ ppm 1.3 (t, J 7.1 Hz, 3 H) 2.9 (m, 4 H) 4.3 (q, J 7.1 Hz, 2 H) 4.4 (s, 3 H) 4.5 (s, 2 H) 6.9 (m, 1 H) 7.3 (t, J 7.8 Hz, 1 H) 7.5 (m, 1 H) 7.8 (s, 1 H) 8.4 (s, 1-H) 9.5 (s, 1 H);

ethyl 8-[(4-methoxyphenyl)amino]-1-methyl-4,5-dihydro-1H-pyrazolo[4,3-h]quinazoline-3-carboxylate [B68-X00-M00(C01)-D01]

¹H NMR (400 MHz, DMSO-d₆) δ ppm 1.3 (t, J 7.1 Hz, 3 H) 2.9 (m, 4 H) 3.7 (s, 3 H) 4.3 (q, J 7.1 Hz, 2 H) 4.3 (s, 3 H) 6.9 (d, J 9.0 Hz, 2 H) 7.6 (d, J 9.0 Hz, 2 H) 8.4 (s, 1 H) 9.3 (s, 1 H);

ethyl 8-{[(4-Bromo-3-chloro)phenyl]amino}-1-methyl-4,5-dihydro-1H-pyrazolo[4,3-h]quinazoline-3-carboxylate [B88-X00-M00(C01)-D01]

¹H NMR (400 MHz, DMSO-d₆) δ ppm 1.3 (t, J 7.1 Hz, 3 H) 2.9 (m, 4 H) 4.3 (q, J 7.1 Hz, 2 H) 4.4 (s, 3 H) 7.6 (dd, J 8.8, 2.4 Hz, 1 H) 7.7 (d, J 8.8 Hz, 1 H) 8.2 (d, J 2.4 Hz, 1 H) 8.5(s, 1 H) 9.9(s, 1 H);

ethyl 8-{[3-bromo-5-(trifluoromethyl)phenyl]amino}-1-methyl-4,5-dihydro-1H-pyrazolo[4,3-h]quinazoline-3-carboxylate [B115-X00-M00(C01)-D01]

¹H NMR (400 MHz, DMSO-d₆) δ ppm 1.33 (t, J=7.1 Hz, 3 H) 2.95 (m, 4 H) 4.31 (q, J=7.2 Hz, 2 H) 4.39 (s, 3 H) 7.49 (s, 1 H) 8.10 (s, 1 H) 8.36 (s, 1 H) 8.54 (s, 1 H) 10.11 (s, 1 H);

ethyl 8-[4-(4-methyl-piperazin-1-yl)-3-(hydroxymethyl)phenylamino]-1-methyl-4,5-dihydro-1H-pyrazolo[4,3-h]quinazoline-3-carboxylate [B116-X00-M00(C01)-D01]

¹H NMR (400 MHz, DMSO-d₆) δ ppm 1.33 (t, J=7.07 Hz, 3 H) 2.28 (s, 3 H) 2.42-2.61 (m, 4 H) 2.79-2.88 (m, 6 H) 2.98 (t, J=7.80 Hz, 2 H) 4.31 (q, J=7.15 Hz, 2 H) 4.36 (s, 3 H) 4.56

(d, J=5.24 Hz, 2 H) 5.06 (t, J=5.30 Hz, 1 H) 7.03 (d, J=8.66 Hz, 1 H) 7.50 (dd, 1 H) 7.81 (d, J=2.68 Hz, 1 H) 8.39 (s, 1 H) 9.42 (s, 1 H);

ethyl 1-methyl-8-{[4-(morpholin-4-ylmethyl)phenyl] amino}-4,5-dihydro-1H-pyrazolo[4,3-h]quinazoline-3-carboxylate [B102-X00-M00(C01)-D01]

$^1$H NMR (400 MHz, DMSO-6) δ ppm 1.33 (t, J=7.13 Hz, 3 H) 2.35 (s, 4 H) 2.86 (t, J=7.62 Hz, 2 H) 2.99 (t, J=7.80 Hz, 2 H) 3.42 (s, 2 H) 3.55-3.61 (m, 4 H) 4.31 (q, J=7.07 Hz, 2 H) 4.37 (s, 3 H) 7.24 (d, J=8.41 Hz, 2 H) 7.66 (d, J=8.41 Hz, 2 H) 8.42 (s, 1 H) 9.52 (s, 1 H);

ethyl 1-methyl-8-({4-[(1-methylpiperidin-4-yl)oxy] phenyl}amino)-4,5-dihydro-1H-pyrazolo[4,3-h]quinazoline-3-carboxylate [B103-X00-M00(C01)-D01]

$^1$H NMR (400 MHz, DMSO-d$_6$) δ ppm 1.32 (t, 3 H) 2.09 (m, 4 H) 2.86 (m, 5 H) 2.98 (t, 2 H) 3.37 (m, 5 H) 4.30 (q, 2 H) 4.34 (s, 3 H) 7.03 (m, 2 H) 7.61 (m, 2 H) 8.39 (s, 1 H) 9.40 (s, 1 H);

ethyl 1-methyl-8-({3-[(4-methylpiperazin-1-yl)methyl]phenyl})amino)-4,5-dihydro-1H-pyrazolo[4,3-h]quinazoline-3-carboxylate [B104-X00-M00(C01)-D01]

$^1$H NMR (400 MHz, DMSO-d$_6$) δ ppm 1.33 (t, 3 H) 2.21 (m, 3 H) 2.40 (m, 8 H) 2.86 (t, 2 H) 2.99 (t, 2 H) 3.44 (s, 2 H) 4.30 (q, 2 H) 4.39 (s, 3 H) 6.91 (m, 1 H) 7.24 (m, 1 H) 7.56 (m, 1 H) 7.75 (dd, 1 H) 8.43 (m, 1 H) 9.54 (s, 1 H);

ethyl 8-{[3-fluoro-4-(4-methylpiperazin-1-yl)phenyl] amino}-1-methyl-4,5-dihydro-1H-pyrazolo[4,3-h] quinazoline-3-carboxylate [B109-X00-M00(C01)-D01]

$^1$H NMR (400 MHz, DMSO-d$_6$) δ ppm 1.33 (t, 3 H) 2.28 (s, 3 H) 2.85 (t, 2 H) 2.99 (m, 6 H) 4.30 (q, 2 H) 4.37 (s, 3 H) 7.01 (, 1 H) 7.35 (dd, 1 H) 7.64 (dd, 1 H) 8.42 (m, 1 H) 9.56 (s, 1 H);

ethyl 8-[(4-chlorophenyl)amino]-1-methyl-4,5-dihydro-1H-pyrazolo[4,3-h]quinazoline-3-carboxylate [B112-X00-M00(C01)-D01]

$^1$H NMR (400 MHz, DMSO-d$_6$) δ ppm 1.33 (t, 3 H) 2.86 (t, 2 H) 2.99 (t, 2 H) 4.30 (q, 2 H) 4.37 (s, 3 H) 7.38 (d, 2 H) 7.74 (d, 2 H) 8.45 (s, 1 H) 9.70 (s, 1 H);

ethyl 8-{[4-(hydroxymethyl)phenyl]amino}-1-methyl-4,5-dihydro-1H-pyrazolo[4,3-h]quinazoline-3-carboxylate [B114-X00-M00(C01)-D01]

$^1$H NMR (400 MHz, DMSO-d$_6$) δ ppm 1.33 (t, 3 H) 2.86 (t, 2 H) 2.99 (t, 2 H) 4.30 (q, 2 H) 4.37 (s, 3 H) 4.45 (s, 2 H) 7.27 (d, 2 H) 7.65 (d, 2 H) 8.42 (s, 1 H) 9.50 (s, 1 H).

Example 43

1-Methyl-8-(pyridin-2-ylamino)-4,5-dihydro-1H-pyrazolo[4,3-h]quinazoline-3-carboxamide [B15-X00-M00(C01)-D03]

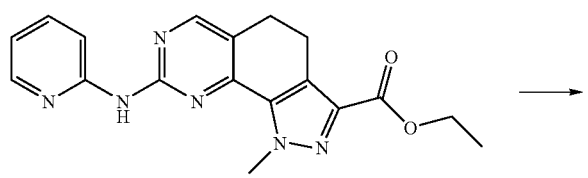

→

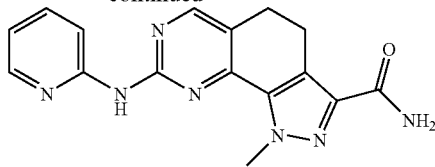

To a solution of ethyl 1-methyl-8-(pyridin-2-ylamino)-4,5-dihydro-1H-pyrazolo[4,3-h]quinazoline-3-carboxylate (220 mg, 0.63 mmol) in methanol (250 mL), 33% aqueous ammonium hydroxide (100 mL) was added and the solution was stirred at 65° C. for 8 hours.

By concentrating the solution, the final compound that precipitated was collected by suction filtration, washed with water and crystallized twice from methanol containing sodium hydroxide, and dried at 40° C. under vacuum. There were thus obtained 60 mg of the title compound.

$^1$H NMR (400 MHz, DMSO-d$_6$) δ 3.0 (m, 4 H) 4.4 (s, 3 H) 7.0 (ddd, J 7.2, 4.9, 1.0 Hz, 1 H) 7.3 (s, 1 H) 7.5 (s, 1 H) 7.8 (ddd, 1 H) 8.2 (d, J 8.4 Hz, 1 H) 8.3 (ddd, J 4.8, 2.0, 0.9 Hz, 1 H) 8.5 (s, 1 H) 9.9 (s, 1 H)

By working according to the same procedure, the following compounds were prepared:

8-[(3,5-dichlorophenyl)amino]-1-methyl-4,5-dihydro-1H-pyrazolo[4,3-h]quinazoline-3-carboxamide [B14-X00-M00(C01)-D03]

$^1$H NMR (400 MHz, DMSO-d$_6$) δ ppm 3.0 (m, 4 H) 4.4 (s, 3 H) 7.1 (t, J 1.8 Hz, 1 H) 7.3 (s, 1 H) 7.5 (s, 1 H) 7.9 (d, J 1.8 Hz, 2 H) 8.5 (s, 1 H) 10.0 (s, 1 H);

8-{[3-methoxy-5-(trifluoromethyl)phenyl]amino}-1-methyl-4,5-dihydro-1H-pyrazolo[4,3-h]quinazoline-3-carboxamide B16-X00-M00(C01)-D03]

$^1$H NMR (400 MHz, DMSO-d$_6$) δ ppm 2.9 (m, 4 H) 3.8 (s, 3 H) 4.3 (s, 3 H) 6.8 (s, 1 H) 7.3 (s, 1 H) 7.5 (s, 1 H) 7.6 (s, 1 H) 7.8 (s, 1 H) 8.5 (s, 1 H) 9.9 (s, 1 H);

8-[(4-hydroxyphenyl)amino]-1-methyl-4,5-dihydro-1H-pyrazolo[4,3-h]quinazoline-3-carboxamide [B18-X00-M00(C01)-D03]

$^1$H NMR (400 MHz, DMSO-d$_6$) δ ppm 2.9 (m, 4 H) 4.3 (s, 3 H) 6.7 (d, J 8.8 Hz, 2 H) 7.2 (s, 1 H) 7.4 (d, J 8.9 Hz, 2 H) 7.5 (s, 1 H) 8.3 (s, 1 H) 9.1 (s, 1 H) 9.2 (s, 1 H);

8-{[4-(1H-imidazol-1-yl)phenyl]amino}-1-methyl-4,5-dihydro-1H-pyrazolo[4,3-h]quinazoline-3-carboxamide [B21-X00-M00(C01)-D03]

$^1$H NMR (400 MHz, DMSO-d$_6$) δ ppm 2.9 (m, 4 H) 4.4 (s, 3 H) 7.1 (s, 1 H) 7.3 (s, 1 H) 7.5 (s, 1 H) 7.6 (d, J 8.9 Hz, 2 H) 7.7 (t, J 1.2 Hz, 1 H) 7.9 (d, J 9.0 Hz, 2 H) 8.2 (s, 1 H) 8.4 (s, 1 H) 9.7 (s, 1 H);

1-methyl-8-(thiazol-2-ylamino)-4,5-dihydro-1H-pyrazolo[4,3-h]quinazoline-3-carboxamide [B86-X00-M00(C01)-D03]

$^1$H NMR (400 MHz, DMSO-d$_6$) δ ppm 3.0 (m, 4 H) 4.4 (s, 3 H) 7.1 (d, J 3.7 Hz, 1 H) 7.3 (s, 1 H) 7.5 (d, J 3.7 Hz, 1 H) 7.5 (s, 1 H) 8.6 (s, 1 H) 11.8 (s, 1 H);

1-methyl-8-(1H-pyrazol-3-ylamino)-4,5-dihydro-1H-pyrazolo[4,3-h]quinazoline-3-carboxamide [B77-X00-M00(C01)-D03]

$^1$H NMR (400 MHz, DMSO-d$_6$) δ ppm 2.9 (m, 4 H) 4.3 (s, 3 H) 6.5 (bs, 1 H) 7.25 (s, 1 H) 7.45 (s, 1 H) 7.6 (bs, 1 H) 8.4 (s, 1 H) 9.9 (s, 1 H);

8-{[4-(N-morpholino)phenyl]amino}-1-methyl-4,5-dihydro-1H-pyrazolo[4,3-h]quinazoline-3-carboxamide [B19-X00-M00(C01)-D03]

$^1$H NMR (400 MHz, DMSO-d$_6$) δ ppm 2.9 (m, 4 H) 3.1 (m, 4 H) 3.8 (m, 4 H) 4.3 (s, 3 H) 6.9 (d, J 9.1 Hz, 2 H) 7.2 (s, 1 H) 7.5 (s, 1 H) 7.6 (d, J 9.0 Hz, 2 H) 8.4 (s, 1 H) 9.3 (s, 1 H);

8-{[4-(diethylamino)phenyl]amino}-1-methyl-4,5-dihydro-1H-pyrazolo[4,3-h]quinazoline-3-carboxamide [B17-X00-M00(C01)-D03]

$^1$H NMR (400 MHz, DMSO-d$_6$) δ ppm 1.1 (t, J 7.0 Hz, 6 H) 2.9 (m, 4 H) 3.3 (m, 4 H) 4.3 (s, 3 H) 6.7 (d, J 9.0 Hz, 2 H) 7.2 (s, 1 H) 7.4 (m, J 9.0 Hz, 1 H) 7.4 (d, J 9.0 Hz, 2 H) 8.3 (s, 1 H) 9.1 (s, 1 H);

8-{[4-(acetylamino)phenyl]amino}-1-methyl-4,5-dihydro-1H-pyrazolo[4,3-h]quinazoline-3-carboxamide [B22-X00-M00(C01)-D03]

$^1$H NMR (400 MHz, DMSO-d$_6$) δ ppm 2.0 (s, 3 H) 2.9 (m, 4 H) 4.3 (s, 3 H) 7.3 (s, 1 H) 7.5 (s, 1 H) 7.5 (d, J 8.9 Hz, 2 H) 7.6 (d, J 9.0 Hz, 2 H) 8.4 (s, 1 H) 9.4 (s, 1 H) 9.8 (s, 1 H);

8-{[3-(hydroxymethyl)phenyl]amino}-1-methyl-4,5-dihydro-1H-pyrazolo[4,3-h]quinazoline-3-carboxamide [B11-X00-M00(C01)-D03]

$^1$H NMR (400 MHz, DMSO-d$_6$) δ ppm 2.9 (m, 4 H) 4.3 (s, 3 H) 4.5 (s, 2 H) 5.2 (s, 1 H) 6.9 (d, J 8.0 Hz, 1 H) 7.2 (m, 2 H) 7.5 (s, 1 H) 7.5 (dd, J 8.1, 1.4 Hz, 1 H) 7.8 (t, J 1.8 Hz, 1 H) 8.4 (s, 1 H) 9.5 (s, 1 H);

8-[(4-methoxyphenyl)amino]-1-methyl-4,5-dihydro-1H-pyrazolo[4,3-h]quinazoline-3-carboxamide [B68-X00-M00(C01)-D03]

$^1$H NMR (400 MHz, DMSO-d$_6$) δ ppm 2.9 (m, 4 H) 3.7 (s, 3 H) 4.3 (s, 3 H) 6.9 (d, J 9.1 Hz, 2 H) 7.3 (s, 1 H) 7.5 (s, 1 H) 7.6 (d, J 9.0 Hz, 2 H) 8.4 (s, 1 H) 9.3 (s, 1 H);

8-{[(4-Bromo-3-chloro)phenyl]amino}-1-methyl-4,5-dihydro-1H-pyrazolo[4,3-h]quinazoline-3-carboxamide [B88-X00-M00(C01)-D03]

$^1$H NMR (400 MHz, DMSO-d$_6$) δ ppm 2.9 (m, 4 H) 4.4 (s, 3 H) 7.3 (s, 1 H) 7.5 (s, 1 H) 7.6 (dd, J 8.8, 2.4 Hz, 1 H) 7.7 (d, J 8.8 Hz, 1 H) 8.2 (d, J 2.4 Hz, 1 H) 8.5 (s, 1 H) 9.9 (s, 1 H);

8-[4-(4-methyl-piperazin-1-yl)-3-(hydroxymethyl)phenylamino]-1-methyl-4,5-dihydro-1H-pyrazolo[4,3-h]quinazoline-3-carboxamide [B116-X00-M00(C01)-D03]

$^1$H NMR (400 MHz, DMSO-d$_6$) δ ppm 2.29 (s, 3 H) 2.45-2.61 (m, 4 H) 2.73-2.87 (m, 6 H) 2.99 (t, J=7.56 Hz, 2 H) 4.34 (s, 3 H) 4.56 (d, J=5.24 Hz, 2 H) 5.06 (t, J=5.37 Hz, 1 H) 7.03 (d, J=8.66 Hz, 1 H) 7.26 (s, 1 H) 7.46 (s, 1 H) 7.50 (dd, J=8.23, 2.99 Hz, 1 H) 7.83 (d, J=2.68 Hz, 1 H) 8.38 (s, 1 H) 9.40 (s, 1 H);

8-[4-(4-methyl-piperazin-1-yl)-3-(hydroxymethyl)phenylamino]-1-methyl-4,5-dihydro-1H-pyrazolo[4,3-h]quinazoline-3-carboxylic acid methylamide [B116-X00-M00(C01)-D04]

$^1$H NMR (400 MHz, DMSO-d$_6$) δ ppm 2.28 (s, 3 H) 2.45-2.55 (m, 4 H) 2.75 (d, J=4.63 Hz, 3 H) 2.81 (t, J=7.19 Hz, 2 H) 2.83 (t, J=4.63 Hz, 4 H) 2.99 (t, J=7.56 Hz, 2 H) 4.34 (s, 3 H) 4.56 (d, J=5.24 Hz, 2 H) 5.05 (t, J=5.37 Hz, 1 H) 7.03 (d, J=8.54 Hz, 1 H) 7.50 (d, J=8.41, 2.56 Hz, 1 H) 7.83 (d, J=2.68 Hz, 1 H) 8.07 (q, J=4.63 Hz, 1 H) 8.37 (s, 1 H) 9.40 (s, 1 H);

8-[4-(4-methyl-piperazin-1-yl)-3-(bromo)phenylamino]-1-methyl-4,5-dihydro-1H-pyrazolo[4,3-h]quinazoline-3-carboxamide trihydrochloride [B117-X00-M00(C01)-D03]

$^1$H NMR (400 MHz, DMSO-d$_6$) δ ppm 2.83 (m, 2 D) 2.88 (d, J=4.68 Hz, 3 H) 3.01 (m, 4 H) 3.19 (m, 2 H) 3.53 (m, 2 H) 4.37 (s, 3 H) 7.23 (m, 1 H) 7.29 (m, 1 H) 7.46 (m, 1 H) 7.63 (m, 1 H) 8.21 (m, 1 H) 8.44 (m, 1 H) 9.67 (s, 1 H) 10.13 (s, 1 H);

8-[3-(4-methyl-piperazin-1-ylmethyl)-phenylamino]-1-methyl-4,5-dihydro-1H-pyrazolo[4,3-h]quinazoline-3-carboxamide [B104-X00-M00(C01)-D03

$^1$H NMR (400 MHz, DMSO-d$_6$) δ ppm 2.27 (s, 3 H) 2.44 (s, 4 H) 2.78-3.03 (m, 4 H) 3.04-3.40 (m, 4 H) 3.45 (s, 2 H) 4.37 (s, 3 H) 6.90 (d, J=7.32 Hz, 1 H) 7.25 (t, J=7.68 Hz, 1 H) 7.27 (s, 1 H) 7.46 (s, 1 H) 7.57 (dd, J=7.68, 1.59 Hz, 1 H) 7.76 (t, J=1.77 Hz, 1 H) 8.42 (s, 1 H) 9.52 (s, 1 H);

8-{[(3-hydroxy)-5-trifluoromethyl]phenylamino}-1-methyl-4,5-dihydro-1H-pyrazolo[4,3-h]quinazoline-3-carboxamide [B118-X00-M00(C01)-D03]

$^1$H NMR (400 MHz, DMSO-d$_6$) δ ppm 2.77-3.07 (m, 4 H) 3.84 (s, 3 H) 4.35 (s, 3 H) 6.84 (s, 1 H) 7.28 (s, 1 H) 7.47 (s, 1 H) 7.57 (s, 1 H) 7.85 (s, 1 H) 8.49 (s, 1 H) 9.86 (s, 1 H);

8-[4-(4-methyl-piperazin-1-yl)-phenylamino]-1-methyl-4,5-dihydro-1H-pyrazolo[4,3-h]quinazoline-3-carboxylic acid methylamide [B10-X00-M00(C01)-D04]

$^1$H NMR (400 MHz, DMSO-d$_6$) δ ppm 2.75 (d, J=4.76 Hz, 3 H) 2.81 (t, J=7.68 Hz, 2 H) 2.85 (d, J=4.39 Hz, 3 H) 2.94-3.07 (m, 4 H) 3.11-3.25 (m, 2 H) 3.51 (d, J=11.83 Hz, 2 H) 3.73 (d, J=13.66 Hz, 2 H) 4.33 (s, 3 H) 6.99 (d, J=9.15 Hz, 2 H) 7.60 (d, J=9.02 Hz, 2 H) 8.08 (q, J=4.67 Hz, 1 H) 8.37 (s, 1 H) 9.40 (s, 1 H) 10.36 (s, 1 H);

8-anilino-1-methyl-4,5-dihydro-1H-pyrazolo[4,3-h]quinazoline-3-carboxylic acid methylamide [B04-X00-M00(C01)-D04]

$^1$H NMR (400 MHz, DMSO-d$_6$) δ ppm 2.72 (d, J=4.76 Hz, 3 H) 2.79 (t, J=7.68 Hz, 2 H) 2.97 (t, J=7.68 Hz, 2 H) 4.31 (s, 3 H) 6.94 (t, J=7.38 Hz, 1 H) 7.21-7.32 (m, 2 H) 7.68 (d, J=7.56 Hz, 2 H) 8.06 (q, J=4.35 Hz, 1 H) 8.38 (s, 1 H) 9.48 (s, 1 H).

Example 44

1-Methyl-8-(pyridin-2-ylamino)-4,5-dihydro-1H-pyrazolo[4,3-h]quinazoline-3-carboxamide hydrochloride

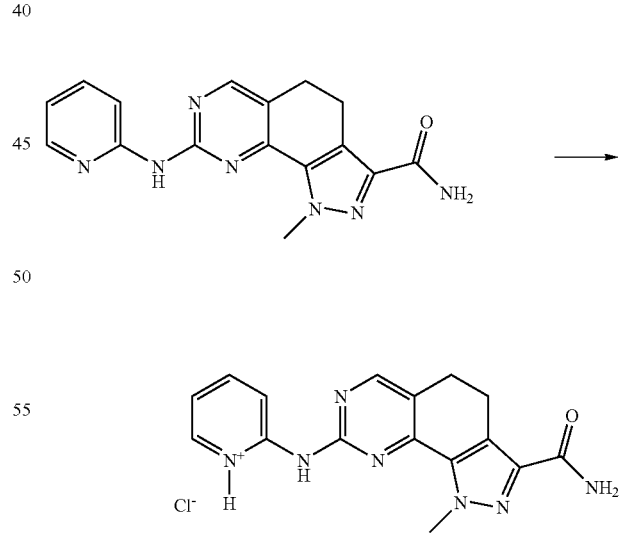

To a solution of 1-methyl-8-(pyridin-2-ylamino)-4,5-dihydro-1H-pyrazolo[4,3-h]quinazoline-3-carboxamide in a 1:1 mixture of methanol and dichloromethane, 4 N HCl in dioxane (1 mL) was added. After 1 hour at room temperature the solvent was removed under vacuum and the solid was triturated with diethyl ether affording the title compound.

¹H NMR (400 MHz, DMSO-d₆) δ ppm 3.0 (, 4 H) 4.4 (s, 3 H) 7.3 (m, 2 H) 7.5 (s, 1 H) 7.8 (d, J 8.8 z, 1 H) 8.2 (t, J 7.7 Hz, 1 H) 8.4 (dd, J 5.9, 1.0 Hz, 2 H) 8.6 (s, 1 H) 11.6 (s, 1 H).

By working according to this method, the following compounds were prepared:

1-methyl-(thiazol-2-ylamino)-4,5-dihydro-1H-pyrazolo[4,3-h]quinazoline-3-carboxamide hydrochloride ¹H NMR (400 MHz, DMSO-d₆) δ ppm 3.0 (m, 4 H) 4.4 (s, 3 H) 7.1 (d, J 3.7 Hz, 1 H) 7.3(s, 1 H) 7.5 (d, J 3.7 Hz, 1 H) 7.5(s, 1 H) 8.6 (s, 1 H) 11.8 (s, 1 H);

8-[4(N-Methylpiperazino)-3-chlorophenylamino]-1-methyl-4,5-dihydro-1H-pyrazolo[4,3-h]quinazoline-3-carboxamide trichlorohydrate ¹H NMR (400 MHz, DMSO-d₆) δ ppm 3.1 (m, 15 H) 4.4 (s, 3 H) 7.2 (d, J 8.9 Hz, 1 H) 7.3 (s, 1 H) 7.5 (s, 1 H) 7.6 (dd, J 8.8, 2.4 Hz, 1 H) 8.0 (d, J 2.6 Hz, 1 H) 8.4 (s, 1 H) 9.7 (s, 1 H) 10.5 (s, 1 H);

8-[4(N-Methylpiperazino)-3-bromophenylamino]-1-methyl-4,5-dihydro-1H-pyrazolo[4,3-h]quinazoline-3-carboxamide trichlorohydrate ¹H NMR (400 MHz, DMSO-d₆) δ ppm 3.1 (m, 15 H) 4.4 (s, 3 H) 7.2 (d, J 8.8 Hz, 1 H) 7.3 (s, 1 H) 7.5 (s, 1 H) 7.6 (dd, J 8.6, 2.4 Hz, 1 H) 8.0 (d, J 2.6 Hz, 1 H) 8.2 (s, 1 H) 9.7 (s, 1 H) 10.5 (s, 1 H);

N-benzyl-1-methyl-8-{[4-(4-methylpiperazin-1-yl)phenyl]amino}-4,5-dihydro-1H-pyrazolo[4,3-h]quinazoline-3-carboxamide (L)-tartrate ¹H NMR (400 MHz, DMSO-d₆) δ ppm 2.40 (s, 3 H) 2.70 (m, 4 H) 2.80 (t, J=7.62 Hz, 2 H) 3.00 (t, J=7.62 Hz, 2 H) 3.14 (m, 4 H) 4.20 (s, 2 H) 4.34 (s, 3 H) 4.43 (d, J=6.34 Hz, 2 H) 6.93 (d, J=9.15 Hz, 2 H) 7.27 (m, 5 H) 7.55 (d, J=9.02 Hz, 2 H) 8.35 (s, 1 H) 8.69 (t, J=6.34 Hz, 1 H) 9.28 (s, 1 H);

1-methyl-8-[(4-morpholin-4-ylphenyl)amino]-N-[(1R)-1-phenylethyl]4,5-dihydro-1H-pyrazolo[4,3-h]quinazoline-3-carboxamide hydrochloride ¹H NMR (400 MHz, DMSO-d₆) δ ppm 1.51 (m, 3 H) 2.97 (m, 4 H) 3.21 (m, 4 H) 3.84 (m, 4 H) 4.37 (m, 3 H) 5.15 (m, 1 H) 7.28 (m, 7 H) 7.63 (m, 2 H) 8.40 (m, 1 H) 8.44 (m, 1 H) 9.50 (m, 1 H);

N-(3-fluorobenzyl)-1-methyl-8-[(4-morpholin-4-ylphenyl)amino]4,5-dihydro-1H-pyrazolo[4,3-h]quinazoline-3-carboxamide hydrochloride ¹H NMR (400 MHz, DMSO-d₆) δ ppm 2.91 (m, J=73.53 Hz, 4 H) 3.16 (m, 4 H) 3.81 (m, 4 H) 4.35 (s, 3 H) 4.43 (m, 2 H) 7.07 (m, 6 H) 7.61 (m, 2 H) 8.37 (m, 1 H) 8.80 (m, 1 H) 9.44 (m, 1 H);

N-(3-fluorobenzyl)-1-methyl-8-[(4-morpholin-4-ylphenyl)amino]-4,5-dihydro-1H-pyrazolo[4,3-h]quinazoline-3-carboxamide methanesulfonate ¹H NMR (400 MHz, DMSO-d₆) δ ppm 2.33 (s, 3 H) 3.00 (s, 4 H) 3.17 (s, 4 H) 3.80 (s, 4 H) 4.35 (s, 3 H) 4.43 (m, 2 H) 7.07 (m, 6 H) 7.61 (m, 2 H) 8.37 (m, 1 H) 8.80 (m, 1 H) 9.46 (m, 1 H).

Example 45

8-anilino-N-(2-hydroxyethyl)-1-methyl-4,5-dihydro-1H-pyrazolo[4,3-h]quinazoline-3-carboxamide [B04-X00-M00(C01)-D06]

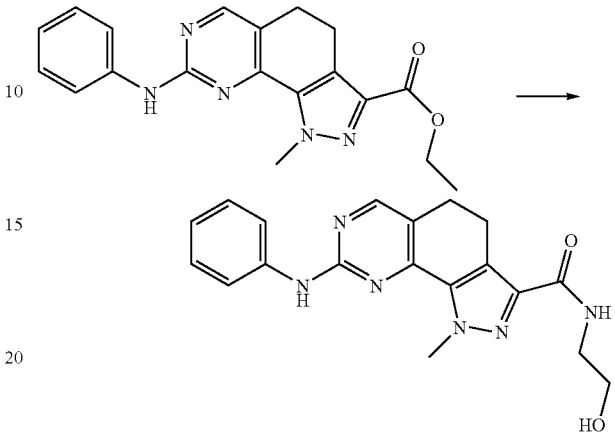

To a suspension of 0.30 g (0.86 mmol) of ethyl 8-anilino-1-methyl-4,5-dihydro-1H-pyrazolo[4,3-h]quinazoline-3-carboxylate in a mixture of 10 mL of methanol and 10 mL of dimethylformamide, 5 mL of ethanolamine were added. The mixture was heated in a close bottle under stirring at 65° C. After 5 hours the solvent was removed, the residue redissolved with dichloromethane and washed with water. The organic layer was dried over Na₂SO₄ and evaporated. The residue was triturated with diethyl ether and the product collected by filtration (60% yield).

¹H NMR (400 MHz, DMSO-d₆) δ ppm: 2.7-3.0 (2m, 4 H) 3.47 (m, 4 H) 4.32 (s, 3 H) 4.71 (t, 1 H) 6.94-7.67 (3m, 5 H) 7.91 (t, J 5.73 Hz, 1 H) 8.38 (bs, 1 H) 9.48 (bs, 1 H).

By working analogously the following compound was prepared:

8-anilino-N,1-dimethyl-4,5-dihydro-1H-pyrazolo[4,3-h]quinazoline-3-carboxamide [B04-X00-M00(C01)-D04]

¹H NMR (400 MHz, DMSO-d₆) δ ppm 2.72 (d, J 4.76 Hz, 3 H) 2.79 (t, J 7.68 Hz, 2 H) 2.97 (t, J 7.68 Hz, 2 H) 4.31 (s, 3 H) 6.94 (t, J 7.38 Hz, 1 H) 7.28 (m, 2 H) 7.68 (d, J 7.56 Hz, 2 H) 8.06 (q, J 4.35 Hz, 1 H) 8.38 (s, 1 H) 9.48 (s, 1 H).

Example 46

8-[(4-methoxy-3-chlorophenyl)amino]-1-methyl-4,5-dihydro-1H-pyrazolo[4,3-h]quinazoline-3-carboxamide [B20-X00-M00(C01)-D03]

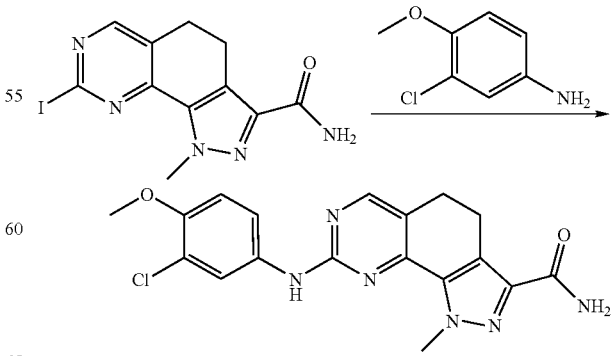

Pd(OAc)₂ (20 mg, 0.09 mmol, 10%), (±)-BINAP (55 mg, 0.09 mmol, 10%) and dimethylformamide (15 mL) were charged in a round-bottom flask flushed with argon. The mixture was stirred under argon for 30 minutes. Then 3-chloro-p-anisidine (153 mg, 0.97 mmol), 8-iodo-1-methyl-4,5-dihydro-1H-pyrazolo[4,3-h]quinazoline-3-carboxamide (300 mg, 0.84 mmol), $K_2CO_3$ (2.45 g, 17.8 mmol) and dimethylformamide (6 mL) were added. The resulting mixture was stirred at room temperature for 1 hour and then heated to 120° C. in an oil bath under argon with good stirring for 18 hours. After cooling to room temperature, the reaction mixture was poured into water (300 mL) and extracted with dichloromethane (5×60 mL). The organic extracts were washed with water (2×20 mL) and dried over anhydrous $Na_2SO_4$. The solvent was removed under vacuum, the crude solid was taken up with diethyl ether, filtered, washed with diethyl ether and purified by flash chromatography on silica gel (eluant: dichloromethane/methanol 97.5:2.5) to afford 95 mg of pure title compound.

$^1$H NMR (400 MHz, DMSO-$d_6$) δ ppm 2.9 (m, 4 H) 3.8 (s, 3 H) 4.3 (s, 3 H) 7.1 (d, J 9.0 Hz, 1 H) 7.3 (s, 1 H) 7.5 (s, 1 H) 7.5 (dd, J 9.0, 2.6 Hz, 1 H) 7.9 (d, J 2.6 Hz, 1 H) 8.4 (s, 1 H) 9.5 (s, 1 H)

By working according to the same procedure the following compound was prepared:

8-[4(N-Methyl-N-piperazinyl)-3-chlorophenylamino]-1-methyl-4,5-dihydro-1H-pyrazolo[4,3-h]quinazoline-3-carboxamide [B13-X00-M00(C01)-D03]

$^1$H NMR (400 MHz, DMSO-$d_6$) δ ppm 2.3 (s, 3 H) 2.5 (m, 4 H) 2.9 (m, 8 H) 4.4 (s, 3 H) 7.1 (d, J 8.8 Hz, 1 H) 7.3 (s, 1 H) 7.5 (s, 1 H) 7.5 (dd, J 8.8, 2.4 Hz, 1 H) 8.0 (d, J 2.6 Hz, 1 H) 8.4 (s, 1 H) 9.6 (s, 1 H).

Example 47

8-[(4-methoxybenzyl)amino]-1-methyl-4,5-dihydro-1H-pyrazolo[4,3-h]quinazoline-3-carboxamide [B60-X00-M00(C01)-D03]

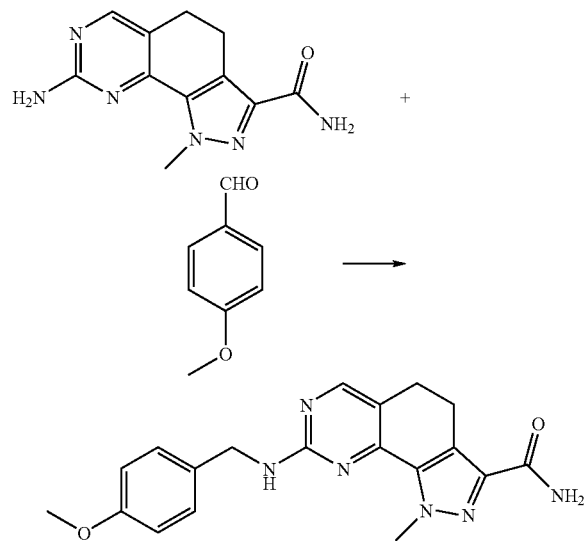

To a solution of 8-amino-1-methyl-4,5-dihydro-1H-pyrazolo[4,3-h]quinazoline-3-carboxamide (244 mg, 1.0 mmol) in a mixture of glacial acetic acid/methanol/water (1:1:1) (30 mL) in a round-bottom flask were added p-methoxybenzaldehyde (0.44 mL, 450 mg, 3.0 mmol) and then 85% sodium cyanoborohydride (210 mg, 2.0 mmol). The solution was stirred at room temperature for 7 hours. At that time further amount of aldehyde (0.44 mL) and sodium cyanoborohydride (210 mg) were added and stirring was continued overnight.

The reaction mixture was poured into ice-water (200 mL), the pH was adjusted to 10 by addition of saturated sodium carbonate and the solution extracted with ethyl acetate (4×20 mL). The collected organic extracts were washed with brine until neutral, with water and dried over $Na_2SO_4$.

Evaporation of the solvent under vacuum left a yellow solid residue that was purified by flash chromatography on silica gel (eluant: dichloromethane/methanol 95:5) to yield 250 mg of yellow pure compound. Crystallization from methanol afforded 225 mg of crystalline title compound.

$^1$H NMR (400 MHz, DMSO-$d_6$) δ ppm 2.8 (m, 4 H) 3.7 (s, 3 H) 4.2 (s, 3 H) 4.5 (d, J 6.1 Hz, 2 H) 7.2 (s, 1 H) 6.8 (d, J 8.8 Hz, 2 H) 7.4 (s, 1 H) 7.3 (d, J 8.8 Hz, 2 H) 7.6 (m, 1 H) 8.2 (s, 1 H)

By working according to this method, the following compounds were prepared:

1-methyl-8-[(thien-3-ylmethyl)amino]4,5-dihydro-1H-pyrazolo[4,3-h]quinazoline-3-carboxamide [B43-X00-M00(C01)-D03]

$^1$H NMR (400 MHz, DMSO-$d_6$) δ ppm 2.8 (m, 4 H) 4.2 (s, 3 H) 4.5 (d, J 6.1 Hz, 2 H) 7.1 (m, 1 H) 7.2 (s, 1 H) 7.3 (m, 1 H) 7.4 (s, 1 H) 7.5 (m, 1 H) 7.6 (m, 1 H) 8.2 (s, 1 H);

8-[(3,5-dihydroxybenzyl)amino]-1-methyl-4,5-dihydro-1H-pyrazolo[4,3-h]quinazoline-3-carboxamide [B62-X00-M00(C01)-D03]

$^1$H NMR (400 MHz, DMSO-$d_6$) δ ppm 2.8 (m, 4 H) 4.2 (m, 2 H) 4.3 (s, 3 H) 4.4 (d, J 6.2 Hz, 2 H) 6.0 (m, 1 H) 6.2 (m, 2 H) 7.2 (s, 1 H) 7.4 (s, 1 H) 7.6 (m, 1 H) 8.2 (s, 1 H);

8-({4-[3-(dimethylamino)propoxy]benzyl}amino)-1-methyl-4,5-dihydro-1H-pyrazolo[4,3-h]quinazoline-3-carboxamide [B61-X00-M00(C01)-D03]

$^1$H NMR (400 MHz, DMSO-$d_6$) δ ppm 1.8 (m, 2 H) 2.2 (s, 6 H) 2.4 (t, 2 H) 2.8 (m, 4 H) 4.0 (t, 2 H) 4.3 (s, 3 H) 4.5 (d, J 6.5 Hz, 2 H) 6.9 (m, J 9.0 Hz, 2 H) 7.2 (d, J 8.7 Hz, 2 H) 7.2 (s, 1 H) 7.4 (s, 1 H) 7.6 (m, 1 H) 8.2 (s, 1 H);

[5-({[3-(aminocarbonyl)-1-methyl-4,5-dihydro-1H-pyrazolo[4,3-h]quinazolin-8-yl]amino}methyl)-2-furyl]methyl acetate [B65-X00-M00(C01)-D03]

$^1$H NMR (400 M DMSO-$d_6$) δ ppm 2.0 (s, 3 H) 2.8 (m, 4 H) 4.3 (s, 3 H) 4.5 (d, J 6.1 Hz, 2 H) 5.0(s, 2 H) 6.2 (d, J 3.2 Hz, 1 H) 6.4 (d, J 3.2 Hz, 1 H) 7.2 (s, 1 H) 7.4 (s, 1 H) 7.6 (t, J 6.0 Hz, 1 H) 8.2 (s, 1 H);

8-[(3-cyanobenzyl)amino]-1-methyl-4,5-dihydro-1H-pyrazolo[4,3-h]quinazoline-3-carboxamide [B63-X00-M00(C01)-D03]

$^1$H NMR (400 MHz, DMSO-$d_6$) δ ppm 2.8 (m, 4 H) 4.1 (s, 3 H) 4.6 (d, J 6.1 Hz, 2 H) 7.2 (s, 1 H) 7.4 (s, 1 H) 7.5 (t, J 7.7 MHz, 1 H) 7.7 (m, 4 H) 8.2 (s, 1 H);

8-[(4-Bromobenzyl)amino]-1-methyl-4,5-dihydro-1H-pyrazolo[4,3-h]quinazoline-3-carboxamide [B64-X00-M00(C01)-D03]

$^1$H NMR (400 MHz, DMSO-$d_6$) δ ppm 2.8 (m, 4 H) 4.2 (s, 3 H) 4.5 (d, J 6.3 Hz, 2 H) 7.2 (s, 1 H) 7.3 (d, J 8.5 Hz, 2 H) 7.4 (s, 1 H) 7.5 (d, J 8.5 Hz, 2 H) 7.7 (m, 1 H) 8.2 (s, 1 H);

8-{[4-(acetylamino)benzyl]amino}-1-methyl-4,5-dihydro-1H-pyrazolo[4,3-h]quinazoline-3-carboxamide [B80-X00-M00(C01)-D03]

$^1$H NMR (400 MHz, DMSO-$d_6$) δ ppm 2.0 (s, 3 H) 2.7 (m, 2 H) 2.9 (t, J 7.7 Hz, 2 H) 4.2 (s, 3 H) 4.5 (d, J 6.2 Hz, 2 H) 7.2 (s, 1 H) 7.3 (d, J 8.5 Hz, 2 H) 7.4 (s, 1 H) 7.5 (d, J 8.5 Hz, 2 H) 7.6 (t, J 7.4 Hz, 1 H) 8.2 (s, 1 H) 9.9 (s, 1 H);

B81-X00-M00(C01)-D03

$^1$H NMR (400 MHz, DMSO-d$_6$) δ ppm 2.7 (m, 2 H) 2.9 (t, J 7.6 Hz, 2 H) 4.3 (s, 3 H) 4.3 (s, 2 H) 4.5 (d, J 6.0 Hz, 2 H) 5.1 (s, 1 H) 6.2 (m, 2 H) 7.2 (s, 1 H) 7.4 (s, 1 H) 7.6 (t, J 5.9 Hz, 1 H) 8.2 (s, 1 H);

8-[(1-Methylimidazol-2-yl)methylamino]-1-methyl-4,5-dihydro-1-pyrazolo[4,3-h]quinazoline-3-carboxamide [B82-X00-M00(C01)-D03]

$^1$H NMR (400 MHz, DMSO-d$_6$) δ ppm 2.8 (m, 4 H) 3.7 (s, 3 H) 4.3 (s, 3 H) 4.6 (m, 2 H) 6.9 (s, 1 H) 7.17 (s, 1 H) 7.24 (s, 1 H) 7.43 (s, 1 H) 7.5 (m, 1 H) 8.3 (s, 1 H);

8-[(4-Aminobenzyl)amino]-1-methyl-4,5-dihydro-1H-pyrazolo[4,3-h]quinazoline-3-carboxamide [B83-X00-M00(C01)-D03]

$^1$H NMR (400 MHz, DMSO-d$_6$) δ ppm 2.7 (m, 2 H) 2.9 (t, J 7.7 Hz, 2 H) 4.3 (s, 3 H) 4.4 (d, J 6.1 Hz, 2 H) 5.1 (s, 2 H) 6.5 (d, J 8.4 Hz, 2 H) 7.0 (d, J 8.3 Hz, 2 H) 7.2 (s, 1 H), 7.4 (m, 2 H) 8.2 (s, 1 H);

8-[(4-Fluorobenzyl)amino]-1-methyl-4,5-dihydro-1H-pyrazolo[4,3-h]quinazoline-3-carboxamide $^1$H NMR (400 MHz, DMSO-d$_6$) δ ppm 2.73 (t, J=7.74 Hz, 2 H) 2.94 (t, J=7.56 Hz, 2 H) 4.18 (s, 3 H) 4.52 (d, 6.22 Hz, 2 H) 7.13 (t, J=8.90 Hz, 2 H) 7.23 (s, 1 H) 7.38 (dd, J=8.66, 5.61 Hz, 2 H) 7.42 (t, 1 H) 7.71 (t, J=5.97 Hz, 1 H) 8.23 (s, 1 H).

Example 48

8-{[4-(2-morpholinoethoxy)benzyl]amino}-1-methyl-4,5-dihydro-1H-pyrazolo[4,3-h]quinazoline-3-carboxamide [B84-X00-M00(C01)-D03]

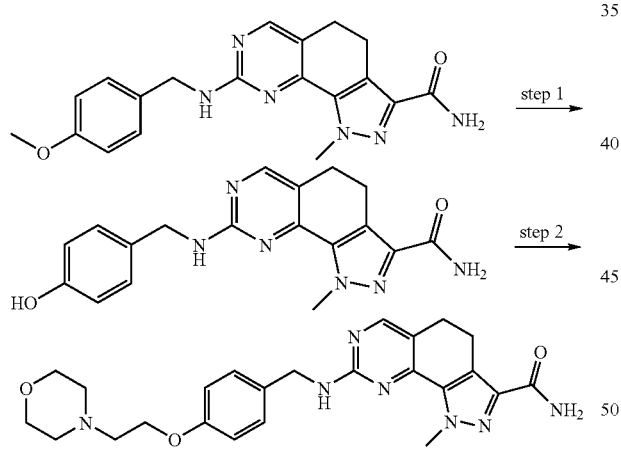

Step 1. 8-[(4-Hydroxybenzyl)amino]-1-methyl-4,5-dihydro-1H-pyrazolo[4,3-h]quinazoline-3-carboxamide [B85-X00-M00(C01)-D03]

To a well stirred solution of 8-[(4-methoxybenzyl)amino]-1-methyl-4,5-dihydro-1H-pyrazolo[4,3-h]quinazoline-3-carboxamide (242 mg, 0.7 mmol) in chloroform (30 mL) boron tribromide (1M in dichloromethane, 5.12 mL, 5.1 mmol) was added dropwise over a 5 minutes period, at room temperature. The mixture was heated to reflux for 8 hours. A solution of 10% aqueous ammonium hydroxide (30 mL) was added dropwise at 0° C. over a 10 minutes period. A precipitate was formed and, after 2 hours, it was filtered and washed with water and dried at 40° C. under vacuum. There were obtained 130 mg of the title compound.

$^1$H NMR (400 MHz, DMSO-d$_6$) δ ppm 2.8 (m, 4 H) 4.2 (s, 3 H) 4.5 (m, 2 H) 6.7 (d, J 8.65 Hz, 2 H) 7.2 (d, J 8.5 Hz, 2 H) 7.25 (s, 1 H) 7.4 (s, 1 H) 7.8 (m, 1 H) 8.2 (s, 1 H)

Step 2. 8-{[4-(2-morpholinoethoxy)benzyl]amino}-1-methyl-4,5-dihydro-1H-pyrazolo[4,3-h]quinazoline-3-carboxamide [B84-X00-M00(C01)-D03]

To a solution of 8-[(4-hydroxybenzyl)amino]-1-methyl-4,5-dihydro-1H-pyrazolo[4,3-h]quinazoline-3-carboxamide (70 mg, 0.2 mmol) in anhydrous dimethylformamide (3 mL), N-morpholinoethylchloride hydrochloride (47 mg, 0.3 mmol) and powdered potassium carbonate (45 mg, 3.3 mmol) were added. The mixture was heated to reflux for 1 hour. The reaction mixture was poured into iced water (70 mL) and extracted with dichloromethane; the organic extracts were washed with brine until neutral pH, then with water and dried over Na$_2$SO$_4$. The crude was purified by flash chromatography on silica gel (eluant: dichloromethane/methanol 96:4) to yield a white solid that was crystallized from methanol, affording 47.0 mg of the title compound.

$^1$H NMR (400 MHz, DMSO-d$_6$) δ ppm 2.5 (m, 4 H) 2.7 (t, 2 H) 2.8 (m, 4 H) 3.6 (m, 4 H) 4.0 (t, 2 H) 4.2 (s, 3 H) 4.5 (m, 2 H) 6.9 (d, J 8.42 Hz, 2 H) 7.2 (s, 1 H) 7.25 (d, J 8.54 Hz, 2 H) 7.4 (s, 1 H) 7.6 (m, 1 H) 8.2 (s, 1 H).

Analogously the following compound was prepared:

8-{[3-(2-morpholinoethoxy)-5-trifluoromethyl]phenylamino}-1-methyl-4,5-dihydro-1H-pyrazolo[4,3-h]quinazoline-3-carboxamide [B119-X00-M00(C01)-D03]

$^1$H NMR (400 MHz, DMSO-d$_6$) δ ppm 2.47-2.56 (m, 4 H) 2.73 (t, J=7.26 Hz, 2 H) 2.85 (t, J=7.80 Hz, 2 H) 3.01 (t, J=7.80 Hz, 2 H) 3.57-3.64 (m, 4 H) 4.17 (t, J=5.49 Hz, 2 H) 4.35 (s, 3 H) 6.86 (t, J=1.83 Hz, 1 H) 7.28 (s, 1 H) 7.48 (s, 1 H) 7.61 (t, J=2.32 Hz, 1 H) 7.80 (t, J=1.46 Hz, 1 H) 8.49 (s, 1 H) 9.85 (s, 1 H).

Example 49

2-anilino-5,6,8,9,10,11-hexahydro-7H-[1,4]diazepino[1',2':1,5]pyrazolo[4,3-h]quinazolin-7-one [B04-X00-M06]

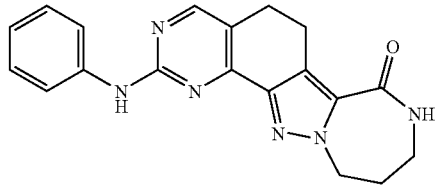

Step 1. Ethyl 7-oxo-4,5,6,7-tetrahydro-1H-indazole-3-carboxylate

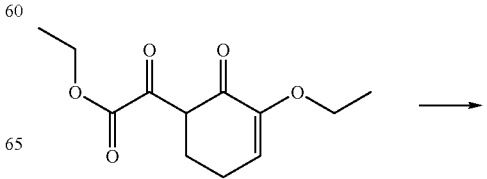

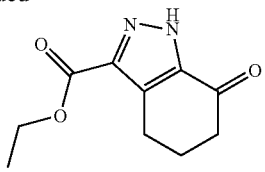

1 g (4.2 mmol) of ethyl (3-ethoxy-2-oxocyclohex-3-en-1-yl)(oxo)acetate were dissolved in 10 mL of ethanol, 0.21 mL of hydrazine hydrate were added and the solution stirred at reflux for a day. The solvent was then evaporated and the residue redissolved with dichloromethane. The organic layer was washed with water, dried over Na$_2$SO$_4$ and concentrated. The crude was triturated with diethyl ether and filtered to give (70% yield) the title compound.

$^1$H NMR (400 MHz, DMSO-d$_6$) δ ppm 1.16 (t, J 6.83 Hz 3 H) 2.25-3.27 (3m, 6 H) 4.18 (q, J 6.83 Hz, 2 H) 8.45 (bs, 1 H).

Analogously the following compound was prepared:

Ethyl 4,4-dimethyl-7-oxo-4,5,6,7-tetrahydro-1H-indazole-3-carboxylate $^1$H NMR (400 MHz, DMSO-d$_6$) δ ppm 1.33 (t, J=6.95 Hz, 3 H) 1.42 (s, 6 H) 1.90-2.02 (m, 2 H) 2.55-2.63 (m, 2 H) 4.33 (q, J=6.95 Hz, 2 H) 14.34 (s, 1 H).

Step 2. Ethyl 7-oxo-1 (and 2)-trityl-4,5,6,7-tetrahydro-1H-indazole-3-carboxylate

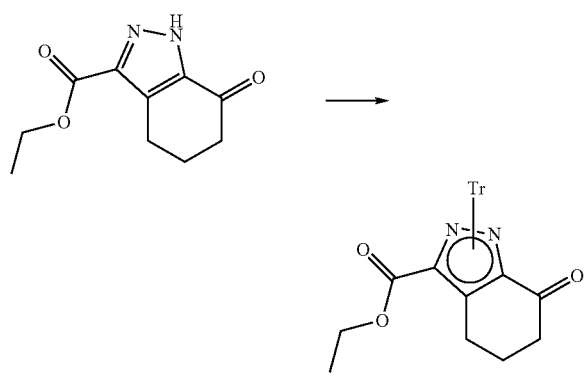

1.20 g (4.8 mmol) of ethyl 7-oxo-4,5,6,7-tetrahydro-1H-indazole-3-carboxylate were dissolved in 40 mL of dichloromethane and 0.76 mL of triethylamine and 1.47 g (5.3 mmol) of triphenylmethyl chloride were added. The solution was stirred at room temperature for 6 hours. Then the solution was diluted with further dichloromethane and washed with water. The organic layer was treated with anhydrous Na$_2$SO$_4$ and evaporated to dryness. The product, as a mixture of regioisomers, was finally obtained by crystallization from diethyl ether (80% yield).

$^1$H NMR (400 MHz, DMSO-d$_6$) δ ppm 1.25 (t, 3 H) 1.94-2.98 (3m, 6 H) 4.25 (q, 2 H) 6.85-7.36 (2m, 15 H).

Analogously the following compounds were prepared:

Ethyl 1-trityl-4,4-dimethyl-7-oxo-4,5,6,7-tetrahydro-1H-indazole-3-carboxylate $^1$H NMR (400 MHz, DMSO-D6) δ ppm 1.26 (t, J=7.07 Hz, 3 H) 1.45 (s, 6 H) 1.79-1.88 (m, 2 H) 2.18-2.26 (m, 2 H) 4.27 (q, J=7.15 Hz, 2 H) 6.84-7.01 (m, 6 H) 7.14-7.33 (m, 9 H);

Ethyl 2-trityl-4,4-dimethyl-7-oxo-4,5,6,7-tetrahydro-1H-indazole-3-carboxylate $^1$H NMR (400 MHz, DMSO-d$_6$) δ ppm 0.88 (t, J=7.13 Hz, 3 H) 1.27 (s, 6 H) 1.92-1.99 (m, 2 H) 2.56-2.63 (m, 2 H) 3.44 (q, J=7.15 Hz, 2 H) 6.99-7.05 (m, 6 H) 7.31-7.37 (m, 9 H).

Step 3. Ethyl-6-[(dimethylamino)methylene]-7-oxo-1(2)-trityl-4,5,6,7-tetrahydro-1H-indazole-3-carboxylate

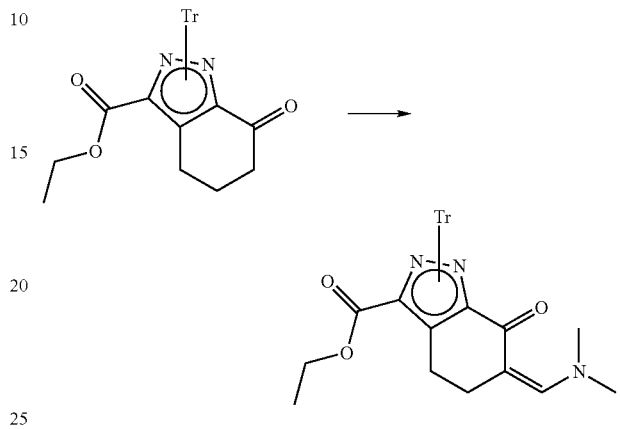

3.0 g (6.6 mmol) of ethyl 7-oxo-1(2)-trityl-4,5,6,7-tetrahydro-1H-indazole-3-carboxylate were dissolved in 20 mL of dimethylformamide and 3.2 mL (13.2 mmol) of dimethylformamide ditertbutylacetale were added. The solution was heated at 65° C. under stirring for a day and then evaporated to dryness. The product was obtained by crystallization from a mixture diethyl ether/ethyl acetate (90% yield).

$^1$H NMR (400 MHz, DMSO-d$_6$) δ ppm 1.24 and 0.79 (2t, J 7.07 Hz, 3 H) 2.70-2.90 (2t, J 6.71 Hz, 6 H) 2.94 and 2.99 (2m, 6 H) 4.21 (q, J 7.07 Hz, 2 H) 6.90-7.30 (m, 15 H).

Analogously the following compounds were prepared:

Ethyl 6-[(dimethylamino)methylene]-1-trityl-4,4-dimethyl-7-oxo-4,5,6,7-tetrahydro-1H-indazole-3-carboxylate $^1$H NMR (400 MHz, DMSO-d$_6$) δ ppm 1.26 (t, J=7.13 Hz, 3 H) 1.36 (s, 6 H) 2.66 (s, 2 H) 2.98 (s, 6 H) 4.25 (q, J=7.15 Hz, 2 H) 6.96 (t, 7 H) 7.15-7.29 (m, 9 H);

Ethyl 6-[(dimethylamino)methylene]-2-trityl-4,4-dimethyl-7-oxo-4,5,6,7-tetrahydro-1H-indazole-3-carboxylate $^1$H NMR (400 MHz, DMSO-d$_6$) δ ppm 0.90 (t, J=7.19 Hz, 3 H) 1.19 (s, 6 H) 2.78 (s, 2 H) 3.11 (s, 6 H) 3.42 (q, J=7.23 Hz, 2 H) 6.97-7.09 (m, 6 H) 7.30-7.37 (m, 9 H) 7.48 (s, 1 H).

Step 4. Ethyl 8-anilino-1 (and 2)-trityl-4,5-dihydro-1H-pyrazolo[4,3-h]quinazoline-3-carboxylate

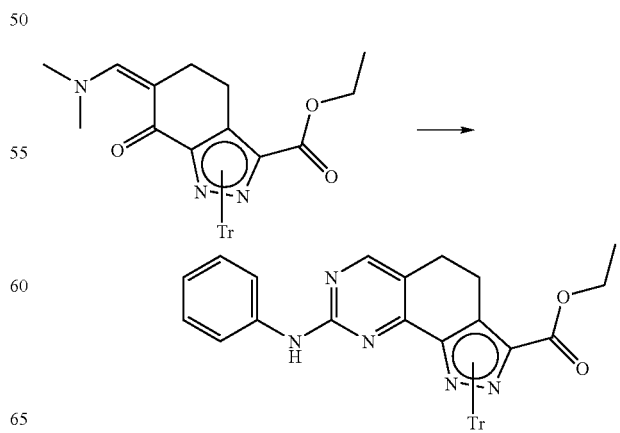

To a solution of 636 mg of ethyl 6-[(dimethylamino)methylene]-7-oxo-1(2)-trityl-4,5,6,7-tetrahydro-1H-indazole-3-carboxylate (1.18 mmol) and 440 mg (1.18 mmol) of phenylguanidine carbonate in 100 mL of absolute ethanol, 0.5 mL of diazabicycloundecene were added. The mixture was stirred at reflux for 48 hours and then the solvent evaporated under reduced pressure. The residue was redissolved with dichloromethane and washed with water. The organic layer was dried over $Na_2SO_4$ and purified by chromatography on a silica gel column (eluant cyclohexane/ethyl acetate 8/2) to give 240 mg of the title compound (35% yield).

$^1$H NMR (400 MHz, DMSO-$d_6$) δ ppm 0.81 (t, J 7.20 Hz, 3 H) 2.80-2.95 (m, 4 H) 3.58 (q, J 7.20 Hz, 2 H) 6.85-7.80 (5m, 20H) 8.38 (bs, 1 H) 9.49 (bs, 1 H).

According to the same method but employing the suitable guanidine derivatives, the following compounds were prepared:

Ethyl 8-{[4-(4-methylpiperazin-1-yl)-3-(trifluoromethyl) phenyl]amino}-1 (and 2)-trityl-4,5-dihydro-1H-pyrazolo [4,3-h]quinazoline-3-carboxylate Ethyl 8-{[3-chloro-4-(4-methylpiperazin-1-yl)phenyl] amino}-1 (and 2)-trityl-4,5-dihydro-2H-pyrazolo[4,3-h] quinazoline-3-carboxylate Ethyl 8-{[4-(4-methylpiperazin-1-yl)phenyl]amino}-1 (and 2)-trityl-4,5-dihydro-2H-pyrazolo[4,3-h]quinazoline-3-carboxylate Ethyl 8-amino-1 (and 2)-trityl-4,5-dihydro-2H-pyrazolo[4,3-h]quinazoline-3-carboxylate Ethyl 8-[4-(4-methyl-piperazin-1-yl)-phenylamino]-1-trityl-4,4dimethyl-4,5-dihydro-1H-pyrazolo[4,3-h]quinazoline-3-carboxylate $^1$H NMR (400 MHz, DMSO-$d_6$) δ ppm 1.24 (t, J 7.20 Hz, 3 H) 1.31 (s, 6H) 2.20 (s, 3 H) 2.43 (m, 4 H) 2.56 (m, 2 H) 2.99 (m, 4 H) 4.24 (q, J 7.20 Hz, 2 H) 6.61 (d, J=8.79 Hz, 2 H) 6.92-7.37 (m, 17 H) 8.07 (bs, 1 H);

Ethyl 8-[4-(4-methyl-piperazin-1-yl)-phenylamino]-2-trityl-4,4dimethyl-4,5-dihydro-1H-pyrazolo[4,3-h]quinazoline-3-carboxylate $^1$H NMR (400 MHz, DMSO-$d_6$) δ ppm 0.89 (t, J 7.20 Hz, 3 H) 1.17 (s, 6H) 2.21 (s, 3 H) 2.46 (m, 4H) 2.71 (m, 2 H) 3.04 (m, 4 H) 3.40 (q, J 7.20 Hz, 2 H) 6.80 (d, J=8.79 Hz, 2 H) 6.96-7.43 (m, 15 H) 7.60 (d, J=8.79 Hz, 2 H) 8.31 (bs, 1 H) 9.31 (bs, 1 H);

Ethyl 8-amino-1 (and 2)-trityl-4,4dimethyl-4,5-dihydro-1H-pyrazolo[4,3-h]quinazoline-3-carboxylate;

Ethyl 8-amino-1-trityl-4,4-dimethyl-4,5-dihydro-1H-pyrazolo[4,3-h]quinazoline-3-carboxylate $^1$H NMR (400 MHz, DMSO-$d_6$) δ ppm 1.27 (t J=7.13 Hz, 3 H) 1.31 (s, 6 H) 2.52 (s, 2 H) 4.27 (q, J=7.07 Hz, 2 H) 5.20 (s, 2 H) 7.03-7.09 (m, 6 H) 7.16-7.34 (m, 9 H) 7.93 (s, 1 H);

Ethyl 8-amino-2-trityl-4,4-dimethyl-4,5-dihydro-1H-pyrazolo[4,3-h]quinazoline-3-carboxylate $^1$H NMR (400 MHz, DMSO-$d_6$) δ ppm 0.95 (t, J=7.13 Hz, 3 H) 1.16 (s, 6 H) 2.63 (s, 2 H) 3.46 (q, J=7.07 Hz, 2 H) 6.47 (s, 2 H) 7.09-7.16 (, 6 H) 7.24-7.41 (m, 9 H) 8.14 (s, 1 H).

Step 5. Ethyl 8-anilino-4,5-dihydro-1H-pyrazolo[4,3-h] quinazoline-3-carboxylate [B04-X00-M00(C00)-D01]

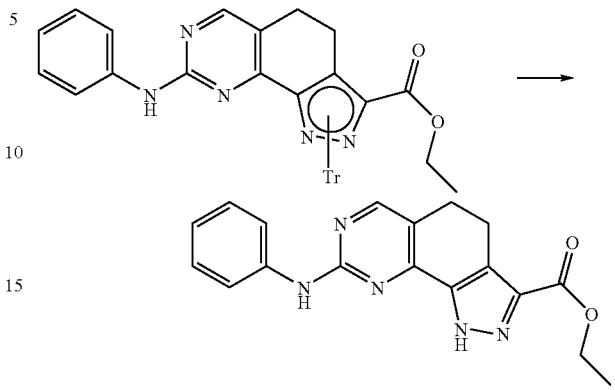

1.50 g (2.6 mmol) of ethyl 8-anilino-1(2)-trityl-4,5-dihydro-1H-pyrazolo[4,3-h]quinazoline-3-carboxylate were dissolved in 50 mL of dichloromethane and 5 mL of trifluoroacetic acid were added. The solution was stirred overnight and the solvent removed in vacuo. The residue was redissolved in dichloromethane and washed with a saturated solution of $NaHCO_3$. The organic layer was then dried over $Na_2SO_4$ and the solvent evaporated to dryness. By crystallization from diisopropyl ether 0.70 mg of the title compound were obtained (80% yield).

$^1$H NMR (400 MHz, DMSO-$d_6$) δ ppm 1.17 (t, 3 H, J 7.07 Hz) 3.05-3.28 (2m, 4 H) 4.18 (q, 2 H, J 7.07 Hz) 6.83-7.63 (3m, 5 H) 8.31 (bs, 1 H) 9.10 (m, 2 H).

According to the same method the following compounds were prepared:

Ethyl 8-{[4-(4-methylpiperazin-1-yl)-3-(trifluoromethyl) phenyl]amino}-4,5-dihydro-2H-pyrazolo[4,3-h]quinazoline-3-carboxylate [B12-X00-M00(C00)-D01]

Ethyl 8-{[3-chloro-4-(4-methylpiperazin-1-yl)phenyl] amino}-4,5-dihydro-2H-pyrazolo[4,3-h]quinazoline-3-carboxylate [B13-X00-M00(C00)-D01]

Ethyl 8-{[4-(4-methylpiperazin-1-yl)phenyl]amino}-4,5-dihydro-2H-pyrazolo[4,3-h]quinazoline-3-carboxylate [B10-X00-M00(C00)-D01]

$^1$H NMR (400 MHz, DMSO-$d_6$) δ ppm 1.35 (t J 7.20 Hz, 3 H) 2.30 (s, 3 H) 2.50-2.60 (m, 4 H) 2.86 (m, 2 H) 2.99 (m, 2 H) 3.10 (m, 4 H) 4.33 (q, J 7.20 Hz, 2 H) 6.90 (d, J=8.90 Hz, 2 H) 7.71 (d, J=8.90 Hz, 2 H) 8.34 (s, 1 H) 9.27 (bs, 1 H) 14.22 (bs, 1 H)

Ethyl 8-amino-4,5-dihydro-1H-pyrazolo[4,3-h]quinazoline-3-carboxylate [B00-X00-M00(C00)-D01]

$^1$H NMR (400 MHz, DMSO-$d_6$) δ ppm 1.33 (t, 3 H, J 7.2 Hz) 2.78 (m, 2 H) 2.96 (m, 2 H) 4.31 (q, 2 H, J 7.2 Hz) 6.64 (m, 2 H) 8.19 (bs, 1 H);

Ethyl 8-[4-(4-methyl-piperazin-1-yl)-phenylamino]-4,4-dimethyl-4,5-dihydro-1H-pyrazolo[4,3-h]quinazoline-3-carboxylate [B10-X00-M03(C00)-D01]

$^1$H NMR (400 MHz, DMSO-$d_6$) δ ppm 1.31 (t J 7.20 Hz, 3 H) 1.33 (s, 6 H) 2.22 (s, 3 H) 2.40-2.50 (m, 4 H) 2.73 (m, 2 H) 3.07 (m, 4 H) 4.35 (q, J 7.20 Hz, 2 H) 6.91 (d, J=9.02 Hz, 2 H) 7.70 (d, J=9.02 Hz, 2 H) 8.33 (bs, 1 H) 9.30 (bs, 1 H) 14.13 (bs, 1 H);

Ethyl 8-amino-4,4-dimethyl-4,5-dihydro-1H-pyrazolo[4,3-h]quinazoline-3-carboxylate [B00-X00-M03(C00)-D01]

$^1$H NMR (400 MHz, DMSO-$d_6$) δ ppm 1.32 (m, 9 H) 2.66 (s, 2 H) 4.22-4.42 (m, 2 H) 6.36 (d, 2 H) 8.19 (d, 1 H) 14.11 (d, 1 H);

Ethyl 8-anilino-4,4-dimethyl-4,5-dihydro-1H-pyrazolo[4,3-h]quinazoline-3-carboxylate [B04-X00-M03(C00)-D01].

Step 6. Ethyl 8-anilino-2-{3-[(tert-butoxycarbonyl)amino]propyl}-4,5-dihydro-2H-pyrazolo[4,3-h]quinazoline-3-carboxylate

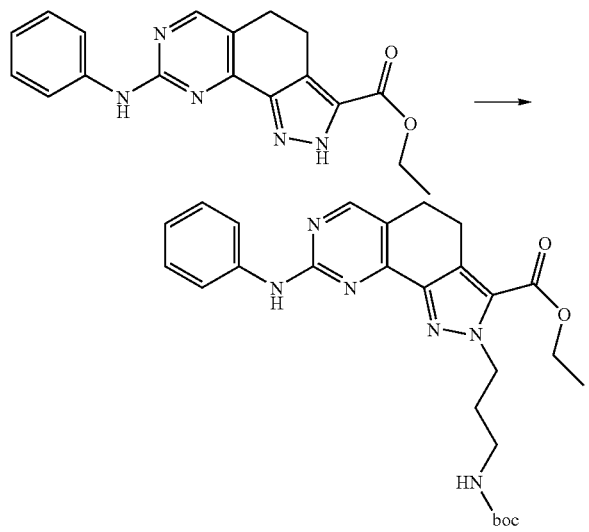

500 mg of ethyl 8-anilino-4,5-dihydro-1H-pyrazolo[4,3-h]quinazoline-3-carboxylate (1.5 mmol) were dissolved in 10 mL of dry dimethylformamide and 1.63 mL of 1 H lithium tert-butoxide in tetrahydrofuran were added to the cooled solution. After 30 minutes under stirring at 0° C. a solution of 432 mg of tert-butoxycarbonylaminopropyl bromide in 8 mL of dry tetrahydrofuran were added dropwise. After a night at room temperature the mixture was poured into a solution of $NaH_2PO_4$ and extracted with dichloromethane. The organic layer was then dried over $Na_2SO_4$ and the solvent evaporated, giving an oil that was treated according to the following step 7, without any further purification.

Analogously the following compounds can be prepared:

Ethyl 2-{3-[(tert-butoxycarbonyl)amino]propyl}-8-{[4-(4-methylpiperazin-1-yl)phenyl]amino}-4,5-dihydro-2H-pyrazolo[4,3-h]quinazoline-3-carboxylate Ethyl 2-{3-[(tert-butoxycarbonyl)amino]propyl})-8-{[4-(4-methylpiperazin-1-yl)-3-(trifluoromethyl)phenyl]amino}-4,5-dihydro-2H-pyrazolo[4,3-h]quinazoline-3-carboxylate Ethyl 2-{3-[(tert-butoxycarbonyl)amino]propyl}-8-{[3-chloro-4-(4-methylpiperazin-1-yl)phenyl]amino}-4,5-dihydro-2H-pyrazolo[4,3-h]quinazoline-3-carboxylate Ethyl 8-amino-2-{3-[(tert-butoxycarbonyl)amino]propyl}-4,5-dihydro-2H-pyrazolo[4,3-h]quinazoline-3-carboxylate;

Ethyl 8-amino-2-{3-[(tert-butoxycarbonyl)amino]propyl}-4,4-dimethyl-4,5-dihydro-1H-pyrazolo[4,3-h]quinazoline-3-carboxylate;

Ethyl 8-[4-(4-methyl-piperazin-1-yl)-phenylamino]-2-{3-[(tert-butoxycarbonyl)amino]propyl}-4,4-dimethyl-4,5-dihydro-1H-pyrazolo[4,3-h]quinazoline-3-carboxylate;

Ethyl 8-anilino-2-{3-[(tert-butoxycarbonyl)amino]propyl}-4,4-dimethyl-4,5-dihydro-1H-pyrazolo[4,3-h]quinazoline-3-carboxylate.

Following the above method, but employing tert-butoxycarbonylaminoethyl bromide, the following compounds were prepared:

Ethyl 8-anilino-2-{2-[(tert-butoxycarbonyl)amino]ethyl}-4,5-dihydro-2H-pyrazolo[4,3-h]quinazoline-3-carboxylate;

Ethyl 2-{2-[(tert-butoxycarbonyl)amino]ethyl}-8-{[4-(4-methylpiperazin-1-yl)phenyl]amino}-4,5-dihydro-2H-pyrazolo[4,3-h]quinazoline-3-carboxylate Ethyl 2-{2-[(tert-butoxycarbonyl)amino]ethyl}-8-{[4-(4-methylpiperazin-1-yl)-3-(trifluoromethyl)phenyl]amino}-4,5-dihydro-2H-pyrazolo[4,3-h]quinazoline-3-carboxylate Ethyl 2-{2-[(tert-butoxycarbonyl)amino]ethyl}-8-{[3-chloro-4-(4-methylpiperazin-1-yl)phenyl]amino}-4,5-dihydro-2H-pyrazolo[4,3-h]quinazoline-3-carboxylate Ethyl 8-amino-2-{2-[(tert-butoxycarbonyl)amino]ethyl}-4,5-dihydro-2H-pyrazolo[4,3-h]quinazoline-3-carboxylate $^1$H NMR (400 MHz, DMSO-$d_6$) δ ppm 1.31 (s, 9H) 1.36(t, 3 H, J 7.2 Hz) 2.74 (m, 2 H) 2.94 (m, 2 H) 3.34 (m, 2 H) 4.33 (q, 2H, J 7.2 Hz) 4.57 (t, 2 H) 6.50 (m, 2 H) 6.87 (t, 1 H) 8.15 (bs, 1 H);

Ethyl 8-amino-2-{2-[(tert-butoxycarbonyl)amino]ethyl}-4,4-dimethyl-4,5-dihydro-2H-pyrazolo[4,3-h]quinazoline-3-carboxylate;

Ethyl 8-[4-(4-methyl-piperazin-1-yl)-phenylamino]-2-{2-[(tert-butoxycarbonyl)amino]ethyl}-4,4-dimethyl-4,5-dihydro-1H-pyrazolo[4,3-h]quinazoline-3-carboxylate;

Ethyl 8-anilino-2-{2-[(tert-butoxycarbonyl)amino]ethyl}-4,4-dimethyl-4,5-dihydro-2H-pyrazolo[4,3-h]quinazoline-3-carboxylate.

Step 7. Ethyl 2-(3-aminopropyl)-8-anilino-4,5-dihydro-2H-pyrazolo[4,3-h]quinazoline-3-carboxylate hydrochloride [B04-X00-M04(C13)-D01]

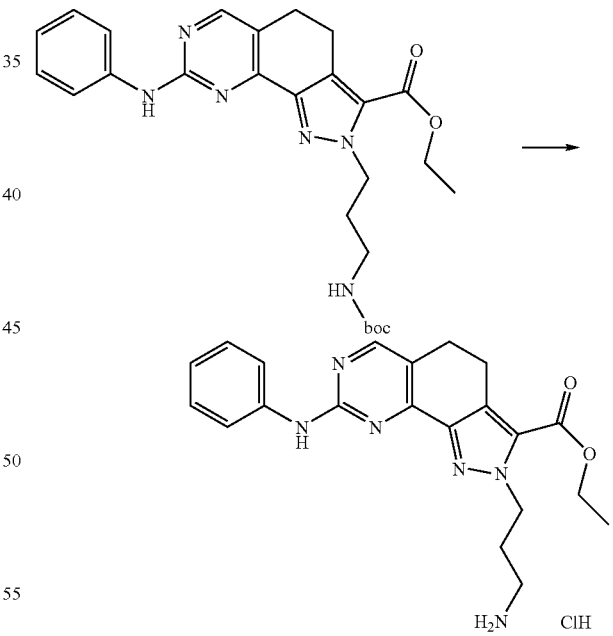

The crude of previous step 6 was dissolved in 20 mL of dioxane and 8 mL of HCl 37% were added. After 6 hours under stirring at room temperature the solvent was removed in vacuo, the residue triturated with ethanol and the product collected by filtration (80% yield).

By working according to the above method, the following compounds were prepared:

B04-X00-M04(C12)-D01
B00-X00-M04(C12)-D01

$^1$H NMR (400 MHz, DMSO-d$_6$) δ ppm 1.37 (t, 3 H, J 7.2 Hz) 2.85 (m, 2 H) 3.02 (m, 2 H) 3.50 (m, 2 H) 4.37 (q. 2 H, J 7.2 Hz) 4.84 (t, 2 H) 7.47 (m, 1 H) 8.08 (m, 3 H) 8.29 (s, 1 H);

B12-X00-M04(C12)-D01
B13-X00-M04(C12)-D01
B10-X00-M04(C12)-D01
B12-X00-M04(C13)-D01
B13-X00-M04(C13)-D01
B10-X00-M04(C13)-D01

Ethyl 8-amino-2-(3-aminopropyl)-4,5-dihydro-1H-pyrazolo[4,3-h]quinazoline-3-carboxylate hydrochloride B00-X00-M04(C13)-D01;

Ethyl 8-amino-2-(3-aminopropyl)-4,4-dimethyl-4,5-dihydro-1H-pyrazolo[4,3-h]quinazoline-3-carboxylate hydrochloride B00-X00-M09(C13)-D01;

Ethyl 2-(3-aminopropyl)-[4-(4-methyl-piperazin-1-yl)-phenylamino]4,4-dimethyl-4,5-dihydro-1H-pyrazolo[4,3-h]quinazoline-3-carboxylate hydrochloride B10-X00-M09(C13)-D01;

Ethyl 8-anilino-2-(3-aminopropyl)-4,4-dimethyl-4,5-dihydro-1H-pyrazolo[4,3-h]quinazoline-3-carboxylate hydrochloride B04-X00-M09(C13)-D01;

Ethyl 8-amino-2-(3-aminoethyl)-4,4-dimethyl-4,5-dihydro-1H-pyrazolo[4,3-h]quinazoline-3-carboxylate hydrochloride B00-X00-M09(C12)-D01;

Ethyl 2-(3-aminoethyl)-8-[4-(4-methyl-piperazin-1-yl)-phenylamino]-4,4-dimethyl-4,5-dihydro-1H-pyrazolo[4,3-h]quinazoline-3-carboxylate hydrochloride B10-X00-M09(C12)-D01;

Ethyl 8-anilino-2-(3-aminoethyl)-4,4-dimethyl-4,5-dihydro-1H-pyrazolo[4,3-h]quinazoline-3-carboxylate hydrochloride B04-X00-M09(C12)-D01.

Step 8. 2-anilino-5,6,8,9,10,11-hexahydro-7H-[1,4]diazepino[1',2':1,5]pyrazolo[4,3-h]quinazolin-7-one [B04-X00-M06]

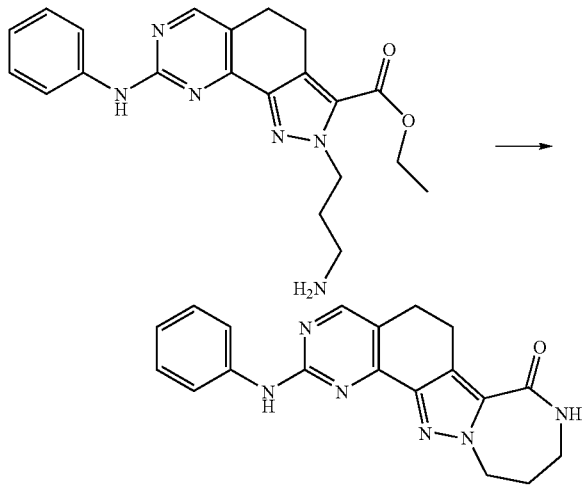

185 mg (0.43 mmol) of ethyl 2-(3-aminopropyl)-8-anilino-4,5-dihydro-2H-pyrazolo[4,3-h]quinazoline-3-carboxylate hydrochloride were dissolved in 10 mL of methanol and 400 mg of cesium carbonate were added. After 3 hours under stirring at room temperature the solvent was removed at reduced pressure. Water was then added to the residue and the solid collected by filtration and washed with water and acetone to give 100 mg (70% yield) of the title compound.

$^1$H NMR (400 MHz, DMSO-d$_6$) δ ppm 2.18 (ddd, J 13.02, 6.65, 6.55 Hz, 2 H) 2.88 (m, 4 H) 3.21 (q, J 5.89 Hz, 2 H) 4.50 (t, J 6.77 Hz, 2 H) 6.93 (t, J 7.32 Hz, 1 H) 7.28 (dd, J 829, 7.56 Hz, 2 H) 7.85 (d, J 7.68 Hz, 2 H) 8.27 (t, J 5.18 Hz, 1 H) 8.38 (s, 1 H) 9.62 (s, 1 H)

By working according to this method the following compounds were prepared:

2-anilino-5,6,9,10-tetrahydropyrazino[1',2':1,5]pyrazolo[4,3-h]quinazolin-7(8H)-one [B04-X00-M05]

$^1$H NMR (400 MHz, DMSO-d$_6$) δ ppm 2.92 (m, 4 H) 3.65 (m, 2 H) 4.41 (m, 2 H) 6.93 (m, 1 H) 7.28 (m, 2 H) 7.85 (m, 2 H) 8.26 (m, 1 H) 8.39 (s, 1 H) 9.61 (s, 1 H);

2-{[4-(4-methylpiperazin-1-yl)-3-(trifluoromethyl)phenyl]amino}-5,6,9,10-tetrahydropyrazino[1',2':1,5]pyrazolo[4,3-h]quinazolin-7(8 H)-one [B12-X00-M05]

2-{[3-chloro-4-(4-methylpiperazin-1-yl)phenyl]amino}-5,6,9,10-tetrahydropyrazino[1',2':1,5]pyrazolo[4,3-h]quinazolin-7(8H)-one [B13-X00-M05]

2-{[4-(4-methylpiperazin-1-yl)phenyl]amino}-5,6,9,10-tetrahydropyrazino[1',2':1,5]pyrazolo[4,3-h]quinazolin-7(8H)-one[B10-X00-M05]

2-amino-5,6,9,10-tetrahydropyrazino[1',2':1,5]pyrazolo[4,3-h]quinazolin-7(8H)-one [B00-X00-M05]

$^1$H NMR (400 MHz, DMSO-d$_6$) δ ppm 2.74 (t, J=7.56 Hz, 2 H) 2.88-2.98 (m, 2 H) 3.60-3.68 (m, 2 H) 4.29-4.42 (m, 2 H) 6.48 (s, 2 H) 8.15 (s, 1 H) 8.21-8.32 (m, 1 H);

2-amino-5,6,8,9,10,11-hexahydro-7H-[1,4]diazepino[1',2':1,5]pyrazolo[4,3-h]quinazolin-7-one[B00-X00-M06]

$^1$H NMR (400 MHz, DMSO-d$_6$) δ ppm 2.18 (ddd, J 13.02, 6.65, 6.55 Hz, 2 H) 2.74 (m, 2 H) 2.92 (m, 2 H) 3.21 (q, J 5.89 Hz, 2 H) 4.50 (t, J 6.77 Hz, 2 H) 6.48 (m, 2 H) 8.17 (s, 1 H) 8.23 (m, 1 H);

2-{[4-(4-methylpiperazin-1-yl)-3-(trifluoromethyl)phenyl]amino}-5,6,8,9,10,11-hexahydro-7H-[1,4]diazepino[1',2':1,5]pyrazolo[4,3-h]quinazolin-7-one[B12-X00-M06]

2-{[3-chloro-4-(4-methylpiperazin-1-yl)phenyl]amino}-5,6,8,9,10,11-hexahydro-7H-[1,4]diazepino[1',2':1,5]pyrazolo[4,3-h]quinazolin-7-one [B13-X00-M06]

2-{[4-(4-methylpiperazin-1-yl)phenyl]amino}-5,6,8,9,10,11-hexahydro-7H-[1,4]diazepino[1',2':1,5]pyrazolo[4,3-h]quinazolin-7-one [B10-X00-M06]

2-amino-6,6-dimethyl-5,9,10-trihydropyrazino[1',2':1,5]pyrazolo[4,3-h]quinazolin-7(8H)-one [B00-X00-M07];

2-anilino-6,6-dimethyl-5,9,10-trihydropyrazino[1',2':1,5]pyrazolo[4,3-h]quinazolin-7(8H)-one [B04-X00-M07];

2-[4-(4-methyl-piperazin-1-yl)-phenylamino]-6,6-dimethyl-5,9,10-trihydropyrazino[1',2':1,5]pyrazolo[4,3-h]quinazolin-7(8H)-one [B10-X00-M07]

$^1$H NMR (400 MHz, DMSO-d$_6$) δ ppm 1.33 (s, 6) 2.23 (s, 3 H) 2.47 (m, 4 H) 2.92 (m, 2 H) 3.07 (m, 4 H) 3.65 (m, 2 H) 4.41 (m, 2 H) 6.91 (d, J=9.02 Hz, 2 H) 7.53 (d, J=9.02 Hz, 2 H) 8.23 (m, 1 H) 8.34 (s, 1 H) 9.12 (s, 1 H);

2-amino-6,6-dimethyl-5,8,9,10,11-pentahydro-7H-[1,4]diazepino[1',2':1,5]pyrazolo[4,3-h]quinazolin-7-one [B00-X00-M08];

2-anilino-6,6-dimethyl-5,8,9,10,11-pentahydro-7H-[1,4]diazepino[1',2':1,5]pyrazolo[4,3-h]quinazolin-7-one [B04-X00-M08];

2-[4-(4-methyl-piperazin-1-yl)-phenylamino]-6,6-dimethyl-5,8,9,10,11-pentahydro-7H-[1,4]diazepino[1',2':1,5]pyrazolo[4,3-h]quinazolin-7-one [B10-X00-M08]

$^1$H NMR (400 MHz, DMSO-d$_6$) δ ppm 1.33 (s, 6 H) 2.18 (ddd, J 13.02, 6.65, 6.55 Hz, 2 H) 2.23 (s, 3 H) 2.47 (m, 4 H) 2.92 (m, 2 H) 3.07 (m, 4 H) 3.21 (q, J 5.89 Hz, 2 H) 4.50 (t, J 6.77 Hz, 2 H) 6.91 (d, J 9.02 Hz, 2 H) 7.53 (d, J=9.02 Hz, 2 H) 8.27 (m, 1 H) 8.34 (s, 1 H) 9.12 (s, 1 H).

Example 50

8-anilino-1-methyl-4,5-dihydro-1H-pyrazolo[4,3-h]quinazoline-3-carboxylic acid [B04-X00-M00(C01)-D02]

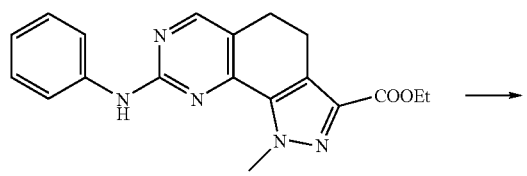

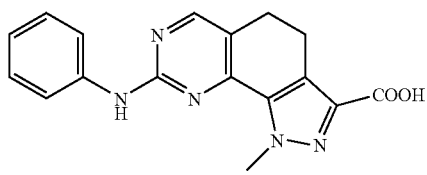

0.63 g (1.80 mmol) of ethyl 8-anilino-1-methyl-4,5-dihydro-1H-pyrazolo[4,3-h]quinazoline-3-carboxylate were dissolved in 100 mL of a mixture tetrahydrofuran/methanol/water 8/1/1 and 0.19 g (4,53 mmol) of lithium hydroxide hydrate were added. The solution was stirred at 60° C. for 1.5 hours. The mixture was then cooled to room temperature and 1 N HCl added until neutral pH. Water was added and the resulting precipitate collected by filtration (87% yield).

$^1$H NMR (400 MHz, DMSO-$d_6$) δ ppm 2.85 (t, J 7.74 Hz, 2 H) 2.99 (m, 2 H) 4.36 (s, 3 H) 6.98 (tt, J 7.35, 1.07 Hz, 1 H) 7.31 (dd, J 8.47, 7.50 Hz, 2 H) 7.72 (dd, J 8.60, 0.91 Hz, 2 H) 8.42 (s, 1 H) 9.52 (s, 1 H) 12.68 (s, 1 H)

By working according to the same procedure the following compounds were prepared:

B00-X00-M00(C01)-D02

$^1$H NMR (400 MHz, DMSO-$d_6$) δ ppm 2.48 and 3.64 (2t, J 7.25 Hz, 4 H) 3.84 (s, 3 H) 8.04 (bs, 2 H) 8.46 (bs, 1 H);

B09-X00-M00(C03)-D02

$^1$H NMR (400 MHz, DMSO-$d_6$ Hz) 6.49 (m, 1 H) 7.07 (m, 2 H) 7.94 (bs, 1 H) 8.30 (s, 1 H) 9.35 (bs, 1 H);

B09-X00-M04(C03)-D02

$^1$H NMR (400 MHz, DMSO-$d_6$) δ ppm 0.80 (s, 9 H) 1.62 (m, 2 H) 2.26 (s, 2 H) 2.52 (m, 4 H) 3.13 (m, 4 H) 4.86 (m, 2 H) 6.58 (m, 1 H) 7.13 (m, 1 H) 7.20 (m, 1 H) 8.41 (s, 1 H) 9.20 (bs, 1 H);

B10-X00-M00(C01)-D02

$^1$H NMR (400 MHz, DMSO-$d_6$) δ ppm 1.89 (s, 3 H) 2.74 (m, 2 H) 2.95 (m, 2 H) 4.30 (s, 3 H) 6.93 (m, 2 H) 7.52 (m, 2 H) 8.33 (s, 1 H) 9.28 (bs, 1 H);

B103-X00-M00(C01)-D02

$^1$H NMR (400 MHz, DMSO-$d_6$) δ ppm 2.09 (m, 4 H) 2.83 (m, 5 H) 2.97 (t, 2 H) 4.33 (s, 3 H) 7.02 (m, 2 H) 7.61 (m, 2 H) 8.38 (s, 1 H) 9.39 (s, 1 H);

B09-X00-M00(C01)-D02

$^1$H NMR (400 MHz, DMSO-$d_6$) δ ppm 2.81 (m, 5 H) 2.93 (t, 2 H) 3.09 (m, 4 H) 3.71 (m, 4 H) 4.32 (s, 3 H) 6.64 (m, 1 H) 7.17 (m, 1 H) 7.29 (m, 2 H) 8.38 (s, 1 H) 9.42 (s, 1 H) 10.33 (s, 1 H);

B04-X04-M00(C01)-D02

$^1$H NMR (400 MHz, DMSO-$d_6$) δ ppm 2.89 (t, 2 H) 2.97 (t, 2 H) 3.70 (s, 3 H) 7.51 (m, 3 H) 7.67 (m, 2 H) 8.56 (s, 1 H) 12.81 (bs, 1 H),

B05-X06-M00(C01)-D02

$^1$H NMR (400 MHz, DMSO-$d_6$) δ ppm 2.92 (t, 2 H) 2.97 (t, 2 H) 4.23 (s, 2 H) 4.26 (s, 3 H) 7.23 (m, 1 H) 7.32 (m, 2 H) 7.36 (m, 2 H) 8.65(s, 1 H) 12.82 (bs, 1 H);

B10-X00-M04(C15)-D02

$^1$H NMR (400 MHz, DMSO-$d_6$) δ ppm 2.60 (m, 5 H) 2.89 (m, 2 H) 3.04 (m, 4 H) 3.33 (m, 4 H) 6.31 (s, 2 H) 6.78 (d, 2 H) 7.39 (m, 3 H) 7.47 (m, 2 H) 7.63 (m, 2 H) 7.67 (s, 1 H) 8.42 (s, 1 H) 9.33(s, 1 H) 13.55 (s, 1 H).

Example 51

8-anilino-1-methyl-N-phenyl-4,5-dihydro-1H-pyrazolo[4,3-h]quinazoline-3-carboxamide [B04-X00-M00(C00)-D20]

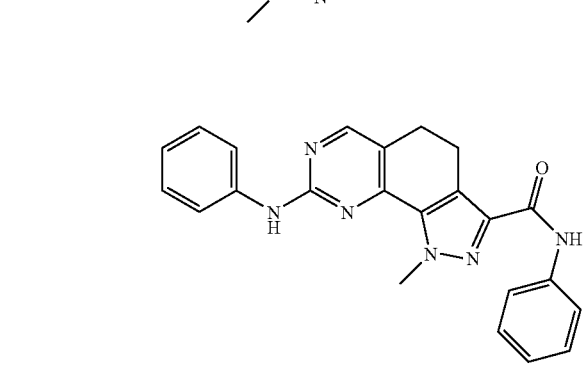

45 mg (0.14 mmol) of 8-anilino-1-methyl-4,5-dihydro-1H-pyrazolo[4,3-h]quinazoline-3-carboxylic acid were dissolved in 7 mL of dimethylformamide and 145.6 mg (0.28 mmol) of (benzotriazol-1-yloxy)tripyrrolidinophosphonium hexafluorophosphate (PyBOP); 0.12 mL (0.70 mmol) of N,N-diisopropyl-N-ethyl amine and 0.08 mL (0.70 mmol) of aniline were then added. After 6 hours the solvent was removed, the residue was redissolved with dichloromethane and washed with water. The organic layer was dried over $Na_2SO_4$ and evaporated to dryness. The product crystallized from methanol (60% yield).

$^1$H NMR (400 MHz, DMSO-$d_6$) δ ppm: 2.88 (m, 2 H) 3.07 (m, 2 H) 4.43 (s, 3 H,) 6.97-7.85 (6m, 10 H) 8.45 (s, 1 H) 9.55 (s, 1 H) 10.09 (s, 1 H).

By working analogously the following compounds were prepared:

TABLE XIII

| | |
|---|---|
| B04-X00-M00(C01)-D04 | $^1$H NMR(400MHz, DMSO-$d_6$) δ ppm 2.72(d, J=4.76Hz, 3H) 2.79(t, J=7.68Hz, 2H) 2.97(t, J=7.68Hz, 2H) 4.31(s, 3H) 6.94(t, J=7.38Hz, 1H) 7.21–7.32(m, 2H) 7.68(d, J=7.56Hz, 2H) 8.06(q, J=4.35Hz, 1H) 8.38(s, 1H) 9.48(s, 1H) |
| B04-X00-M00(C01)-D08 | $^1$H NMR(400MHz, DMSO-$d_6$) δ ppm 1.89(m, 4H) 2.83(m, 2H) 2.94(m, 2H) 3.49(t, J 6.77Hz, 2H) 3.83(t, J 6.58Hz, 2H) 4.34(s, 3H) 6.97(t, J 7.32Hz, 1H) 7.31(dd, J 8.29, 7.56Hz, 2H) 7.73(d, J 7.44Hz, 2H) 8.42(s, 1H) 9.51(s, 1H) |
| B04-X00-M00(C01)-D09 | $^1$H NMR(400MHz, DMSO-$d_6$) δ ppm 2.65(m, 2H) 3.01(m, 2H) 4.36(s, 3H) 4.43(d, J 6.34Hz, 2H) 6.97(t, J 7.32Hz, 1H) 7.31(m, 7H) 7.72(d, J 7.5Hz, 2H) 8.42(s, 1H) 8.71(t, J 6.4Hz, 1H) 9.52(s, 1H) |
| B04-X00-M00(C01)-D10 | $^1$H NMR(400MHz, DMSO-$d_6$) δ ppm 2.65–3.5(m, 15H) 4.35(s, 3H) 6.98(t, J 7.4Hz, 1H) 7.32(dd, J 8.29, 7.56Hz, 2H) H) 7.73(d, J 7.5Hz, 2H) 8.44(s, 1H) 9.55(s, 1H) |
| B04-X00-M00(C01)-D11 | $^1$H NMR(400MHz, DMSO-$d_6$) δ ppm 0.88(d, J 6.71Hz, 6H) 1.86(m, 1H) 2.83(dd, J 8.05, 7.19Hz, 2H) 3.00(t, J 7.74Hz, 2H) 3.07(t, J 6.58Hz, 2H) 4.36(s, 3H) 6.97(tt, J 7.32, 1.10Hz, 1H) 7.31(dd, J 8.47, 7.50Hz, 2H) 7.72(dd, J 8.54, 0.98Hz, 2H) 8.09(t, J 6.16Hz, 1H) 8.42(s, 1H) 9.52(s, 1H) |
| B04-X00-M00(C01)-D12 | $^1$H NMR(400MHz, DMSO-$d_6$) δ ppm 2.83(m, 2H) 3.01(m, 2H) 3.28(s, 3H) 3.43(m, 4H) 4.36(s, 3H) 6.98(m, 1H) 7.31(dd, J 8.41, 7.44Hz, 2H) 7.72(dd, J 8.66, 0.98Hz, 2H) 7.99(t, J 5.49Hz, 1H) 8.42(s, 1H) 9.52(s, 1H) |
| B04-X00-M00(C01)-D13 | $^1$H NMR(400MHz, DMSO-$d_6$) δ ppm 1.16(m, 6H) 1.83(m, 2H) 2.83(m, 2H) 3.01(m, 2H) 2.9–3.5(m, 8H) 4.36(s, 3H) 6.97(m, 1H) 7.31(m, 2H) 7.72(dd, J 8.54, 0.98Hz, 2H) 8.09(t J 6.16Hz, 1H) 8.43(s, 1H) 9.53(s, 1H) |
| B04-X00-M00(C01)-D14 | $^1$H NMR(400MHz, DMSO-$d_6$) δ ppm 1.54(m, 4H) 1.70(m, 2H) 1.85(m, 2H) 2.83(m, 2H) 3.0(m, 2H) 4.21(m, 1H) 4.35(s, 3H) 6.97(t, J 7.32Hz, 1H) 7.31(dd, J 8.29, 7.56Hz, 2H) 7.73(d, J 7.44Hz, 2H) 8.42(s, 1H) 9.51(s, 1H) |
| B04-X00-M00(C01)-D15 | $^1$H NMR(400MHz, DMSO-$d_6$) δ ppm 2.65(s, 3H) 2.83(m, 2H) 3.01(m, 2H) 3.06(m, 8H) 4.42(s, 3H) 6.75(m, 1H) 6.99(t, J 7.32Hz, 1H) 7.20(t, J 8.05Hz, 1H) 7.32(m, 3H) 7.55(bs, 1H) 7.72(dd, J 8.66, 0.98Hz, 2H) 8.45(s, 1H) 9.55(s, 1H) 9.91(s, 1H) |
| B04-X00-M00(C01)-D16 | $^1$H NMR(400MHz, DMSO-$d_6$) δ ppm 2.84(m, 2H) 3.01(m, 2H) 4.35(s, 3H) 4.43(d, J 6.10Hz, 2H) 6.25(dd, J 3.17, 0.85Hz, 1H) 6.40(dd, J 3.17, 1.83Hz, 1H) 6.97(m, 1H) 7.31(dd, J 8.54, 7.44Hz, 2H) 7.57(dd, J 1.83, 0.85Hz, 1H) 7.72(dd, J 8.60, 1.04Hz, 2H) 8.42(s, 1H) 8.54(t, J 6.04Hz, 1H) 9.52(s, 1H) |
| B04-X00-M00(C01)-D17 | $^1$H NMR(400MHz, DMSO-$d_6$) δ ppm 1.7(m, 2H) 2.83(m, 2H) 3.01(m, 2H) 3.2–3.7(m, 12H) 4.35(s, 3H) 6.98(m, 1H) 7.32(dd, J 8.54, 7.44Hz, 2H) 7.72(dd, J 8.54, 0.98Hz, 2H) 8.38(m, 1H) 8.42(s, 1H) 9.52(s, 1H) |
| B00-X00-M00(C21)-D04] | $^1$H NMR(400MHz, DMSO-$d_6$) δ ppm 1.94(d, J=10.73Hz, 2H) 2.11–2.31(m, 4H) 2.70(1, J=7.93Hz, 2H) 2.76(d, J=4.76Hz, 3H) 2.86–3.02(m, J=7.56, 7.56Hz, 4H) 3.55(s, 2H) 5.50–5.62(m, 1H) 6.51(s, 2H) 7.19–7.39(m, 5H) 7.93–8.04(m, 1H) 8.17(s, 1H) |
| B00-X00-M00(C01)-D18 | $^1$H NMR(400MHz, DMSO-$d_6$) δ ppm 2.79(m, 2H) 3.03(m, 2H) 4.40(s, 3H) 6.61(bs, 2H) 7.18(m, 1H) 7.87(m, 1H) 8.18(m, 1H) 8.22(m, 1H) 8.37(m, 1H) 9.46(s, 1H). |
| B04-X00-M00(C01)-D27 | |
| B04-X00-M04(C01)-D27 | |
| B04-X00-M00(C21)-D09 | $^1$H NMR(400MHz, DMSO-$d_6$) δ ppm 1.93(d, J=9.76Hz, 2H) 2.00–2.10(m, 2H) 2.13–2.28(m, 2H) 2.81(t, J=7.44Hz, 2H) 2.88(d, J=11.22Hz, 2H) 3.00(t, J=7.62Hz, 2H) 3.51(s, 2H) 4.42–4.50(m, J=6.46Hz, 2H) 5.49–5.62(m, 1H) 6.99–7.40(m, 13H) 7.61(d, J=8.66Hz, 2H) 8.42(s, 1H) 8.68(t, J=6.16Hz, 1H) 9.44(s, 1H) |
| B04-X00-M00(C01)-D19 | $^1$H NMR(400MHz, DMSO-$d_6$) δ ppm 2.85(m, 4H) 3.01(m, 2H) 3.49(m, 2H) 4.35(s, 3H) 6.97(m, 1H) 7.31(m, 7H) 7.72(dd, J 8.60, 1.04Hz, 2H) 8.18(m, 1H) 8.42(s, 1H) 9.52(s, 1H) |

TABLE XIII-continued

| | |
|---|---|
| B10-X00-M00(C01)-D04 | $^1$H NMR(400MHz, DMSO-d$_6$) δ ppm 2.75(d, J=4.76Hz, 3H) 2.81(t, J=7.68Hz, 2H) 2.85(d, J=4.39Hz, 3H) 2.94–3.07(m, 4H) 3.11–3.25(m, 2H) 3.51(d, J=11.83Hz, 2H) 3.73(d, J=13.66Hz, 2H) 4.33(s, 3H) 6.99(d, J=9.15Hz, 2H) 7.60(d, J=9.02Hz, 2H) 8.08(q, J=4.67Hz, 1H) 8.37(s, 1H) 9.40(s, 1H) 10.36(s, 1H) |
| B10-X00-M00(C01)-D09 | $^1$H NMR(400MHz, DMSO-d$_6$) δ ppm 2.29(s, 3H) 2.55(m, 4H) 2.80(m, 2H) 2.99(m, 2H) 3.10(m, 2H) 4.34(s, 3H) 4.44(d, J 6.34Hz, 2H) 6.92(d, J 9.02Hz, 2H) 7.25(d, 1H) 7.32(m, 4H) 7.72(d, J 7.5Hz, 2H) 8.35(s, 1H) 8.69(t, J 6.4Hz, 1H) 9.26(s, 1H) |
| B10-X00-M00(C01)-D21 | $^1$H NMR(400MHz, DMSO-d$_6$) δ ppm 2.27(s, 3H), 2.80(t, 2H), 2.99(t, 2H), 3.09(bs, 4H), 3.34(m, 4H), 4.34(s, 3H), 4.40(d, 2H), 6.93(d, 2H), 7.15(t, 2H), 7.37(t, 2H), 7.53(d, 2H), 8.35(s, 1H), 8.74(t, 1H), 9.26(s, 1H). |
| B10-X00-M00(C01)-D22 | $^1$H NMR(400MHz, DMSO-d$_6$) δ ppm 2.27(s, 3H), 2.80(t, 2H), 2.99(t, 2H), 3.09(bs, 4H), 3.34(m, 4H), 3.74,(s, 3H), 4.33(d+s, 5H), 6.90(t, 4H), 7.25(d, 2H), 7.53(d, 2H), 8.35(s, 1H), 8.60(t, 1H), 9.26(s, 1H). |
| B10-X00-M00(C01)-D23 | $^1$H NMR(400MHz, DMSO-d$_6$) δ ppm 2.27(s, 3H), 2.52(m, 4H), 2.80(t, 2H), 2.99(t, 2H), 3.09(bs, 4H), 4.35(s, 3H), 4.50(d, 2H), 6.93(d, 2H), 7.55(m, 4H), 7.69(d, 2H), 8.35(s, 1H), 8.87(t, 1H), 9.26(s, 1H). |
| B10-X00-M00(C01)-D24 | $^1$H NMR(400MHz, DMSO-d$_6$) δ ppm 1.50(d, 3H), 2.24(s, 3H), 2.47(m, 4H), 2.78(t, 2H), 2.96(t, 2H), 3.08(m, 4H), 4.35(s, 3H), 5.15(m, 1H), 6.91(d, 2H), 7.24(t, 1H), 7.33(t, 2H), 7.42(m, 2H), 7.53(d, 2H), 8.34(s, 1H), 8.43(d, 1H), 9.25(s, 1H). |
| B10-X00-M00(C19)-D04 | $^1$H NMR(400MHz, DMSO-d$_6$) δ ppm 2.23(s, 3H) 2.24(s, 3H) 2.48(m, 4H) 3.12(m, 4H) 5.44(m, 1H) 6.95(m, 2H) 7.38(m, 2H) 7.94(s, 1H) 8.34(s, 1H) 9.12(s, 1H). |
| B10-X00-M00(C01)-D40 | $^1$H NMR(400MHz, DMSO-d$_6$) δ ppm 2.26(s, 3H) 2.80(t, 2H) 2.99(t, 3H) 3.09(m, 4H) 4.35(s, 3H) 4.43(d, 2H) 6.93(d, 2H) 7.07(m, 1H) 7.14(m, 1H) 7.18(m, 1H) 7.37(m, 1H) 7.53(d, 2H) 8.35(m, 1H) 8.79(t, 1H) 9.26(s, 1H) |
| B10-X00-M00(C01)-D16 | $^1$H NMR(400MHz, DMSO-d$_6$) δ ppm 2.95(m, 15H) 4.33(s, 3H) 4.43(d, J=5.97Hz, 2H) 6.25(dd, J=3.17, 0.85Hz, 1H) 6.40(dd, J=3.23, 1.89Hz, 1H) 6.94(d, J=9.02Hz, 2H) 7.56(d, J=9.02Hz, 2H) 7.57(dd, J=1.83, 0.85Hz, 1H) 8.36(s, 1H) 8.52(t, J=6.16Hz, 1H) 9.29(s, 1H) |
| B10-X00-M00(C01)-D76 | $^1$H NMR(400MHz, DMSO-d$_6$) δ ppm 2.26(s, 3H) 2.52(m, 12H) 2.80(t, 2H) 2.99(t, 2H) 3.08(m, 4H) 3.59(m, 4H) 4.33(s, 3H) 6.92(d, 2H) 7.52(d, 2H) 7.99(t, 1H) 8.35(s, 1H) 9.25(s, 1H) |
| B10-X00-M00(C01)-D47 | $^1$H NMR(400MHz, DMSO-d$_6$) δ ppm 2.36(s, 3H) 2.64(m, 4H) 2.78(t, 2H) 2.96(t, 2H) 3.13(m, 4H) 4.35(s, 3H) 5.15(m, 1H) 6.94(d, 2H) 7.24(m, 1H) 7.33(m, 2H) 7.41(m, 2H) 7.54(d, 2H) 8.34(s, 1H) 8.42(d, 1H) 9.27(s, 1H) |
| B10-X00-M00(C01)-D61 | $^1$H NMR(400MHz, DMSO-d$_6$) δ ppm 1.49(d, 3H) 2.27(s, 3H) 2.78(t, 2H) 2.96(t, 2H) 3.09(m, 4H) 4.35(s, 3H) 5.15(m, 1H) 6.93(d, 2H) 7.24(m, 1H) 7.33(m, 2H) 7.41(m, 2H) 7.52(d, 2H) 8.34(s, 1H) 8.42(d, 1H) 9.25(s, 1H) |
| B10-X00-M00(C01)-D50 | $^1$H NMR(400MHz, DMSO-d$_6$) δ ppm 2.25(s, 3H) 2.52(m, 4H) 2.80(t, 2H) 2.99(t, 2H) 3.08(m, 4H) 3.60(s, 3H) 4.32(s, 3H) 4.39(d, 2H) 5.89(m, 1H) 5.97(m, 1H) 6.64(m, 1H) 6.92(d, 2H) 7.52(d, 2H) 8.26(t, 1H) 8.35(s, 1H) 9.25(s, 1H) |
| B10-X00-M00(C01)-D44 | $^1$H NMR(400MHz, DMSO-d$_6$) δ ppm 2.26(s, 3H) 2.49(m, 4H) 2.82(t, 2H) 3.01(t, 2H) 3.10(m, 4H) 4.38(s, 3H) 4.46(d, 2H) 6.94(d, 2H) 7.33(d, 2H) 7.55(d, 2H) 8.37(s, 1H) 8.52(d, 2H) 8.88(t, 1H) 9.29(s, 1H) |
| B10-X00-M00(C01)-D45 | $^1$H NMR(400MHz, DMSO-d$_6$) δ ppm 2.27(s, 3H) 2.80(t, 2H) 2.99(t, 2H) 3.09(m, 4H) 4.34(s, 3H) 4.44(d, 2H) 6.93(d, 2H) 7.38(m, 1H) 7.53(d, 2H) 7.72(m, 1H) 8.35(s, 1H) 8.46(m, 1H) 8.55(m, 1H) 8.83(t, 1H) 9.26(s, 1H) |
| B10-X00-M00(C01)-D34 | $^1$H NMR(400MHz, DMSO-d$_6$) δ ppm 2.28(m, 3H) 2.53(m, 4H) 2.78(m, 2H) 2.94(m, 2H) 3.10(m, 4H) 3.74(m, 2H) 4.37(m, 3H) 5.00(t, 1H) 5.03(m, 1H) 6.92(m, 2H) 7.25(m, 1H) 7.33(m, 2H) 7.39(m, 2H) 7.54(m, 2H) 8.27(d, 1H) 8.34(m, 1H) 9.26(m, 1H) |
| B10-X00-M00(C01)-D60 | $^1$H NMR(400MHz, DMSO-d$_6$) δ ppm 2.27(s, 3H) 2.52(m, 4H) 2.78(t, J=7.74Hz, 2H) 2.95(t, 2H) 3.09(m, 4H) 3.74(m, 2H) 4.37(s, 3H) 5.01(m, 2H) 6.92(d, 2H) |

TABLE XIII-continued

| | |
|---|---|
| | 7.30(m, 5H) 7.53(d, 2H) 8.27(d, J=8.29Hz, 1H) 8.34(s, 1H) 9.26(s, 1H) |
| B10-X00-M00(C01)-D42 | ¹H NMR(400MHz, DMSO-d₆) δ ppm 2.27(s, 3H) 2.52(m, 4H) 2.80(t, 2H) 2.99(s, 2H) 3.09(m, 4H) 4.34(s, 3H) 4.39(d, 2H) 6.93(d, 2H) 7.18(m, 1H) 7.37(m, 2H) 7.53(d, 2H) 8.35(s, 1H) 8.81(t, 1H) 9.26(m, 1H) |
| B10-X00-M00(C01)-D41 | ¹H NMR(400MHz, DMSO-d₆) δ ppm 0.89(t, J=7.32Hz, 3H) 1.87(m, 2H) 2.27(s, 3H) 2.52(m, 4H) 2.77(m, 2H) 2.95(m, 2H) 3.09(m, 4H) 4.35(s, 3H) 4.88(td, J=8.75, 6.40Hz, 1H) 6.91(d, J=9.15Hz, 2H) 7.23(m, 1H) 7.33(t, J=7.50Hz, 2H) 7.42(m, 2H) 7.54(d, J=9.02Hz, 2H) 8.34(s, 1H) 8.41(d, J=8.78Hz, 2H) 9.25(s, 1H) |
| B10-X00-M00(C01)-D54 | ¹H NMR(400MHz, DMSO-d₆) δ ppm 2.24(s, 3H) 2.52(t, 10H) 2.78(t, 2H) 2.95(m, 4H) 3.08(m, 4H) 3.59(m, 4H) 4.37(s, 3H) 5.16(m, 1H) 6.92(d, 2H) 7.24(m, 1H) 7.33(m, 2H) 7.42(m, 2H) 7.53(d, 2H) 8.34(s, 1H) 8.40(d, 1H) 9.25(s, 1H) |
| B10-X00-M00(C01)-D67 | ¹H NMR(400MHz, DMSO-d₆) δ ppm 2.20(s, 3H) 2.26(s, 3H) 2.51(m, 4H) 2.80(t, J=7.68Hz, 2H) 2.99(t, J=7.68Hz, 2H) 3.08(m, 4H) 3.66(s, 3H) 4.30(d, J=5.97Hz, 2H) 4.32(s, 3H) 5.94(s, 1H) 6.91(d, J=9.15Hz, 2H) 7.54(d, J=9.02Hz, 2H) 8.23(t, J=5.97Hz, 1H) 8.35(s, 1H) 9.25(s, 1H) |
| B10-X00-M00(C01)-D49 | ¹H NMR(400MHz, DMSO-d₆) δ ppm 2.25(s, 3H) 2.51(m, 4H) 2.80(t, J=7.68Hz, 2H) 3.00(t, J=7.68Hz, 2H) 3.08(m, 4H) 4.33(s, 3H) 4.58(d, J=6.22Hz, 2H) 6.91(d, J=9.02Hz, 2H) 6.96(dd, J=5.06, 3.48Hz, 1H) 7.01(dd, J=3.41, 1.10Hz, 1H) 7.37(dd, J=5.06, 1.28Hz, 1H) 7.53(d, J=9.15Hz, 2H) 8.35(s, 1H) 8.74(t, J=6.22Hz, 1H) 9.25(s, 1H) |
| B10-X00-M00(C01)-D68 | ¹H NMR(400MHz, DMSO-d₆) δ ppm 0.89(t, J=7.26Hz, 3H) 1.86(m, 2H) 2.25(s, 3H) 2.49(m, 4H) 2.78(m, 2H) 2.95(m, 2H) 3.08(m, 4H) 4.35(s, 3H) 4.88(m, 1H) 6.91(d, J=9.15Hz, 2H) 7.23(m, 1H) 7.33(m, 2H) 7.42(m, 2H) 7.53(d, J=9.02Hz, 2H) 8.34(s, 1H) 8.41(d, J=8.78Hz, 1H) 9.25(s, 1H) |
| B10-X00-M00(C01)-D64 | ¹H NMR(400MHz, DMSO-d₆) δ ppm 2.27(s, 3H) 2.52(m, 4H) 2.83(m, 4H) 2.90(m, 3H) 3.09(m, 4H) 3.18(s, 3H) 4.30(d, J=17.68Hz, 6H) 4.69(s, 2H) 4.97(s, 2H) 6.91(m, J=9.02Hz, 2H) 7.29(m, 5H) 7.52(m, 2H) 8.36(s, 1H) 9.27(s, 1H) |
| B10-X00-M00(C01)-D53 | ¹H NMR(400MHz, DMSO-d₆) δ ppm 1.50(d, 3H) 2.27(s, 3H) 2.52(m, 4H) 2.78(t, 2H) 2.95(t, 2H) 3.09(m, 4H) 4.37(s, 3H) 5.13(m, 1H) 6.93(d, 2H) 7.41(d, 2H) 7.53(d, 2H) 8.35(s, 1H) 8.51(m, 2H) 8.66(d, 1H) 9.26(s, 1H) |
| B10-X00-M00(C01)-D52 | ¹H NMR(400MHz, DMSO-d₆) δ ppm 1.72(s, 6H) 2.26(s, 3H) 2.50(m, 4H) 2.79(t, 2H) 2.92(t, 2H) 3.10(m, 4H) 4.38(s, 3H) 6.94(d, 2H) 7.22(m, 1H) 7.34(m, 2H) 7.43(m, 2H) 7.54(d, 2H) 7.81(s, 1H) 8.36(s, 1H) 9.28(s, 1H) |
| B10-X00-M00(C01)-D57 | ¹H NMR(400MHz, DMSO-d₆) δ ppm 2.26(s, 3H) 2.52(m, 4H) 2.81(t, 2H) 3.01(t, 2H) 3.09(m, 4H) 4.33(s, 3H) 4.92(d, 2H) 6.92(d, 2H) 7.57(m, 6H) 7.85(m, 1H) 7.96(m, 1H) 8.24(m, 1H) 8.35(s, 1H) 8.69(t, 1H) 9.26(s, 1H) |
| B10-X00-M00(C01)-D59 | ¹H NMR(400MHz, DMSO-d₆) δ ppm 2.27(s, 3H) 2.52(m, 4H) 2.80(t, J=7.68Hz, 2H) 2.99(t, J=7.62Hz, 2H) 3.09(m, 4H) 4.32(d, J=5.85Hz, 2H) 4.33(s, 3H) 5.98(s, 2H) 6.80(dd, J=7.93, 1.59Hz, 1H) 6.86(d, J=7.80Hz, 1H) 6.91(d, J=2.56Hz, 1H) 6.91(d, J=8.05Hz, 2H) 7.54(d, J=9.15Hz, 2H) 8.35(s, 1H) 8.63(t, J=6.40Hz, 1H) 9.26(s, 1H) |
| B10-X00-M00(C01)-D37 | ¹H NMR(400MHz, DMSO-d₆) δ ppm 1.49(d, J=7.07Hz, 3H) 2.27(s, 3H) 2.51(m, 4H) 2.78(t, J=7.68Hz, 2H) 2.95(t, J=7.74Hz, 2H) 3.09(m, 4H) 4.35(s, 3H) 5.15(m, 1H) 6.91(d, J=9.15Hz, 2H) 7.15(d, J=8.96Hz, 2H) 7.46(dd, J=8.54, 5.61Hz, 2H) 7.53(d, J=9.15Hz, 2H) 8.34(s, 1H) 8.49(d, J=8.41Hz, 1H) 9.25(s, 1H) |
| B10-X00-M00(C01)-D74 | ¹H NMR(400MHz, DMSO-d₆) δ ppm 0.92(m, 2H) 1.18(m, 4H) 1.67(m, 5H) 2.27(s, 3H) 2.52(m, 4H) 2.79(t, 2H) 2.98(t, 2H) 3.08(m, 6H) 4.33(s, 3H) 6.92(d, 2H) 7.53(d, 2H) 8.05(t, 1H) 8.35(s, 1H) 9.25(s, 1H) |
| B10-X00-M00(C01)-D39 | ¹H NMR(400MHz, DMSO-d₆) δ ppm 1.68(m, 4H) 2.24(s, 3H) 2.52(m, 8H) 2.78(t, 2H) 2.95(t, 2H) 3.08(m, 4H) 4.36(s, 3H) 5.11(m, 1H) 6.92(d, 2H) 7.33(m, 3H) 7.41(m, 2H) 7.52(d, 2H) 8.34(s, 1H) 9.25(s, 1H) |

TABLE XIII-continued

| | |
|---|---|
| B10-X00-M00(C01)-D51 | ¹H NMR(400MHz, DMSO-d₆) δ ppm 2.27(s, 3H) 2.52(m, 4H) 2.79(t, J=7.80Hz, 2H) 2.95(m, 2H) 3.09(m, 4H) 4.37(s, 3H) 5.53(d, J=7.80Hz, 1H) 6.92(d, J=9.15Hz, 2H) 7.31(m, 1H) 7.38(m, 2H) 7.38(m, 1H) 7.47(m, 2H) 7.54(d, J=9.15Hz, 2H) 7.86(s, 1H) 8.12(d, J=7.80Hz, 1H) 8.35(s, 1H) 9.27(s, 1H) |
| B10-X00-M00(C01)-D38 | ¹H NMR(400MHz, DMSO-d₆) δ ppm 2.26(s, 3H) 2.53(m, 10H) 2.80(t, 2H) 2.95(m, 4H) 3.10(m, 4H) 3.58(m, 4H) 4.39(s, 3H) 5.18(m, 1H) 6.94(d, 2H) 7.26(m, 1H) 7.35(m, 2H) 7.44(m, 2H) 7.55(d, 2H) 8.36(s, 1H) 8.42(d, 1H) 9.28(s, 1H) |
| B10-X00-M00(C01)-D62 | ¹H NMR(400MHz, DMSO-d₆) δ ppm 2.27(s, 3H) 2.52(m, 4H) 2.80(t, J=7.68Hz, 2H) 2.98(t, J=7.56Hz, 2H) 3.09(m, 4H) 4.35(s, 3H) 6.36(d, J=8.78Hz, 1H) 6.91(d, J=9.15Hz, 2H) 7.28(m, 2H) 7.36(t, J=7.50Hz, 4H) 7.41(m, 4H) 7.54(d, J=9.15Hz, 2H) 8.35(s, 1H) 8.70(d, J=8.90Hz, 1H) 9.26(s, 1H) |
| B10-X00-M00(C01)-D75 | ¹H NMR(400MHz, DMSO-d₆) δ ppm 1.33(m, 11H) 1.12(d, J=6.83Hz, 3H) 2.26(s, 3H) 2.51(m, 4H) 2.80(t, J=7.62Hz, 2H) 2.95(m, 2H) 3.09(m, 4H) 3.82(m, 1H) 4.33(s, 3H) 6.91(d, J=9.02Hz, 2H) 7.54(d, J=9.02Hz, 2H) 7.65(d, J=9.27Hz, 1H) 8.35(s, 1H) 9.25(s, 1H) |
| B10-X00-M00(C01)-D46 | ¹H NMR(400MHz, DMSO-d₆) δ ppm 2.26(s, 3H) 2.50(m, 4H) 2.78(t, J=7.80Hz, 2H) 2.96(m, 2H) 3.09(m, 4H) 3.30(s, 3H) 3.60(dd, J=9.94, 5.18Hz, 1H) 3.78(dd, J=10.00, 7.93Hz, 1H) 4.37(s, 3H) 5.23(m, 1H) 6.92(d, J=9.15Hz, 2H) 7.30(m, 3H) 7.43(m, 2H) 7.54(d, J=9.02Hz, 2H) 8.34(s, 1H) 8.41(d, J=8.54Hz, 1H) 9.26(s, 1H) |
| B10-X00-M00(C01)-D56 | ¹H NMR(400MHz, DMSO-d₆) δ ppm 0.68(m, 6H) 2.04(m, 4H) 2.25(s, 3H) 2.49(m, 4H) 2.78(t, J=7.68Hz, 2H) 2.91(t, J=7.80Hz, 2H) 3.08(m, 4H) 4.37(s, 3H) 6.91(d, J=9.15Hz, 2H) 7.28(m, 5H) 7.42(m, 1H) 7.54(d, J=9.02Hz, 2H) 8.34(s, 1H) 9.26(s, 1H) |
| B10-X00-M00(C01)-D69 | ¹H NMR(400MHz, DMSO-d₆) δ ppm 1.86(m, 4H) 2.25(s, 3H) 2.49(m, 4H) 2.77(m, 2H) 2.83(t, J=7.68Hz, 2H) 3.03(m, 2H) 3.08(m, 4H) 4.31(s, 3H) 5.20(m, 1H) 6.91(d, J=9.15Hz, 2H) 7.16(m, 4H) 7.53(d, J=9.15Hz, 2H) 8.14(d, J=9.02Hz, 1H) 8.36(s, 1H) 9.25(s, 1H) |
| B10-X00-M00(C01)-D63 | ¹H NMR(400MHz, DMSO-d₆) δ ppm 2.25(s, 3H) 2.49(m, 4H) 2.80(t, J=7.68Hz, 2H) 2.99(t, J=7.68Hz, 2H) 3.08(m, 4H) 3.15(t, J=8.66Hz, 2H) 4.33(s, 3H) 4.33(s, 3H) 4.50(t, J=8.72Hz, 2H) 6.69(d, J=8.17Hz, 1H) 6.91(d, J=9.15Hz, 2H) 7.05(dd, J=8.11, 1.89Hz, 1H) 7.20(d, J=1.22Hz, 1H) 7.53(d, J=9.02Hz, 2H) 8.35(s, 1H) 8.56(t, J=6.34Hz, 1H) 9.25(s, 1H) |
| B10-X00-M00(C01)-D65 | ¹H NMR(400MHz, DMSO-d₆) δ ppm 2.60(m, 4H) 2.25(s, 3H) 2.48(m, 4H) 2.93(m, 4H) 3.08(m, 4H) 4.32(s, 3H) 5.52(q, J=8.17Hz, 1H) 6.91(d, J=9.02Hz, 2H) 7.24(m, 4H) 7.54(d, J=9.15Hz, 2H) 8.27(d, J=8.66Hz, 1H) 8.36(s, 1H) 9.25(s, 1H) |
| B10-X00-M00(C01)-D43 | ¹H NMR(400MHz, DMSO-d₆) δ ppm 1.28(m, 4H) 2.26(s, 3H) 2.52(m, 4H) 2.79(t, 2H) 2.96(t, 2H) 3.09(m, 4H) 4.35(s, 3H) 6.93(d, 2H) 7.16(m, 1H) 7.25(m, J=10.00Hz, 4H) 7.53(d, 2H) 8.35(s, 1H) 8.86(s, 1H) 9.26(s, 1H) |
| B10-X00-M00(C01)-D66 | ¹H NMR(400MHz, DMSO-d₆) δ ppm 1.67(s, 6H) 2.24(s, 3H) 2.50(m, 4H) 2.76(t, 2H) 2.88(t, 2H) 3.08(m, 4H) 4.37(s, 3H) 6.93(d, 2H) 7.37(m, 2H) 7.52(d, 2H) 8.04(s, 1H) 8.33(s, 1H) 8.48(m, 2H) 9.26(s, 1H) |
| B10-X00-M00(C01)-D55 | ¹H NMR(400MHz, DMSO-d₆) δ ppm 2.25(s, 3H) 2.52(m, 4H) 2.80(t, 2H) 2.99(t, 2H) 3.08(m, 4H) 4.35(s, 3H) 4.48(d, 2H) 6.93(d, 2H) 7.18(m, 2H) 7.31(m, 2H) 7.53(d, 2H) 8.35(s, 1H) 8.68(t, 1H) 9.26(s, 1H) |
| B10-X00-M00(C01)-D35 | ¹H NMR(400MHz, DMSO-d₆) δ ppm 2.24(s, 3H) 2.51(m, 4H) 2.80(t, 2H) 2.99(t, 2H) 3.08(m, 4H) 3.75(s, 3H) 4.34(s, 3H) 4.39(d, 2H) 6.83(m, 1H) 6.90(m, 4H) 7.24(t, 1H) 7.53(d, 2H) 8.35(s, 1H) 8.67(t, 1H) 9.25(s, 1H) |
| B10-X00-M00(C01)-D48 | ¹H NMR(400MHz, DMSO-d₆) δ ppm 2.24(s, 3H) 2.47(m, 4H) 2.80(t, 2H) 2.99(t, 2H) 3.08(m, 4H) 3.85(s, 3H) 4.35(s, 3H) 4.41(d, 2H) 6.92(m, 3H) 7.01(m, 1H) 7.17(m, 1H) 7.24(m, 1H) 7.53(d, 2H) 8.35(s, 1H) 8.38(t, 1H) 9.26(s, 1H) |
| B10-X00-M00(C01)-D77 | ¹H NMR(400MHz, DMSO-d₆) δ ppm 1.12(t, J=7.56Hz, 6H) 2.29(s, 3H) 2.55(m, 4H) 2.56(q, J=7.68Hz, 4H) 2.83(t, J=7.62Hz, 2H) 3.00(t, J=7.62Hz, 2H) |

TABLE XIII-continued

| | |
|---|---|
| | 3.11(m, 4H) 4.40(s, 3H) 6.93(d, J=9.15Hz, 2H) 7.14(d, J=7.68Hz, 2H) 7.22(dd, J=8.29, 6.83Hz, 1H) 7.56(d, J=9.02Hz, 2H) 8.37(s, 1H) 9.28(s, 1H) 9.57(s, 1H) |
| B10-X00-M00(C01)-D58 | $^1$H NMR(400MHz, DMSO-d$_6$) δ ppm 2.26(s, 3H) 2.51(m, 4H) 2.80(t, J=7.74Hz, 2H) 2.99(t, J=7.62Hz, 2H) 3.08(m, 4H) 3.73(s, 6H) 4.34(s, 3H) 4.36(d, J=6.71Hz, 2H) 6.38(t, J=2.32Hz, 1H) 6.50(d, J=2.19Hz, 2H) 6.91(d, J=9.15Hz, 2H) 7.54(d, J=9.15Hz, 2H) 8.35(s, 1H) 8.64(t, J=6.28Hz, 1H) 9.26(s, 1H) |
| B10-X00-M00(C01)-D20 | $^1$H NMR(400MHz, DMSO-d$_6$) δ ppm 2.26(s, 3H) 2.52(m, 4H) 2.84(t, J=7.74Hz, 2H) 3.05(t, J=7.74Hz, 2H) 3.09(m, 4H) 4.41(s, 3H) 6.92(d, J=9.15Hz, 2H) 7.10(tt, J=7.39, 1.14Hz, 1H) 7.34(dd, J=8.29, 7.56Hz, 2H) 7.55(d, J=9.02Hz, 2H) 7.83(dd, J=8.66, 1.10Hz, 2H) 8.38(s, 1H) 9.28(s, 1H) 10.07(s, 1H) |
| B10-X00-M00(C01)-D36 | $^1$H NMR(400MHz, DMSO-d$_6$) δ ppm 1.49(m, 6H) 2.27(s, 3H) 2.52(m, 10H) 2.78(t, 2H) 2.95(t, 2H) 3.09(m, 4H) 4.37(s, 3H) 5.12(m, 1H) 6.93(d, 2H) 7.24(m, 1H) 7.33(m, 2H) 7.39(m, 2H) 7.53(d, 2H) 8.34(m, 2H) 9.26(s, 1H) |
| B10-X00-M00(C01)-D70 | $^1$H NMR(400MHz, DMSO-d$_6$) δ ppm 2.28(s, 3H) 2.79(t, 2H) 2.97(t, 2H) 3.09(m, 4H) 3.35(m, 4H) 3.65(dd, 1H) 3.90(dd, 1H) 4.37(s, 3H) 5.25(m, 1H) 6.92(d, J=8.78Hz, 2H) 7.29(m, 1H) 7.37(m, 2H) 7.47(m, 2H) 7.53(d, 2H) 8.35(s, 1H) 8.82(d, 1H) 9.26(s, 1H) |
| B10-X00-M00(C01)-D73 | $^1$H NMR(400MHz, DMSO-d$_6$) δ ppm 2.27(s, 3H) 2.81(m, 4H) 3.11(m, 6H) 3.34(m, 4H) 4.33(s, 3H) 4.52(m, 1H) 5.38(m, 1H) 5.44(d, 1H) 6.92(d, 2H) 7.22(m, 3H) 7.53(d, 2H) 7.70(m, 1H) 8.38(s, 1H) 9.27(s, 1H) |
| B10-X00-M00(C01)-D165 | $^1$H NMR(400MHz, DMSO-d$_6$) δ ppm 2.04(s, 3H) 2.27(s, 3H) 2.52(m, 4H) 2.74(t, 2H) 2.87(t, 2H) 3.09(m, 4H) 3.35(m, 8H) 4.34(s, 3H) 6.92(d, 2H) 7.31(m, 1H) 7.43(m, 4H) 7.52(d, 2H) 8.32(s, 1H) 9.10(s, 1H) 9.25(s, 1H) |
| B10-X00-M00(C01)-D144 | $^1$H NMR(400MHz, DMSO-d$_6$) δ ppm 1.81(s, 3H) 2.24(m, 7H) 2.47(m, 4H) 2.78(m, 6H) 3.08(m, 4H) 3.46(m, 2H) 3.55(m, 2H) 4.37(s, 3H) 6.93(d, 2H) 7.21(m, 1H) 7.35(m, 4H) 7.54(d, 2H) 8.35(m, 2H) 9.27(s, 1H) |
| B10-X00-M00(C01)-D164 | $^1$H NMR(400MHz, DMSO-d$_6$) δ ppm 2.27(s, 3H) 2.52(m, 4H) 2.78(t, 2H) 2.96(t, 2H) 3.09(m, 4H) 3.55(m, 8H) 4.34(s, 3H) 6.00(d, 1H) 6.92(d, 2H) 7.34(m, 1H) 7.43(m, 4H) 7.52(d, 2H) 8.24(d, 1H) 8.34(s, 1H) 9.26(s, 1H) |
| B109-X00-M00(C01)-D09 | $^1$H NMR(400MHz, DMSO-d$_6$) δ ppm 2.28(s, 3H) 2.53(m, 4H) 2.83(m, 2H) 3.00(m, 6H) 4.36(s, 3H) 4.44(d, J=6.34Hz, 2H) 7.01(dd, J=9.94, 8.96Hz, 1H) 7.27(m, 5H) 7.37(dd, J=8.29, 2.19Hz, 1H) 7.67(dd, J=15.36, 2.44Hz, 1H) 8.41(s, 1H) 8.71(t, J=6.34Hz, 1H) 9.55(s, 1H) |
| B109-X00-M00(C01)-D21 | $^1$H NMR(400MHz, DMSO-d$_6$) δ ppm 2.27(s, 3H) 2.54(m, 4H) 2.82(t, J=7.68Hz, 2H) 2.99(m, 6H) 4.36(s, 3H) 4.41(d, J=6.34Hz, 2H) 7.01(dd, J=9.94, 8.96Hz, 1H) 7.15(t, J=8.96Hz, 2H) 7.37(m, 3H) 7.67(dd, J=15.43, 2.38Hz, 1H) 8.41(s, 1H) 8.75(t, J=6.28Hz, 1H) 9.55(s, 1H) |
| B108-X00-M00(C01)-D03 | $^1$H NMR(400MHz, DMSO-d$_6$) δ ppm 1.08(s, 9H) 2.71(m, 4H) 2.80(t, 2H) 2.99(t, 2H) 3.06(m, 4H) 4.34(s, 3H) 6.91(d, 2H) 7.25(s, 1H) 7.46(s, 1H) 7.51 d, 2H) 8.34(s, 1H) 9.24(s, 1H) |
| B108-X00-M00(C01)-D09 | $^1$H NMR(400MHz, DMSO-d$_6$) δ ppm 1.07(s, 9H) 2.71(m, 4H) 2.80(t, 2H) 2.99(t, 2H) 3.06(m, 4H) 4.34(s, 3H) 4.42(d, 2H) 6.91(d, 2H) 7.34(m, 5H) 8.35(s, 1H) 8.69(t, 1H) 9.24(s, 1H) |
| B108-X00-M00(C01)-D44 | $^1$H NMR(400MHz, DMSO-d$_6$) δ ppm 1.08(s, 9H) 2.69(m, 4H) 2.80(t, 2H) 2.99(t, 2H) 3.06(m, 4H) 4.36(s, 3H) 4.44(d, 2H) 6.92(d, 2H) 7.31(m, 2H) 7.54(d, 2H) 8.35(s, 1H) 8.50(m, 2H) 8.86(t, 1H) 9.26(s, 1H) |
| B108-X00-M00(C01)-D52 | $^1$H NMR(400MHz, DMSO-d$_6$) δ ppm 1.08(s, 9H) 1.70(s, 6H) 2.69(m, 4H) 2.77(t, 2H) 2.90(t, 2H) 3.06(m, 4H) 4.36(s, 3H) 6.92(d, 2H) 7.20(m, 1H) 7.32(m, 2H) 7.41(m, 2H) 7.51(d, 2H) 7.79(s, 1H) 8.33(s, 1H) 9.25(s, 1H) |
| B108-X00-M00(C01)-D51 | $^1$H NMR(400MHz, DMSO-d$_6$) δ ppm 1.09(s, 9H) 2.69(s, 4H) 2.79(t, J=7.68Hz, 2H) 2.95(t, J=7.86Hz, 2H) 3.08(s, 4H) 4.37(s, 3H) 5.53(d, J=7.80Hz, 1H) |

TABLE XIII-continued

| | |
|---|---|
| | 6.91(d, J=9.15Hz, 2H) 7.31(m, 1H) 7.38(m, 3H) 7.47(d, J=7.19Hz, 2H) 7.53(d, J=9.15Hz, 2H) 7.87(s, 1H) 8.12(d, J=7.68Hz, 1H) 8.34(s, 1H) 9.26(s, 1H) |
| B108-X00-M00(C01)-D38 | $^1$H NMR(400MHz, DMSO-$d_6$) δ ppm 1.09(s, 9H) 2.52(m, 4H) 2.68(m, 4H) 2.78(t, 2H) 2.92(m, 4H) 3.07(m, 4H) 3.56(m, 4H) 4.37(s, 3H) 5.16(m, 1H) 6.92(d, 2H) 7.24(m, 1H) 7.33(m, 2H) 7.42(m, 2H) 7.51(d, 2H) 8.34(s, 1H) 8.40(d, 1H) 9.25(s, 1H) |
| B108-X00-M00(C01)-D35 | $^1$H NMR(400MHz, DMSO-$d_6$) δ ppm 1.07(s, 9H) 2.66(s, 4H) 2.80(t, J=7.68Hz, 2H) 2.99(t, J=7.62Hz, 2H) 3.06(s, 4H) 3.75(s, 3H) 4.34(s, 3H) 4.40(d, J=6.22Hz, 2H) 6.82(ddd, J=8.20, 2.59, 0.91Hz, 1H) 6.90(m, 4H) 7.24(t, J=8.05Hz, 1H) 7.53(d, J=8.90Hz, 2H) 8.35(s, 1H) 8.67(t, J=6.34Hz, 1H) 9.25(s, 1H) |
| B19-X00-M00(C01)-D09 | $^1$H NMR(400MHz, DMSO-$d_6$) δ ppm 2.80(t, 2H) 3.00(t, 2H) 3.05(m, 4H) 3.75(m, 4H) 4.34(s, 3H) 4.44(d, 2H) 6.94(d, 2H) 7.34(m, 5H) 7.55(d, 2H) 8.35(s, 1H) 8.69(t, 1H) 9.28(s, 1H) |
| B19-X00-M00(C01)-D21 | $^1$H NMR(400MHz, DMSO-$d_6$) δ ppm 2.80(t, 2H) 2.99(t, 2H) 3.05(m, 4H) 3.75(m, 4H) 4.34(s, 3H) 4.41(d, 2H) 6.94(d, 2H) 7.15(m, 2H) 7.36(m, 2H) 7.55(d, 2H) 8.35(s, 1H) 8.74(t, 1H) 9.28(s, 1H) |
| B19-X00-M00(C01)-D24 | $^1$H NMR(400MHz, DMSO-$d_6$) δ ppm 1.51(d, 3H) 2.79(t, 2H) 2.96(t, 2H) 3.05(m, 4H) 3.75(m, 4H) 4.35(s, 3H) 5.15(m, 1H) 6.94(d, 2H) 7.23(m, 1H) 7.33(m, 2H) 7.41(m, 2H) 7.55(d, 2H) 8.35(s, 1H) 8.42(d, 1H) 9.27(s, 1H) |
| B19-X00-M00(C01)-D47 | $^1$H NMR(400MHz, DMSO-$d_6$) δ ppm 1.51(m, 3H) 2.78(m, 2H) 2.96(m, 2H) 3.05(m, 4H) 3.75(m, 4H) 4.35(s, 3H) 5.15(m, 1H) 6.94(m, 2H) 7.24(t, 1H) 7.33(t, 2H) 7.41(m, 2H) 7.55(m, 2H) 8.35(s, 1H) 8.42(s, 1H) 9.27(s, 1H) |
| B19-X00-M00(C01)-D42 | $^1$H NMR(400MHz, DMSO-$d_6$) δ ppm 2.90(m, 4H) 3.05(m, 4H) 3.76(m, 4H) 4.35(s, 3H) 4.40(m, 2H) 6.94(m, 2H) 7.37(m, 3H) 7.55(m, 2H) 8.36(s, 1H) 8.81(m, 1H) 9.28(s, 1H) |
| B19-X00-M00(C01)-D41 | $^1$H NMR(400MHz, DMSO-$d_6$) δ ppm 0.89(m, 3H) 1.81(m, 2H) 2.78(m, 4H) 3.05(m, 4H) 3.76(m, 4H) 4.36(s, 3H) 4.88(m, 1H) 6.93(m, 2H) 7.23(m, 1H) 7.33(m, 2H) 7.41(m, 2H) 7.55(m, 2H) 8.34(m, 1H) 8.37(d, 1H) 9.27(s, 1H) |
| B19-X00-M00(C01)-D68 | $^1$H NMR(400MHz, DMSO-$d_6$) δ ppm 1.81(m, 2H) 2.78(m, 4H) 3.05(m, 4H) 3.75(m, 4H) 4.36(s, 3H) 4.88(m, 1H) 6.93(m, 2H) 7.33(m, 5H) 7.55(m, 2H) 8.34(m, 1H) 8.40(m, 1H) 9.27(m, 1H) |
| B19-X00-M00(C01)-D61 | $^1$H NMR(400MHz, DMSO-$d_6$) δ ppm 1.51(m, 3H) 2.96(m, 4H) 3.05(m, 4H) 3.75(m, 4H) 4.35(s, 3H) 5.15(m, 1H) 6.94(m, 2H) 7.33(m, 5H) 7.55(m, 2H) 8.35(m, 1H) 8.42(m, 1H) 9.27(m, 1H) |
| B19-X00-M00(C01)-D40 | $^1$H NMR(400MHz, DMSO-$d_6$) δ ppm 2.91(m, 4H) 3.05(m, 4H) 3.75(m, 4H) 4.35(s, 3H) 4.43(m, 2H) 6.94(d, 2H) 7.18(m, 4H) 7.55(d, 2H) 8.36(s, 1H) 8.79(s, 1H) 9.28(s, 1H) |
| B19-X00-M00(C01)-D34 | $^1$H NMR(400MHz, DMSO-$d_6$) δ ppm 2.79(t, J=7.68Hz, 2H) 2.96(t, J=7.74Hz, 2H) 3.05(m, 4H) 3.74(m, 6H) 4.37(s, 3H) 5.02(m, 2H) 6.93(d, J=9.15Hz, 2H) 7.24(m, 1H) 7.33(m, 2H) 7.39(m, 2H) 7.56(d, J=9.02Hz, 2H) 8.27(d, J=8.29Hz, 1H) .35(s, 1H) 9.28(s, 1H) |
| B19-X00-M00(C01)-D44 | $^1$H NMR(400MHz, DMSO-$d_6$) δ ppm 3.01(m, 4H) 3.07(s, 4H) 3.77(m, 4H) 4.38(s, 3H) 4.46(m, 2H) 6.95(m, 1H) 7.33(m, 2H) 7.57(m, 2H) 8.38(s, 1H) 8.58(m, 2H) 8.88(m, 1H) 9.31(s, 1H) |
| B19-X00-M00(C01)-D52 | $^1$H NMR(400MHz, DMSO-$d_6$) δ ppm 1.70(s, 6H) 2.77(t, J=7.80Hz, 2H) 2.90(m, 2H) 3.06(m, 4H) 3.76(m, 4H) 4.36(s, 3H) 6.93(d, J=9.15Hz, 2H) 7.20(m, 1H) 7.32(t, J=7.68Hz, 2H) 7.42(m, 2H) 7.56(d, J=9.15Hz, 2H) 7.79(s, 1H) 8.34(s, 1H) 9.27(s, 1H) |
| B19-X00-M00(C01)-D38 | $^1$H NMR(400MHz, DMSO-$d_6$) δ ppm 2.52(m, 5H) 2.78(m, 5H) 3.05(m, 4H) 3.56(m, 4H) 3.76(m, 4H) 4.37(s, 3H) 5.17(m, 1H) 7.30(m, 9H) 8.34(m, 1H) 8.40(m, 1H) 9.28(s, 1H) |
| B19-X00-M00(C01)-D51 | $^1$H NMR(400MHz, DMSO-$d_6$) δ ppm 2.87(m, 4H) 3.06(m, 4H) 3.76(m, 4H) 4.37(s, 3H) 5.54(m, 1H) 6.94(m, 2H) 7.42(m, 8H) 7.86(m, 1H) 8.11(d, 1H) 8.35(m, 1H) 9.28(m, 1H) |
| B19-X00-M00(C01)-D39 | $^1$H NMR(400MHz, DMSO-$d_6$) δ ppm 1.69(m, 4H) 2.52(s, 6H) 2.87(d, 4H) 3.05(s, 4H) 3.76(s, 4H) 4.37(s, 3H) 5.10(m, 1H) 7.30(m, 9H) 8.35(m, 2H) 9.28(m, 1H) |

TABLE XIII-continued

| | |
|---|---|
| B09-X00-M00(C01)-D35 | $^1$H NMR(400MHz, DMSO-d$_6$) δ ppm 2.27(s, 3H) 2.52(m, 4H) 2.82(t, 2H) 3.00(t, 2H) 3.13(m, 4H) 3.75(s, 3H) 4.36(s, 3H) 4.40(d, 2H) 6.59(m, 1H) 6.83(m, 1H) 6.90(m, 2H) 7.14(m, 1H) 7.24(m, 3H) 8.40(s, 1H) 8.67(t, 1H) 9.33(s, 1H) |
| B09-X00-M00(C01)-D34 | $^1$H NMR(400MHz, DMSO-d$_6$) δ ppm 2.26(s, 3H) 2.52(m, 4H) 2.80(t, 2H) 2.97(t, 2H) 3.13(m, 4H) 3.73(m, 2H) 4.39(s, 3H) 5.00(m, 2H) 6.59(m, 1H) 7.14(m, 1H) 7.25(m, 7H) 8.26(d, 1H) 8.40(s, 1H) 9.33(s, 1H) |
| B09-X00-M00(C01)-D43 | $^1$H NMR(400MHz, DMSO-d$_6$) δ ppm 1.29(m, 4H) 2.28(s, 3H) 2.52(m, 4H) 2.81(t, 2H) 2.97(t, 2H) 3.14(m, 4H) 4.37(s, 3H) 6.59(m, 1H) 6.71(m, 1H) 7.24(m, 7H) 8.40(s, 1H) 8.86(s, 1H) 9.33(s, 1H) |
| B09-X00-M00(C01)-D39 | $^1$H NMR(400MHz, DMSO-d$_6$) δ ppm 1.70(m, 4H) 2.25(s, 3H) 2.48(m, 4H) 2.83(m, 10H) 3.12(m, 4H) 4.38(s, 3H) 5.10(m, 1H) 6.58(ddd, J=8.14, 2.29, 0.67Hz, 1H) 7.14(t, J=7.99Hz, 1H) 7.24(m, 3H) 7.33(m, 2H) 7.42(m, 2H) 8.35(d, J=8.66Hz, 1H) 8.39(s, 1H) 9.33(s, 1H) |
| B09-X00-M00(C01)-D51 | $^1$H NMR(400MHz, DMSO-d$_6$) δ ppm 2.28(s, 3H) 2.52(m, 4H) 2.81(t, J=7.80Hz, 2H) 2.97(m, 2H) 3.14(m, 4H) 4.39(s, 3H) 5.53(d, J=7.68Hz, 1H) 6.58(dd, J=8.11, 2.26Hz, 1H) 7.14(t, J=8.05Hz, 1H) 7.26(m, 2H) 7.31(m, 1H) 7.38(m, 3H) 7.48(m, 2H) 7.87(s, 1H) 8.12(d, J=7.68Hz, 1H) 8.40(s, 1H) 9.34(s, 1H) |
| B09-X00-M00(C01)-D36 | $^1$H NMR(400MHz, DMSO-d$_6$) δ ppm 1.49(m, 6H) 2.29(s, 3H) 2.49(m, 8H) 2.80(t, J=7.68Hz, 3H) 2.97(m, 3H) 3.14(m, 4H) 4.39(s, 3H) 5.14(m, 1H) 6.58(dd, J=8.17, 1.83Hz, 1H) 7.15(t, J=8.11Hz, 1H) 7.26(m, 3H) 7.33(t, J=7.50Hz, 2H) 7.41(m, 2H) 8.36(s, 1H) 8.40(s, 1H) 9.34(s, 1H) |
| B101-X00-M00(C01)-D09 | $^1$H NMR(400MHz, DMSO-d$_6$) δ ppm 2.16(s, 3H) 2.34(m, 8H) 2.83(t, 2H) 3.01(t, 2H) 3.40(s, 2H) 4.36(s, 3H) 4.43(d, 2H) 7.23(m, 3H) 7.34(m, 3H) 7.65(d, 2H) 8.41(s, 1H) 8.71(t, 1H) 9.50(s, 1H) |
| B101-X00-M00(C01)-D44 | $^1$H NMR(400MHz, DMSO-d$_6$) δ ppm 2.16(s, 3H) 2.34(m, 8H) 2.83(t, 2H) 3.00(t, 2H) 3.40(s, 2H) 4.38(s, 3H) 4.44(d, 2H) 7.23(d, 2H) 7.30(m, 2H) 7.65(d, 2H) 8.41(s, 1H) 8.50(m, 2H) 8.87(t, 1H) 9.51(s, 1H) |
| B101-X00-M00(C01)-D52 | $^1$H NMR(400MHz, DMSO-d$_6$) δ ppm 1.70(s, 6H) 2.16(s, 3H) 2.34(m, 8H) 2.79(t, 2H) 2.91(t, 2H) 3.40(s, 2H) 4.38(s, 3H) 7.21(m, 3H) 7.32(m, 2H) 7.42(m, 2H) 7.64(d, 2H) 7.80(s, 1H) 8.39(s, 1H) 9.50(s, 1H) |
| B101-X00-M00(C01)-D37 | $^1$H NMR(400MHz, DMSO-d$_6$) δ ppm 1.50(d, 3H) 2.16(s, 3H) 2.34(m, 8H) 2.81(t, 2H) 2.97(t, 2H) 3.41(m, 2H) 4.37(s, 3H) 5.15(m, 1H) 7.15(dd, 2H) 7.23(d, 2H) 7.46(dd, 2H) 7.64(d, 2H) 8.40(s, 1H) 8.50(d, 1H) 9.49(s, 1H) |
| B101-X00-M00(C01)-D51 | $^1$H NMR(400MHz, DMSO-d$_6$) δ ppm 2.16(s, 3H) 2.34(m, 8H) 2.81(t, 2H) 2.97(t, 2H) 3.40(s, 2H) 4.39(s, 3H) 5.52(d, 1H) 7.23(d, 2H) 7.31(m, 1H) 7.38(m, 4H) 7.46(m, 2H) 7.64(d, 2H) 7.87(s, 2H) 8.12(d, 1H) 8.40(s, 1H) 9.50(s, 1H) |
| B102-X00-M00(C01)-D09 | $^1$H NMR(400MHz, DMSO-d$_6$) δ ppm 2.36(m, 4H) 2.83(t, J=7.74Hz, 2H) 3.01(t, J=7.68Hz, 2H) 3.43(m, 2H) 3.59(m, 4H) 4.36(s, 3H) 4.44(d, J=6.46Hz, 2H) 7.25(m, 3H) 7.32(m, 4H) 7.68(d, J=8.17Hz, 2H) 8.41(s, 1H) 8.71(t, J=6.28Hz, 1H) 9.52(s, 1H) |
| B102-X00-M00(C01)-D38 | $^1$H NMR(400MHz, DMSO-d$_6$) δ ppm 2.52(m, 10H) 2.81(t, 2H) 2.95(t, 2H) 3.43(s, 2H) 3.59(m, 8H) 4.39(s, 3H) 5.18(m, 1H) 7.25(m, 3H) 7.33(m, 2H) 7.42(m, 2H) 7.66(d, 2H) 8.40(m, 2H) 9.51(s, 1H) |
| B102-X00-M00(C01)-D52 | $^1$H NMR(400MHz, DMSO-d$_6$) δ ppm 1.70(s, 6H) 2.36(m, 4H) 2.79(t, 2H) 2.91(t, 2H) 3.42(s, 2H) 3.59(m, 4H) 4.38(s, 3H) 7.25(m, 3H) 7.32(m, 2H) 7.42(m, 2H) 7.66(d, 2H) 7.80(s, 1H) 8.40(s, 1H) 9.51(s, 1H) |
| B102-X00-M00(C01)-D51 | $^1$H NMR(400MHz, DMSO-d$_6$) δ ppm 2.37(m, 4H) 2.81(t, 2H) 2.97(t, 2H) 3.42(s, 2H) 3.59(m, 4H) 4.39(s, 3H) 5.54(d, 1H) 7.25(d, 2H) 7.31(m, 1H) 7.38(m, 2H) 7.46(m, 2H) 7.66(d, 2H) 7.87(s, 2H) 8.12(d, 1H) 8.41(s, 1H) 9.52(s, 1H) |
| B102-X00-M00(C01)-D43 | $^1$H NMR(400MHz, DMSO-d$_6$) δ ppm 1.26(m, 4H) 2.37(m, 4H) 2.82(t, 2H) 2.97(t, 2H) 3.44(m, 2H) 3.59(m, 4H) 4.37(s, 3H) 7.16(m, 1H) 7.24(m, 6H) 7.66(d, 2H) 8.40(s, 1H) 8.87(s, 1H) 9.51(s, 1H) |
| B102-X00-M00(C01)-D39 | $^1$H NMR(400MHz, DMSO-d$_6$) δ ppm 1.71(m, 4H) 2.36(m, 4H) 2.81(t, 2H) 2.97(t, 2H) 3.35(m, 6H) 3.42(s, 2H) 3.59(m, 4H) 4.39(s, 3H) 5.11(m, 1H) 7.25(m, 3H) |

TABLE XIII-continued

| | |
|---|---|
| | 7.35(m, 2H) 7.43(m, 2H) 7.66(d, 2H) 8.40(m, 2H) 9.51(s, 1H) |
| B102-X00-M00(C01)-D36 | $^1$H NMR(400MHz, DMSO-$d_6$) δ ppm 1.49(m, 6H) 2.38(m, 10H) 2.81(t, 2H) 2.97(t, 2H) 3.42(s, 2H) 3.59(m, 4H) 4.39(s, 3H) 5.11(m, 1H) 7.25(m, 3H) 7.33(m, 2H) 7.40(m, 2H) 7.66(d, 2H) 8.35(d, 1H) 8.40(s, 1H) 9.51(s, 1H) |
| B105-X00-M00(C01)-D35 | $^1$H NMR(400MHz, DMSO-$d_6$) δ ppm 2.38(m, 4H) 2.92(m, 4H) 3.44(m, 2H) 3.59(m, 4H) 3.75(s, 3H) 4.39(m, 5H) 6.90(m, 4H) 7.25(m, 2H) 7.57(m, 1H) 7.77(m, 1H) 8.42(m, 1H) 8.68(s, 1H) 9.54(m, 1H) |
| B105-X00-M00(C01)-D51 | $^1$H NMR(400MHz, DMSO-$d_6$) δ ppm 2.38(m, 4H) 2.90(m, 4H) 3.44(m, 2H) 3.59(m, 4H) 4.42(s, 3H) 5.53(m, 1H) 6.93(m, 1H) 7.47(m, 8H) 7.82(m, J=39.51Hz, 2H) 8.12(m, 1H) 8.42(m, 1H) 9.55(m, 1H) |
| B105-X00-M00(C01)-D39 | $^1$H NMR(400MHz, DMSO-$d_6$) δ ppm 2.09(m, 4H) 2.38(m, 4H) 2.90(m, 4H) 3.45(m, 4H) 3.59(m, 4H) 4.42(s, 3H) 6.93(m, 1H) 7.25(m, 7H) 7.57(m, 1H) 7.76(m, 1H) 8.42(m, 1H) 9.54(m, 1H) |
| B105-X00-M00(C01)-D34 | $^1$H NMR(400MHz, DMSO-$d_6$) δ ppm 2.38(m, 4H) 2.90(m, 4H) 3.45(m, 2H) 3.60(m, 4H) 3.73(m, 2H) 4.42(m, 3H) 5.00(m, 2H) 6.92(m, 1H) 7.32(m, 6H) 7.57(m, 1H) 7.77(m, 1H) 8.27(m, 1H) 8.42(m, 1H) 9.54(m, 1H) |
| B105-X00-M00(C01)-D43 | $^1$H NMR(400MHz, DMSO-$d_6$) δ ppm 1.29(m, 4H) 2.38(m, 4H) 2.98(m, 4H) 3.44(m, 2H) 3.60(m, 4H) 4.40(s, 3H) 6.92(m, 1H) 7.20(m, 6H) 7.58(m, 1H) 7.77(s, 1H) 8.42(s, 1H) 9.20(m, 2H) |
| B105-X00-M00(C01)-D36 | $^1$H NMR(400MHz, DMSO-$d_6$) δ ppm 1.49(m, 6H) 2.52(m, 8H) 2.81(m, 4H) 3.45(m, 2H) 3.60(s, 4H) 4.42(s, 3H) 5.11(m, 1H) 6.92(m, 1H) 7.25(m, 6H) 7.57(m, 1H) 7.76(m, 1H) 8.34(m, 1H) 8.42(m, 1H) 9.54(m, 1H) |
| B104-X00-M00(C01)-D52 | $^1$H NMR(400MHz, DMSO-$d_6$) δ ppm 1.71(s, 6H) 2.21(s, 3H) 2.40(m, 8H) 2.80(t, 2H) 2.92(t, 2H) 3.44(s, 2H) 4.40(s, 3H) 6.91(m, 1H) 7.32(m, 4H) 7.42(m, 2H) 7.55(m, 1H) 7.75(m, 1H) 7.81(m, 1H) 8.41(s, 1H) 9.53(s, 1H) |
| B104-X00-M00(C01)-D43 | $^1$H NMR(400MHz, DMSO-$d_6$) δ ppm 1.29(m, 4H) 2.20(m, 3H) 2.40(m, 8H) 2.82(t, 2H) 2.98(t, 2H) 3.44(s, 2H) 4.39(s, 3H) 6.90(m, 1H) 7.25(m, 6H) 7.56(m, 1H) 7.76(m, 1H) 8.42(s, 1H) 8.87(s, 1H) 9.53(s, 1H) |
| B104-X00-M00(C01)-D51 | $^1$H NMR(400MHz, DMSO-$d_6$) δ ppm 2.22(s, 3H) 2.42(m, 8H) 2.82(t, 2H) 2.97(t, 2H) 3.44(s, 2H) 4.41(s, 3H) 5.53(d, 1H) 6.91(d, 1H) 7.24(m, 1H) 7.38(m, 3H) 7.46(m, 2H) 7.56(m, 1H) 7.75(m, 1H) 7.87(s, 2H) 8.12(m, 1H) 8.42(s, 1H) 9.54(m, 1H) |
| B104-X00-M00(C01)-D35 | $^1$H NMR(400MHz, DMSO-$d_6$) δ ppm 2.19(s, 3H) 2.39(m, 8H) 2.83(t, 2H) 3.01(t, 2H) 3.43(s, 2H) 3.75(s, 3H) 4.38(s, 3H) 4.41(d, 2H) 6.83(m, 1H) 6.90(m, 3H) 7.24(m, 2H) 7.56(m, 1H) 7.76(m, 1H) 8.42(s, 1H) 8.68(t, 1H) 9.53(s, 1H) |
| B103-X00-M00(C01)-D09 | $^1$H NMR(400MHz, DMSO-$d_6$) δ ppm 1.74(m, 1H) 1.95(m, 1H) 2.09(m, 1H) 2.26(m, 1H) 2.82(m, 5H) 3.00(t, 2H) 3.34(m, 4H) 4.34(s, 3H) 4.43(d, 2H) 4.65(m, 1H) 7.02(m, 2H) 7.25(m, 1H) 7.33(m, 4H) 7.62(m, 2H) 8.38(s, 1H) 8.67(t, 1H) 9.39(s, 1H) |
| B103-X00-M00(C01)-D52 | $^1$H NMR(400MHz, DMSO-$d_6$) δ ppm 1.70(s, 6H) 1.79(m, 2H) 2.00(m, 2H) 2.56(s, 3H) 2.68(m, 2H) 2.78(t, 2H) 2.90(t, 2H) 2.99(m, 2H) 4.35(s, 3H) 4.42(m, 1H) 6.97(d, 2H) 7.21(m, 2H) 7.32(m, 2H) 7.41(m, 2H) 7.58(d, 2H) 7.78(s, 1H) 8.35(s, 1H) 9.34(s, 1H) |
| B103-X00-M00(C01)-D37 | $^1$H NMR(400MHz, DMSO-$d_6$) δ ppm 1.48(d, 3H) 1.84(m, 2H) 2.01(m, 2H) 2.79(m, 4H) 2.96(m, 4H) 4.34(s, 3H) 4.43(m, 1H) 5.15(m, 1H) 6.97(d, 2H) 7.15(m, 2H) 7.46(m, 2H) 7.58(d, 2H) 8.36(s, 1H) 8.47(d, 1H) 9.34(s, 1H) |
| B103-X00-M00(C01)-D51 | $^1$H NMR(400MHz, DMSO-$d_6$) δ ppm 1.71(m, 2H) 1.96(m, 2H) 2.34(s, 3H) 2.42(m, 2H) 2.79(m, 6H) 4.36(m, 4H) 5.52(d, 1H) 6.94(d, 2H) 7.31(m, 1H) 7.38(m, 2H) 7.46(m, 2H) 7.56(d, 2H) 7.87(s, 2H) 8.11(d, 1H) 8.36(s, 1H) 9.34(s, 1H) |
| B103-X00-M00(C01)-D44 | $^1$H NMR(400MHz, DMSO-$d_6$) δ ppm 1.69(m, 2H) 1.94(m, 2H) 2.32(s, 3H) 2.39(m, 2H) 2.80(m, 4H) 2.99(t, 2H) 4.35(m, 4H) 4.44(d, 2H) 6.94(d, 2H) 7.31(m, 2H) 7.57(d, 2H) 8.37(s, 1H) 8.50(m, 2H) 8.85(t, 1H) 9.34(s, 1H) |

TABLE XIII-continued

| | |
|---|---|
| B103-X00-M00(C01)-D36 | $^1$H NMR(400MHz, DMSO-$d_6$) δ ppm 1.91(m, 4H) 2.20(m, 3H) 2.37(m, 4H) 2.55(m, 4H) 2.88(m, J=59.63Hz, 6H) 4.28(m, 1H) 4.35(s, 3H) 5.10(m, 1H) 5.35(none, 1H) 6.93(m, 2H) 7.31(m, 5H) 7.56(m, 2H) 8.35(m, 2H) 9.32(m, 6H) |
| B103-X00-M00(C01)-D39 | $^1$H NMR(400MHz, DMSO-$d_6$) δ ppm 1.68(s, 4H) 1.91(m, 4H) 2.20(m, 3H) 2.52(m, 8H) 2.87(m, J=66.33Hz, 4H) 3.04(m, 2H) 4.28(m, 1H) 4.35(s, 3H) 5.08(m, 1H) 6.93(m, 2H) 7.38(m, 7H) 8.35(m, 2H) 9.32(m, 1H) |
| B103-X00-M00(C01)-D34 | $^1$H NMR(400MHz, DMSO-$d_6$) δ ppm 1.78(m, J=106.57Hz, 4H) 2.41(m, 7H) 2.87(m, J=68.16Hz, 4H) 3.73(m, 2H) 4.28(m, 1H) 4.36(s, 3H) 5.00(m, 2H) 6.93(m, 2H) 7.32(m, 5H) 7.56(m, 2H) 8.26(m, 1H) 8.36(m, 1H) 9.32(m, 1H) |
| B103-X00-M00(C01)-D43 | $^1$H NMR(400MHz, DMSO-$d_6$) δ ppm 1.28(m, 4H) 1.79(m, J=107.43Hz, 4H) 2.43(m, 7H) 2.88(m, J=66.33Hz, 4H) 4.29(m, 1H) 4.34(m, 3H) 6.93(m, 2H) 7.22(m, 5H) 7.56(m, 2H) 8.36(s, 1H) 8.86(m, 1H) 9.32(m, 1H) |
| B00-X00-M00(C01)-D38 | $^1$H NMR(400MHz, DMSO-$d_6$) δ ppm 2.52(m, 6H) 2.71(t, 2H) 2.90(t, 2H) 3.57(m, 4H) 4.36(m, 3H) 5.15(m, 1H) 6.55(s, 2H) 7.24(m, 1H) 7.33(m, 2H) 7.41(m, 2H) 8.17(s, 1H) 8.36(d, 1H). |
| B00-X00-M00(C01)-D44 | $^1$H NMR(400MHz, DMSO-$d_6$) δ ppm 2.71(t, 2H) 2.94(t, 2H) 4.35(s, 3H) 4.43(d, 2H) 6.56(s, 2H) 7.31(m, 2H) 8.18(s, 1H) 8.50(m, 2H) 8.82(t, 1H). |
| B113-X00-M00(C01)-D44 | $^1$H NMR(400MHz, DMSO-$d_6$) δ ppm 2.83(t, 2H) 3.00(t, 2H) 4.35(s, 3H) 4.44(d, 2H) 7.16(m, 2H) 7.30(m, 2H) 7.71(m, 2H) 8.41(s, 1H) 8.50(m, 2H) 8.87(t, 1H) 9.55(s, 1H) |
| B112-X00-M00(C01)-D09 | $^1$H NMR(400MHz, DMSO-$d_6$) δ ppm 2.84(t, J=7.68Hz, 2H) 3.01(t, J=7.68Hz, 2H) 4.35(s, 3H) 4.44(d, J=6.34Hz, 2H) 7.26(m, 5H) 7.36(d, J=9.02Hz, 2H) 7.76(d, J=9.02Hz, 2H) 8.44(s, 1H) 8.72(t, J=6.40Hz, 1H) 9.68(s, 1H) |
| B04-X04-M00(C01)-D03 | $^1$H NMR(400MHz, DMSO-$d_6$) δ ppm 2.87(t, 2H) 2.99(t, 2H) 3.71(s, 3H) 7.25(m, 1H) 7.44(s, 1H) 7.51(m, 3H) 7.66(m, 2H) 8.55(s, 1H) |
| B10-X00-M04(C15)-D03 | $^1$H NMR(400MHz, DMSO-$d_6$) δ ppm 2.85(m, 6H) 3.05(m, 4H) 3.33(m, 5H) 6.28(s, 2H) 6.80(d, 2H) 7.33(s, 2H) 7.47(m, 7H) 7.63(d, 2H) 7.66(s, 1H) 8.42(s, 1H) 9.34(s, 1H) |
| B09-X00-M04(C03)-D03 | $^1$H NMR(400MHz, DMSO-$d_6$) δ ppm 0.79(m, 9H) 1.64(t, 2H) 2.86(m, 15H) 4.84(t, 2H) 6.67(m, 1H) 7.21(m, 3H) 7.39(s, 2H) 8.41(s, 1H) 9.25(s, 1H) |
| B10-X00-M00(C14)-D03 | $^1$H NMR(400MHz, DMSO-$d_6$) δ ppm 1.13(t, 3H) 2.25(s, 3H) 2.52(m, 4H) 2.61(q, 2H) 2.84(t, 2H) 3.03(m, 6H) 6.16(s, 2H) 6.75(d, 2H) 6.83(s, 1H) 7.29(br. s, 2H) 7.36(d, 2H) 7.45(br. s, 1H) 8.38(s, 1H) 9.25(s, 1H) |
| B10-X00-M00(C14)-D09 | $^1$H NMR(400MHz, DMSO-$d_6$) δ ppm 1.12(t, 3H) 2.24(s, 3H) 2.46(m, 4H) 2.60(q, 2H) 2.85(t, 2H) 3.02(m, 6H) 4.41(d, 2H) 6.18(s, 2H) 6.74(d, 2H) 6.83(s, 1H) 7.23(m, 1H) 7.31(m, 4H) 7.37(d, 2H) 8.38(s, 1H) 8.69(t, 1H) 9.26(s, 1H) |
| B08-X00-M00(C01)-D03 | $^1$H NMR(400MHz, DMSO-$d_6$) δ ppm 2.79(m, 2H) 2.96(m, 2H) 3.83(s, 3H) 4.23(s, 3H) 6.96(m, 3H) 7.22(s, 1H) 7.43(s, 1H) 8.00(m, 1H) 8.11(s, 1H) 8.35(s, 1H) |
| B36-X00-M00(C01)-D03 | $^1$H NMR(400MHz, DMSO-$d_6$) δ ppm 2.78(t, 2H) 2.95(t, 2H) 4.28(s, 3H) 5.95(s, 2H) 6.84(d, 1H) 7.06(dd, 1H) 7.22(s, 1H) 7.34(d, 1H) 7.42(s, 1H) 8.34(s, 1H) 9.34(s, 1H) |

Example 52

8-iodo-1-methyl-N-[(1S)-2-morpholin-4-yl-1-phenylethyl]-4,5-dihydro-1H-pyrazolo[4,3-h]quinazolin-3-carboxamide

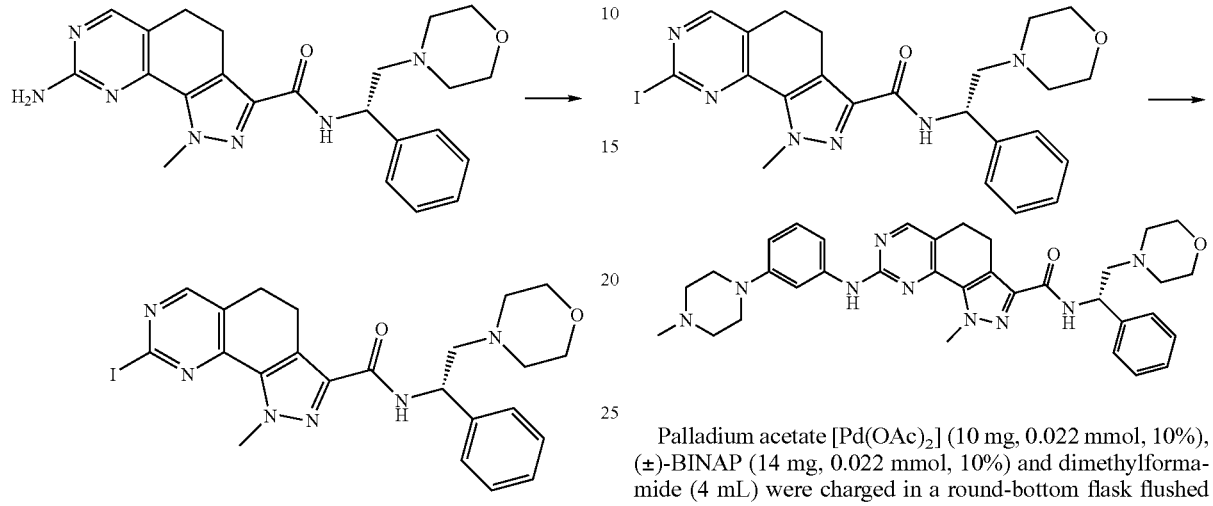

Example 53

1-methyl-8-{[3-(4-methylpiperazin-1-yl)phenyl]amino}-N-[(1S)-2-morpholin-4-yl-1-phenylethyl]-4,5-dihydro-1H-pyrazolo[4,3-h]quinazoline-3-carboxamide [B09-X00-M00(C01)-D38]

To a well stirred and warm suspension of 8-amino-1-methyl-N-[(1S)-2-morpholin-4-yl-1-phenylethyl]-4,5-dihydro-1H-pyrazolo[4,3-h]quinazoline-3-carboxamide (3 g, 6.92 mmol) in dimethoxyethane (240 mL), maintained in an inert atmosphere of argon, cesium iodide (2.16 g, 8.3 mmol), bisublimated iodine (870 mg, 3.46 mmol), copper iodide (460 mg, 2.42 mmol) and isopentyl nitrite (1.71 mL, 1.5 g, 12.46 mmol) were added, in sequence. The reaction mixture was stirred vigorously at 65-70° C. for 18 hours. After cooling in an ice-water bath, the solid was filtered off and the filtrate was diluted with dichloromethane (100 mL), washed with 30% ammonium hydroxide (50 mL), sodium thiosulphate (100 mL), brine and dried over anhydrous $Na_2SO_4$. The crude was purified by flash chromatography on silica gel (eluant: dichloromethane/methanol 95:59) and 1.48 g of the title compound was isolated (40% yield).

$^1$H NMR (400 MHz, DMSO-$d_6$) δ ppm 2.52 (m, 6 H) 2.89 (t, 2 H) 2.99 (t, 2 H) 4.30 (s, 3 H) 5.17 (m, 1 H) 7.22 (m, 1 H) 7.34 (m, 2 H) 7.41 (m, 2 H) 8.47 (s, 1 H)

Palladium acetate [Pd(OAc)$_2$] (10 mg, 0.022 mmol, 10%), (±)-BINAP (14 mg, 0.022 mmol, 10%) and dimethylformamide (4 mL) were charged in a round-bottom flask flushed with argon. The mixture was stirred under argon for 30 minutes. Then, 3-(4-methylpiperazin-1-yl)phenylamine (84 mg, 0.44 mmol), 8-iodo-1-methyl-N-[(1S)-2-morpholin-4-yl-1-phenylethyl]-4,5-dihydro-1H-pyrazolo[4,3-h]quinazoline-3-carboxamide (120 mg, 0.22 mmol), potassium carbonate (670 mg, 4.85 mmol) and dimethylformamide (1.5 mL) were added The resulting mixture was heated at 80° C. in an oil bath under argon with good stirring for 1.5 hours.

After cooling to room temperature, the reaction mixture was poured into water and extracted with dichloromethane. The organic extracts were washed with brine and dried over $Na_2SO_4$. The solvent was removed under vacuo, the crude was purified by flash chromatography on silica gel (eluant: dichloromethane/methanol 95:5) to afford 40 mg (30% yield) of the title compound.

$^1$H NMR (400 MHz, DMSO-$d_6$) δ ppm 2.27 (s, 3 H) 2.52 (m, 8 H) 2.80 (t, 2 H) 2.94 (m, 4 H) 3.13 (m, 4 H) 3.56 (m, 4 H) 4.39 (s, 3 H) 5.16 (m, 1 H) 6.59 (m, 1 H) 7.14 (m, 1 H) 7.24 (m, 2 H) 7.33 (m, 2 H) 7.42 (m, 2 H) 8.39 (m, 2 H) 9.33 (s, 1 H).

By working analogously the following compounds were prepared:

TABLE XIV

| | |
|---|---|
| B107-X00-M00(C01)-D38 | $^1$H NMR(400MHz, DMSO-$d_6$) δ ppm 2.52(m, 6H) 2.80(t, 2H) 2.97(m, 2H) 3.09(m, 4H) 3.57(m, 4H) 3.76(m, 4H) 4.39(s, 3H) 5.18(m, 1H) 6.60(m, 1H) 7.16(m, 1H) 7.42(m, 6H) 8.40(m, 2H) 9.35(s, 1H) |
| B105-X00-M00(C01)-D38 | $^1$H NMR(400MHz, DMSO-$d_6$) δ ppm 2.52(m, 10H) 2.81(t, 2H) 2.97(t, 2H) 3.34(m, 10H) 4.41(s, 3H) 5.17(m, 1H) 6.93(m, 1H) 7.34(m, 4H) 7.42(m, 2H) 7.58(m, 1H) 7.77(m, 1H) 8.41(m, 2H) 9.54(s, 1H) |
| B103-X00-M00(C01)-D38 | $^1$H NMR(400MHz, DMSO-$d_6$) δ ppm 1.66(m, 2H) 1.92(m, 2H) 2.21(m, 5H) 2.52(m, 4H) 2.65(m, 2H) 2.79(t, 2H) 2.95(m, 4H) 3.56(m, 4H) 4.29(m, 1H) 4.36(s, 3H) 5.17(m, 1H) 6.93(d, 2H) 7.24(m, 1H) 7.33(m, 2H) 7.42(m, 2H) 7.56(d, 2H) 8.35(s, 1H) 8.40(d, 1H) 9.32(s, 1H) |

TABLE XIV-continued

| | |
|---|---|
| B101-X00-M00(C01)-D38 | ¹H NMR(400MHz, DMSO-d₆) δ ppm 2.19(s, 3H) 2.52(m, 8H) 2.80(t, 2H) 2.95(m, 4H) 3.33(m, 6H) 3.56(m, 4H) 4.39(s, 3H) 5.17(m, 1H) 7.23(m, 3H) 7.33(m, 2H) 7.42(m, 2H) 7.65(d, 2H) 8.40(m, 2H) 9.50(s, 1H) |
| B104-X00-M00(C01)-D38 | ¹H NMR(400MHz, DMSO-d₆) δ ppm 2.21(s, 3H) 2.42(m, 13H) 2.81(t, J=7.80Hz, 2H) 2.95(m, 3H) 3.44(s, 2H) 3.57(m, 4H) 4.41(s, 3H) 5.17(m, 1H) 6.90(d, J=7.56Hz, 1H) 7.24(t, J=7.68Hz, 2H) 7.33(t, J=7.50Hz, 2H) 7.43(m, 2H) 7.57(dd, J=8.29, 0.98Hz, 1H) 7.76(t, J=1.95Hz, 1H) 8.41(d, J=7.68Hz, 1H) 8.41(s, 1H) 9.53(s, 1H) |
| B110-X00-M00(C01)-D38 | ¹H NMR(400MHz, DMSO-d₆) δ ppm 1.45(m, 6H) 2.73(m, 16H) 3.57(m, 4H) 4.39(s, 3H) 5.17(m, 1H) 7.26(m, 2H) 7.25(m, 1H) 7.33(t, J=7.56Hz, 2H) 7.43(m, 2H) 7.70(s, 2H) 8.42(m, 2H) 9.55(s, 1H) |
| B106-X00-M00(C01)-D38 | ¹H NMR(400MHz, DMSO-d₆) δ ppm 1.74(m, 2H) 1.98(m, 2H) 2.52(m, 7H) 2.81(m, 8H) 3.56(m, 4H) 4.41(m, 4H) 5.17(m, 1H) 6.60(m, 1H) 7.26(m, 5H) 7.44(m, 3H) 8.42(m, 2H) 9.50(s, 1H) |
| B111-X00-M00(C01)-D38 | ¹H NMR(400MHz, DMSO-d₆) δ ppm 1.30(t, J=7.19Hz, 3H) 2.46(m, 5H) 2.80(t, J=7.74Hz, 2H) 2.93(m, 3H) 3.56(q, 4H) 4.03(q, J=7.19Hz, 2H) 4.20(s, 3H) 5.16(m, 1H) 6.20(d, J=1.71Hz, 1H) 7.24(t, J=7.32Hz, 1H) 7.33(t, J=7.44Hz, 2H) 7.42(m, 3H) 8.36(s, 1H) 8.41(d, J=6.95Hz, 1H) 9.23(s, 1H) |

Example 54

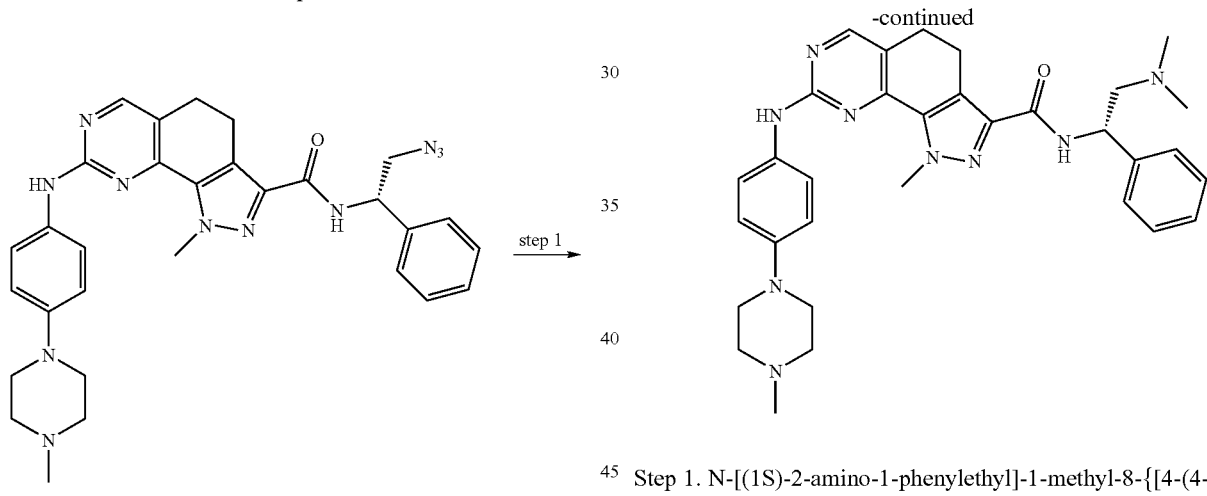

Step 1. N-[(1S)-2-amino-1-phenylethyl]-1-methyl-8-{[4-(4-methylpiperazin-1-yl)phenyl]amino}-4,5-dihydro-1H-pyrazolo[4,3-h]quinazoline-3-carboxamide [B10-X00-M00(C01)-D71]

To a solution of 129 mg (0.228 mmol) of N-[(1S)-2-azido-1-phenylethyl]-1-methyl-8-{[4-(4-methylpiperazin-1-yl)phenyl]amino}-4,5-dihydro-1H-pyrazolo[4,3-h]quinazoline-3-carboxamide in 16 mL of methanol, 65 mg (1.2 mmol) of NH₄Cl dissolved in 3.2 mL of water and 39 mg of iron (0.7 mmol) were added and the mixture refluxed overnight. The suspension was cooled to room temperature and filtered. After removal of methanol, solid Na₂CO₃ was added portionwise to the aqueous phase up to pH 10 and the product was then extracted with dichloromethane. Flash chromatography of the crude (eluant dichloromethane/methanol 95/5) yielded 94 mg of the title compound.

¹H NMR (400 MHz, DMSO-d₆) δ ppm 2.24 (s, 3 H) 2.47 (m, 4 H) 2.78 (t, J=7.68 Hz, 2 H) 2.96 (m, 3 H) 3.08 (m, 5 H) 4.37 (s, 3 H) 5.01 (m, 1 H) 6.91 (d, J=9.15 Hz, 2 H) 7.31 (m, 5 H) 7.54 (d, J=9.02 Hz, 2 H) 8.34 (s, 1 H) 8.54 (d, J=8.17 Hz, 1 H) 9.26 (s, 1 H).

By working according to the above method the following compound was prepared:

B10-X00-M03(C01)-D71

$^1$H NMR (400 MHz, DMSO-$d_6$) δ ppm 1.21 (s, 3 H) 1.34 (s, 3 H) 2.24 (s, 3 H) 2.45-2.49 (m, 4 H) 2.62-2.72 (m, 2 H) 2.90-3.05 (m, 2 H) 3.06-3.10 (m, 4 H) 4.35 (s, 3 H) 5.01 (td, J=8.20, 5.67 Hz, 1 H) 6.91 (d, J=9.15 Hz, 2 H) 7.24-7.29 (m, 1 H) 7.33-7.38 (m, 2 H) 7.38-7.41 (m, 2 H) 7.53 (d, J=9.15 Hz, 2 H) 8.34 (s, 1 H) 8.65 (d, J=8.29 Hz, 1 H) 9.26 (s, 1 H).

Step 2. N-[(1S)-2-(dimethylamino)-4-phenylethyl]-1-methyl-8-{[4-(4-methylpiperazin-1-yl)phenyl]amino}-4,5-dihydro-1H-pyrazolo[4,3-h]quinazoline-3-carboxamide [B10-X00-M00(C01)-D72]

To a solution of 50 mg (0.091 mmol) of N-[(1S)-2-amino-1-phenylethyl]-1-methyl-8-{[4-(4-methylpiperazin-1-yl)phenyl]amino}-4,5-dihydro-1H-pyrazolo[4,3-h]quinazoline-3-carboxamide in methanol (5 mL), 0.027 mL of formaldehyde (40% aqueous solution 0.364 mmol) and acetic acid (0.02 mL) were added. After 30 minutes, 77 mg (0.364 mmol) of sodiumtriacetoxyborohydride were added and the mixture was stirred for 5 hours. The solvent was removed under vacuo, the crude was dissolved in water and $Na_2CO_3$ was added portionwise up to basic pH. The product was extracted with dichloromethane as the sole compound (34 mg, 66% yield).

$^1$H NMR (400 MHz, DMSO-$d_6$) δ ppm 2.26 (s, 9 H) 2.52 (m, 4 H) 2.78 (t, 2 H) 2.95 (t, 2 H) 3.09 (, 4 H) 4.37 (s, 3 H) 5.11 (m, 1 H) 6.93 (d, 2 H) 7.24 (m, 1 H) 7.33 (m, 2 H) 7.41 (m, 2 H) 7.53 (d, 2 H) 8.34 (m, 2 H) 9.26 (s, 1 H).

By working analogously the following compounds were prepared:

1-methyl-{[4-(4-methylpiperazin-1-yl)phenyl]amino}-N-{(1S)-2-[(1-methylpiperidin-4-yl)amino]-1-phenylethyl}-4,5-dihydro-1H-pyrazolo[4,3-h]quinazoline-3-carboxamide [B10-X00-M00(C01)-D145]

$^1$H NMR (400 MHz, DMSO-$d_6$) δ ppm 1.76 (m, 4 H) 2.73 (m, 24 H) 4.39 (s, 3 H) 5.34 (m, 1 H) 6.98 (d, 2 H) 7.30 (m, 1 H) 7.38 (m, 2 H) 7.43 (m, 2 H) 7.57 (d, 2 H) 8.36 (s, 1 H) 8.75 (s, 1 H) 9.33 (bs, 1 H)

B10-X00-M03(C01)-D72

$^1$H NMR (400 MHz, DMSO-$d_6$) δ ppm 1.21 (s, 3 H) 1.32 (s, 3 H) 2.24 (s, 6 H) 2.25 (s, 3 H) 2.49 (m, 4 H) 2.67 (m, 2 H) 2.80 (m, 2 H) 3.08 (m, 4 H) 4.34 (s, 3 H) 5.12 (td, J=8.20, 5.67 Hz, 1 H) 6.91 (d, J=9.15 Hz, 2 H) 7.25 (m, 1 H) 7.34 (m, 2 H) 7.42 (m, 2 H) 7.53 (d, J=9.15 Hz, 2 H) 8.33 (s, 1 H) 8.45 (d, J=8.29 Hz, 1 H) 9.26 (s, 1 H)

Example 55

N-benzyl-1-methyl-8-{[4-(4-methyl-4-oxidopiperazin-1-yl)phenyl]amino}-4,5-dihydro-1H-pyrazolo[4,3-h]quinazoline-3-carboxamide

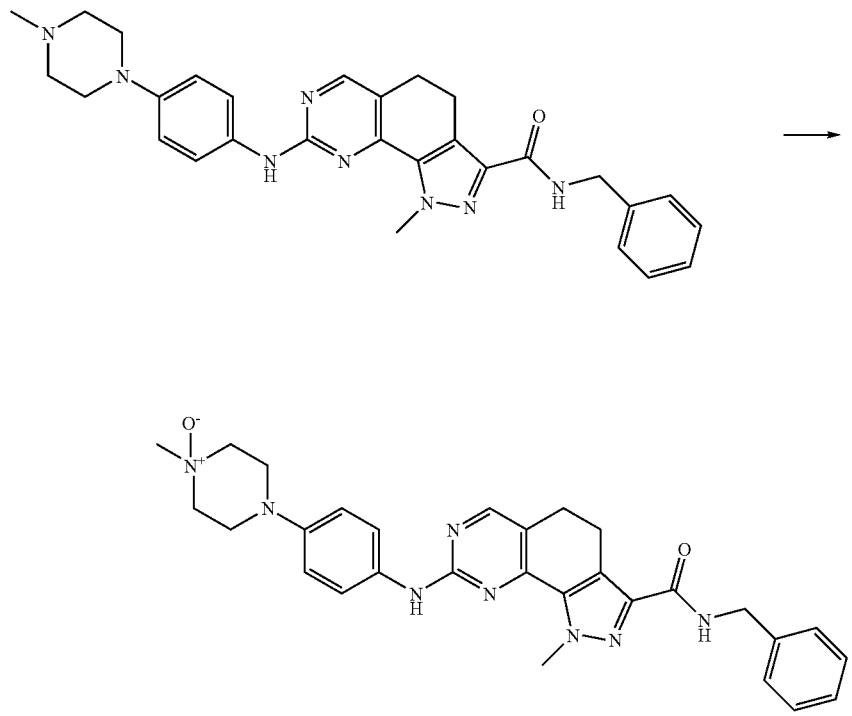

To a solution of 39.4 mg (0.0774 mmol) of N-benzyl-1-methyl-8-{[4-(4-methylpiperazin-1-yl)phenyl]amino}-4,5-dihydro-1H-pyrazolo[4,3-h]quinazoline-3-carboxamide, 17.4 mg (0.0774 mg) of 3-chlorobenzenecarboperoxoic acid were added and the mixture was stirred at room temperature. After 45 minutes an aqueous solution of $NaHCO_3$ was added and the solvent removed. Treatment with methanol and filtration afforded 26.6 mg of the title compound (66% yield).

$^1$H NMR (400 MHz, DMSO-$d_6$) δ ppm 2.81 (t, J=7.74 Hz, 2 H) 3.00 (t, J=7.62 Hz, 2 H) 3.37 (m, 8 H) 3.15 (s, 3 H) 4.34 (s, 3 H) 4.43 (d, J=6.34 Hz, 2 H) 6.98 (d, J=9.15 Hz, 2 H) 7.24 (m, 1 H) 7.33 (m, 4 H) 7.57 (d, J=9.15 Hz, 2 H) 8.36 (s, 1 H) 8.70 (t, J=6.34 Hz, 1 H) 9.30 (s, 1 H).

Example 56

Ethyl 8-[4-(4-methyl-piperazin-1-yl)-phenylamino]-1,4,4-trimethyl-4,5-dihydro-1H-pyrazolo[4,3-h]quinazoline-3-carboxylate [B10-X00-M03(C01)-D01]

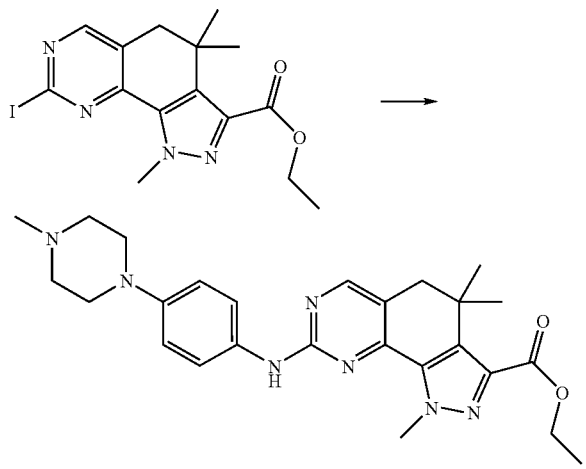

Pd(OAc)$_2$ (762.34 mg, 3.395 mmol), (±)-BINAP (2.145 g, 3.395 mmol) and dimethylformamide (250 mL) were charged in a round-bottom flask flushed with argon. The mixture was stirred under argon for 30 minutes. Then 4-(4-methyl-piperazin-1-yl)-phenylamine (19.493 g, 101.908 mmol), ethyl 8-iodo-1,4,4-trimethyl-4,5-dihydro-1H-pyrazolo[4,3-h]quinazoline-3-carboxylate (14.00 g, 33.961 mmol), K$_2$CO$_3$ (60.00 g, 434.112 mmol) and dimethylformamide (250 mL) were added. The resulting mixture was stirred at room temperature for 1 hour and then heated to 80° C. in an oil bath under argon with good stirring for 3 hours.

After cooling to room temperature, the reaction mixture was filtered by suction filtration washing with dichloromethane and the filtrate was evaporated to dryness. The crude was purified by flash chromatography on silica gel (eluant: dichloromethane/methanol 94:6) to afford 11.60 g (yield 72%) of pure title compound.

$^1$H NMR (400 MHz, DMSO-d$_6$) δ ppm 1.33 (t, J=7.07 Hz, 3 H) 1.33 (s, 6H) 2.27 (s, 3 H) 2.52 (m, 4 H) 2.71 (s, 2 H) 3.03-3.15 (m, 4 H) 4.32 (q, J=7.07 Hz, 2 H) 4.33 (s, 3 H) 6.91 (d, J=9.02 Hz, 2 H) 7.53 (d, J=9.02 Hz, 2 H) 8.35 (s, 1 H) 9.28 (s, 1 H).

By working according to the above method the following compound was prepared:

TABLE XV

| | |
|---|---|
| B19-X00-M03(C01)-D01 | $^1$H NMR(400MHz, DMSO-d$_6$) δ ppm 1.33(t, J=7.07Hz, 3H) 1.33(s, 6H) 2.71(s, 2H) 3.01–3.08(m, 4H) 3.70–3.80(m, 4H) 4.32(q, J=7.07Hz, 2H) 4.33(s, 3H) 6.93(d, J=9.15Hz, 2H) 7.55(d, J=9.02Hz, 2H) 8.36(s, 1H) 9.30(s, 1H) |

Example 57

8-[4-4-methyl-piperazin-1-yl)-phenylamino]-1,4,4-trimethyl-4,5-dihydro-1H-pyrazolo[4,3-h]quinazoline-3-carboxylic acid potassium salt [B10-X00-M03(C01)-D02]

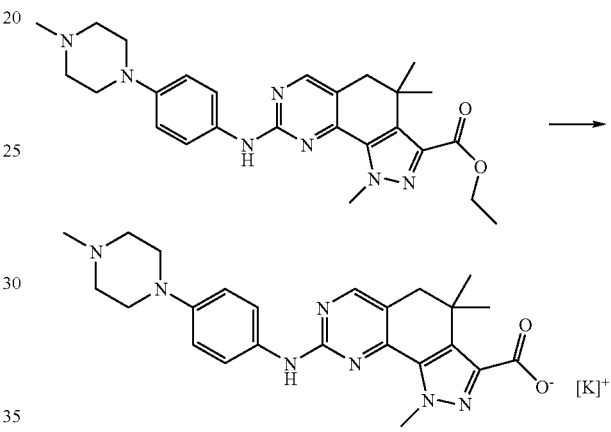

To a suspension of ethyl 8-[4-(4-methyl-piperazin-1-yl)-phenylamino]-1,4,4-trimethyl-4,5-dihydro-1H-pyrazolo[4,3-h]quinazoline-3-carboxylate (11.60 g, 24.390 mmol) in anhydrous ethanol (450 mL), 1.5 M potassium hydroxide in 95% ethanol (63 mL) was added under good stirring and the mixture was heated to reflux for 3 hours. After cooling in an ice bath, a solid was formed, that was filtered washing with ethanol, dried at 40° C. under vacuum to yield 11.8 g (quantitative yield) of white solid title compound $^1$H NMR (400 MHz, DMSO-d$_6$) δ ppm 1.31 (s, 6 H) 2.23 (s, 3 H) 2.47 (m, 4 H) 2.58 (s, 2 H) 3.03-3.15 (m, 4 H) 4.17 (s, 3 H) 6.91 (d, J=9.02 Hz, 2 H) 7.54 (d, J=9.02 Hz, 2 H) 8.24 (s, 1 H) 9.12 (s, 1 H)

By working according to the above method the following compounds were prepared:

TABLE XVI

| | |
|---|---|
| B04-X00-M03(C01)-D02 | $^1$H NMR(400MHz, DMSO-d$_6$) δ ppm 1.35(s, 6H) 2.73(s, 2H) 4.34(s, 3H) 6.98(tt, J 7.36, 1.13, 1.10Hz, 1H) 7.31(dd, J 8.47, 7.38Hz, 2H) 7.71(dd, J 8.66, 0.98Hz, 2H) 8.42(s, 1H) 9.53(s, 1H) 12.84(s, 1H) |
| B12-X00-M03(C01)-D02 | $^1$H NMR(400MHz, DMSO-d$_6$) δ ppm 1.31(s, 6H) 2.24(s, 3H) 2.45(s, 4H) 2.61(s, 2H) 2.84(t, J 4.51Hz, 4H) 4.18(s, 3H) 7.52(d, J 9.02Hz, 1H) 7.94(dd, J 8.90, 2.44Hz, 1H) 8.09(d, J 2.56Hz, 1H) 8.34(s, 1H) 9.63(s, 1H) |
| B13-X00-M03(C01)-D02 | $^1$H NMR(400MHz, DMSO-d$_6$) δ ppm 1.32(s, 6H) 2.25(s, 3H) 2.52(m, 4H) 2.61(s, 2H) 2.94(t, J 4.51Hz, 4H) 4.20(s, 3H) 7.12(d, J 8.90Hz, 1H) 7.53(dd, |

TABLE XVI-continued

| | |
|---|---|
| | J 8.78, 2.56Hz, 1H) 7.99(d, J 2.56Hz, 1H) 8.31(s, 1H) 9.45(s, 1H) |
| B00-X00-M03(C01)-D02 | $^1$H NMR(400MHz, DMSO-d$_6$) δ ppm 1.28(s, 6H) 2.51(s, 2H) 4.16(s, 3H) 6.37(s, 2H) 8.07(s, 1H) |
| B19-X00-M03(C01)-D02 | $^1$H NMR(400MHz, DMSO-d$_6$) δ ppm 1.31(s, 6H) 2.58(s, 2H) 3.01–3.09(m, 4H) 3.71–3.79(m, 4H) 4.18(s, 3H) 6.91(d, J=9.15Hz, 2H) 7.57(d, J=9.15Hz, 2H) 8.25(s, 1H) 9.14(s, 1H) |
| B109-X00-M00(C01)-D02 | $^1$H NMR(400MHz, DMSO-d$_6$) δ ppm 2.24(s, 3H) 2.48(m, 4H) 2.76(t, J=7.68Hz, 2H) 2.96(m, 6H) 4.27(s, 3H) 6.99(dd, J=10.00, 8.90Hz, 1H) 7.38(ddd, J=8.87, 2.47, 0.85Hz, 1H) 7.68(dd, J=15.49, 2.44Hz, 1H) 8.34(s, 1H) 9.45(s, 1H) |
| B13-X00-M02(C01)-D02 | $^1$H NMR(400MHz, DMSO-d$_6$) δ ppm 1.27(s, 6H) 2.25(s, 3H) 2.51(m, 4H) 2.91(s, 2H) 2.94(t, J 4.39Hz, 4H) 4.25(s, 3H) 7.13(d, J 8.78Hz, 1H) 7.53(dd, J 8.78, 2.56Hz, 1H) 8.00(d, J 2.44Hz, 1H) 8.43(s, 1H) 9.49(s, 1H) |
| B12-X00-M02(C01)-D02 | $^1$H NMR(400MHz, DMSO-d$_6$) δ ppm 1.27(s, 6H) 2.24(s, 3H) 2.45(s, 4H) 2.84(t, J 4.63Hz, 4H) 2.91(s, 2H) 4.23(s, 3H) 7.52(d, J 8.78Hz, 1H) 7.93(dd, J 8.78, 2.32Hz, 1H) 8.11(d, J 2.56Hz, 1H) 8.44(s, 1H) 9.67(s, 1H) |
| B04-X00-M02(C01)-D02 | $^1$H NMR(400MHz, DMSO-d$_6$) δ ppm 1.31(s, 6H) 2.92(s, 2H) 4.37(s, 3H) 6.98(tt, J 7.33, 1.10, 1.07Hz, 1H) 7.32(dd, J 8.41, 7.44Hz, 2H) 7.72(dd, J 8.66, 0.98Hz, 2H) 8.52(s, 1H) 9.56(s, 1H) 12.80(s, 1H) |
| B10-X00-M02(C01)-D02 | $^1$H NMR(400MHz, DMSO-d$_6$) δ ppm 1.25(s, 6H) 2.23(s, 3H) 2.47(m, 4H) 2.89(s, 2H) 3.07(m, 4H) 4.21(s, 3H) 6.89(d, J=9.17Hz, 2H) 7.54(d, J=9.17Hz, 2H) 8.35(s, 1H) 9.14(s, 1H) |

Example 58

8-[4-(4-methyl-piperazin-1-yl)-phenylamino]-1,4,4-trimethyl-4,5-dihydro-1H-pyrazolo[4,3-h]quinazoline-3-carboxylic acid methylamide [B10-X00-M03(C01)-D04]

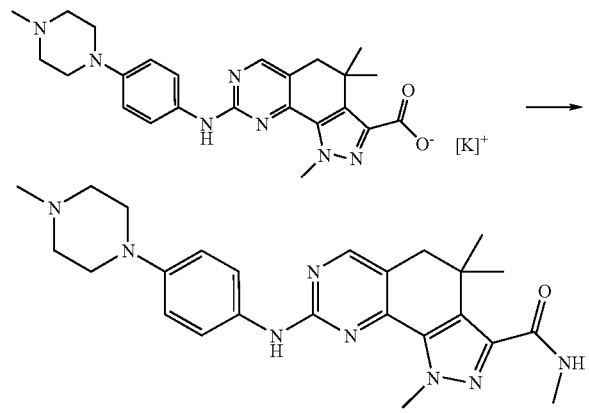

To a suspension of 8-[4-(4-methyl-piperazin-1-yl)-phenylamino]-1,4,4-trimethyl-4,5-dihydro-1H-pyrazolo[4,3-h]quinazoline-3-carboxylic acid potassium salt (9.5 g, 19.561 mmol) in a 1:1 mixture of anhydrous tetrahydrofurane and dimethylformamide (50 mL), 2M methylamine in tetrahydrofurane (21.12 mL, 42.24 mmol), 1-hydroxybenzotriazole (5.332 g, 39.458 mmol) and 1-(3-dimethylaminopropyl)-3-ethylcarbodiimide (EDC) (7.567 g, 39.473 mmol) were added in that order, and the reaction mixture stirred at room temperature for 18 hours.

The reaction mixture was poured into water (2.5 L) and extracted with dichloromethane (4×250 mL). The combined organic extracts were washed with water, essicated over anhydrous sodium sulphate, and the solvent was removed under reduced pressure. The crude was purified by flash chromatography on silica gel (eluant: methylene chloride/methanol 94:6) to afford 8.20 g (yield 92%) of pure title compound.

$^1$H NMR (400 MHz, DMSO-d$_6$) δ ppm 1.33 (s, 6 H) 2.26 (s, 3 H) 2.44-2.54 (m, 4 H) 2.68 (s, 2 H) 2.76 (d, J=4.76 Hz, 3 H) 3.04-3.13 (m, 4 H) 4.31 (s, 3 H) 6.91 (d, J=9.02 Hz, 2 H) 7.53 (d, J=9.02 Hz, 2 H) 8.15 (q, J=4.84 Hz, 1 H) 8.34 (s, 1 H) 9.25 (s, 1 H)

By working according to the above method the following compounds were prepared:

TABLE XVII

| | |
|---|---|
| B19-X00-M03(C01)-D04 | $^1$H NMR(400MHz, DMSO-d$_6$) δ ppm 1.33(s, 6H) 2.68(s, 2H) 2.76(d, J=4.76Hz, 3H) 3.02–3.09(m, 4H) 3.72–3.79(m, 4H) 4.31(s, 3H) 6.93(d, J=9.02Hz, 2H) 7.55(d, J=9.02Hz, 2H) 8.15(q, J=4.63Hz, 1H) 8.34(s, 1H) 9.28(s, 1H) |
| B10-X00-M03(C01)-D25 | $^1$H NMR(400MHz, DMSO-d$_6$) δ ppm 1.35(s, 6H) 2.28(s, 3H) 2.50–2.57(m, 4H) 2.70(s, 2H) 3.04–3.13(m, 4H) 4.26(d, J=5.85Hz, 2H) 4.34(s, 3H) |

TABLE XVII-continued

| | |
|---|---|
| B10-X00-M03(C01)-D30 | 6.92(d, J=9.02Hz, 2H) 7.53(d, J=9.02Hz, 2H) 8.36(s, 1H) 8.94(t, J=5.85Hz, 1H) 9.28(s, 1H) $^1$H NMR(400MHz, DMSO-$d_6$) δ ppm 1.35(s, 6H) 2.28(s, 3H) 2.47–2.59(m, 4H) 2.69(s, 2H) 3.02–3.16(m, 4H) 3.83(d, J=5.73Hz, 2H) 4.34(s, 3H) 6.92(d, J=9.15Hz, 2H) 7.08(s, 1H) 7.36(s, 1H) 7.53(d, J=9.02Hz, 2H) 8.12(t, J=5.67Hz, 1H) 8.35(s, 1H) 9.27(s, 1H) |
| B10-X00-M03(C01)-D162 tri hydrochloride salt | $^1$H NMR(400MHz, DMSO-$d_6$) δ ppm 1.33(s, 6H) 2.70(s, 2H) 2.85(d, J=4.63Hz, 3H) 2.95–3.05(m, 2H) 3.11–3.25(m, 2H) 3.52(d, J=11.46Hz, 2H) 3.67(s, 3H) 3.74(d, J=13.66Hz, 2H) 4.00(d, J=5.97Hz, 2H) 4.34(s, 3H) 6.99(d, J=9.15Hz, 2H) 7.60(d, J=9.02Hz, 2H) 8.37(s, 1H) 8.54(t, J=6.04Hz, 1H) 9.39(s, 1H) 10.23(s, 1H) |
| B10-X00-M03(C01)-D20 | $^1$H NMR(400MHz, DMSO-$d_6$) δ ppm 1.36(s, 6H) 2.27(s, 3H) 2.50–2.57(m, 4H) 2.71(s, 2H) 3.07–3.13(m, 4H) 4.38(s, 3H) 6.92(d, J=9.15Hz, 2H) 7.06–7.15(m, 1H) 7.31–7.40(m, 2H) 7.55(d, J=9.15Hz, 2H) 7.80(dd, J=8.54, 0.98Hz, 2H) 8.37(s, 1H) 9.29(s, 1H) 10.29(s, 1H) |
| B10-X00-M03(C01)-D09 | $^1$H NMR(400MHz, DMSO-$d_6$) δ ppm 1.33(s, 6H) 2.70(s, 2H) 2.84(d, J=4.15Hz, 3H) 3.03(t, J=12.56Hz, 2H) 3.10–3.25(m, 2H) 3.36–3.55(m, 2H) 3.74(d, J=13.05Hz, 2H) 4.32(s, 3H) 4.45(d, J=6.34Hz, 2H) 7.00(d, J=9.02Hz, 2H) 7.21–7.29(m, 1H) 7.31–7.36(m, 4H) 7.59(d, J=9.02Hz, 2H) 8.36(s, 1H) 8.77(t, J=6.34Hz, 1H) 9.46(s, 1H) 10.46(s, 1H) |
| B10-X00-M03(C01)-D34 | $^1$H NMR(400MHz, DMSO-$d_6$) δ ppm 1.23(s, 3H) 1.33(s, 3H) 2.27(s, 3H) 2.48–2.56(m, 4H) 2.67(s, 2H) 3.04–3.14(m, 4H) 3.71(t, J=6.04Hz, 2H) 4.35(s, 3H) 4.96(t, J=5.61Hz, 1H) 5.02(dt, J=7.83, 6.20Hz, 1H) 6.92(d, J=9.15Hz, 2H) 7.22–7.28(m, 1H) 7.34(t, J=7.44Hz, 2H) 7.38–7.42(m, 2H) 7.53(d, J=9.15Hz, 2H) 8.34(s, 1H) 8.42(d, J=8.17Hz, 1H) 9.26(s, 1H) |
| B10-X00-M03(C01)-D70 | $^1$H NMR(400MHz, DMSO-$d_6$) δ ppm 1.23(s, 3H) 1.36(s, 3H) 2.27(s, 3H) 2.45–2.54(m, 4H) 2.61–2.72(m, 2H) 3.07–3.12(m, 4H) 3.61–3.68(m, J=12.44, 5.12Hz, 1H) 3.80(dd, J=12.44, 9.51Hz, 1H) 4.35(s, 3H) 5.27(td, J=9.21, 5.00Hz, 1H) 6.92(d, J=9.15Hz, 2H) 7.27–7.33(m, 1H) 7.38(t, J=7.44Hz, 2H) 7.48(d, J=7.07Hz, 2H) 7.53(d, J=9.02Hz, 2H) 8.34(s, 1H) 8.93(d, J=9.02Hz, 1H) 9.27(s, 1H) |
| B10-X00-M03(C01)-D163 | $^1$H NMR(400MHz, DMSO-$d_6$) δ ppm 1.08(d, J=6.54Hz, 3H) 1.31(s, 6H) 2.17(s, 6H) 2.22(s, 3H) 2.45(m, 6H) 2.65(s, 2H) 3.04(m, 4H) 4.04(m, 1H) 4.29(s, 3H) 6.90(d, J=9.02Hz, 2H) 7.49(d, J=9.02Hz, 2H) 7.91(d, J=8.46Hz, 1H) 8.32(s, 1H) 9.27(s, 1H) |
| B10-X00-M02(C01)-D04 | $^1$H NMR(400MHz, DMSO-$d_6$) δ ppm 1.28(s, 6H) 2.26(s, 3H) 2.47(m, 4H) 2.93(s, 2H) 3.09(m, 4H) 4.33(s, 3H) 6.93(d, J=9.32Hz, 2H) 7.25(s, 1H) 7.46(s, 1H) 7.53(d, J=9.32Hz, 2H) 8.44(s, 1H) 9.28(s, 1H) |

Reported below are the analytical HPLC/Mass data for some representative compounds of the invention.

TABLE XVIII

| | M + H | Time 1 | Method |
|---|---|---|---|
| B10-X00-M03(C01)-D136 | 560.34 | 2.2 | 1 |
| B10-X00-M03(C01)-D26 | 532.34 | 2.25 | 1 |
| B10-X00-M03(C01)-D86 | 518.33 | 2.43 | 1 |
| B10-X00-M03(C01)-D137 | 534.32 | 2.34 | 1 |
| B10-X00-M03(C01)-D116 | 558.36 | 2.45 | 1 |
| B10-X00-M03(C01)-D79 | 535.31 | 2.5 | 1 |
| B10-X00-M03(C01)-D123 | 517.3 | 2.67 | 1 |
| B10-X00-M03(C01)-D135 | 517.3 | 2.64 | 1 |
| B10-X00-M03(C01)-D138 | 505.3 | 2.63 | 1 |
| B10-X00-M03(C01)-D139 | 506.29 | 2.45 | 1 |
| B10-X00-M03(C01)-D95 | 521.29 | 2.77 | 1 |
| B10-X00-M03(C01)-D119 | 521.29 | 2.77 | 1 |
| B10-X00-M03(C01)-D81 | 558.36 | 2.6 | 1 |
| B10-X00-M03(C01)-D115 | 544.34 | 2.45 | 1 |
| B10-X00-M03(C01)-D105 | 531.31 | 2.9 | 1 |
| B10-X00-M03(C01)-D140 | 545.33 | 2.87 | 1 |
| B10-X00-M03(C01)-D100 | 545.33 | 3.05 | 1 |
| B10-X00-M03(C01)-D82 | 505.3 | 3.1 | 1 |
| B10-X00-M03(C01)-D97 | 505.3 | 3.19 | 1 |
| B10-X00-M03(C01)-D121 | 572.34 | 3.23 | 1 |
| B10-X00-M03(C01)-D06 | 491.28 | 2.93 | 1 |
| B10-X00-M03(C01)-D104 | 505.3 | 3.21 | 1 |
| B10-X00-M03(C01)-D113 | 531.31 | 3.07 | 1 |
| B10-X00-M03(C01)-D83 | 549.29 | 3.45 | 1 |
| B10-X00-M03(C01)-D131 | 519.31 | 3.47 | 1 |
| B10-X00-M03(C01)-D102 | 475.29 | 3.54 | 1 |
| B10-X00-M03(C01)-D122 | 545.33 | 3.32 | 1 |
| B10-X00-M03(C01)-D85 | 506.29 | 3.24 | 3 |
| B10-X00-M03(C01)-D93 | 559.34 | 3.61 | 1 |
| B10-X00-M03(C01)-D94 | 493.28 | 3.58 | 1 |

2.95-3.08 (m, 2 H) 3.10-3.26 (m, 2 H) 3.39-3.55 (m, 2 H) 3.74 (d, J=13.41 Hz, 2 H) 4.30 (s, 3 H) 7.00 (d, J=9.02 Hz, 2 H) 7.59 (d, J=8.90 Hz, 2 H) 8.16 (q, J=4.51 Hz, 1 H) 8.36 (s, 1 H) 9.44 (s, 1 H) 10.37 (s, 1 H)

TABLE XVIII-continued

| | M + H | Time 1 | Method |
|---|---|---|---|
| B10-X00-M03(C01)-D60 | 567.31 | 3.92 | 1 |
| B10-X00-M03(C01)-D117 | 533.33 | 3.77 | 1 |
| B10-X00-M03(C01)-D34 | 567.31 | 3.99 | 1 |
| B10-X00-M03(C01)-D87 | 567.31 | 4.21 | 1 |
| B10-X00-M03(C01)-D108 | 634.35 | 4.07 | 1 |
| B10-X00-M03(C01)-D91 | 533.29 | 4.01 | 1 |
| B10-X00-M03(C01)-D114 | 602.35 | 4.1 | 1 |
| B10-X00-M03(C01)-D14 | 515.32 | 4.64 | 1 |
| B10-X00-M03(C01)-D141 | 552.31 | 4.34 | 1 |
| B10-X00-M03(C01)-D109 | 580.34 | 4.89 | 1 |
| B10-X00-M03(C01)-D107 | 531.28 | 3.56 | 1 |

Example 59

8-[4-(4-methyl-piperazin-1-yl)-phenylamino]-1,4,4-trimethyl-4,5-dihydro-1H-pyrazolo[4,3-h]quinazoline-3-carboxylic acid methylamide tri-hydrochloride salt [B10-X00-M03(C01)-D04]

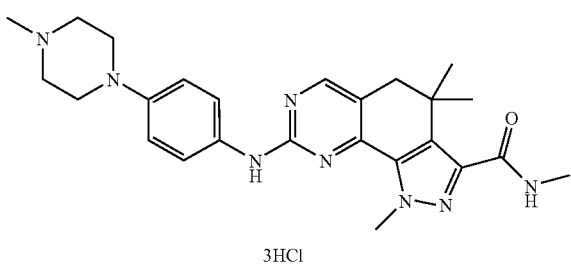

3HCl

To 8-[4-(4-methyl-piperazin-1-yl)-phenylamino]-1,4,4-trimethyl-4,5-dihydro-1H-pyrazolo[4,3-h]quinazoline-3-carboxylic acid methylamide (7.00 g, 15.192 mmol) dissolved into a 1:1 mixture of methanol/dichloromethane (149 mL) 4M hydrochloric acid in dioxane (12.12 mL, 48.48 mL) was added and the solution stirred at room temperature for 2 hours. After removing the solvent under reduced pressure, the reddish solid was dried at 43° C. under vacuum for 10 hours. There were obtained 8.11 g of the title compound as a red solid.

$^1$H NMR (400 M, DMSO-$d_6$) δ ppm 1.34 (s, 6 H) 2.69 (s, 2 H) 2.76 (d, J=4.76 Hz, 3 H) 2.85 (d, J=3.54 Hz, 3 H)

Example 60

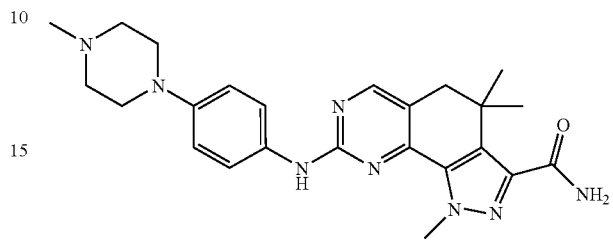

8-[4-(4-methyl-piperazin-1-yl)phenylamino]-1,4,4-trimethyl-4,5-dihydro-1H-pyrazolo[4,3-h]quinazoline-3-carboxamide [B10-X00-M03(C01)-D03]

To a suspension of 8-[4-(4-methyl-piperazin-1-yl)-phenylamino]-1,4,4-trimethyl-4,5-dihydro-1H-pyrazolo[4,3-h]quinazoline-3-carboxylic acid potassium salt (185.5 mg, 0.382 mmol) in a 1:1 mixture of anhydrous tetrahydrofurane and dimethylformamide (4.8 mL), N-ethyldiisopropylamine (0.13 mL, 0.760 mmol), 1-hydroxybenzotriazole ammonium salt (102 mg, 0.760 mmol) were added in that order. The reaction mixture was cooled to 0° C., treated with 1-(3-dimethylaminopropyl)-3-ethylcarbodiimide (EDC) (146 mg, 0.760 mmol) and then stirred at room temperature for 18 hours.

The reaction mixture was poured into water (10 mL) and the precipitate was filtered, washed with water, dried under vacuum at 40° C. for 4 hours. There were obtained 130 mg (yield 76%) of pure title compound.

$^1$H NMR (400 MHz, DMSO-$d_6$) δ ppm 1.34 (s, 6 H) 2.26 (s, 3 M) 2.46-2.56 (m, 4 H) 2.68 (s, 2 H) 3.04-3.14 (m, 4 H) 4.31 (s, 3 H) 6.91 (d, J=9.15 Hz, 2 H) 7.29 (s, 1 H) 7.53 (d, J=9.15 Hz, 2 H) 7.55 (s, 1 H) 8.34 (s, 1 H) 9.25 (s, 1 H)

By working according to the above method the following compounds were prepared:

TABLE XIX

| | |
|---|---|
| B04-X00-M03(C01)-D03 | $^1$H NMR(400MHz, DMSO-$d_6$) δ ppm 1.35(s, 6H) 2.71(s, 2H) 4.33(s, 3H) 6.97(tt, J 7.38, 1.10Hz, 1H) 7.31(m, 3H) 7.56(s, 1H) 7.71(dd, J 8.60, 1.04Hz, 2H) 8.41(s, 1H) 9.52(s, 1H) |
| B12-X00-M03(C01)-D03 | $^1$H NMR(400MHz, DMSO-$d_6$) δ ppm 1.35(s, 6H) 2.72(s, 2H) 2.87(d, J 4.63Hz, 3H) 3.35(m, 8H) 4.34(s, 3H) 7.21(d, J 8.78Hz, 1H) 7.32(s, 1H) 7.56(s, 1H) 7.59(dd, J 8.78, 2.56Hz, 1H) 8.01(d, J 2.44Hz, 1H) 8.43(s, 1H) 9.68(s, 1H) 10.39(s, 1H) |
| B13-X00-M03(C01)-D03 | $^1$H NMR(400MHz, DMSO-$d_6$) δ ppm 1.35(s, 6H) 2.73(s, 2H) 2.88(d, J 4.63Hz, 3H) 3.32(m, 8H) 4.32(s, 3H) 7.33(s, 1H) 7.54(d, J 8.90Hz, 1H) 7.56(s, 1H) 8.01(dd, J 8.72, 2.38Hz, 1H) 8.12(d, J 2.56Hz, 1H) 8.45(s, 1H) 9.86(s, 1H) 10.35(s, 1H) |
| B19-X00-M03(C01)-D03 | $^1$H NMR(400MHz, DMSO-$d_6$) δ ppm 1.34(s, 6H) 2.68(s, 2H) 3.00-3.13(m, 4H) 3.70-3.80(m, 4H) 4.31(s, 3H) 6.92(d, J=9.02Hz, 2H) 7.29(s, 1H) 7.51-7.59(m, 3H) 8.34(s, 1H) 9.27(s, 1H) |

TABLE XIX-continued

| | |
|---|---|
| B13-X00-M02(C01)-D03 | $^1$H NMR(400MHz, DMSO-d$_6$) δ ppm 1.29(m, 6H) 2.86(d, J 4.39Hz, 3H) 2.95(s, 2H) 3.34(m, 8H) 4.37(s, 3H) 7.21(d, J 8.78Hz, 1H) 7.29(s, 1H) 7.45(s, 1H) 7.58(dd, J 8.84, 2.50Hz, 1H) 8.04(d, J 2.44Hz, 1H) 8.53(s, 1H) 9.71(s, 1H) 10.49(s, 1H) |
| B12-X00-M02(C01)-D03 | $^1$H NMR(400MHz, DMSO-d$_6$) δ ppm 1.32(m, 6H) 2.88(d, J 4.39Hz, 3H) 2.96(s, 2H) 3.38(m, 8H) 4.35(s, 3H) 7.29(s, 1H) 7.46(s, 1H) 7.54(d, J 8.90Hz, 1H) 8.00(dd, J 8.66, 2.32Hz, 1H) 8.15(d, J 2.44Hz, 1H) 8.55(s, 1H) 9.89(s, 1H) 10.32(s, 1H) |
| B04-X00-M02(C01)-D03 | $^1$H NMR(400MHz, DMSO-d$_6$) δ ppm 1.30(s, 6H) 2.95(s, 2H) 4.35(s, 3H) 6.98(tt, J 7.35, 1.04, 0.98Hz, 1H) 7.27(s, 1H) 7.31(dd, J 8.35, 7.50Hz, 2H) 7.47(s, 1H) 7.72(dd, J 8.54, 0.98Hz, 2H) 8.51(s, 1H) 9.55(s, 1H) |
| B10-X00-M02(C01)-D03 | $^1$H NMR(400MHz, DMSO-d$_6$) δ ppm 1.28(s, 6H) 2.26(s, 3H) 2.47(m, 4H) 2.93(s, 2H) 3.09(m, 4H) 4.33(s, 3H) 6.93(d, J=9.32Hz, 2H) 7.25(s, 1H) 7.46(s, 1H) 7.53(d, J=9.32Hz, 2H) 8.44(s, 1H) 9.28(s, 1H) |

Example 61

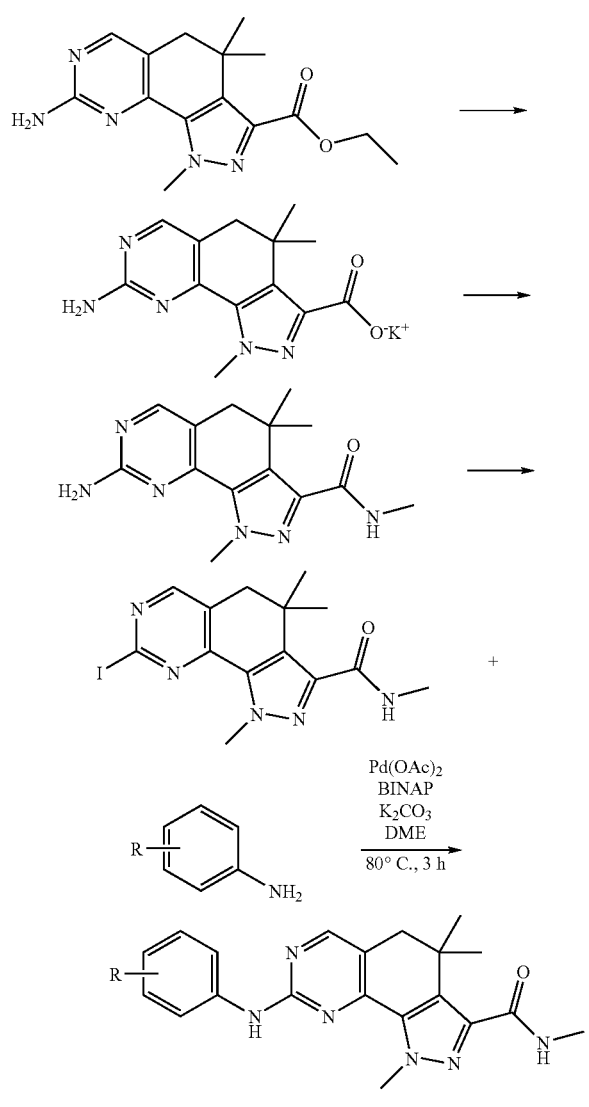

Step 1. 8-amino-1,4,4-trimethyl-4,5-dihydro-1H-pyrazolo[4,3-h]quinazoline-3-carboxylic acid potassium salt [B00-X00-M03(C01)-D02]

A suspension of ethyl 8-amino-1,4,4-trimethyl-4,5-dihydro-1H-pyrazolo[4,3-h]quinazoline-3-carboxylate (20.00 g, 66.368 mmol) in anhydrous ethanol (250 mL), 1.5M potassium hydroxide in ethanol (150 mL) was added under good stirring and the mixture was heated to reflux for 1.5 hours. After cooling in an ice bath, a solid was formed; that was filtered washing with ethanol, dried at 40° C. under vacuum to yield 17.34 g (yield 84%) of white solid compound.

$^1$H NMR (400 MHz, DMSO-d$_6$) δ ppm 1.28 (s, 6 H) 2.51 (s, 2 H) 4.16 (s, 3 H) 6.37 (s, 2 H) 8.07 (s, 1 H)

Step 2. 8-amino-1,4,4-trimethyl-4,5-dihydro-1H-pyrazolo[4,3-h]quinazoline-3-carboxylic acid methylamide [B00-X00-M03(C01)-D04]

To a suspension of 8-amino-1,4,4-trimethyl-4,5-dihydro-1H-pyrazolo[4,3-h]quinazoline-3-carboxylic acid potassium salt (17.00 g, 54.594 mmol) in a 1:1 mixture of anhydrous tetrahydrofurane and dimethylformamide (340 mL), 2 M methylamine in tetrahydrofurane (40.80 mL, 81.60 mmol), 1-hydroxybenzotriazole (8.840 g, 65.418 mmol) and 1-(3-dimethylaminopropyl)-3-ethylcarbodiimide (EDC) (12.540 g, 65.418 mmol) were added in that order, and the thick slurry was stirred at room temperature for 20 hours.

The reaction mixture was poured into water (2.5 L) and extracted with dichloromethane (4×250 mL). The combined organic extracts were washed with water (50 mL), dried over anhydrous sodium sulphate, and the solvent was removed under reduced pressure. There were obtained 17.0 g of yellowish solid that were triturated with diethylether to yield 13.05 g (yield 87%) of the desired compound.

$^1$H NMR (400 MHz, DMSO-d$_6$) δ ppm 1.31 (s, 6 H) 2.60 (s, 2 H) 2.75 (d, J=4.76 Hz, 3 H) 4.30 (s, 3 H) 6.55 (s, 2 H) 8.12 (q, J=4.39 Hz, 1 H) 8.17 (s, 1 H).

By working in an analogous way the following compounds were prepared:

8-amino 4,5-dihydro-1H-pyrazolo[4,3-h]quinazoline-3-carboxylic acid methylamide [B00-X00M00(C01)-D04]

$^1$H NMR (400 MHz, DMSO-d$_6$) δ ppm 2.69-2.74 (m, 2 H) 2.74 (d, J=4.76 Hz, 3 H) 2.94 (t, J=7.56 Hz, 2 H) 4.31 (s, 3 H) 6.54 (s, 2 H) 7.99-8.08 (m, 1 H) 8.18 (s, 1 H);

8-amino-1,4,4-trimethyl-4,5-dihydro-1H-pyrazolo[4,3-h]quinazoline-3-carboxamide [B00-X00-M03(C01)-D03]

¹H NMR (400 MHz, DMSO-d₆) δ ppm 1.32 (s, 6 H) 2.61 (s, 2 H) 4.30 (s, 3 H) 6.57 (s, 2 H) 7.27 (s, 1 H) 7.51 (s, 1 H) 8.17 (s, 1 H)

Step 3. 8-iodo-1,4,4-trimethyl-4,5-dihydro-1H-pyrazolo[4,3-h]quinazoline-3-carboxylic acid methylamide In a round bottom flask maintained under argon atmosphere, ethyl 8-amino-1,4,4-trimethyl-4,5-dihydro-1H-pyrazolo[4,3-h]quinazoline-3-carboxylic acid methylamide (13.00 g, 45.400 mmol) was dissolved into anhydrous dimethoxyethane (800 mL); cesium iodide (11.795 g, 45.400 mmol), bisublimated iodine (5.761 g, 22.698 mmol), copper (I) iodide (2.594 g, 13.621 mmol), and iso-amyl nitrite (9.107 mL, 68.100 mmol) were added in that order and the mixture was heated to 70° C. for 22 hours.

After cooling to room temperature, the solids materials were removed by suction filtration, washing with dichloromethane. The filtrate was concentrated to 400 mL, diluted with dichloromethane (1000 mL), washed with 30% ammonium hydroxide (100 mL), 5% sodium thiosulphate (50 mL), water (4×100 mL), and dried over anhydrous sodium sulphate. The solvent was removed under vacuum to afford 11.00 g of dark oil that was triturated with diethylether to yield 4.300 g of the title compound as a yellow solid. Purification of the mother liquors by flash chromatography on silica gel (eluant dichloromethane/methanol 97:3) afforded further 2.04 g of yellowish solid compound (overall yield 35%).

¹H NMR (400 MHz, DMSO-d₆) δ ppm 1.34 (s, 6 H) 2.76 (d, J=4.76 Hz, 3 H) 2.80 (s, 2 H) 4.24 (s, 3 H) 8.16-8.25 (m, 1 H) 8.48 (s, 1 H)

Step 4. 8-[3-(4-methyl-piperazin-1-ylmethyl)-phenylamino]-1,4,4-trimethyl-4,5-dihydro-1H-pyrazolo[4,3-h]quinazoline-3-carboxylic acid methylamide [B104-X00-M03(C01)-D04]

Pd(OAc)₂ (16.34 mg, 0.0728 mmol), (±)-BINAP (45.33 mg, 0.0728 mmol) and dimethylformamide (12 mL) were charged in a round-bottom flask flushed with argon. The mixture was stirred under argon for 30 minutes. Then 3-(4-methyl-piperazin-1-ylmethyl)-phenylamine (448.4 mg, 2.184 mmol), ethyl 8-iodo-1,4,4-trimethyl-4,5-dihydro-1H-pyrazolo[4,3-h]quinazoline-3-carboxylic acid methylamide (300 mg, 0.728 mmol), K₂CO₃ (1.508 g, 10.910 mmol) and dimethylformamide (10 mL) were added. The resulting mixture was heated to 80° C. in an oil bath under argon with good stirring for 3 hours.

After cooling to room temperature, the reaction mixture was filtered by suction filtration washing with dichloromethane and the filtrate was evaporated to dryness. The crude was purified by flash chromatography on silica gel (eluant: dichloromethane/methanol 95:5) to afford 215 mg (yield 62%) of pure title compound.

¹H NMR (400 MHz, DMSO-d₆) δ ppm 1.35 (s, 6 H) 2.25 (s, 3 H) 2.42 (m, 4 H) 2.71 (s, 2 H) 2.77 (d, J=4.76 Hz, 3 H) 3.44 (m, 4 H) 3.48 (s, 2 H) 4.35 (s, 3 H) 6.91 (d, J=7.31 Hz, 1 H) 7.26 (t, J=7.68 Hz, 1 H) 7.56 (d, J=8.78 Hz, 1 H) 7.76 (s, 1 H) 8.15 (s, 1 H) 8.41 (s, 1 H) 9.5 (s, 1 H)

By working according to the above method the following compounds were prepared:

TABLE XX

| | |
|---|---|
| B10-X00-M03(C01)-D04 | ¹H NMR(400MHz, DMSO-d₆) δ ppm 1.33(s, 6H) 2.26(s, 3H) 2.44-2.54(m, 4H) 2.68(s, 2H) 2.76(d, J=4.76Hz, 3H) 3.04-3.13(m, 4H) 4.31(s, 3H) 6.91(d, J=9.02Hz, 2H) 7.53(d, J=9.02Hz, 2H) 8.15(q, J=4.84Hz, 1H) 8.34(s, 1H) 9.25(s, 1H) |
| B09-X00-M03(C01)-D04 | ¹H NMR(400MHz, DMSO-d₆) δ ppm 1.34(s, 6H) 2.27(s, 3H) 2.52(m, 4H) 2.70(s, 2H) 2.76(d, J=4.76Hz, 3H) 3.13(m, 4H) 4.33(s, 3H) 6.59(d, J=7.31Hz, 1H) 7.14(t, J=7.68Hz, 1H) 7.23(s, 1H) 7.26(d, J=8.78Hz, 1H) 8.15(s, 1H) 8.39(s, 1H) 9.33(s, 1H) |
| B101-X00-M03(C01)-D04 | ¹H NMR(400MHz, DMSO-d₆) δ ppm 1.34(s, 6H) 2.55-3.62(m, 13H) 2.71(s, 2H) 2.75-2.79(m, J=4.76Hz, 3H) 4.33(s, 3H) 7.25(d, J=10.24Hz, 2H) 7.69(d, J=7.80Hz, 2H) 8.10-8.18(m, 1H) 8.41(s, 1H) 9.55(s, 1H) |
| B19-X00-M03(C01)-D04 | ¹H NMR(400MHz, DMSO-d₆) δ ppm 1.33(s, 6H) 2.68(s, 2H) 2.76(d, J=4.76Hz, 3H) 3.02-3.09(m, 4H) 3.72-3.79(m, 4H) 4.31(s, 3H) 6.93(d, J=9.02Hz, 2H) 7.55(d, J=9.02Hz, 2H) 8.15(q, J=4.63Hz, 1H) 8.34(s, 1H) 9.28(s, 1H) |
| B107-X00-M03(C01)-D04 | ¹H NMR(400MHz, DMSO-d₆) δ ppm 1.34(s, 6H) 2.70(s, 2H) 2.76(d, J=4.76Hz, 3H) 3.06-3.13(m, 4H) 3.73-3.78(m, 4H) 4.33(s, 3H) 6.59(dd, J=7.93, 2.07Hz, 1H) 7.16(t, J=8.11Hz, 1H) 7.23(t, J=2.01Hz, 1H) 7.30(dd, J=7.74, 1.40Hz, 1H) 8.16(q, J=4.59Hz, 1H) 8.39(s, 1H) 9.35(s, 1H) |
| B102-X00-M03(C01)-D04 | ¹H NMR(400MHz, DMSO-d₆) δ ppm 1.34(s, 6H) 2.35(s, 4H) 2.70(s, 2H) 2.76(d, J=4.76Hz, 3H) 3.43(s, 2H) 3.58(s, 4H) 4.33(s, 3H) 7.25(s, 2H) 7.66(s, 2H) 8.40(s, 1H) 9.51(s, 1H) |
| B105-X00-M03(C01)-D04 | ¹H NMR(400MHz, DMSO-d₆) δ ppm 1.35(s, 7H) 2.38(s, 4H) 2.71(s, 2H) 2.77(d, J=4.76Hz, 3H) 3.44(s, 2H) 3.58(s, 5H) 4.36(s, 3H) 6.87-6.99(m, 1H) 7.25(t, J=7.56Hz, 1H) 7.58(d, J=6.71Hz, 1H) 7.76(s, 1H) 8.41(s, 1H) |
| B103-X00-M03(C01)-D04 | ¹H NMR(400MHz, DMSO-d₆) δ ppm 1.33(s, 6H) 1.64-2.07(m, 4H) 2.37-2.62(m, 5H) 2.68(s, 2H) 2.76(d, J=4.63Hz, 3H) 2.81-3.00(m, 2H) 4.30(s, 3H) |

TABLE XX-continued

| | |
|---|---|
| | 4.34-4.46(m, 1H) 6.94(d, J=9.02Hz, 2H) 7.58(d, J=9.02Hz, 2H) 8.15(q, J=4.55Hz, 1H) 8.36(s, 1H) 9.34(s, 1H) |
| B106-X00-M03(C01)-D04 | $^1$H NMR(400MHz, DMSO-$d_6$) δ ppm 1.34(s, 6H) 1.70-2.18(m, 4H) 2.59(s, 3H) 2.71(s, 2H) 2.77(d, J=4.76Hz, 3H) 2.93-3.50(m, 4H) 4.35(s, 3H) 4.40-4.57(m, 1H) 6.61(dd, J=7.93, 2.07Hz, 1H) 7.21(t, J=8.11Hz, 1H) 7.26-7.32(m, 1H) 7.47(s, 1H) 8.12-8.19(m, 1H) 8.42(s, 1H) 9.51(s, 1H) |
| B120-X00-M03(C01)-D04 | $^1$H NMR(400MHz, DMSO-$d_6$) δ ppm 1.04-1.24(m, 6H) 1.33(s, 6H) 2.68(s, 2H) 2.76(d, J=4.76Hz, 3H) 2.79-3.52(m, 9H) 4.31(s, 3H) 6.94(d, J=8.78Hz, 2H) 7.55(d, J=8.78Hz, 2H) 8.15(q, J=4.63Hz, 1H) 8.34(s, 1H) 9.28(s, 1H) |
| B173-X00-M03(C01)-D04 | $^1$H NMR(400MHz, DMSO-$d_6$) δ ppm 1.31(s, 6H) 2.40-2.50(m, 4H) 2.68(s, 2H) 2.74(d, J=4.76Hz, 3H) 3.53(s, 2H) 3.60(m, 4H) 4.30(s, 3H) 6.98(d, 1H) 7.06(dd, 1H) 7.23(d, 1H) 8.14(q, 1H) 8.37(s, 1H) 9.39(s, 1H) 10(bs, 1H) |

Reported Below are the Analytical HPLC/Mass Data for some Representative Compounds of the Invention

TABLE XXI

| | M + H | RT | method |
|---|---|---|---|
| B121-X00-M03(C01)-D04 | 442.514 | 4.40 | 1 |
| B122-X00-M03(C01)-D04 | 393.461 | 4.70 | 1 |
| B123-X00-M03(C01)-D04 | 380.422 | 3.42 | 1 |
| B124-X00-M03(C01)-D04 | 379.434 | 4.86 | 1 |
| B125-X00-M03(C01)-D04 | 406.503 | 5.60 | 1 |
| B126-X00-M03(C01)-D04 | 395.433 | 4.37 | 1 |
| B127-X00-M03(C01)-D04 | 442.514 | 4.90 | 1 |
| B128-X00-M03(C01)-D04 | 406.46 | 5.40 | 1 |
| B114-X00-M03(C01)-D04 | 393.461 | 4.35 | 1 |
| B129-X00-M03(C01)-D04 | 406.46 | 4.10 | 1 |
| B11-X00-M03(C01)-D04 | 393.461 | 4.50 | 1 |
| B130-X00-M03(C01)-D04 | 406.46 | 4.10 | 1 |
| B131-X00-M03(C01)-D04 | 449.524 | 6.10 | 1 |
| B168-X00-M03(C01)-D04 | 420.487 | 4.50 | 1 |
| B132-X00-M03(C01)-D04 | 448.54 | 6.14 | 1 |
| B133-X00-M03(C01)-D04 | 412.488 | 4.90 | 1 |
| B134-X00-M03(C01)-D04 | 407.487 | 4.90 | 1 |
| B135-X00-M03(C01)-D04 | 406.46 | 4.80 | 1 |
| B21-X00-M03(C01)-D04 | 429.498 | 4.66 | 1 |
| B136-X00-M03(C01)-D04 | 439.489 | 4.76 | 1 |
| B137-X00-M03(C01)-D04 | 409.46 | 4.7 | 1 |
| B138-X00-M03(C01)-D04 | 393.461 | 5.02 | 1 |
| B139-X00-M03(C01)-D04 | 407.487 | 4.77 | 1 |
| B140-X00-M03(C01)-D04 | 393.46 | 4.62 | 1 |
| B141-X00-M03(C01)-D04 | 407.487 | 4.60 | 1 |
| B142-X00-M03(C01)-D04 | 395.433 | 4.05 | 1 |
| B143-X00-M03(C01)-D04 | 406.503 | 6.10 | 1 |
| B144-X00-M03(C01)-D04 | 446.568 | 6.27 | 1 |
| B145-X00-M03(C01)-D04 | 420.53 | 3.41 | 1 |
| B17-X00-M03(C01)-D04 | 434.557 | 5.27 | 1 |
| B146-X00-M03(C01)-D04 | 488.648 | 4.6 | 1 |
| B147-X00-M03(C01)-D04 | 420.53 | 3.58 | 1 |
| B148-X00-M03(C01)-D04 | 407.487 | 4.33 | 1 |
| B149-X00-M03(C01)-D04 | 407.487 | 4.50 | 1 |
| B150-X00-M03(C01)-D04 | 492.549 | 3.85 | 1 |
| B151-X00-M03(C01)-D04 | 486.566 | 5.38 | 1 |
| B152-X00-M03(C01)-D04 | 510.632 | 6.60 | 1 |
| B153-X00-M03(C01)-D04 | 512.604 | 5.55 | 1 |
| B154-X00-M03(C01)-D04 | 506.576 | 5.34 | 1 |
| B155-X00-M03(C01)-D04 | 504.604 | 5.03 | 1 |
| B156-X00-M03(C01)-D04 | 489.593 | 4.45 | 1 |
| B13-X00-M03(C01)-D04 | 496.028 | 4.28 | 1 |
| B117-X00-M03(C01)-D04 | 540.479 | 4.38 | 1 |
| B157-X00-M03(C01)-D04 | 512.604 | 5.60 | 1 |
| B158-X00-M03(C01)-D04 | 466.53 | 5.73 | 1 |
| B159-X00-M03(C01)-D04 | 510.632 | 4.94 | 1 |
| B160-X00-M03(C01)-D04 | 491.609 | 3.71 | 1 |
| B161-X00-M03(C01)-D04 | 490.577 | 5.41 | 1 |
| B162-X00-M03(C01)-D04 | 448.584 | 3.95 | 1 |
| B163-X00-M03(C01)-D04 | 476.594 | 3.82 | 1 |
| B164-X00-M03(C01)-D04 | 434.557 | 3.69 | 1 |
| B165-X00-M03(C01)-D04 | 436.486 | 4.44 | 1 |
| B109-X00-M03(C01)-D04 | 479.573 | 3.93 | 1 |
| B166-X00-M03(C01)-D04 | 483.545 | 5.07 | 1 |
| B12-X00-M03(C01)-D04 | 529.58 | 4.66 | 1 |
| B167-X00-M03(C01)-D04 | 505.635 | 3.75 | 1 |

Example 62

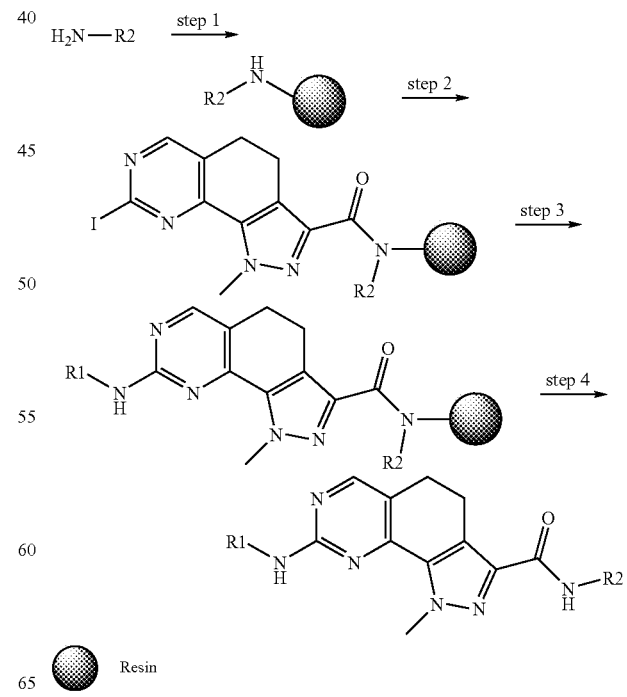

Step. 1 loading primary amines to a solid support (resin)

A: Case where the "resin" is 4-(4-formyl-3-methoxyphenoxy)butyryl polyethylene glycol grafted aminomethylpolystyrene-1% DVB:

For each variant of R2 primary amine, 1 gram (0.39 mmol) of the aforementioned resin was charged to a 10 mL Argonaut Quest 210 reaction tube. Trimethyl orthoformate (7 mL) was added to the tube along with 5 equivalents (1.95 mmol) of each primary amine (indicated as R2 in the scheme). The reaction was mixed on the Quest at 25° C. for 16 hours followed by a 2-hour period of heating at 70° C. After cooling and removal of the reaction solution, the resin was washed once with trimethyl orthoformate (7 mL each) and three times with anhydrous methanol (7 mL). Anhydrous methanol (5 mL) was then added to the resin, followed by the addition of 148 mg (3.9 mmol, 10 equiv) of sodium borohydride. After vigorous gas evolution had ceased, the tube was capped and mixed for 8 hours at room temperature. The resin was washed 3 times with methanol (5 mL), three times with methanol/water (1:1, 5 mL), and three times with DMF (5 mL). The resin was then treated with 20% piperidine in DMF for 1 hour at room temperature. Again, the resin was washed three times with DMF (5 mL), three times with methanol (5 mL), and three times with dichloromethane (5 mL). A sample of the resin was tested for quantitative amine loading by using the Fmoc UV-spectrometric method described below. Qualitatively, the resin was analyzed using the chloranil test method described below.

B: Case where the "resin" is Rink amide, 4-(2',4'-dimethoxyphenyl-fmoc-aminomethyl)phenoxy (copolystyrene-1% DVB):

1 g (0.39 mmol) of the aforementioned resin were charged into a 10 mL Argonaut Quest 210 reaction tube. The resin was treated with 20% piperidine in DMF for 5 minutes and a then a second treatment occurred for 30 minutes at room temperature. The resin was washed with DMF (3×5 mL), with methanol (3×5 mL) and with dichloromethane (3×5 mL).

Quantitative amine loading by using the Fmoc UV-spectrometric method:

A precisely tarred quantity (25 mg±5 mg) of dry, loaded resin was charged into a 3 mL polypropylene syringe, fitted with a filter disk. To the syringe, 3 equivalents of 9-fluorenylmethyl chloroformate dissolved in 1 mL of dichloromethane were charged and 1.5 equivalents of N,N-diisopropylethylamine were then added. The resin was shaken by means of orbital shaker, for 1 hour. The resin was washed with DMF (3×2 mL, 5 min.), with methanol (3×2 mL, 5 min.), and with DCM (3×2 mL, 5 min.).

1 mL of a 20% piperidine solution in DMF was drawn from the syringe and agitated for 5 minutes at room temperature. The solution was dispensed into a 10 mL volumetric flask. A second aliquot of the 20% piperidine solution in DMF was drawn and agitated for 30 minutes at room temperature. Again, the solution was dispensed into the same 10 mL volumetric flask (stock solution). DMF was added to the volumetric flask to achieve a 10 mL total volume. This volumetric flask containing the stock solution was agitated thoroughly and exactly 0.5 mL were transferred into a second 10 mL volumetric flask (test solution). Again, DMF was added to the volumetric flask up to a 10 mL total volume. The absorbance of this test solution was measured through an *Amerasham Pharmacia Biotech Ultrospec* 3000 *Pro*, UV-Vis spectrometer at λ=302 nm against DMF as the blank. The post reaction resin substitution was calculated using the following formula:

$$\text{loading (mmol/g)} = (A_{302} \times 20 \text{ fold} \times 10 \text{ mL})/8100 \times wt$$

where $A_{302}$ is the UV absorbance at λ=302 nm, ϵ=8100 is the extinction coefficient of the piperidine-fluorenone adduct and wt is the tare of the resin in milligrams.

Qualitative chloranil (3,4,5,6-tetrachloro-1,2-benzoquinone) test for resin bound secondary amines: A small aliquot of pre-washed resin containing the attached amine was placed in a micro-test tube. The beads were washed once with acetone and the solvent was removed by decantation. One drop of the chloranil test solution was added to the test tube and allowed to stand at room temperature for 5 minutes. A dark green to brown color was a positive indication of a secondary amine. The intensity of the color was a non-quantitative indication of secondary amine concentration.

Test solution: a saturated solution of 3,4,5,6-tetrachloro-1,2-benzoquinone in toluene at room temperature.

Step. 2 Acylation of the solid supported amine with 8-iodo-1-methyl-4,5-dihydro-1H-pyrazolo[4,3-h]quinazoline-3-carbonyl fluoride For each variant of R2 primary amine loaded onto 1 g (0.39 mmol) of the resin in step 1 above, the following pre-activated carboxylic acid fluoride reagent was added. In 5 mL of dichloromethane, 166 mg (0.47 mol, 1.2 equivalents) of 8-iodo-1-methyl-4,5-dihydro-1H-pyrazolo[4,3-h]quinazoline-3-carboxylate, 155 mg (0.585 mmol, 1.5 equivalents) of tetramethylfluoroformamidinium hexafluorophosphate and 0.102 mL (0.585 mmol, 1.5 equivalents) of N,N-diisopropylethylamine were dissolved N,N-Dimethylacetamide was added dropwise to the solution until all reagents were in solution with sonication. The reaction system was stirred at room temperature for 30 minutes. Additional 0.102 mL (0.585 mmol, 1.5 equivalents) of N,N-diisopropylethylamine were added to the solution, in 30 minutes, and the entire content was charged to the resin on the Quest 210 synthesizer. The resin was mixed for 18 hours at room temperature. The resin was drained of the acylation cocktail and washed with DMF (3×5 mL, 5 min.), with methanol (3×5 mL, 5 min.) and with DCM (3×5 mL, 5 min.). The resin was dried from DCM under vacuum. The resin was qualitatively tested for the acylation reaction completion using the chloranil test method. A sample of each dried resin was subjected to the quantitative Fmoc UV-spectrometric analysis to determine the extent of resin bound acylation.

Step. 3 Catalytic amination of the solid supported 8-iodo-1-methyl-4,5-dihydro-1H-pyrazolo[4,3-h]quinazoline-3-carboxamide Using a 4 mL Argonaut Trident synthesizer cassette, 200 mg (0.078 mmol) of each resin type from step 2 above, were charged into separate vials. To each of the reactor vials flushed with argon, potassium carbonate (0.158 g, 1.56 mmol), palladium acetate [Pd(OAc)$_2$] (1.8 mg, 0.008 mmol, 10%), (±)-BINAP (5.0 mg, 0.008 mmol, 10%) and the corresponding R1 amine (0.156 mmol, 2 equivalents) in dimethyacetamide (2 mL) were added. The resulting mixture was agitated at room temperature for 1 hour and then heated to 60° C. for 16 hours on the Argonaut Trident External Agitation Thermal Unit (EATU) synthesis station.

The resin was drained from the synthesis cocktail and washed using the Argonaut Trident EATU synthesis station with DMF (1×2 mL, 5 min.), with water (1×2 mL, 5 min.), with DMF/water (1:1) (3×2 mL, 5 min.), with DMF (3×2 mL, 5 min.), with methanol (3×2 mL, 5 min.) and with DCM (3×2 mL, 5 min.).

Step. 4 Cleavage of the differentially substituted 8-amino-1-methyl-4,5-dihydro-1H-pyrazolo[4,3-h]quinazoline-3-carboxamide from the solid support To each Argonaut Trident reactor vial, 2 mL of the following resin cleavage cocktail were added: dichloromethane (50 mL), trifluoroacetic acid (49 mL) and water (1 mL). The resin suspended in the cleavage cocktail was shaken for 1 hour at room temperature on the Argonaut Trident EATU synthesis station. The solution containing the crude products was captured into separate vials where three additional resin washing with dichloromethane (2 mL each) were also captured to the same corresponding vials.

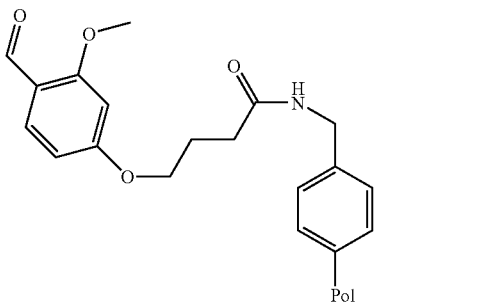

4-(4-formyl-3-methoxyphenoxy)butynyl polyethylene glycol grafted aminomethylpolystyrene-1% DVB

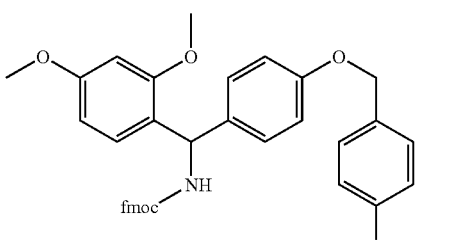

4-(2',4',-dimethoxyphenyl-fmoc-aminomethyl)phenoxy (copolystyrene-1% DVB)

Example 63

N-[3-chloro-4-(4-methylpiperazin-1-yl)phenyl] guanidine

Step 1. 1,3-bis(tert-butoxycarbonyl)guanidine

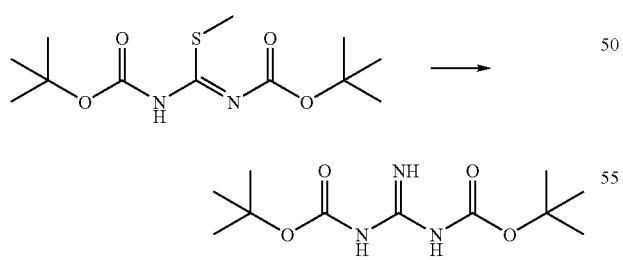

15 g of 1,3-bis(tert-butoxycarbonyl)-2-methyl-2-thiopseudourea (0.052 mol) were suspended in 150 mL of gaseous ammonia in methanol and the mixture was stirred at room temperature in a close bottle at room temperature. The resulting solution was concentrated in vacuo until 10 g (74% yield) of the title compound precipitated which were collected by filtration.

Step 2. 1,3-bis(tort-butoxycarbonyl)-2-trifluoromethanesulfonylguanidine

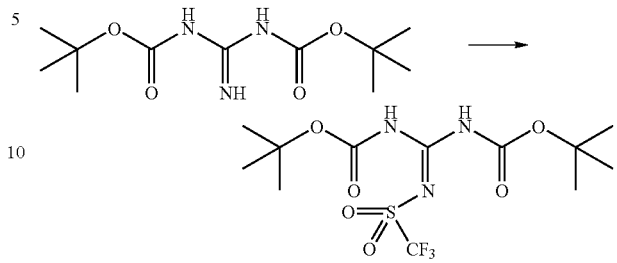

A solution of 5.2 g (20 mmol) of 1,3-bis(tert-butoxycarbonyl)guanidine in 100 mL of dry dichloromethane was cooled to −78° C. under stirring and 5.6 g (20 mmol) of trifluoromethanesulfonic anhydride were added dropwise. The reaction mixture was allowed to come to room temperature and stirred for 5 hours. An aqueous solution of $NaHSO_4$ was added and the organic layer dried over $Na_2SO_4$ and evaporated to dryness. The residue was purified by chromatography on a silica gel column (eluant petroleum ether/ethyl acetate 7/3) to give 4.0 g (51% yield) of the title compound.

Step 3. N-[3-chloro-4-(4-methylpiperazin-1-yl)phenyl] guanidine

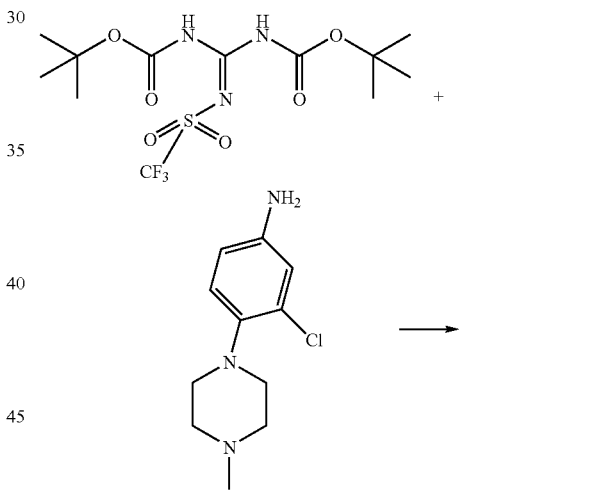

To a solution of 3.0 g (13.3 mmol) of 4-(3-chloro-4-methylpiperazin-1-yl)aniline and 2.22 mL (16.0 mmol) of triethylamine in 36 mL of dichloromethane, 6.0 g (15.3 mmol) of 1,3-bis(tert-butoxycarbonyl)-2-trifluoromethanesulfonylguanidine were added. The reaction mixture was stirred at room temperature for 72 hours. The solution was diluted with further dichloromethane, washed with water and the solvent dried over Na₂SO₄ and evaporated in vacuo. The residue was purified by chromatography on a silica gel column (eluant dichloromethane/methanol 92/8) giving 5.4 g (86.2% yield) of a protected intermediate, that was treated with 60 mL of 4 N HCl in dioxane. The mixture was stirred at room temperature overnight. The solvent was removed under reduced pressure, the residue redissolved in water, the resulting solution neutralized and the product extracted with ethyl acetate. The solvent was removed under reduced pressure to give 2.4 g (78.7% yield) of the title compound.

¹H NMR (400 MHz, DMSO-d₆) δ ppm 2.23 (s, 3 H) 2.48 (m, 4 H) 2.90 (m, 4 H) 5.38 (bs, 4 H) 6.72 (dd, J 2.44, 8.42 Hz, 1 H) 6.82 (d, J 2.44, 1 H) 7.01 (d, J 8.42 Hz, 1 H).

By working analogously, but employing the suitable substituted aniline derivative, the following compounds were prepared:

N-[3-(4-methylpiperazin-1-yl)phenyl]guanidine;
N-[4-(4-methylpiperazin-1-yl)phenyl]guanidine;

¹H NMR (400 MHz, DMSO-d₆) δ ppm 2.80 (s, 3 H) 7.09 (m 4 H) 7.41 (s, 2 H) 9.85 (s, 1 H) 11.39 (s, 1 H) (as dihydrochloride);

N-[4-(4-methylpiperazin-1-yl)-3-(trifluoromethyl)phenyl] guanidine;

¹H NMR (400 MHz, DMSO-d₆) δ ppm 2.22 (s, 3 H) 2.43 (m, 4 H) 2.80 (m, 4 H) 5.46 (bs, 4) 7.02 (m, 2 H) 7.37 (d, 1 H, J 8.42 Hz);

N-(3-chlorophenyl)guanidine.

Example 64

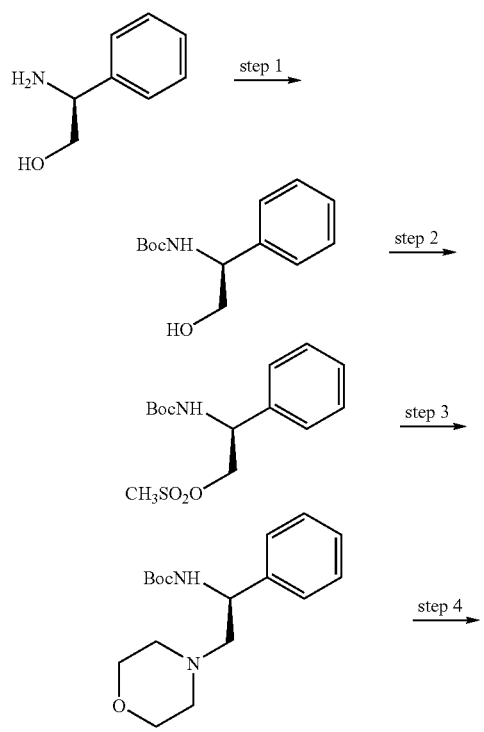

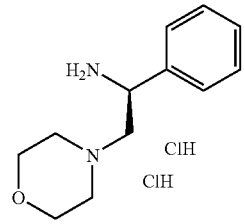

Step 1. Tert-butyl (1S)-2-hydroxy-1-phenylethylcarbamate

A solution of 40 g (0.291 mol) of (2S)-2-amino-2-phenylethanol in 1250 mL of ethylacetate and 99.83 mL (0.583 mol) of N-ethyl-N,N-diisopropylamine was cooled to 0° C. and 76.21 g (0.349 mol) of di-tert-butyl dicarbonate were added portionwise. The mixture was stirred at room temperature for 3 hours then it was washed with 400 mL of 1M KHSO₄. The organic layer was dried over Na₂SO₄ thus affording 69.88 g of the title compound.

Step 2. (2S)-2-[(tert-butoxycarbonyl)amino]-2-phenylethyl methanesulfonate

The solution of 68.9 g (0.29 mol) of tert-butyl (1S)-2-hydroxy-1-phenylethylcarbamate and triethylamine (40.36 mL, 0.29 mol) in 700 mL of dry dichloromethane under inert atmosphere was cooled to −10° C. and 24.79 mL (0.319 mol) of mesylchloride were added dropwise. After 2 hours at 0° C. the mixture was poured into ice and water and extracted with dichloromethane. The organic phase was washed with diluted HCl, aqueous NaHCO₃, brine and dried over Na₂SO₄ yielding 89.8 g of the product (98% yield).

Step 3. Tert-butyl (1S)-2-morpholin-4-yl-1-phenylethylcarbamate

The mixture of 25 g (0.0792 mol) of (2S)-2-[(tert-butoxycarbonyl)amino]-2-phenylethyl methanesulfonate and morpholine (69.37 mL, 0.792 mol) in 250 mL of dry THF under inert atmosphere was refluxed for 8 hours. The reaction was then cooled to room temperature, treated with diethylether and the solid filtered. The solution was evaporated affording the crude as a yellow oil that was purified through silica gel chromatography (eluant hexane/ethylacetate 6/4). 11.59 g of the title product were isolated (48% yield).

Step 4. (1S)-2-morpholin-4-yl-1-phenylethanamine dihydrochloride

A solution of 11.58 g (0.0378 mol) of tert-butyl (1S)-2-morpholin-4-yl-1-phenylethylcarbamate in 100 mL of dichloromethane was treated with 120 mL of HCl 4M in dioxane and stirred for 18 hours. The mixture was diluted with diethylether and the product filtered (9.48 g, 90% yield).

¹H NMR (400 MHz, DMSO-d₆) δ ppm 3.37 (m, 6 H) 3.83 (m, 4 H) 4.90 (m, 1 H) 7.51 (m, 5 H) 8.84 (bs, 3 H).

By working analogously the following compounds was prepared:

(1S)-2-(4-methylpiperazin-1-yl)-1-phenylethanamine trihydrochloride

¹H NMR (400 MHz, DMSO-d₆) δ ppm 2.78 (m, 13 H) 4.47 (m, 1 H) 7.46 (m, 5 H) 8.45 (bs, 3 H) 10.40 (bs, 1 H).

Example 65

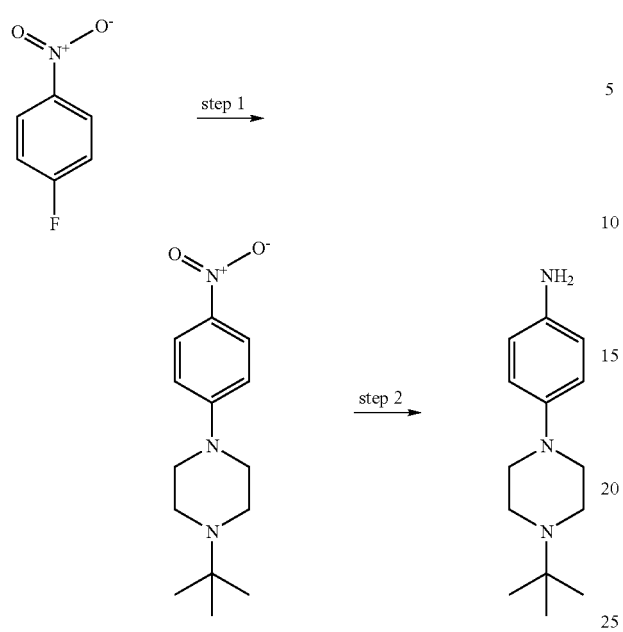

Step. 1 1-tert-butyl-4-(4-nitrophenyl)piperazine

A solution of 800 mg (5.67 mmol) of 1-fluoro-4-nitrobenzene, 2.07 g (1.2 mmol) of 1-tert-butylpiperazine dihydrobromide and 3.2 mL (20.41 mmol) of triethylamine, in 22 mL of acetonitrile, was refluxed for 10 hours. The mixture was cooled to room temperature, diluted with water and extracted with dichloromethane. The organic layer was washed with water and brine, dried over Na$_2$SO$_4$ and evaporated. Purification by flash chromatography (eluant dichloromethane/methanol 7/3) yielded 860 mg of the title compound as yellow solid.

$^1$H NMR (400 MHz, DMSO d$_6$) δ ppm 1.05 (s, 9 H) 2.63 (m, 4 H) 3.43 (m, 4 H) 7.03 (d, 2 H) 8.05 (d, 2 H).

Step 2. 4-(4-tert-butylpiperazin-1-yl)phenylamine

To a solution of 840 mg (3.189 mmol) of 1-tert-butyl-4-(4-nitrophenyl)piperazine in 24 mL of methanol, 904 mg (16.9 mmol) of ammonium chloride dissolved in 6 mL of water and 552 mg (9.886 mmol) of iron were added. After 7 hours, the suspension was cooled and filtered pH was adjusted to 10 through portionwise addition of Na$_2$CO$_3$ to the aqueous phase. Extraction with dichloromethane yielded 667 mg of the title amine.

$^1$H NMR (400 MHz, DMSO-d$_6$) δ ppm 1.05 (s, 9 H) 2.62 (m, 4 H) 2.89 (m, 4 H) 4.52 (s, 2 H) 6.50 (d, J=8.78 Hz, 2 H) 6.67 (d, J=8.78 Hz, 2 H).

Example 66

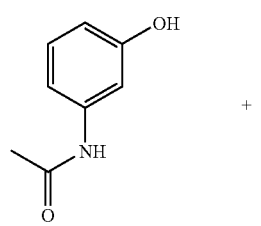 +

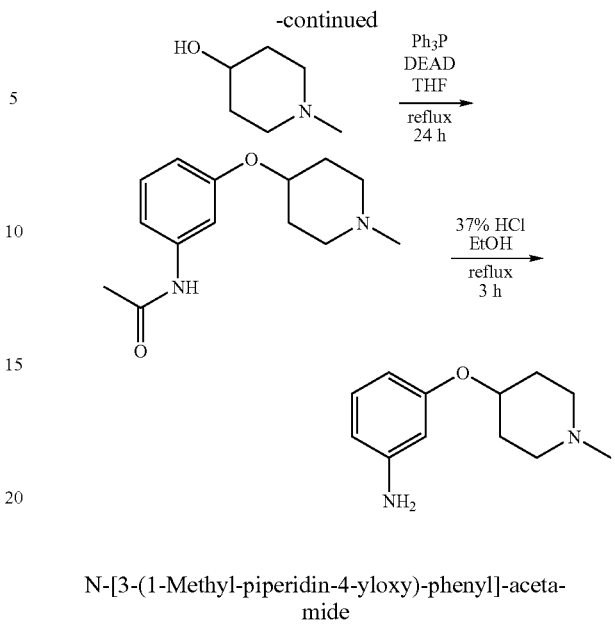

N-[3-(1-Methyl-piperidin-4-yloxy)-phenyl]-acetamide

A suspension of N-(3-Hydroxy-phenyl)-acetamide (30.2 g) in anhydrous tetrahydrofuran (600 mL) was treated with 4-hydroxy-N-methylpiperidine (30.54 mL) and triphenylphosphine (68.18 g); a solution of diethylazadicarboxylate in anhydrous tetrahydrofuran (THF) (40.94 mL in 60 mL of THF) was added dropwise and the mixture was stirred at room temperature for 2 hours and then heated to 50° C. overnight. Further amounts of triphenylphosphine (28.00 g) and diethylazadicarboxylate (14 mL) were added and the heating was continued for additional 24 hours.

The solvent was removed under vacuum and the residue was taken up with ethyl acetate (600 mL), and extracted with 2N hydrochloric acid (3×200 mL). The aqueous layer was washed with ethyl acetate and pH was brought to 10 by addition of 20% sodium hydroxide. Extraction with ethyl acetate (4×100 mL) was carried out and the combined organic extracts were washed with brine and dried over anhydrous sodium sulphate. The solvent was removed under vacuum and the crude was purified by flash chromatography on silica gel (eluant dichloromethane/methanol 85:15 then +0.1% triethylamine) to yield 21 g of the desired compound.

$^1$H NMR (400 MHz, DMSO-d$_6$) δ ppm 1.52-1.68 (m, 2 H) 1.83-1.96 (m, 2 H) 2.01 (s, 3 H) 2.14 (s, 3 H) 2.46-2.52 (m, 2 H) 2.52-2.63 (m, 2 H) 4.18-4.20 (m, 1 H) 6.59 (d, 1 H) 7.05 (d, 1 H) 7.14 (t, 1 H) 7.26 (s, 1 H) 9.83 (s, 1 H).

3-(1-Methyl-piperidin-4-yloxy)-phenylamine

A solution of N-[3-(1-Methyl-piperidin-4-yloxy)-phenyl]-acetamide (2.604 g) in absolute ethanol (40 mL) was treated with 37% hydrochloric acid and the solution was heated to reflux for 3 hours.

After removing the solvent under vacuum, the residue was dissolved in water and washed with ethyl acetate (30 mL). The aqueous solution was basified by 20% sodium hydroxide and extracted with ethyl acetate (4×50 mL); the combined organic layers were washed with brine (4×20 mL), with water (2×10 mL) and dried over anhydrous sodium sulphate. After removing the solvent, the crude (2.00 g) was crystallized from n-hexane and ethyl acetate to yield 1.00 g of pure compound.

$^1$H NMR (400 MHz, DMSO-d$_6$) δ ppm 1.54-1.68 (m, 2 H) 1.82-1.94 (m, 2 H) 2.12-2.27 (m, 2 H) 2.21 (s, 3 H) 2.58-2.71

(m, 2 H) 4.14-4.29 (m, 1 H) 4.98 (s, 2 H) 6.09 (ddd, J=8.11, 2.32, 0.79 Hz, 1 H) 6.14 (ddd, J=7.83, 2.04, 0.98 Hz, 1 H) 6.16 (t, J=2.19 Hz, 1 H) 6.88 (t, J=7.99 Hz, 1 H)

$^1$H NMR (400 MHz, DMSO-d$_6$) δ ppm 2.25 (s, 3 H) 2.46 (m, 4 H) 3.27 (m, 4 H) 3.87 (s, 3 H) 7.22 (d J=9.27 Hz, 1 H) 8.08 (dd J=9.27 Hz J=2.80 Hz, 1 H) 8.33 (d J=2.80 Hz, 1 H).

Example 67

5-Amino-2-(4-methyl-piperazin-1-yl)-phenyl]-methanol

2-(4-Methyl-piperazin-1-yl)-5-nitro-phenyl]-methanol

A suspension of methyl 2-(4-methyl-piperazin-1-yl)-5-nitro-benzoate (1.40 g, 5.00 mmol) in anhydrous diethyl ether

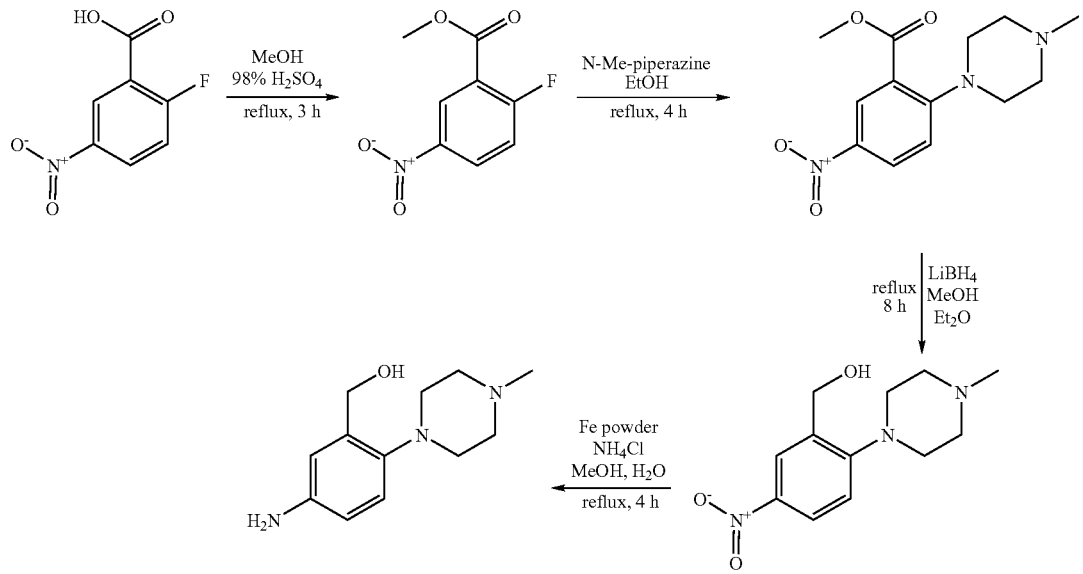

Methyl 2-fluoro-5-nitro-benzoate

A solution of 2-fluoro-5-nitro-benzoic acid (3.702 g, 20 mmol) in anhydrous methanol (10.00 mL) was treated with 98% sulphuric acid and the solution was heated to reflux for 4 hours. The solvent was removed under vacuum and the residue was dissolved in ethyl acetate (50 mL). The solution was washed with saturated aqueous sodium bicarbonate (3×10 mL), brine until neutrality ant then water, and dried over anhydrous sodium sulphate. The solvent was removed under vacuum to afford a thick oil that started to crystallize, After adding n-hexane (3 mL) the crude was stored for 2 days in the fridge. The crystalline compound was filtered and washed with n-hexane to yield 3.147 g of the pure compound.

By concentrating the mother liquors a second crop was obtained (390 mg) (y=89%).

$^1$H NMR (400 MHz, DMSO-d$_6$) δ ppm 3.94 (s, 3 H) 7.69 (m, 1 H) 8.55 (m, 1 H) 8.65 (m, 1 H).

Methyl 2-(4-methyl-piperazin-1-yl)-5-nitro-benzoate

A solution of methyl 2-fluoro-5-nitro-benzoate (3.487 g, 17.511 mmol) and N-methylpiperazine (3.855 mL, 3.508 g, 35.022 mmol) in 30 mL of anhydrous methanol was heated to reflux for 5 hours.

After removing the volatiles at reduced pressure, the crude orange oil was treated slowly with water (about 20 mL) and stirred in an ice bath for 1 hour. The crystalline compound formed was filtered by suction filtration, washed with water and dried at 40° C. under vacuum for 24 hours. There were obtained 4.627 g of yellow compound (y=96%).

(60 mL) was treated with litium borum hydride (190.5 mg, 8.75 mmol) and the formation of a precipitate was observed. Anhydrous methanol (0.350 mL, 280.3 mg, 8.75 mmol) was then added and the solution heated to reflux for 2 hours. As the reaction was not complete, further litium borum hydride (190.5 mg) and methanol (0.350 mL) were added twice every 4 hours.

After cooling in ice bath, the reaction mixture was treated with water, with 1N HCl (6 mL) and stirred at room temperature for 15 minutes. The solution was then basified to pH 11 by 1N sodium hydroxide and extracted with dichloromethane; the organic extracts were washed with brine and with water and dried over anhydrous sodium sulphate. The solvent was evaporated to dryness to afford 1.35 g of a brownish solid that was purified by flash chromatography on silica gel (eluant dichloromethane/methanol 95:5) to yield 1.10 g of desired compound (y=87%).

$^1$H NMR (400 MHz, DMSO-d$_6$) δ ppm 2.28 (s, 3 H) 2.52 (m, 4 H) 3.03 (m, 4 H) 4.54 (m, 2 H) 5.53 (t, 1 H) 7.17 (d J=8.90 Hz, 1 H) 8.08 (dd J=8.90 Hz J=2.92 Hz, 1 H) 8.33 (d J=2.92 Hz, 1 H).

5-Amino-2-(4-methyl-piperazin-1-yl)-phenyl]-methanol

To a solution of crude [2-(4-Methyl-piperazin-1-yl)-5-nitro-phenyl]-methanol (437 mg, 1.74 mmol) in methanol (1.5 mL), ammonium chloride (NH$_4$Cl) (465 mg), water (4.9 mL) and Fe powder (290 mg) were added and the mixture was heated at 100° C. for 3 hours.

The reaction mixture was filtered and the black precipitate washed with MeOH/water 1:1 (10 mL). Methanol was removed under vacuum and the remaining water was basified with sodium carbonate (NaCO₃) and extracted with ethyl acetate (5×20 mL). The organic extracts were washed with brine (2×10 mL) and with water (2×5 mL) and dried over anhydrous sodium sulphate. After evaporation, the resultant crude orange solid was purified by flash chromatography on silica gel (eluant dichloromethane/methanol/triethylamine 90:10:0.1) to yield 357 mg of pure title compound (y=92%).

$^1$H NMR (400 MHz, DMSO-$d_6$) δ ppm 2.26 (s, 3 H) 2.52 (m, 4 H) 2.73 (m, 4 H) 4.48 (m, 2 H) 4.75 (bs, 2 H) 4.95 (t, 1 H) 6.43 (dd J=8.42 Hz J=2.68 Hz, 1 H) 6.67 (d J=2.68 Hz, 1 H) 6.80 (d J=8.42 Hz, 1 H).

Example 68

1-(4-Methyl-piperazine-1-carbonyl)-piperidin-4-one hydrochloride

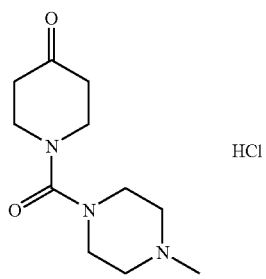

To a suspension of 4-methylpiperazine-1-carbonyl chloride hydrochloride (19.9 g 0.1 mol) and piperidone monohydrate hydrochloride (15.3 g 0.1 mol), in 200 mL of dichloromethane, dry triethylamine (45 mL, 0.33 mol) was added dropwise. The mixture was stirred for 2 hours. The organic phase was washed with brine (2×20 mL) and dried over sodium sulfate. After filtration, the solvent was evaporated in vacuo and the crude product was dissolved in EtOH (50 mL) and diethylether (100 mL) and treated with HCl 4N in dioxane (25 mL). After 1 hour, the precipitate was filtered and dried in oven to give 13 g (yield 50%) of the title compound.

1 H NMR (400 MHz, DMSO-D6) δ ppm 2.40 (t, J=6.16 Hz, 4 H) 2.81 (s, 3 H) 3.00-3.11 (m, 2 H) 3.12-3.23 (m, 2 H) 3.28-3.42 (m, 2 H) 3.51 (t, J=6.16 Hz, 4 H) 3.73 (d, J=14.27 Hz, 2 H) 10.12 (s, 1 H)

Example 69

1-acetyl-4-hydrazinopiperidine hydrochloride

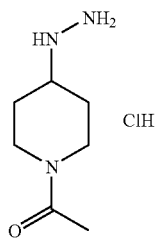

Step 1: N'-(1-acetylpiperidin-4-ylidene)benzohydrazide

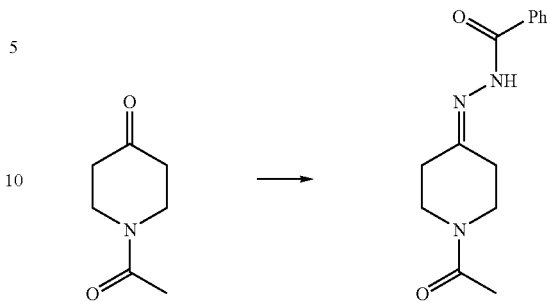

20 g (0.142 mol) of 1-acetyl-4-piperidone were dissolved in 400 mL of absolute ethanol and 21.2 g (0.156 mol) of benzoylhydrazine were added. The resulting solution was refluxed for 6 hours under stirring. The solvent was then removed in vacuo and the residue partitioned between dichloromethane and water. The organic layer was dried over sodium sulfate and evaporated to dryness. The residue was triturated with diethylether and 30 g (83% yield) of the title compound were collected by filtration.

$^1$H NMR (400 MHz, DMSO-$d_6$) δ ppm 2.07 (s, 3 H) 2.43-2.62 (m, 4 H) 3.45-3.74 (m, 4 H) 7.51 (m, 3 H) 7.84 (m, 2 H) 10.7 (bs, 1 H).

Step 2: N'-(1-acetylpiperidin-4-yl)benzohydrazide

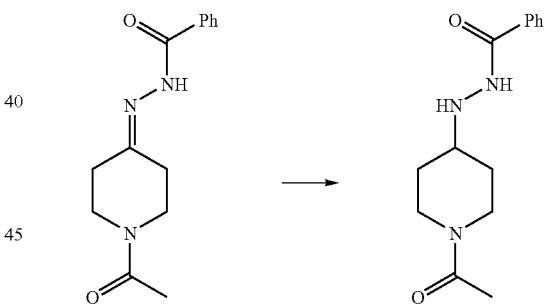

30 g (0.12 mol) of N'-(1-acetylpiperidin-4-ylidene)benzohydrazide were dissolved in 500 mL of glacial acetic acid and 1 g of PtO₂ were added. The mixture was hydrogenated at 40 psi for 12 hours at room temperature. The catalyst was then filtered on celite and the filtrate evaporated in vacuo. The residue was redissolved with dichloromethane and washed with aqueous NaHCO₃. The solvent was dried over sodium sulfate and removed under reduced pressure to give, after trituration with diethylether, 28.6 g (92% yield) of the title compound.

$^1$H NMR (400 MHz, DMSO-$d_6$) δ ppm 1.25 (m, 2 H) 1.81 (m, 2 H) 2.00 (s, 3 H) 3.75 (m, 2 H) 4.10 (m, 2 H) 4.19 (s, 1 H) 7.49-7.51 (m, 3 H) 7.84 (m, 2 H) 10.01 (s, 1 H).

Step 3: di-tert-butyl1-(1-acetylpiperidin-4-yl)-2-benzoylhydrazine-1,2-dicarboxylate

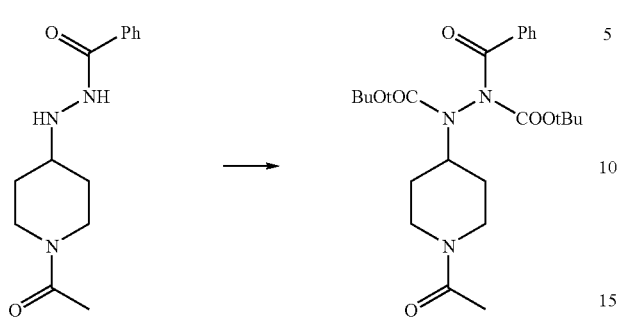

To a solution of 28.6 g (0.11 mol) of N-(1-acetylpiperidin-4-yl)benzohydrazide in 700 mL of acetonitrile, 53.19 g (0.44 mol) of 4-diethylaminopyridine (DMAP) and 77.2 g (0.35 mol) of di-tert-butyldicarbonate were added. The mixture was stirred overnight, the solvent removed and the residue taken up with dichoromethane and washed with aqueous KHSO₄ to remove DMAP. The organic layer was dried over sodium sulfate and evaporated to give 45 g of the title compound as an oil.

$^1$H NMR (400 MHz, DMSO-$d_6$) δ ppm 1.18 and 1.40 (2s, 18H) 1.97 (s, 3 H) 4.28 (m, 1 H) 7.51-7.53 (m, 4 H).

Step 4: di-tert-butyl1-(1-acetylpiperidin-4-yl)hydrazine-1,2-dicarboxylate

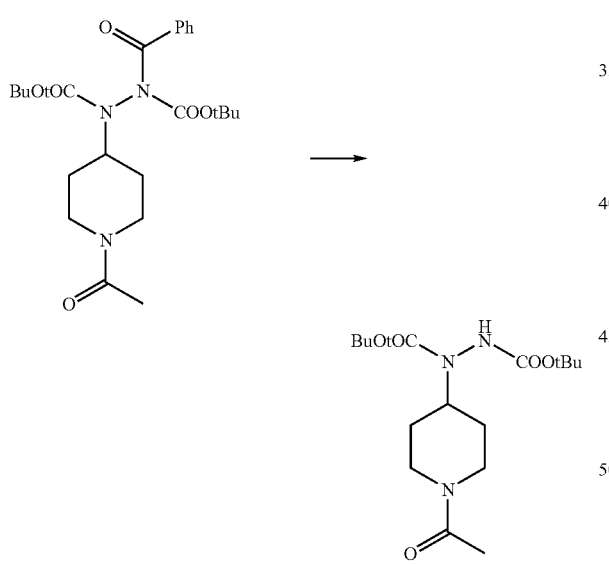

45 g (0.1 mol) of di-tert-butyl1-(1-acetylpiperidin-4-yl)-2-benzoylhydrazine-1,2-dicarboxylate were dissolved in 1 L of tetrahydrofuran and a solution of 5.8 g (0.14 mol) of lithium hydroxide monohydrate in 1 L of water were added. The mixture was stirred at room temperature for 16 hours, the tetrahydrofuran removed in vacuo and the aqueous layer extracted several times with dichloromethane. The organic phase was dried over sodium sulfate and evaporated to dryness, giving 32 g (84% yield) of the title compound.

$^1$H NMR (400 MHz, DMSO-$d_6$) δ ppm 1.41 and 1.42 (2s, 18H) 1.99 (s, 3 H) 4.09 (m, 1 H) 2.52 and 3.05/2m, 4 H) 3.95 and 4.41 (2m, 4 H) 8.81 (bs, 1 H).

Step 5: 1-acetyl-4-hydrazinopiperidine hydrochloride

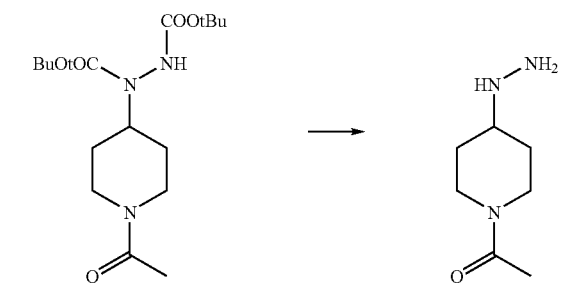

32 g (0.09 mol) of di-tert-butyl 1-(1-acetylpiperidin-4-yl)hydrazine-1,2-dicarboxylate were dissolved in 300 mL of methanol and 30 mL of HCl 4 M in dioxane were added. The mixture was stirred at room temperature overnight. The solvent was then evaporated and the residue crystallized from ethanol, giving 14 g (77% yield) of the title compound.

Example 70

(1S)-1-methyl-2-morpholin-4-yl-1-phenylethylamine dihydrochloride

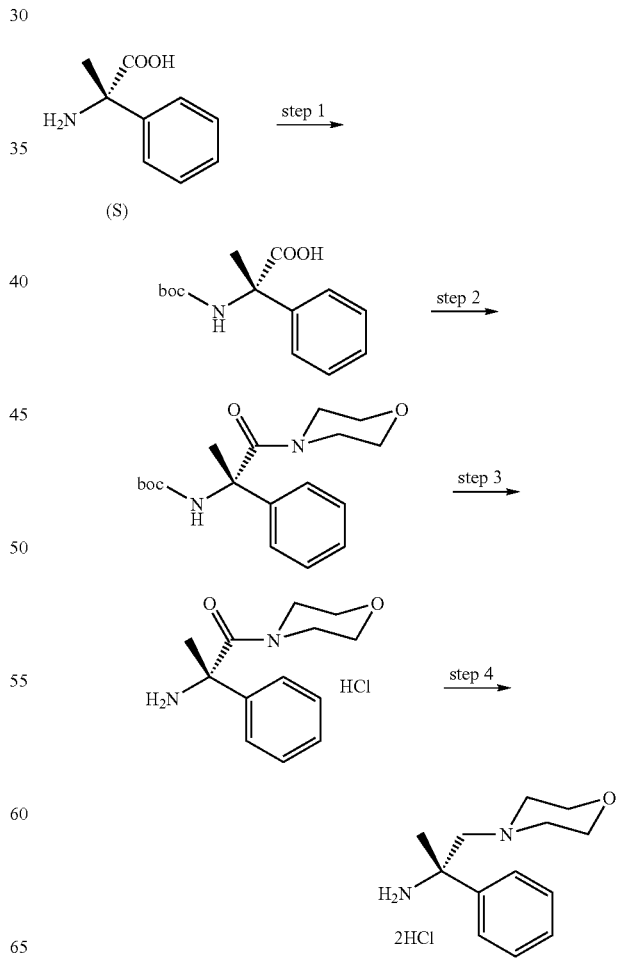

Step 1. N-(tert-butoxycarbonyl)-2-phenyl-D-alanine

To a suspension of 500 mg of 2-phenyl-D-alanine (3.02 mmol) and trimethylammonium hydroxide (aqueous solution 10%, 2.8 mL, 3.02 mmol) in 15 mL of acetonitrile, diterbutylcarbonate (1.047 g, 4.8 mmol) was added and the mixture was stirred at room temperature for 2 days. The solvent was then removed under vacuo, the residue was dissolved in water and washed with diethylether. The aqueous layer was acidified to pH=3-4 with citric acid and the product was extracted with ethyl acetate (3×20 mL). The combined organic phase was washed with water, dried over $Na_2SO_4$ and evaporated. The title product was recovered as white solid (630 mg, yield 78%).

Step 2. N-(tert-butoxycarbonyl-(1S)-1-methyl-2-morpholin-4-yl-2-oxo-1-phenylethylamine 630 mg (2.374 mmol) of N-(tert-butoxycarbonyl)-2-phenyl-D-alanine were dissolved in 20 mL of dry DMF and O-(benzotriazol-1-yl)-1,1,3,3-tetramethyluronium tetrafluoborate (TBTU, 1.37 g, 4.27 mmol), morpholine (0.412 mL, 4.73 mmol) and diisopropylethylamine (1.63 mL, 9.5 mol) were added. The mixture was stirred at room temperature for 1 hour, then the solvent was removed and the residue dissolved with dichloromethane. The solution was washed with saturated $NaHCO_3$, brine, water and dried over $Na_2SO_4$. 700 mg of the title compound were recovered (88% yield).

$^1$H NMR (400 MHz, DMSO-$d_6$) δ ppm 1.40 (s, 9 H) 1.65 (s, 3 H) 3.33 (m, 8 H) 7.35 (m, 6 H).

Step 3. (1S)-1-methyl-2-morpholin-4-yl-2-oxo-1-phenylethylamine hydrochloride

A solution of 630 mg (1.884 mmol) of N-(tert-butoxycarbonyl)-(1S)-1-methyl-2-morpholin-4-yl-2-oxo-1-phenylethylamine in 20 mL of dioxane was treated with 2.5 mL of HCl 4N in dioxane overnight. The solvent was removed under vacuo and the solid was triturated with diethylether yielding 560 mg of the title compound.

$^1$H NMR (400 MHz, DMSO-$d_6$) δ ppm 1.94 (s, 3 H) 3.35 (m, 8 H) 7.51 (m, 5 H) 8.52 (bs, 3 H).

Step 4. (1S)-1-methyl-2-morpholin-4-yl-1-phenylethylamine dihydrochloride

Under an argon atmosphere 412 mg of (1S)-1-methyl-2-morpholin-4-yl-2-oxo-1-phenylethylamine hydrochloride (1.522 mol) were dissolved in 30 mL of dry THF. A 2 M solution of borane dimethylsulfide (4.4 mL, 5.78 mmol) was added dropwise at 0° C. and the mixture stirred for 10 minutes at 0° C. and then allowed to reach room temperature (gas evolution). After 4 hours the reaction was quenched with methanol (added very carefully) and diluted with methanol when effervescence ceased. THF was removed under vacuo and the methanolic solution was heated at 60° C. for 30 minutes. The solvent was at last completely removed recovering 330 mg of the amine that was subsequently dissolved in 15 mL of dioxane and treated with 1.35 mL of HCl 4 N in dioxane. After 1 hour the solvent was evaporated and the product was triturated with diethylether to yield 350 mg of the expected salt.

$^1$H NMR (400 MHz, DMSO-$d_6$) δ ppm 1.66 (s, 3 H) 2.52 (m, 6 H) 3.57 (m, 4 H) 7.51 (m, 5 H) 8.53 (s, 3 H).

Example 71

(1S)-2-morpholin-4-yl-2-oxo-1-phenylethylamine hydrochloride

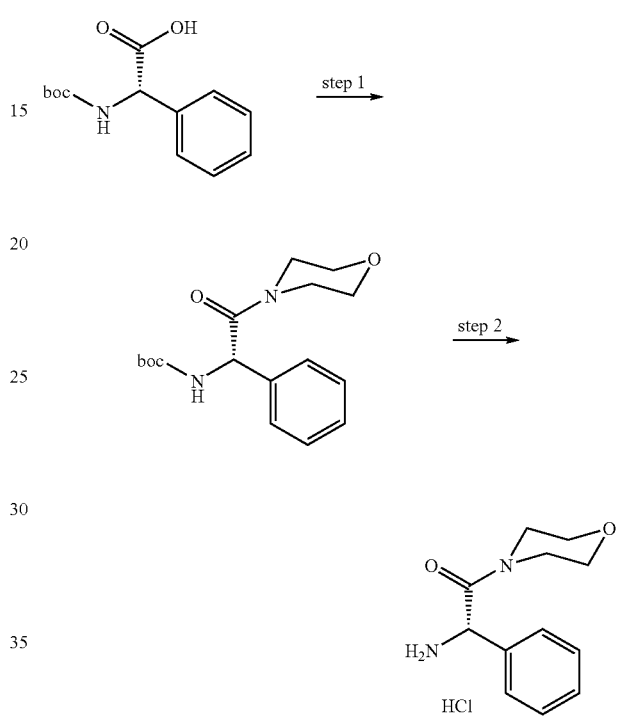

Step 1. N-(tert-butoxycarbonyl)-(1S)-2-morpholin-4-yl-2-oxo-1-phenylethylamine 1 g (3.98 mmol) of Boc-L-phenylglicine was dissolved in 18 mL of dry DMF and O-(benzotriazol-1-yl)-1,1,3,3-tetramethyluronium tetrafluoborate (TBTU, 1.92 g, 5.97 mmol), morpholine (0.555 mL, 6.37 mmol) and diisopropylethylamine (2.72 mL, 15.92 mol) were added. The mixture was stirred at room temperature for 1 hour, then the solvent was removed and the residue dissolved with dichloromethane. The solution was washed with saturated $NaHCO_3$, brine, water and dried over $Na_2SO_4$. 1.327 g of the title compound were recovered.

Step 2. (1S)-2-morpholin-4-yl-2-oxo-1-phenylethylamine hydrochloride 1.327 g of N-(tert-butoxycarbonyl)-(1S)-2-morpholin-4-yl-2-oxo-1-phenylethylamine was dissolved in 15 mL of dioxane and treated with 3.5 mL of HCl 4 M in dioxane overnight. The solvent was removed and the solid was triturated with diethylether yielding 920 mg of the product (yield 90%).

$^1$H NMR (400 MHz, DMSO-$d_6$) δ ppm 3.13 (m, 4 H) 3.54 (m, 4 H) 5.58 (m, 1 H) 7.50 (s, 5 H) 8.58 (s, 3 H).

What is claimed is:

1. A pyrazolo-quinazoline derivative represented by formula (Ia) or (Ib)

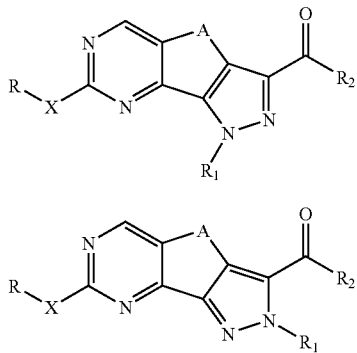

wherein

R is hydrogen or an optionally substituted group selected from amino, straight or branched $C_1$-$C_6$ alkyl, $C_3$-$C_{10}$ cycloalkyl, aryl, arylalkyl, heterocyclyl or heterocyclylalkyl;

X is a single bond or a divalent radical selected from —NR'—, —CONR'—, —NH—CO—NH—, —O—, —S— or $SO_2$—, wherein R' is hydrogen or an optionally substituted group selected from straight or branched $C_1$-$C_6$ alkyl, $C_3$-$C_6$ cycloalkyl, aryl, arylalkyl, heterocyclyl, heterocyclylalkyl or, together with the nitrogen atom to which they are bonded, R and R' may form a 5 to 6 membered heteroaryl or heterocyclyl group optionally containing one additional heteroatom selected among N, O or S;

$R_1$, bonded to any one of the nitrogen atoms of the pyrazole ring as per formulae (Ia) or (Ib), represents a hydrogen atom or an optionally substituted group selected from straight or branched $C_1$-$C_6$ alkyl, $C_3$-$C_6$ cycloalkyl, aryl, arylalkyl, heterocyclyl or heterocyclylalkyl or, in formula (Ib), $R_1$ is a divalent —(CH2)n-NH— group being linked to $R_2$, wherein n is 2 or 3; wherein $R_1$ is optionally substituted in an of its free positions by one or more groups independently selected from: halogen, nitro, oxo groups (=O), cyano, azido, alkyl, polyfluorinated alkyl, hydroxyalkyl, aryl, arylalkyl, heterocyclyl, heterocyclylalkyl, cycloalkyl, alkylaryl, alkylheterocyclyl, hydroxy, alkoxy, polyfluorinated alkoxy, aryloxy, arylalkyloxy, heterocyclyloxy, heterocyclylalkyloxy, methylenedioxy, alkylcarbonyloxy, arylcarbonyloxy, carboxy, alkoxycarbonyl, alkoxycarbonylalkyl, aryloxycarbonyl, cycloalkyloxycarbonyl, amino, aminoalkyl, alkylaminoalkyl, alkylaminoalkyloxy, ureido, alkylamino, dialkylamino, arylamino, diarylamino, formylamino, alkylcarbonylamino, arylcarbonylamino, heterocyclylcarbonylamino, alkoxycarbonylamino, alkoxyimino, alkylsulfonylamino, arylsulfonylamino, formyl, alkylcarbonyl, arylcarbonyl, heterocyclylcarbonyl, cycloalkylcarbonyl, aminocarbonyl, alkylaminocarbonyl, dialkylaminocarbonyl, arylaminocarbonyl, alkylsulfonyl, arylsulfonyl, alkylaminosulfonyl, arylthio and alkylthio;

$R_2$ is a group selected from —NR"R'", —N(OH)R", —OR" or —R", wherein R" and R'" are, each independently, hydrogen or an optionally substituted group selected from straight or branched $C_1$-$C_6$ alkyl, $C_3$-$C_6$ cycloalkyl or cycloalkyl-alkyl, aryl, arylalkyl, heterocyclyl or heterocyclylalkyl or, together with the nitrogen atom to which they are bonded, R" and R'" may form a 5 to 6 membered heteroaryl or heterocyclyl group, optionally containing one additional heteroatom selected among N, O or S;

A is a divalent group selected from —$CH_2$—, —$(CH_2)_2$—, —$CH_2$—$C(CH_3)_2$—, —$C(CH_3)_2$—$CH_2$— or —CH=CH—;

or a pharmaceutically acceptable salt thereof.

2. A compound of formula (Ia) or (Ib), according to claim 1, wherein X is a group —NH— and $R_2$ is a group selected from —NHR", —N(OH)R", —OR" or —R", wherein R" is an optionally substituted group selected from $C_3$-$C_6$ cycloalkyl or cycloalkyl-alkyl, aryl, arylalkyl, heterocyclyl or heterocyclylalkyl; and R, $R_1$ and A are as above defined.

3. A compound of formula (Ia) or (Ib), according to claim 1, wherein X is a group —O— and $R_2$ is a group selected from —NHR", —N(OH)R", —OR" or —R", wherein R" is an optionally substituted group selected from $C_3$-$C_6$ cycloalkyl or cycloalky-alkyl, aryl, arylalkyl, heterocyclyl or heterocyclylalkyl; and R, $R_1$ and A are as above defined.

4. A compound of formula (Ia) or (Ib), according to claim 1, wherein X is a group —S— and $R_2$ is a group selected from —NHR", —N(OH)R", —OR" or —R", wherein R" is an optionally substituted group selected from $C_3$-$C_6$ cycloalkyl or cycloalkyl-alkyl, aryl, arylalkyl, heterocyclyl or heterocyclyalkyl; and R, $R_1$ and A are as above defined.

5. A compound of formula (Ia) or (Ib), according to claim 1, wherein X is a group —NH— and $R_2$ is a group —NHR" or —N(OH)R" wherein R" is a hydrogen atom or a straight or branched $C_1$-$C_4$ alkyl group; and wherein A, R and $R_1$ are as above defined.

6. A compound of formula (Ia) or (Ib), according to claim 1, wherein X is a group —O— and $R_2$ is a group —NHR" or —N(OH)R" wherein R" is a hydrogen atom or a straight or branched $C_1$-$C_4$ alkyl group; and wherein A, R and $R_1$ are as above defined.

7. A compound of formula (Ia) or (Ib), according to claim 1, wherein X is a group —S— and $R_2$ is a group —NHR" or —N(OH)R" wherein R" is a hydrogen atom or a straight or branched $C_1$-$C_4$ alkyl group; and wherein A, R and $R_1$ are as above defined.

8. A compound of formula (Ib), according to claim 1, wherein R, X and A are as above defined and $R_1$ and $R_2$ are linked together through a divalent —$(CH_2)_n$—NH— wherein n is as above defined.

9. A compound of formula (Ia) or (Ib) according to claim 1, wherein A is a group selected from —$(CH_2)_2$—, —$CH_2$—C$(CH_3)_2$— or —C$(CH_3)_2$—$CH_2$—.

10. A compound of formula (Ia) or (Ib), according to claim 1, wherein any of R, R', R" and R'" may be optionally substituted in any of their free positions by one or more groups independently selected from: halogen, nitro, oxo groups (=O), cyano, azido, alkyl, polyfluorinated alkyl, hydroxyalkyl, aryl, arylalkyl, heterocyclyl, heterocyclylalkyl, cycloalkyl, alkylaryl, alkylheterocyclyl, hydroxyl, alkoxy, polyfluorinated alkoxy, aryloxy, arylalkyloxy, heterocyclyloxy, heterocyclylalkyloxy, methylenedioxy, alkylcarbonyloxy, alkylcarbonyloxyalkyl, arylcarbonyloxy, carboxy, alkoxycarbonyl, alkoxycarbonylalkyl, aryloxycarbonyl, cycloalkyloxycarbonyl, amino, aminoalkyl, alkylaminoalkyl, alkylaminoalkyloxy, ureido, alkylamino, dialkylamino, arylamino, diarylamino, formylamino, alkylcarbonylamino, arylcarbonylamino, heterocyclylcarbonylamino, alkoxycarbonylamino, alkoxyimino, alkylsulfonylamino, arylsulfonylamino, formyl, alkylcarbonyl, arylcarbonyl, heterocyclylcarbonyl, cycloalkylcarbonyl, heterocyclylcarbonyl, aminocarbonyl, alkylaminocarbonyl, dialkylaminocarbonyl, arylaminocarbonyl, alkylsuflonyl, arylsulfonyl, heterocyclylsulfonyl, aminosulfonyl, alkylaminosulfonyl, dialkylaminosulfonyl, arylthio and alkylthio.

11. Any specific compound of formula (Ia) or (Ib), according to claim 1, optionally in the form of a pharmaceutically acceptable salt, among those defined in tables from VI to XXI.

12. A pharmaceutical composition comprising a therapeutically effective amount of a pyrazolo-quinazoline derivative of formula (Ia) or (Ib) as defined in claim 1, and at least one pharmaceutically acceptable excipient, cater and/or diluent.

13. A pharmaceutical composition according to claim 12 further comprising one or more chemotherapeutics agents.

\* \* \* \* \*

UNITED STATES PATENT AND TRADEMARK OFFICE
CERTIFICATE OF CORRECTION

PATENT NO. : 7,482,354 B2
APPLICATION NO. : 10/557565
DATED : January 27, 2009
INVENTOR(S) : Gabriella Traquandi et al.

It is certified that error appears in the above-identified patent and that said Letters Patent is hereby corrected as shown below:

Column 1, Line 8:

"The present application is application is a 371 of PCT/"

should read

--The present application is a 371 of PCT/--

Column 75, line 9:

"control, data acquisition and data processing were providen"

should read

--control, data acquisition and data processing were provided--

Column 75, Line 29:

"control, data acquisition and data processing were providen"

should read

--control, data acquisition and data processing were provided--

Column 76, Line 57, Example 2:

"LIN(1MS)$_2$"  should read  --LIN(TMS)$_2$--

Column 77, Line 32:

"chlorform"  should read  --chloroform--

Column 125, Line 35, Example 32:

"8-(cyclopentylamio)"  should read  --8-(cyclopentylamino)--

Column 134, Line 17, Example 33:

"M00(C01)-D03]"  should read  --M00(C01)-D04]--

UNITED STATES PATENT AND TRADEMARK OFFICE
CERTIFICATE OF CORRECTION

PATENT NO. : 7,482,354 B2
APPLICATION NO. : 10/557565
DATED : January 27, 2009
INVENTOR(S) : Gabriella Traquandi et al.

It is certified that error appears in the above-identified patent and that said Letters Patent is hereby corrected as shown below:

Column 137, Line 51, Example 38:

"triphenylmethylhydroxylanine"

should read

--triphenylmethylhydroxylamine--

Column 141, Line 30, Example 41:

"dissolved in 6 mL of ethanol and 0.03 g (o.66 mmol) of is"

should read

--dissolved in 6 mL of ethanol and 0.03 g (o.66 mmol) of--

Column 159, Line 31, Example 43:

"1 H"   should read   --1 M--

Column 219, Line 44, Claim 1:

"substituted in an of"   should read   --substituted in of--

Signed and Sealed this

Twenty-ninth Day of September, 2009

David J. Kappos
*Director of the United States Patent and Trademark Office*